(12) United States Patent
Li et al.

(10) Patent No.: US 10,822,312 B2
(45) Date of Patent: *Nov. 3, 2020

(54) SUBSTITUTED QUINAZOLINE COMPOUNDS AND METHODS OF USE

(71) Applicant: ARAXES PHARMA LLC, San Diego, CA (US)

(72) Inventors: Liansheng Li, San Diego, CA (US); Jun Feng, San Diego, CA (US); Pingda Ren, San Diego, CA (US); Yi Liu, San Diego, CA (US)

(73) Assignee: ARAXES PHARMA LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/089,000

(22) PCT Filed: Mar. 29, 2017

(86) PCT No.: PCT/US2017/024839
§ 371 (c)(1),
(2) Date: Sep. 27, 2018

(87) PCT Pub. No.: WO2017/172979
PCT Pub. Date: Oct. 5, 2017

(65) Prior Publication Data
US 2019/0127336 A1     May 2, 2019

Related U.S. Application Data

(60) Provisional application No. 62/315,532, filed on Mar. 30, 2016, provisional application No. 62/404,539, filed on Oct. 5, 2016.

(51) Int. Cl.
| | | |
|---|---|---|
| *C07D 403/04* | (2006.01) | |
| *C07D 403/12* | (2006.01) | |
| *C07D 403/14* | (2006.01) | |
| *C07D 239/95* | (2006.01) | |
| *A61K 45/06* | (2006.01) | |
| *A61K 31/517* | (2006.01) | |
| *C11D 3/50* | (2006.01) | |
| *C07D 401/14* | (2006.01) | |
| *A61P 35/00* | (2006.01) | |

(52) U.S. Cl.
CPC .......... *C07D 239/95* (2013.01); *A61K 31/517* (2013.01); *A61K 45/06* (2013.01); *A61P 35/00* (2018.01); *C07D 401/14* (2013.01); *C07D 403/04* (2013.01); *C07D 403/12* (2013.01); *C07D 403/14* (2013.01); *C11D 3/50* (2013.01)

(58) Field of Classification Search
CPC ... C07D 403/04; C07D 403/12; C07D 403/14
See application file for complete search history.

(56) References Cited

U.S. PATENT DOCUMENTS

| | | |
|---|---|---|
| 3,702,849 A | 11/1972 | Cronin et al. |
| 3,752,660 A | 8/1973 | Little |
| 4,649,219 A | 3/1987 | Itoh et al. |
| 4,861,760 A | 8/1989 | Mazuel et al. |
| 4,911,920 A | 3/1990 | Jani et al. |
| 5,010,175 A | 4/1991 | Rutter et al. |
| 5,033,252 A | 7/1991 | Carter et al. |
| 5,052,558 A | 10/1991 | Carter et al. |
| 5,212,162 A | 5/1993 | Missel et al. |
| 5,288,514 A | 2/1994 | Ellman et al. |
| 5,323,907 A | 6/1994 | Kalvelage et al. |
| 5,403,841 A | 4/1995 | Lang et al. |
| 5,538,848 A | 7/1996 | Livak et al. |
| 5,539,083 A | 7/1996 | Cook et al. |
| 5,593,853 A | 1/1997 | Chen et al. |
| 5,605,798 A | 2/1997 | Koester |
| 5,731,352 A | 3/1998 | Lesieur et al. |
| 5,777,324 A | 7/1998 | Hillenkamp |

(Continued)

FOREIGN PATENT DOCUMENTS

| | | |
|---|---|---|
| CN | 1267291 A | 9/2000 |
| EP | 0094498 A2 | 11/1983 |

(Continued)

OTHER PUBLICATIONS

US 5,962,233 A, 10/1999, Livak et al. (withdrawn)
Hillig et al. PNAS, vol. 116 No. 7, pp. 2551-2560. (Year: 2019).*
Devos et al., Practical limits of function prediction. Proteins: Structure, Function and Genetics. 41(1):98-107 (2000).
Kisselev. Polypeptide release factors in prokaryotes and eukaryotes: same function, different structure. Structure. 10(1):8-9 (2002).
Nitrogen Mustard HN-2 : Blister Agent. National Institute for Occupational Safety and Health (NIOSH). Available from: https://www.cdc.gov/niosh/ershdb/emergencyresponsecard_29750011.html (2011).
U.S. Appl. No. 16/013,271 Office Action dated Jun. 27, 2019.
U.S. Appl. No. 15/713,297 Office Action dated Jun. 25, 2019.

(Continued)

*Primary Examiner* — Emily A Bernhardt
(74) *Attorney, Agent, or Firm* — Wilson Sonsini Goodrich & Rosati

(57) ABSTRACT

The present disclosure provides inhibitors of Ras protein of Formula (I-A):

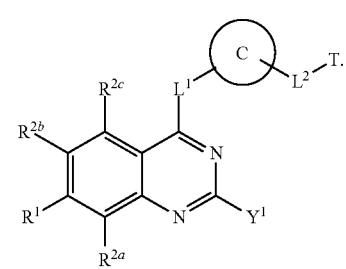

(I-A)

Also disclosed are methods to modulate the activity of Ras protein and methods of treatment of disorders mediated by Ras protein with compounds of Formula (I-A).

12 Claims, 3 Drawing Sheets

(56) References Cited

U.S. PATENT DOCUMENTS

| | | | |
|---|---|---|---|
| 5,858,659 A | 1/1999 | Sapolsky et al. |
| 5,861,510 A | 1/1999 | Piscopio et al. |
| 5,863,949 A | 1/1999 | Robinson et al. |
| 5,919,626 A | 7/1999 | Shi et al. |
| 5,925,525 A | 7/1999 | Fodor et al. |
| 5,952,174 A | 9/1999 | Nikiforov et al. |
| 6,017,696 A | 1/2000 | Heller |
| 6,043,031 A | 3/2000 | Koester et al. |
| 6,045,996 A | 4/2000 | Cronin et al. |
| 6,051,380 A | 4/2000 | Sosnowski et al. |
| 6,068,818 A | 5/2000 | Ackley et al. |
| 6,214,872 B1 | 4/2001 | Robinson |
| 6,251,639 B1 | 6/2001 | Kurn |
| 6,903,118 B1 | 6/2005 | Biedermann et al. |
| 7,465,454 B2 | 12/2008 | Franzusoff et al. |
| 7,595,397 B2 | 9/2009 | Zindell et al. |
| 8,399,454 B2 | 3/2013 | Bian et al. |
| 8,426,401 B2 | 4/2013 | Bian et al. |
| 8,604,017 B2 | 12/2013 | Bian et al. |
| 8,697,684 B2 | 4/2014 | Bian et al. |
| 8,741,887 B2 | 6/2014 | Bian et al. |
| 8,759,333 B2 | 6/2014 | Connolly et al. |
| 9,227,978 B2 | 1/2016 | Ren et al. |
| 9,376,559 B2 | 6/2016 | Holtcamp et al. |
| 9,810,690 B2 | 11/2017 | Patricelli et al. |
| 10,011,600 B2 * | 7/2018 | Li ................. C07D 403/12 |
| 10,023,588 B2 | 7/2018 | Ostrem et al. |
| 2002/0169300 A1 | 11/2002 | Waterman et al. |
| 2003/0022344 A1 | 1/2003 | Williams et al. |
| 2003/0166620 A1 | 9/2003 | Lee et al. |
| 2003/0171400 A1 | 9/2003 | Pikul et al. |
| 2005/0012070 A1 | 1/2005 | Inoue et al. |
| 2005/0227997 A1 | 10/2005 | Noe et al. |
| 2008/0004348 A1 | 1/2008 | Yous et al. |
| 2008/0039450 A1 | 2/2008 | Jensen et al. |
| 2009/0054402 A1 | 2/2009 | Wang et al. |
| 2009/0124636 A1 | 5/2009 | Barber et al. |
| 2009/0298075 A1 | 12/2009 | Travers et al. |
| 2010/0331300 A1 | 12/2010 | Bian et al. |
| 2011/0230476 A1 | 9/2011 | Niu et al. |
| 2011/0269244 A1 | 11/2011 | Petter et al. |
| 2011/0311447 A1 | 12/2011 | Tu et al. |
| 2011/0319290 A1 | 12/2011 | Raymond et al. |
| 2013/0012489 A1 | 1/2013 | Mederski et al. |
| 2013/0274252 A1 | 10/2013 | Pandey et al. |
| 2013/0302407 A1 | 11/2013 | Rao et al. |
| 2014/0288045 A1 | 9/2014 | Ren et al. |
| 2015/0087628 A1 | 3/2015 | Ostrem et al. |
| 2015/0239900 A1 | 8/2015 | Li et al. |
| 2016/0031898 A1 | 2/2016 | Ren et al. |
| 2016/0108019 A1 | 4/2016 | Li et al. |
| 2016/0159738 A1 | 6/2016 | Ren et al. |
| 2016/0166571 A1 | 6/2016 | Janes et al. |
| 2016/0297774 A1 | 10/2016 | Li et al. |
| 2016/0368930 A1 | 12/2016 | Ostrem et al. |
| 2017/0022184 A1 | 1/2017 | Li et al. |
| 2018/0246102 A1 | 8/2018 | Patricelli et al. |

FOREIGN PATENT DOCUMENTS

| | | |
|---|---|---|
| EP | 0606046 A1 | 7/1994 |
| EP | 0780386 A1 | 6/1997 |
| EP | 0818442 A2 | 1/1998 |
| EP | 0931788 A2 | 7/1999 |
| EP | 1004578 A2 | 5/2000 |
| EP | 1736465 A1 | 12/2006 |
| GB | 939516 A | 10/1963 |
| JP | S58203966 A | 11/1983 |
| JP | S59163372 A | 9/1984 |
| JP | 2005502623 A | 1/2005 |
| JP | 2008524154 A | 7/2008 |
| JP | 4775259 B2 | 9/2011 |
| WO | WO-9005719 A1 | 5/1990 |
| WO | WO-9119735 A1 | 12/1991 |
| WO | WO-9200091 A1 | 1/1992 |
| WO | WO-9320242 A1 | 10/1993 |
| WO | WO-9605309 A2 | 2/1996 |
| WO | WO-9627583 A1 | 9/1996 |
| WO | WO-9633172 A1 | 10/1996 |
| WO | WO-9700271 A1 | 1/1997 |
| WO | WO-9803516 A1 | 1/1998 |
| WO | WO-9807697 A1 | 2/1998 |
| WO | WO-9830566 A1 | 7/1998 |
| WO | WO-9833496 A1 | 8/1998 |
| WO | WO-9833768 A1 | 8/1998 |
| WO | WO-9834915 A1 | 8/1998 |
| WO | WO-9834918 A1 | 8/1998 |
| WO | WO-9857948 A1 | 12/1998 |
| WO | WO-9907675 A1 | 2/1999 |
| WO | WO-9929667 A1 | 6/1999 |
| WO | WO-9952889 A1 | 10/1999 |
| WO | WO-9952910 A1 | 10/1999 |
| WO | WO-9967641 A2 | 12/1999 |
| WO | WO-0039587 A1 | 7/2000 |
| WO | WO-03004480 A2 | 1/2003 |
| WO | WO-03088908 A3 | 5/2004 |
| WO | WO-2004074283 A1 | 9/2004 |
| WO | WO-2005070891 A2 | 8/2005 |
| WO | WO-2005082892 A2 | 9/2005 |
| WO | WO-2006066948 A1 | 6/2006 |
| WO | WO-2007144394 A2 | 12/2007 |
| WO | WO-2008009078 A2 | 1/2008 |
| WO | WO-2008112440 A1 | 9/2008 |
| WO | WO-2010087399 A1 | 8/2010 |
| WO | WO-2010121918 A1 | 10/2010 |
| WO | WO-2011002816 A1 | 1/2011 |
| WO | WO-2011031896 A2 | 3/2011 |
| WO | WO-2011093524 A1 | 8/2011 |
| WO | WO-2012016082 A1 | 2/2012 |
| WO | WO-2012054716 A1 | 4/2012 |
| WO | WO-2012174489 A2 | 12/2012 |
| WO | WO-2013064068 A1 | 5/2013 |
| WO | WO-2013140148 A1 | 9/2013 |
| WO | WO-2013155223 A1 | 10/2013 |
| WO | WO-2014143659 A1 | 9/2014 |
| WO | WO-2014152588 A1 | 9/2014 |
| WO | WO-2014159837 A1 | 10/2014 |
| WO | WO-2014201435 A1 | 12/2014 |
| WO | WO-2015054572 A1 | 4/2015 |
| WO | WO-2015144001 A1 | 10/2015 |
| WO | WO-2015184349 A2 | 12/2015 |
| WO | WO-2016044772 A1 | 3/2016 |
| WO | WO-2016049524 A1 | 3/2016 |
| WO | WO-2016049565 A1 | 3/2016 |
| WO | WO-2016049568 A1 | 3/2016 |
| WO | WO-2016164675 A1 | 10/2016 |
| WO | WO-2016168540 A1 | 10/2016 |
| WO | WO-2017015562 A1 | 1/2017 |
| WO | WO-2017058728 A1 | 4/2017 |
| WO | WO-2017058768 A1 | 4/2017 |
| WO | WO-2017058792 A1 | 4/2017 |
| WO | WO-2017058805 A1 | 4/2017 |
| WO | WO-2017058807 A1 | 4/2017 |
| WO | WO-2017058902 A1 | 4/2017 |
| WO | WO-2017058915 A1 | 4/2017 |
| WO | WO-2017070256 A2 | 4/2017 |
| WO | WO-2017070256 A3 | 5/2017 |
| WO | WO-2017087528 A1 | 5/2017 |
| WO | WO-2017100546 A1 | 6/2017 |
| WO | WO-2017172979 A1 | 10/2017 |
| WO | WO-2018064510 A1 | 4/2018 |
| WO | WO-2018068017 A1 | 4/2018 |
| WO | WO-2018140512 A1 | 8/2018 |
| WO | WO-2018140513 A1 | 8/2018 |
| WO | WO-2018140514 A1 | 8/2018 |
| WO | WO-2018140598 A1 | 8/2018 |
| WO | WO-2018140599 A1 | 8/2018 |
| WO | WO-2018140600 A1 | 8/2018 |
| WO | WO-2018218069 A1 | 11/2018 |
| WO | WO-2018218070 A2 | 11/2018 |
| WO | WO-2018218071 A1 | 11/2018 |

(56) References Cited

OTHER PUBLICATIONS

Whisstock et al., Prediction of protein function from protein sequence and structure. Quarterly Reviews of Biophysics. 36(3):307-340 (2003).
Witkowski et al., Conversion of a beta-ketoacyl synthase to a malonyl decarboxylase by replacement of the active-site cysteine with glutamine. Biochemistry. 38(36):11643-11650 (1999).
Knickelbein et al. Mutant KRAS as a critical determinant of the therapeutic response of colorectal cancer. Genes & Disease 2(1):4-12 (2015).
Adibekian, A., et al., Optimization and characterization of a triazole urea dual inhibitor for lysophospholipase 1 (LYPLA1) and lysophospholipase 2 (LYPLA2), in Probe Reports from the NIH Molecular Libraries Program. 2010: Bethesda (MD).
"Allen, Lloyd. The art, science, and technology of pharmaceutical compounding. American Pharmacists Association, 1997."
Al-Muhammed, et al. In-vivo studies on dexamethasone sodium phosphate liposomes. J Microencapsul. May-Jun. 1996;13(3):293-306.
"Sambrook, et al. (1989) Molecular Cloning—A Laboratory Manual (2nd ed.) vol. 1-3, Cold Spring Harbor Laboratory, Cold Spring Harbor Press, N.Y.,".
American Chemical Society. STN Database. Nov. 16, 1984. RN5530-21-2.
"Appel et al., "Supramolecular Cross-Linked Networks via Host-Guest Complexation with Cucurbit[8]uril," 1 Am. Chem. Soc. 132(40):14251-14260, Jul. 2010."
Arkin, et al. Binding of small molecules to an adaptive protein-protein interface. Proc Natl Acad Sci U S A. Feb. 18, 2003;100(4):1603-8. Epub Feb. 11, 2003.
"Sasaki, et al. "Selective Formation of Stable Triplexes Including a TA or a CG Interrupting Site with New Bicyclic Nucleoside Analogues (WNA)," J. Am. Chem. Soc. 126(2):516-528, Jan. 2004."
"Ausubel et al. Current Protocols in Molecular Biology. 1987."
Bachovchin, D.A., et al., Identification of selective inhibitors of uncharacterized enzymes by high-throughput screening with fluorescent activity-based probes. Nat Biotechnol, 2009. 27(4): p. 387-94.
"Banker et al. (eds.), Modern Pharmaceutics, New York, Marcel Dekker, Inc., 1996, pp. 451 and 596. (3 pages)".
"Barbe et al., "Highly Chemoselective Metal-Free Reduction of Tertiary Amides," I Am. Chem. Soc. 130:18-19, 2008."
"Begue et al., "Ions a-Cetocarbenium. Influence De La Structure Sur L'Evolution Des Ions a-Cetocyclohexylcarbenium," Tetrahedron 31(20):2505-2511, 1975. (English Abstract Only)".
Berge, et al. Pharmaceutical salts. J Pharm Sci. Jan. 1977;66(1):1-19.
Campbell, et al. Phosphonate Ester Synthesis Using a Modified Mitsunobu Condensation. J. Org. Chem., 1994, 59 (3), pp. 658-660.
Chemocare.com "Taxol." 2016. Available from:<http://www.chemocare.com/chemotherapy/drug-info/taxol.aspx>.
"Chemocare.com "Taxol." (c) 2016. Available from:<http://www.chemocare.com/chemotherapy/drug-info/taxol.aspx>."
Chen, et al. "Analogous" Organic Synthesis of Small-Compound Libraries: Validation of Combinatorial Chemistry in Small-Molecule Synthesis. J. Am. Chem. Soc., 1994, 116 (6), pp. 2661-2662.
Cho, et al. An unnatural biopolymer. Science. Sep. 3, 1993;261(5126):1303-5.
Chonn, et al. Recent advances in liposomal drug-delivery systems. Curr Opin Biotechnol. Dec. 1995;6(6):698-708.
Choong, et al. Identification of potent and selective small-molecule inhibitors of caspase-3 through the use of extended tethering and structure-based drug design. J Med Chem. Nov. 7, 2002;45(23):5005-22.
Cox, A.D., et al., Drugging the undruggable RAS: Mission Possible? Nat Rev Drug Discov, 2014. 13(11): p. 828-51.
"Database Pubchem Substance [Online] NCBI. Database accession No. SID22405303. Mar. 5, 2007."

Dewitt, et al. "Diversomers": an approach to nonpeptide, nonoligomeric chemical diversity. Proc Natl Acad Sci U S A. Aug. 1, 1993;90(15):6909-13.
Dillon, M.B., et al., Novel inhibitors for PRMT1 discovered by high-throughput screening using activity-based fluorescence polarization. ACS Chem Biol, 2012. 7(7): p. 1198-204.
"Duncan et al., "N-Dialkylaminoalkybiphenylamines as Antimalarial and Antischistosomal Agents," Journal of Medicinal Chemistry 12:25-29, Jan. 1969."
Erlanson, et al. Site-directed ligand discovery. Proc Natl Acad Sci U S A. Aug. 15, 2000;97(17):9367-72.
European search report dated Nov. 6, 2015 for EP13775551.8.
Eyles, et al. Oral delivery and fate of poly(lactic acid) microsphere-encapsulated interferon in rats. J Pharm Pharmacol. Jul. 1997;49(7):669-74.
Fingl, et al. In: The Pharmacological basis of therapeutics, Ch. 1, p. 1. 1975.
"Forbes et al., "COSMIC 2005," British Journal of Cancer 94:318-322, 2006."
Furka et al. General method for rapid synthesis of multicomponent peptide mixtures. Int J Pept Protein Res. 37(6):487-493 (1991).
Gao, et al. Controlled release of a contraceptive steroid from biodegradable and injectable gel formulations: in vitro evaluation. Pharm Res. Jun. 1995;12(6):857-63.
Gorfe, et al. Mapping the nucleotide and isoform-dependent structural and dynamical features of Ras proteins. Structure. Jun. 2008;16(6):885-96. doi: 10.1016/j.str.2008.03.009.
Hagihara, et al. Vinylogous polypeptides : an alternative peptide backbone. J. Amer. Chem. Soc. 1992, 114:6568-70.
Hall, et al. The effect of Mg2+ on the guanine nucleotide exchange rate of p21N-ras. J Biol Chem. Aug. 25, 1986;261(24):10963-5.
Hall, et al. The structural basis for the transition from Ras-GTP to Ras-GDP. Proc Natl Acad Sci U S A. Sep. 17, 2002;99(19):12138-42. Epub Sep. 4, 2002.
Hara, et al. Guanine nucleotide binding properties of purified v-Ki-ras p21 protein produced in *Escherichia coli.* Oncogene Res. May 1988;2(4):325-33.
Hardy, et al. Discovery of an allosteric site in the caspases. Proc Natl Acad Sci U S A. Aug. 24, 2004;101(34):12461-6. Epub Aug. 16, 2004.
"Hattori et al., "Neutralizing Monoclonal Antibody Against ras Oncogene Product p21 Which Impairs Guanine Nucleotide Exchange," Mol. Cell. Biol. 7(5):1999-2002, May 1987."
Hirschmann, et al. Nonpeptidal peptidomimetics with .beta.-D-glucose scaffolding. A partial somatostatin agonist bearing a close structural relationship to a potent, selective substance P antagonist. J. Am. Chem. Soc., 1992, 114 (23), pp. 9217-9218.
Houghton, et al. Generation and use of synthetic peptide combinatorial libraries for basic research and drug discovery. Nature. Nov. 7, 1991;354(6348):84-6.
"Singh et al., "A Gene Expression Signature Associated with "K-Ras Addiction" Reveals Regulators of EMT and Tumor Cell Survival," Cancer Cell 15:489-500, Jun. 2009."
International preliminary report on patentability dated Oct. 14, 2014 for PCT/2013/036031.
International search report and written opinion dated Apr. 13, 2017 for PCT Application No. PCT/US2016/057774.
"International search report and written opinion dated Jul. 22, 2013 for PCT/US2013/036031."
International search report and written opinion dated Aug. 16, 2017 for PCT Application No. PCT/US17/24839.
"International search report with written opinion dated Feb. 2, 2016 for PCT/US15/52437".
"International search report with written opinion dated Feb. 6, 2014 for PCT/US2014/027454".
"International search report with written opinion dated Feb. 18, 2016 for PCT/US2015/051030".
"International search report with written opinion dated Mar. 2, 2016 for PCT/US2015/052427".
"International search report with written opinion dated May 30, 2016 for PCT/US2016/027673".
"International search report with written opinion dated Jul. 8, 2016 for PCT/US2016/026573".

(56) References Cited

OTHER PUBLICATIONS

"International search report with written opinion dated Jul. 25, 2014 for PCT/US2014/027504".
"International search report with written opinion dated Dec. 9, 2015 for PCT/US2015/052349".
"International search report with written opinion dated Dec. 17, 2014 for PCT/US2014/060036".
"Ito et al., "Regional Polysterism in the GTP-Bound Form of the Human c-Ha-Ras Protein," Biochemistry 36(30):9109-1919, Jul. 1997."
"Johnson et al., "The Chemistry of fl-Bromopropionyl Isocyanate. I. Synthesis of 1-Aryldihydrouracils," The Journal of Organic Chemistry 24(9):1391-1392, Sep. 1959."
Jones, et al. Increased frequency of the k-ras G12C mutation in MYH polyposis colorectal adenomas. Br J Cancer. Apr. 19, 2004;90(8):1591-3.
"Jordan, "Tamoxifen: A Most Unlikely Pioneering Medicine," Nature Reviews 2:205-213, Mar. 2003."
"Kelly et al., "Synthesis of Isomeric 3-Piperidinyl and 3-Pyrrolidinyl Benzo[5,6]cyclohepta[1,2-b]pyridines: Sulfonamido Derivatives as Inhibitors of Ras Prenylation," Bioorganic & Medicinial Chemistry 6:673-686, 1998."
"Kimmel, et al. Preparation of cDNA and the Generation of cDNA Libraries: Overview. Methods Enzymol. 1987;152:307-16."
Kraulis, et al. Solution structure and dynamics of ras p21.GDP determined by heteronuclear three- and four-dimensional NMR spectroscopy. Biochemistry. Mar. 29, 1994;33(12):3515-31.
"Kumar et al., "Synthesis of 3-Sulfonylamino Quinolines form 1-(2-Aminophenyl) Propargyl Alcohols through a Ag(I)-Catalyzed Hydroamination, (2+3) Cycloaddition, and an Unusual Strain-Driven Ring Expansion," Organic Letters 17(9):2226-2229, Apr. 2015."
Lachman, et al. Pharmaceutical dosage forms. vol. 1-3. Marcel Dekker, 1992.
"Le Picard et al., "Design and Synthesis of Naphthalenic Derivatives as Potential Inhibitors of Hydroxyindole-0-methyltransferase," Pharm. Pharmacol. Commun. 5:183-188, 1999."
Lee, et al. The mutation spectrum revealed by paired genome sequences from a lung cancer patient. Nature. May 27, 2010;465(7297):473-7. doi: 10.1038/nature09004.
Lenzen, et al. Analysis of intrinsic and CDC25-stimulated guanine nucleotide exchange of p21ras-nucleotide complexes by fluorescence measurements. Methods Enzymol. 1995;255:95-109.
Liang, et al. Parallel synthesis and screening of a solid phase carbohydrate library. Science. Nov. 29, 1996;274(5292):1520-2.
"Liu et al., "Polygonatum cyrtonema lectin induces murine fibrosarcoma L929 cell apoptosis and autophagy via blocking Ras-Raf and PI3K-Akt signaling pathways," Biochimie 92:1934-1938, 2010."
"Loboda et al., "A gene expression signature of RAS pathway dependence predicts response to PI3K and RAS pathway inhibitors and expands the population of RAS pathway activated tumors," BMC Medical Genomics 3(26):1-11, 2010."
Lone, A.M., et al., A substrate-free activity-based protein profiling screen for the discovery of selective PREPL inhibitors. J Am Chem Soc, 2011. 133(30): p. 11665-74.
Long, D. "Taxol: An important compound with an impressive structure." 2016. Available from<https://longscience.com/2011/09/10/taxol-an-organic-compound-you-should-know-about/>.
"Long, D. "Taxol: An important compound with an impressive structure." (c) 2016. Available from:< https://longscience.com/2011/09/10/taxol-an-organic-compound-you-should-know-about/>".
"Malani et al., "Synthesis, characterization and in vitro screening on bacterial, fungal and malarial strain of piprazinyl cyano biphenyl based compounds," Bioorganic Chemistry 51:16-23, 2013."
Margarit, et al. Structural evidence for feedback activation by Ras.GTP of the Ras-specific nucleotide exchange factor SOS. Cell. Mar. 7, 2003;112(5):685-95.
Maurer, T., et al., Small-molecule ligands bind to a distinct pocket in Ras and inhibit SOS-mediated nucleotide exchange activity. Proc Natl Acad Sci U S A, 2012. 109(14): p. 5299-304.

"McMahon, et al. The case for colorectal cancer screening. Semin Roentgenol. Oct. 2000;35(4):325-32."
McMahon, G. VEGF receptor signaling in tumor angiogenesis. Oncologist. 2000;5 Suppl 1:3-10.
"Milburn et al., "Molecular Switch for Signal Transduction: Structural Differences Between Active and Inactive Forms of Protooncogenic ras Proteins," Science 247(4945):939-945, Feb. 1990."
Minto, et al. Pharmacokinetics and pharmacodynamics of nandrolone esters in oil vehicle: effects of ester, injection site and injection volume. J Pharmacol Exp Ther. Apr. 1997;281(1):93-102.
"Notice of allowance dated Feb. 27, 2017 for U.S. Appl. No. 14/933,734."
"Notice of allowance dated Mar. 2, 2017 for U.S. Appl. No. 14/511,425."
Notice of allowance dated Aug. 2, 2017 for U.S. Appl. No. 15/342,100.
"Notice of allowance dated Aug. 6, 2015 for U.S. Appl. No. 14/212,656".
"Office action dated Jan. 15, 2016 for U.S. Appl. No. 14/511,425".
"Office action dated Mar. 27, 2015 for U.S. Appl. No. 14/212,656".
Office action dated May 31, 2017 for U.S. Appl. No. 14/934,184.
"Office action dated Jun. 20, 2016 for U.S. Appl. No. 14/511,425".
Office action dated Sep. 27, 2017 for U.S. Appl. No. 15/508,387.
"Office action dated Oct. 7, 2016 for U.S. Appl. No. 14/933,734".
"Office action dated Oct. 18, 2016 for U.S. Appl. No. 14/866,147".
"Office action dated Oct. 26, 2016 for U.S. Appl. No. 15/093,951".
"Office action dated Nov. 3, 2016 for U.S. Appl. No. 14/511,425".
Office action dated Nov. 28, 2018 for U.S. Appl. No. 15/713,297.
"Ohnmacht, Jr. et al., "Antimalarials. 5. a-Dibutylaminomethyl- and a-(2-Piperidyl)-3-quinolinemethanols," Journal of Medicinal Chemistry 14(1):17-24, 197."
Ostrem, J.M., et al., K-Ras(G12C) inhibitors allosterically control GTP affinity and effector interactions. Nature, 2013. 503(7477): p. 548-51.
Ostro, et al. Use of liposomes as injectable-drug delivery systems. Am J Hosp Pharm. Aug. 1989;46(8):1576-87.
"Pacold et al., "Crystal Structure and Functional Analysis of Ras Binding to Its Effector Phosphoinositide 3-Kinase y," Cell 103(6):931-943, Dec. 2000."
Palmioli, et al. First experimental identification of Ras-inhibitor binding interface using a water-soluble Ras ligand. Bioorg Med Chem Lett. Aug. 1, 2009;19(15):4217-22. doi: 10.1016/j.bmcl.2009.05.107. Epub May 30, 2009.
Palmioli, et al. Selective cytotoxicity of a bicyclic Ras inhibitor in cancer cells expressing K-Ras(G13D). Biochem Biophys Res Commun. Sep. 4, 2009;386(4):593-7. doi: 10.1016/j.bbrc.2009.06.069. Epub Jun. 18, 2009.
"Pardin, et al. Synthesis and evaluation of peptidic irreversible inhibitors of tissue transglutaminase. Bioorg Med Chem. Dec. 15, 2006;14(24):8379-85. Epub Sep. 27, 2006."
Pathan, et al. Lead identification for the K-Ras protein: virtual screening and combinatorial fragment-based approaches. OncoTargets and therapy 9 (2016): 2575-2584.
Patricelli, et al. Selective inhibition of oncogenic KRAS output with small molecules targeting the inactive state. Cancer discovery 6.3 (2016): 316-329.
Pautsch, A. et al., Crystal structure of the C3bot-RalA complex reveals a novel type of action of a bacterial exoenzyme. EMBO J, 2005, 24:3670-3680.
"Pedeboscq et al., "Synthesis and evaluation of apoptosis induction of thienopyrimidine compounds on KRAS and BRAF mutated colorectal cancer cell lines," Bioorganic & Medicinal Chemistry 20:6724-6731, 2012."
"Peri et al., "Arabinose-derived bicyclic amino acids: synthesis, conformational analysis and construction of an a,,(33-selective RGD peptide," I Am. Chem. Soc., Perkins Trans 1(5):638-644, Feb. 2002."
"Peri et al., "Sugar-Derived Ras Inhibitors: Group Epitope Mapping by NMR Spectroscopy and Biological Evaluation," Eur. I Org. Chem. 2006(16):3707-3720, Aug. 2006."
"Peri et al., "Synthesis of bicyclic sugar azido acids and their incorporation in cyclic peptides," Chem. Commun. 23:2303-2304, Jan. 2000."
"Pickar. Dosage Calculations. 1999."

(56) References Cited

OTHER PUBLICATIONS

"Spiegel et al., "Small-molecule modulation of Ras signaling," Nature Chemical Biology 10:613-622, Aug. 2014."

"Pinedo, et al. Aggressive combination therapy to cure patients with metastatic cancer. Lancet Oncol. Oct. 2000;1:72-3."

Pinedo, et al. Introduction Translational Research: The Role of VEGF in Tumor Angiogenesis. The Oncologist 2000; 5 (suppl 1):1-2.

"Pubchem CID 10375614" Create Date: Oct. 25, 2006 (Oct. 25, 2006) Date Accessed: Aug. 8, 2017 (Aug. 8, 2017); p. 3.

"PubChem Compound, "(25,6R)-hexahydrofuro[3,2-blfuran-2,6-diyldicarbonochloridate:Compound Summary CID 53396983," Oct. 30, 2011, retrieved from http://pubchem.ncbi.nlm.nih.gov/compound/53396983, 6 pages."

"PubChem Compound, "(4-hydroxypiperidin-l-yl)-pyridin-4-ylmethanone: AC1L5BNJ," retrieved on Feb. 17, 2014, from http://pubchem.ncbi.nlm.nih.gov/summary/summary.cgi?cid=76837, Jul. 8, 2005, 5 pages."

"PubChem Compound, "AKOS024742141," Nov. 27, 2010, retrieved from http://pubchem.ncbi.nim.nih.gov/compound/49702158#x304, CID 49702158, 12 pages."

"PubChem Compound, "SCHEMBL6674271," Dec. 1, 2012, retrieved from http://pubchem.ncbi.nim.nih.gov/compound/69861127#x304, CID 69861127, 12 pages."

"PubChem Compound, "SCHEMBL6797439," Dec. 1, 2012, retrieved from http://pubchem.ncbi.nim.nih.gov/compound/69898605#x304, CID 69898605, 12 pages."

"PubChem Compound, "Compound Summary for CID 21765509: Molecular Formula C18H21N508," Dec. 5, 2007, retrieved from http//pubchem.ncbi.nlm.nih.gov/compound/21765509, 4 pages."

"PubChem Compound, "Compound Summary for CID 21765511: Molecular Formula C18H2IN508," Dec. 5, 2007, retrieved from http://pubchem.ncbi.nlm.nih.gov/compound/21765511, 4 pages."

"PubChem Compound, "Compound Summary for CID 60018735: Molecular Formula C30I-13o013," Aug. 20, 2012, retrieved from http://pubchem.ncbi.nlm.nih.gov/compound/60018735#section=Top, 1 page."

"PubChem Compound, "Compound Summary for CID 72623693: AGN-PC-0D83J7," Jan. 9, 2014, retrieved from http://pubchem.ncbi.nlm.nih.gov/compound/72623693, 6 pages."

"PubChem Compound, "Compound Summary for CID 9897840: Molecular Formula C501446020," Oct. 25, 2006, retrieved from http://pubchem.ncbi.nlm.nih.gov/compound/9897840, 6 pages."

"PubChem, Substance Record for SID 44253980. Create Date: Dec. 5, 2007. Retrieved from the Internet.< URL: https://pubchem.ncbi.nlm.nih.gov/substance/44253980>".

Rao. Recent developments of collagen-based materials for medical applications and drug delivery systems. J Biomater Sci Polym Ed. 1995;7(7):623-45.

Remington. Remington's Pharmaceutical Sciences. 17th Edition. Mack Publishing Company, Easton, PA. 1985.

Remington. Remington: The science and practice of pharmacy. 20th Edition. Gennaro, Eds. Lippincott Williams & Wilkins, 2003.

Rensland, et al. Substrate and product structural requirements for binding of nucleotides to H-ras p21: the mechanism of discrimination between guanosine and adenosine nucleotides. Biochemistry. Jan. 17, 1995;34(2):593-9.

Schubbert, et al. Biochemical and functional characterization of germ line KRAS mutations. Mol Cell Biol. Nov. 2007;27(22):7765-70. Epub Sep. 17, 2007.

Shima, F., et al., Discovery of small-molecule Ras inhibitors that display antitumor activity by interfering with Ras.GTP-effector interaction. Enzymes, 2013. 34 Pt. B: p. 1-23.

Stefanachi, et al. 1-, 3- and 8-substituted-9-deazaxanthines as potent and selective antagonists at the human A2B adenosine receptor. Bioorg Med Chem. Mar. 15, 2008;16(6):2852-69.

Sun, Q., et al., Discovery of small molecules that bind to K-Ras and inhibit Sos-mediated activation. Angew Chem Int Ed Engl, 2012. 51(25): p. 6140-3.

"Taveras et al., "Ras Oncoprotein Inhibitors: The Discovery of Potent, Ras Nucleotide Exchange Inhibitors and the Structural Determination of a Drug-Protein Complex," Bioorganic and Medicinal Chemistry 5(1):125-133, 1997."

"Streuff et al., "First asymmetric aminohydroxylation of acrylamides," Tetrahedron: Asymmetry 16(21):3492-3496, Oct. 2005."

"Tsubaki et al., "Reduction of metastasis, cell invasion, and adhesion in mouse osteosarcoma by YM529/ONO-5920-induced blockade of the Ras/MEK/ERK and Ras/PI3K/Akt pathway," Toxicology and Applied Pharmacology 259(3):402-410, Jan. 2012."

"Tulshian et al., "Synthesis and Phosphodiesterase Activity of Carboxylic Acid Mimetics of Cyclic Guanosine 3',5'-Monophosphate," 1 Med. Chem. 36(9):1210-1220, Jan. 1993."

"Sunaga et al., "Knockdown of Oncogenic KRAS in Non-Small Cell Lung Cancers Suppresses Tumor Growth and Sensitizes Tumor Cells to Targeted Therapy," Molecular Cancer Therapeutics 10(2):336-346, Feb. 2011."

U.S. Appl. No. 14/934,184 Office Action dated Dec. 29, 2017.

"U.S. Appl. No. 15/508,387 Notice of Allowance dated Apr. 17, 2018."

Vaughan, et al. Human antibodies with sub-nanomolar affinities isolated from a large non-immunized phage display library. Nat Biotechnol. Mar. 1996;14(3):309-14.

"Vetter et al., "The Guanine Nucleotide-Binding Switch in Three Dimensions," Science 294(5545):1299-1304, Nov. 2001."

"Vippagunta et al. Crystalline solids. Adv Drug Deliv Rev. May 16, 2001;48(1):3-26."

"Wolff, (ed.), Burger's Medicinal Chemistry and Drug Discovery, Fifth Edition, vol. 1: Principles and Practice, San Diego, California, John Wiley & Sons, 1994, pp. 975-977. (4 pages)".

"Wu et al., "Stereoselective synthesis of dioxabicycles from 1-C-allyl-2-O-benzyl-glycosides—An intramolecular cyclization between 2-O-benzyl oxygen and the allyl double bond," Can. I Chem. 84(1):597-602, Jan. 2006."

Yan et. al., Discovery and characterization of small molecules that target the GTPase Ral. Nature, 2014, 515:443-447.

"Yang et al., "Fragment-Based Discovery of Nonpeptidic BACE-1 Inhibitors Using Tethering," Biochemistry 48:4488-4496, 2009."

"Sydor et al., "Transient Kinetic Studies on the Interaction of Ras and the Ras-Binding Domain of c-Raf-1 Reveal Rapid Equilibration of the Complex," Biochemistry 37:14292-14299, 1998."

"Young et al., "Oncogenic and Wild-type Ras Play Divergent Roles in the Regulation of Mitogen-Activated Protein Kinase Signaling," Cancer Discovery 3(1):112-123, Jan. 2013."

"Zenkl et al., "Sugar-Responsive Fluorescent Nanospheres," Macromol. Biosci. 8:146-152, 2008."

Co-pending U.S. Appl. No. 16/013,271, filed Jun. 20, 2018.

\* cited by examiner

| Oncogene | Tumor Type | Cumulative Mutation Frequency (All Tumors) |
|---|---|---|
| Bcr-Abl | 90% CML | < 1% |
| EGFR | 10% NSCLC | < 5% |
| ALK | 5% NSCLC | < 1% |
| B-Raf | 66% Melanoma | < 5% |
| Flt3 | 25% AML | < 1% |
| PI3Kα | 25% Breast; 25% Endometrial, 15% CRC | 15-20% |
| K-Ras | > 80% Pancreatic; >40% colon >20% lung | ~20% |

FIG. 3

SUBSTITUTED QUINAZOLINE COMPOUNDS AND METHODS OF USE

CROSS REFERENCE TO RELATED APPLICATIONS

This application is a National Stage Entry of PCT/US2017/024839, filed Mar. 29, 2017, which claims the benefit of U.S. Provisional Application No. 62/315,532, filed on Mar. 30, 2016, and U.S. Provisional Application No. 62/404,539, filed on Oct. 5, 2016, each of which is incorporated herein by reference in its entirety.

BACKGROUND

Ras represents a group of closely related monomeric globular proteins of 189 amino acids (21 kDa molecular mass) which are associated with the plasma membrane and which bind either GDP or GTP. Ras acts as a molecular switch. When Ras contains bound GDP it is in the resting or off position and is "inactive". In response to exposure of the cell to certain growth promoting stimuli, Ras is induced to exchange its bound GDP for a GTP. With GTP bound, Ras is "switched on" and is able to interact with and activate other proteins (its "downstream targets"). The Ras protein itself has a very low intrinsic ability to hydrolyze GTP back to GDP, thus turning itself into the off state. Switching Ras off requires extrinsic proteins termed GTPase-activating proteins (GAPs) that interact with Ras and greatly accelerate the conversion of GTP to GDP. Any mutation in Ras which affects its ability to interact with GAP or to convert GTP back to GDP will result in a prolonged activation of the protein and consequently a prolonged signal to the cell telling it to continue to grow and divide. Because these signals result in cell growth and division, overactive Ras signaling may ultimately lead to cancer.

Structurally, Ras proteins contain a G domain which is responsible for the enzymatic activity of Ras (e.g., guanine nucleotide binding and hydrolysis (GTPase reaction)). It also contains a C-terminal extension, known as the CAAX box, which may be post-translationally modified and is responsible for targeting the protein to the membrane. The G domain is approximately 21-25 kDa in size and contains a phosphate binding loop (P-loop). The P-loop represents the pocket where the nucleotides are bound in the protein; this is the rigid part of the domain with conserved amino acid residues which are essential for nucleotide binding and hydrolysis (Glycine 12, Threonine 26 and Lysine 16). The G domain also contains the so called Switch I (residues 30-40) and Switch II (residues 60-76) regions, both of which are the dynamic parts of the protein which are often represented as the "spring-loaded" mechanism because of their ability to switch between the resting and loaded state. Threonine-35 and glycine-60 form key hydrogen bonds with the γ-phosphate of GTP, which maintain Switch I and Switch II regions, respectively, in their active conformation. After hydrolysis of GTP and release of phosphate, the regions relax into the inactive GDP conformation.

The most notable members of the Ras subfamily are HRAS, KRAS and NRAS, mainly for being implicated in many types of cancer. However, there are many other members including DIRAS1; DIRAS2; DIRAS3; ERAS; GEM; MRAS; NKIRAS1; NKIRAS2; NRAS; RALA; RALB; RAP1A; RAP1B; RAP2A; RAP2B; RAP2C; RASD1; RASD2; RASL10A; RASL10B; RASL11A; RASL11B; RASL12; REM1; REM2; RERG; RERGL; RRAD; RRAS; and RRAS2.

Mutations in any one of the three main isoforms of RAS (H-Ras, N-Ras, or K-Ras) genes are among the most common events in human tumorigenesis. About 30% of all human tumors are found to carry some mutation in Ras genes. Remarkably, K-Ras mutations are detected in 25-30% of tumors. By comparison, the rates of oncogenic mutation occurring in the N-Ras and H-Ras family members are much lower (8% and 3%, respectively). The most common K-Ras mutations are found at residue G12 and G13 in the P-loop and at residue Q61.

G12C is a frequent mutation of K-Ras gene (glycine-12 to cysteine). This mutation has been found in about 13% of cancer occurrences, including about 43% of lung cancer occurrences and almost 100% of MYH-associates polyposis (familial colon cancer syndrome). However targeting this gene with small molecules is a challenge.

SUMMARY OF THE INVENTION

In view of the foregoing, there is a need in the art for small molecules that target Ras (e.g., K-Ras, H-Ras and/or N-Ras) and for use of such compounds in the treatment of various diseases, such as cancer. The present disclosure provides these and other related advantages.

In certain aspects, the present disclosure provides a compound of Formula (I):

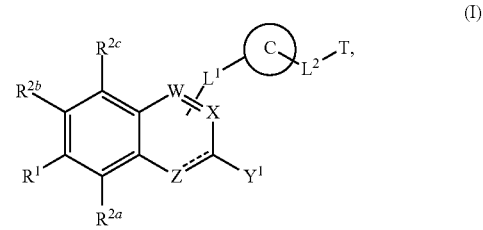

or a salt or prodrug thereof, wherein:
$R^1$, $R^{2a}$, $R^{2b}$ and $R^{2c}$ are each independently selected from hydrogen and $R^{50}$;
W and X are each independently selected from N, $NR^5$ and $CR^6$;
Z is selected from bond, N, and $CR^6$;
$Y^1$ is selected from $-OR^{55}$; and alkyl, alkenyl, alkynyl, $C_{3-12}$ carbocycle and 3- to 12-membered heterocycle, each of which is substituted with $-OR^{55}$ and optionally futher substituted with one or more $R^{50}$;
$L^1$ is selected from bond, $-O-$, $-S-$, $-N(R^{51})-$, $-N(R^{51})CH_2-$, $-C(O)-$, $-C(O)O-$, $-OC(O)-$, $-OC(O)O-$, $-C(O)N(R^{51})-$, $-C(O)N(R^{51})C(O)-$, $-C(O)N(R^{51})C(O)N(R^{51})-$, $-N(R^{51})C(O)-$, $-N(R^{51})C(O)N(R^{51})-$, $-N(R^{51})C(O)O-$, $-OC(O)N(R^{51})-$, $-C(NR^{51})-$, $-N(R^{51})C(NR^{51})-$, $-C(NR^{51})N(R^{51})-$, $-N(R^{51})C(NR^{51})N(R^{51})-$, $-S(O)_2-$, $-OS(O)-$, $-S(O)O-$, $-S(O)-$, $-OS(O)_2-$, $-S(O)_2O-$, $-N(R^{51})S(O)_2-$, $-S(O)_2N(R^{51})-$, $-N(R^{51})S(O)-$, $-S(O)N(R^{51})-$, $-N(R^{51})S(O)_2N(R^{51})-$, $-N(R^{51})S(O)N(R^{51})-$; alkylene, alkenylene, alkynylene, heteroalkylene, heteroalkenylene, and heteroalkynylene, each of which is optionally substituted with one or more $R^{50}$;
$L^2$ is selected from bond and alkylene;
C is selected from 3- to 12-membered heterocycle, optionally substituted with one or more $R^{57}$;
T is hydrogen or a polar group capable of forming a complex with a Ras protein via an interaction other than one resulting in a covalent bond with the cysteine residue at position 12 of a K-Ras, H-Ras or N-Ras G12C mutant protein;

==== indicates a single or double bond such that all valences are satisfied;

$R^5$ is independently selected at each occurrence from $R^{51}$;

$R^6$ is independently selected at each occurrence from hydrogen, $R^{50}$, and a bond to $L^1$;

$R^{50}$ is independently selected at each occurrence from:
halogen, —$NO_2$, —CN, —$OR^{52}$, —$SR^{52}$, —$N(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, =O, =S, =$N(R^{52})$;

$C_{1-10}$ alkyl, $C_{2-10}$ alkenyl, and $C_{2-10}$ alkynyl, each of which is independently optionally substituted at each occurrence with one or more substituents selected from halogen, —$NO_2$, —CN, —$OR^{52}$, —$SR^{52}$, —$N(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, =O, =S, =$N(R^{52})$, $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^{50}$ is independently optionally substituted with one or more substituents selected from halogen, —$NO_2$, —CN, —$OR^{52}$, —$SR^{52}$, —$N(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, =O, =S, =$N(R^{52})$, $C_{1-6}$ alkyl, $C_{1-6}$ haloalkyl, $C_{2-6}$ alkenyl, and $C_{2-6}$ alkynyl;

$R^{51}$ is independently selected at each occurrence from: hydrogen, —$C(O)R^{52}$, —$C(O)OR^{52}$, —$C(O)N(R^{52})_2$, —$C(O)NR^{53}R^{54}$;

$C_{1-6}$ alkyl, $C_{2-6}$ alkenyl, and $C_{2-6}$ alkynyl, each of which is independently optionally substituted at each occurrence with one or more substituents selected from halogen, —$NO_2$, —CN, —$OR^{52}$, —$SR^{52}$, —$N(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, =O, =S, =$N(R^{52})$, $C_{3-12}$ carbocycle and 3- to 12-membered heterocycle; and $C_{3-12}$ carbocycle and 3- to 12-membered heterocycle, wherein each $C_{3-12}$ carbocycle and 3- to 12-membered heterocycle in $R^{51}$ is independently optionally substituted with one or more substituents selected from halogen, —$NO_2$, —CN, —$OR^{52}$, —$SR^{52}$, —$N(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, =O, =S, =$N(R^{52})$, $C_{1-6}$ alkyl, $C_{1-6}$ haloalkyl, $C_{2-6}$ alkenyl, and $C_{2-6}$ alkynyl;

$R^{52}$ is independently selected at each occurrence from hydrogen; and $C_{1-20}$ alkyl, $C_{2-20}$ alkenyl, $C_{2-20}$ alkynyl, 2- to 6-membered heteroalkyl, $C_{3-12}$ carbocycle, and 3- to 12-membered heterocycle, each of which is optionally substituted by halogen, —CN, —$NO_2$, —$NH_2$, —$NHCH_3$, —$NHCH_2CH_3$, =O, —OH, —$OCH_3$, —$OCH_2CH_3$, $C_{3-12}$ carbocycle, or 3- to 6-membered heterocycle;

$R^{53}$ and $R^{54}$ are taken together with the nitrogen atom to which they are attached to form a heterocycle, optionally substituted with one or more $R^{50}$;

$R^{55}$ is selected from:
alkyl, alkenyl, and alkynyl, each of which is independently optionally substituted at each occurrence with one or more substituents selected from halogen, —$NO_2$, —CN, —$OR^{52}$, —$SR^{52}$, —$N(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, =O, =S, =$N(R^{52})$, $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^{55}$ is independently optionally substituted with one or more substituents selected from halogen, —$NO_2$, —CN, —$OR^{52}$, —$SR^{52}$, —$N(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, =O, =S, =$N(R^{52})$, $C_{1-6}$ alkyl, $C_{1-6}$ haloalkyl, $C_{2-6}$ alkenyl, and $C_{2-6}$ alkynyl; and $R^{57}$ is independently selected at each occurrence from:
halogen, —CN, —OH, —OMe, —$NH_2$, —$NHC_{1-6}$ alkyl, —$N(C_{1-6}$ alkyl$)_2$, —C(O)OH, —C(O)H, —$C(O)C_{1-6}$ alkyl, —$NHC(O)C_{1-6}$ alkyl, —$N(C_{1-6}$ alkyl$)C(O)C_{1-6}$ alkyl, —$C(O)NH_2$, —$C(O)NH(C_{1-6}$ alkyl), —$C(O)N(C_{1-6}$ alkyl$)_2$, =O, =N(OH); and $C_{1-10}$ alkyl, optionally substituted at each occurrence with one or more substituents selected from —CN, —OH, —$NH_2$, —OMe, —$NH_2$, —$NHC_{1-6}$ alkyl, —$N(C_{1-6}$ alkyl$)_2$, —C(O)OH, —C(O)H, —$C(O)C_{1-6}$ alkyl, —$NHC(O)C_{1-6}$ alkyl, —$N(C_{1-6}$ alkyl$)C(O)C_{1-6}$ alkyl, —$C(O)NH_2$, —$C(O)NH(C_{1-6}$ alkyl), —$C(O)N(C_{1-6}$ alkyl$)_2$, =O, and =N(OH);

wherein one of W, X and Z is CR⁶ where R⁶ is a bond to L¹; and wherein the compound of Formula (I) is not:

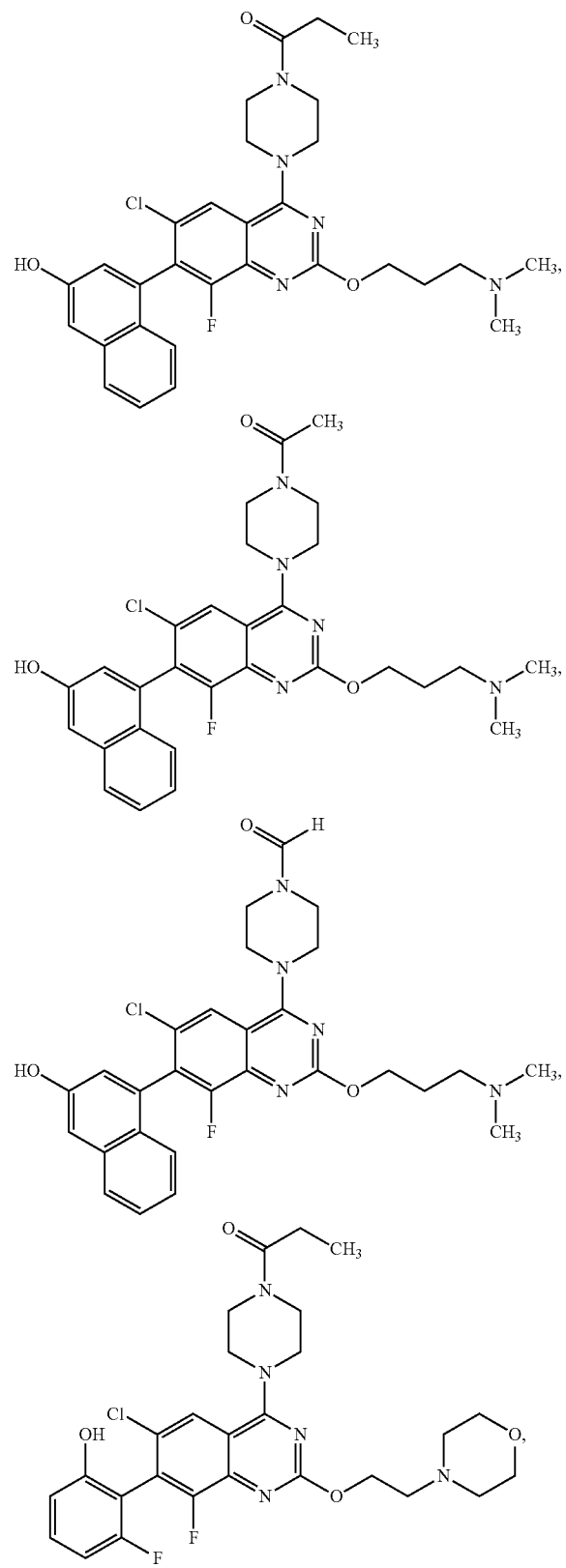

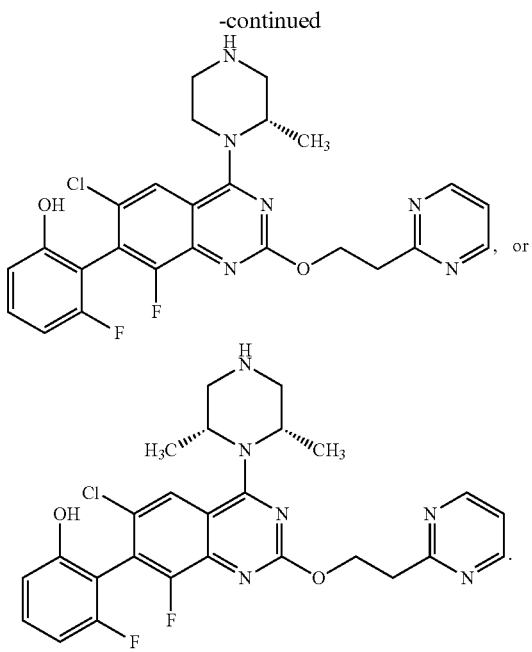

In certain aspects, a compound of Formula (I) is represented by Formula (I-A):

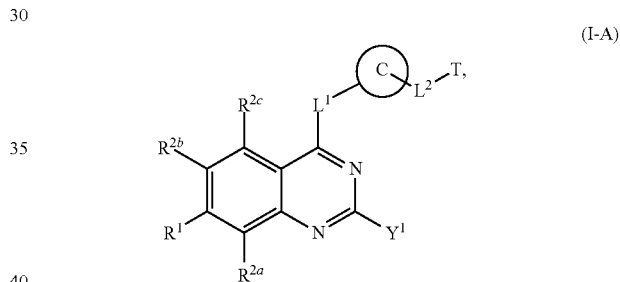

or a salt or prodrug thereof.

In certain aspects, the present disclosure provides a stereoisomer of a compound of Formula (I-A):

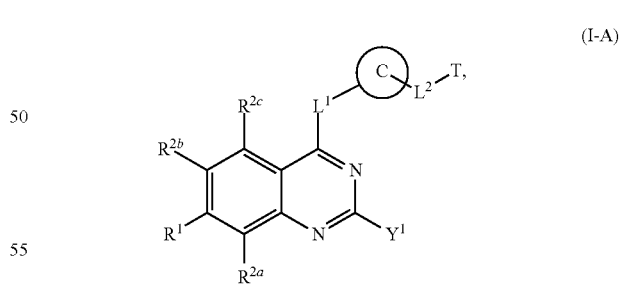

or a salt or prodrug thereof, wherein:

R¹ is selected from C₃₋₁₂ carbocycle and 3- to 12-membered heterocycle, each of which is substituted with one or more substituents independently selected from halogen, —OH, —OR⁵², —NH₂, —NHMe, —NMe₂, C₁₋₃ alkyl, C₁₋₃ haloalkyl, C₃₋₁₂ carbocycle and 3- to 12-membered heterocycle;

R²ᵃ and R²ᵇ are each independently selected from hydrogen, halogen, —OH, —OR⁵², C₁₋₄ alkyl, and C₁₋₄ haloalkyl, wherein at least one of R²ᵃ and R²ᵇ is not hydrogen;

$R^{2c}$ is selected from hydrogen, halogen, —OH, —OR$^{52}$, $C_{1-4}$ alkyl, and $C_{1-4}$ haloalkyl; and $Y^1$ is selected from —OR$^{55}$; and $C_{1-10}$ alkyl, $C_{2-10}$ alkenyl and $C_{2-10}$ alkynyl, each of which is substituted with —OR$^{55}$ and optionally further substituted with one or more R$^{50}$;

$L^1$ is selected from bond, —O—, —S—, —N(R$^{51}$)—, —N(R$^{51}$)CH$_2$—, —C(O)—, —C(O)O—, —OC(O)—, —OC(O)O—, —C(O)N(R$^{51}$)—, —C(O)N(R$^{51}$)C(O)—, —C(O)N(R$^{51}$)C(O)N(R$^{51}$)—, —N(R$^{51}$)C(O)—, —N(R$^{51}$)C(O)N(R$^{51}$)—, —N(R$^{51}$)C(O)O—, —OC(O)N(R$^{51}$)—, —C(NR$^{51}$)—, —N(R$^{51}$)C(NR$^{51}$)—, —C(NR$^{51}$)N(R$^{51}$)—, —N(R$^{51}$)C(NR$^{51}$)N(R$^{51}$)—, —S(O)$_2$—, —OS(O)—, —S(O)O—, —S(O)—, —OS(O)$_2$—, —S(O)$_2$O—, —N(R$^{51}$)S(O)$_2$—, —S(O)$_2$N(R$^{51}$)—, —N(R$^{51}$)S(O)—, —S(O)N(R$^{51}$)—, —N(R$^{51}$)S(O)$_2$N(R$^{51}$)—, —N(R$^{51}$)S(O)N(R$^{51}$)—; alkylene, alkenylene, alkynylene, heteroalkylene, heteroalkenylene, and heteroalkynylene, each of which is optionally substituted with one or more R$^{50}$;

$L^2$ is selected from bond and alkylene;

C is selected from 3- to 12-membered heterocycle, optionally substituted with one or more R$^{57}$;

T is hydrogen or a polar group capable of forming a complex with a Ras protein via an interaction other than one resulting in a covalent bond with the cysteine residue at position 12 of a K-Ras, H-Ras or N-Ras G12C mutant protein;

$R^{50}$ is independently selected at each occurrence from: halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$);

$C_{1-10}$ alkyl, $C_{2-10}$ alkenyl, and $C_{2-10}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in R$^{50}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), $C_{1-6}$ alkyl, $C_{1-6}$ haloalkyl, $C_{2-6}$ alkenyl, and $C_{2-6}$ alkynyl;

$R^{51}$ is independently selected at each occurrence from: hydrogen, —C(O)R$^{52}$, —C(O)OR$^{52}$, —C(O)N(R$^{52}$)$_2$, —C(O)NR$^{53}$R$^{54}$;

$C_{1-6}$ alkyl, $C_{2-6}$ alkenyl, and $C_{2-6}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), $C_{3-12}$ carbocycle and 3- to 12-membered heterocycle; and $C_{3-12}$ carbocycle and 3- to 12-membered heterocycle, wherein each $C_{3-12}$ carbocycle and 3- to 12-membered heterocycle in R$^{51}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), $C_{1-6}$ alkyl, $C_{1-6}$ haloalkyl, $C_{2-6}$ alkenyl, and $C_{2-6}$ alkynyl;

$R^{52}$ is independently selected at each occurrence from hydrogen; and $C_{1-20}$ alkyl, $C_{2-20}$ alkenyl, $C_{2-20}$ alkynyl, 2- to 6-membered heteroalkyl, $C_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, $C_{3-12}$ carbocycle, or 3- to 6-membered heterocycle;

$R^{53}$ and $R^{54}$ are taken together with the nitrogen atom to which they are attached to form a heterocycle, optionally substituted with one or more R$^{50}$;

$R^{55}$ is selected from:

$C_{1-10}$ alkyl, $C_{2-10}$ alkenyl, and $C_{2-10}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in R$^{55}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl; and R$^{57}$ is independently selected at each occurrence from: halogen, —CN, —OH, —OMe, —NH$_2$, —NHC$_{1-6}$ alkyl, —N(C$_{1-6}$ alkyl)$_2$, —C(O)OH, —C(O)H, —C(O)C$_{1-6}$ alkyl, —NHC(O)C$_{1-6}$ alkyl, —N(C$_{1-6}$ alkyl)C(O)C$_{1-6}$ alkyl, —C(O)NH$_2$, —C(O)NH(C$_{1-6}$ alkyl), —C(O)N(C$_{1-6}$ alkyl)$_2$, =O, =N(OH); and C$_{1-10}$ alkyl, optionally substituted at each occurrence with one or more substituents selected from —CN, —OH, —NH$_2$, —OMe, —NH$_2$, —NHC$_{1-6}$ alkyl, —N(C$_{1-6}$ alkyl)$_2$, —C(O)OH, —C(O)H, —C(O)C$_{1-6}$ alkyl, —NHC(O)C$_{1-6}$ alkyl, —N(C$_{1-6}$ alkyl)C(O)C$_{1-6}$ alkyl, —C(O)NH$_2$, —C(O)NH(C$_{1-6}$ alkyl), —C(O)N(C$_{1-6}$ alkyl)$_2$, =O, and =N(OH).

In certain aspects, a compound of Formula (I) is represented by Formula (I-B):

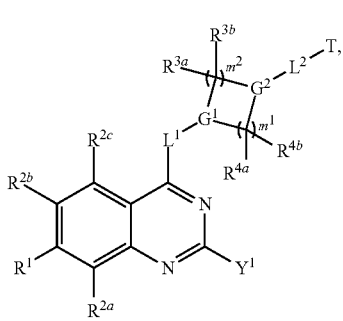

(I-B)

or a salt thereof, wherein:

G$^1$ and G$^2$ are each independently N or CH;

R$^{3a}$ and R$^{3b}$ are independently selected at each occurrence from H, —OH, —NH$_2$, —CO$_2$H, halo, cyano, C$_{1-6}$ alkyl, C$_{2-6}$ alkynyl, hydroxylalkyl, aminoalkyl, alkylaminoalkyl, cyanoalkyl, carboxyalkyl, aminocarbonylalkyl and aminocarbonyl; or R$^{3a}$ and R$^{3b}$ join to form oxo or a carbocyclic or heterocyclic ring; or R$^{3a}$ is independently selected at each occurrence from H, —OH, —NH$_2$, —CO$_2$H, halo, cyano, C$_{1-6}$ alkyl, C$_{2-6}$ alkynyl, hydroxylalkyl, aminoalkyl, alkylaminoalkyl, cyanoalkyl, carboxyalkyl, aminocarbonylalkyl and aminocarbonyl, and R$^{3b}$ joins with R$^{4b}$ to form a carbocyclic or heterocyclic ring;

R$^{4a}$ and R$^{4b}$ are independently selected at each occurrence from H, —OH, —NH$_2$, —CO$_2$H, halo, cyano, C$_{1-6}$ alkyl, C$_{2-6}$ alkynyl, hydroxylalkyl, aminoalkyl, alkylaminoalkyl, cyanoalkyl, carboxyalkyl, aminocarbonylalkyl and aminocarbonyl; or R$^{4a}$ and R$^{4b}$ join to form oxo or a carbocyclic or heterocyclic ring; or R$^{4a}$ is independently selected at each occurrence from H, —OH, —NH$_2$, —CO$_2$H, halo, cyano, C$_{1-6}$ alkyl, C$_{2-6}$ alkynyl, hydroxylalkyl, aminoalkyl, alkylaminoalkyl, cyanoalkyl, carboxyalkyl, aminocarbonylalkyl and aminocarbonyl, and R$^{4b}$ joins with R$^{3b}$ to form a carbocyclic or heterocyclic ring; and m$^1$ and m$^2$ are each independently 1, 2 or 3.

For a compound of Formula (I), (I-A) or (I-B), Y$^1$ may be —OR$^{55}$. In some embodiments, R$^{55}$ is selected from: alkyl, alkenyl, and alkynyl, each of which is independently optionally substituted at each occurrence with one or more substituents selected from halogen, —OR$^{52}$, —SR$^{52}$, —N(R$^{52}$)$_2$, —NR$^{53}$R$^{54}$, and 3- to 12-membered heterocycle; and C$_{3-12}$ carbocycle and 3- to 12-membered heterocycle, wherein each C$_{3-12}$ carbocycle and 3- to 12-membered heterocycle is independently optionally substituted with one or more substituents selected from halogen, =O, C$_{1-6}$ alkyl, and C$_{1-6}$ haloalkyl. In some embodiments, R$^{55}$ is selected from C$_{1-4}$ alkyl substituted with —N(R$^{52}$)$_2$, —NR$^{53}$R$^{54}$, or 3- to 12-membered heterocycle; and 3- to 12-membered heterocycle, wherein each 3- to 12-membered heterocycle is optionally substituted with one or more substituents selected from halogen, =O, C$_{1-6}$ alkyl, and C$_{1-6}$ haloalkyl. In some embodiments, Y$^1$ is

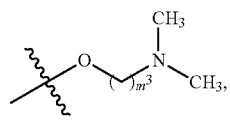

wherein m$^3$ is an integer from 1 to 6, such as m$^3$ is 2 or 3. In some embodiments, Y$^1$ is selected from:

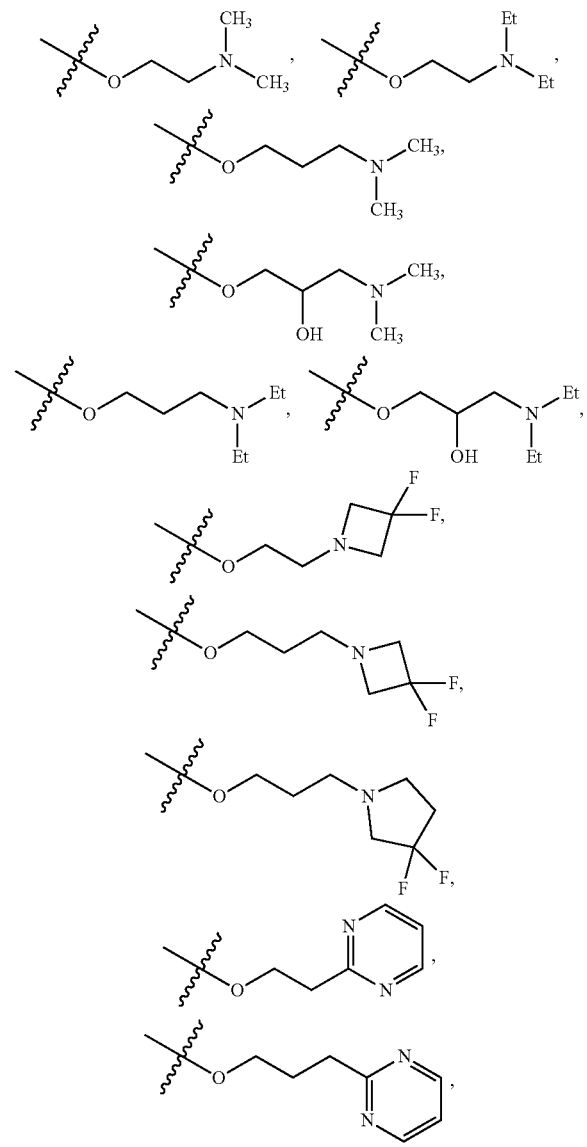

-continued

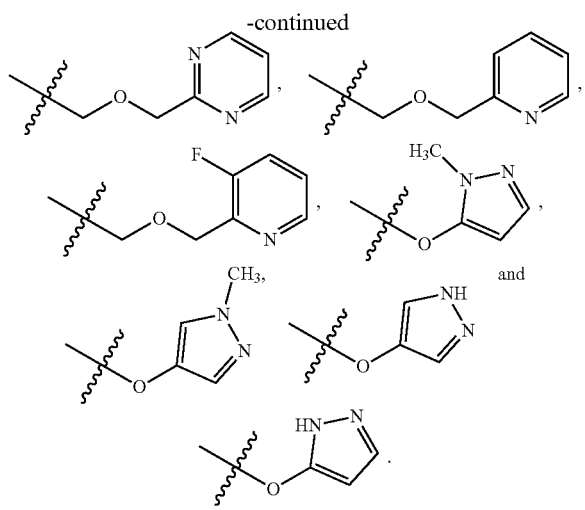

In certain aspects, the present disclosure provides a compound of Formula (II):

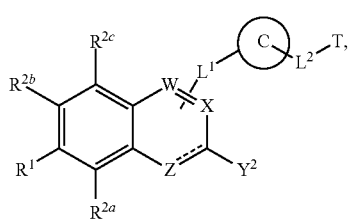

or a salt or prodrug thereof, wherein:

$R^1$, $R^{2a}$, $R^{2b}$ and $R^{2c}$ are each independently selected from hydrogen and $R^{50}$;

W and X are each independently selected from N, $NR^5$ and $CR^6$;

Z is selected from bond, N, and $CR^6$;

$Y^2$ is selected from $-N(R^{56})_2$; and alkyl, alkenyl, alkynyl, $C_{3-12}$ carbocycle and 3- to 12-membered heterocycle, each of which is substituted with $-N(R^{56})_2$ and optionally futher substituted with one or more $R^{50}$;

$L^1$ is selected from bond, $-O-$, $-S-$, $-N(R^{51})-$, $-N(R^{51})CH_2-$, $-C(O)-$, $-C(O)O-$, $-OC(O)-$, $-OC(O)O-$, $-C(O)N(R^{51})-$, $-C(O)N(R^{51})C(O)-$, $-C(O)N(R^{51})C(O)N(R^{51})-$, $-N(R^{51})C(O)-$, $-N(R^{51})C(O)N(R^{51})-$, $-N(R^{51})C(O)O-$, $-OC(O)N(R^{51})-$, $-C(NR^{51})-$, $-N(R^{51})C(NR^{51})-$, $-C(NR^{51})N(R^{51})-$, $-N(R^{51})C(NR^{51})N(R^{51})-$, $-S(O)_2-$, $-OS(O)-$, $-S(O)O-$, $-S(O)-$, $-OS(O)_2-$, $-S(O)_2O-$, $-N(R^{51})S(O)_2-$, $-S(O)_2N(R^{51})-$, $-N(R^{51})S(O)-$, $-S(O)N(R^{51})-$, $-N(R^{51})S(O)_2N(R^{51})-$, $-N(R^{51})S(O)N(R^{51})-$; alkylene, alkenylene, alkynylene, heteroalkylene, heteroalkenylene, and heteroalkynylene, each of which is optionally substituted with one or more $R^{50}$;

$L^2$ is selected from bond and alkylene;

C is selected from 3- to 12-membered heterocycle, optionally substituted with one or more $R^{57}$;

T is hydrogen or a polar group capable of forming a complex with a Ras protein via an interaction other than one resulting in a covalent bond with the cysteine residue at position 12 of a K-Ras, H-Ras or N-Ras G12C mutant protein;

===== indicates a single or double bond such that all valences are satisfied;

$R^5$ is independently selected at each occurrence from $R^{51}$;

$R^6$ is independently selected at each occurrence from hydrogen, $R^{50}$, and a bond to $L^1$;

$R^{50}$ is independently selected at each occurrence from:

halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $=O$, $=S$, $=N(R^{52})$;

$C_{1-10}$ alkyl, $C_{2-10}$ alkenyl, and $C_{2-10}$ alkynyl, each of which is independently optionally substituted at each occurrence with one or more substituents selected from halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $=O$, $=S$, $=N(R^{52})$, $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^{50}$ is independently optionally substituted with one or more substituents selected from halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $=O$, $=S$, $=N(R^{52})$, $C_{1-6}$ alkyl, $C_{1-6}$ haloalkyl, $C_{2-6}$ alkenyl, and $C_{2-6}$ alkynyl;

$R^{51}$ is independently selected at each occurrence from: hydrogen, $-C(O)R^{52}$, $-C(O)OR^{52}$, $-C(O)N(R^{52})_2$, $-C(O)NR^{53}R^{54}$;

$C_{1-6}$ alkyl, $C_{2-6}$ alkenyl, and $C_{2-6}$ alkynyl, each of which is independently optionally substituted at each occurrence with one or more substituents selected from halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $=O$, $=S$, $=N(R^{52})$, $C_{3-12}$ carbocycle and 3- to 12-membered heterocycle; and $C_{3-12}$ carbocycle and 3- to 12-membered heterocycle, wherein each $C_{3-12}$ carbocycle and 3- to 12-membered heterocycle in $R^{51}$ is independently optionally substituted with one or more substituents selected from halogen, $-NO_2$, $-CN$, $-OR^{52}$, $-SR^{52}$, $-N(R^{52})_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl;

R$^{52}$ is independently selected at each occurrence from hydrogen; and C$_{1-20}$ alkyl, C$_{2-20}$ alkenyl, C$_{2-20}$ alkynyl, 2- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle;

R$^{53}$ and R$^{54}$ are taken together with the nitrogen atom to which they are attached to form a heterocycle, optionally substituted with one or more R$^{50}$;

R$^{56}$ is independently selected at each occurrence from: hydrogen;

C$_{1-10}$ alkyl, C$_{2-10}$ alkenyl, and C$_{2-10}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{3-12}$ carbocycle, and 3- to 12-membered heterocycle; and C$_{3-12}$ carbocycle and 3- to 12-membered heterocycle, wherein each C$_{3-12}$ carbocycle and 3- to 12-membered heterocycle in R$^{56}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl, or two R$^{56}$ groups are taken together with the nitrogen atom to which they are attached to form a heterocycle, optionally substituted with one or more R$^{50}$; and R$^{57}$ is independently selected at each occurrence from: halogen, —CN, —OH, —OMe, —NH$_2$, —NHC$_{1-6}$ alkyl, —N(C$_{1-6}$ alkyl)$_2$, —C(O)OH, —C(O)H, —C(O)C$_{1-6}$ alkyl, —NHC(O)C$_{1-6}$ alkyl, —N(C$_{1-6}$ alkyl)C(O)C$_{1-6}$ alkyl, —C(O)NH$_2$, —C(O)NH(C$_{1-6}$ alkyl), —C(O)N(C$_{1-6}$ alkyl)$_2$, =O, =N(OH); and C$_{1-10}$ alkyl, optionally substituted at each occurrence with one or more substituents selected from —CN, —OH, —NH$_2$, —OMe, —NH$_2$, —NHC$_{1-6}$ alkyl, —N(C$_{1-6}$ alkyl)$_2$, —C(O)OH, —C(O)H, —C(O)C$_{1-6}$ alkyl, —NHC(O)C$_{1-6}$ alkyl, —N(C$_{1-6}$ alkyl)C(O)C$_{1-6}$ alkyl, —C(O)NH$_2$, —C(O)NH(C$_{1-6}$ alkyl), —C(O)N(C$_{1-6}$ alkyl)$_2$, =O, and =N(OH);

wherein one of W, X and Z is CR$^6$ where R$^6$ is a bond to L$^1$.

In certain aspects, a compound of Formula (II) is represented by Formula (II-A):

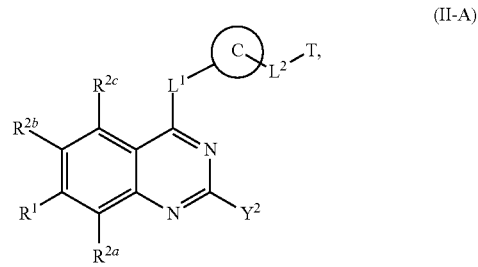

(II-A)

or a salt or prodrug thereof.

In certain aspects, the present disclosure provides a stereoisomer of a compound of Formula (II-A):

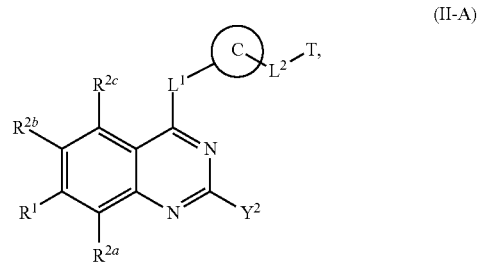

(II-A)

or a salt or prodrug thereof, wherein:

R$^1$ is selected from C$_{3-12}$ carbocycle and 3- to 12-membered heterocycle, each of which is substituted with one or more substituents independently selected from halogen, —OH, —OR$^{52}$, —NH$_2$, —NHMe, —NMe$_2$, C$_{1-3}$ alkyl, C$_{1-3}$ haloalkyl, C$_{3-12}$ carbocycle and 3- to 12-membered heterocycle;

R$^{2a}$ and R$^{2b}$ are each independently selected from hydrogen, halogen, —OH, —OR$^{52}$, C$_{1-4}$ alkyl, and C$_{1-4}$ haloalkyl, wherein at least one of R$^{2a}$ and R$^{2b}$ is not hydrogen;

R$^{2c}$ is selected from hydrogen, halogen, —OH, —OR$^{52}$, C$_{1-4}$ alkyl, and C$_{1-4}$ haloalkyl; and Y$^2$ is selected from —N(R$^{56}$)$_2$; and C$_{1-10}$ alkyl, C$_{2-10}$ alkenyl and C$_{2-10}$ alkynyl, each of which is substituted with —N(R$^{56}$)$_2$ and optionally futher substituted with one or more R$^{50}$;

L$^1$ is selected from bond, —O—, —S—, —N(R$^{51}$)—, —N(R$^{51}$)CH$_2$—, —C(O)—, —C(O)O—, —OC(O)—, —OC(O)O—, —C(O)N(R$^{51}$)—, —C(O)N(R$^{51}$)C(O)—, —C(O)N(R$^{51}$)C(O)N(R$^{51}$)—, —N(R$^{51}$)C(O)—, —N(R$^{51}$)C(O)N(R$^{51}$)—, —N(R$^{51}$)C(O)O—, —OC(O)N(R$^{51}$)—, —C(NR$^{51}$)—, —N(R$^{51}$)C(NR$^{51}$)—, —C(NR$^{51}$)N(R$^{51}$)—, —N(R$^{51}$)C(NR$^{51}$)N(R$^{51}$)—, —S(O)$_2$—, —OS(O)—, —S(O)O—, —S(O)—, —OS(O)$_2$—, —S(O)$_2$O—, —N(R$^{51}$)S(O)$_2$—, —S(O)$_2$N(R$^{51}$)—, —N(R$^{51}$)S(O)—, —S(O)N(R$^{51}$)—, —N(R$^{51}$)S(O)$_2$N(R$^{51}$)—, —N(R$^{51}$)S(O)N(R$^{51}$)—; alkylene, alkenylene, alkynylene, heteroalkylene, heteroalkenylene, and heteroalkynylene, each of which is optionally substituted with one or more R$^{50}$;

L$^2$ is selected from bond and alkylene;

C is selected from 3- to 12-membered heterocycle, optionally substituted with one or more R$^{57}$;

T is hydrogen or a polar group capable of forming a complex with a Ras protein via an interaction other than one resulting in a covalent bond with the cysteine residue at position 12 of a K-Ras, H-Ras or N-Ras G12C mutant protein;

$R^{50}$ is independently selected at each occurrence from:
halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $=O$, $=S$, $=N(R^{52})$;

$C_{1-10}$ alkyl, $C_{2-10}$ alkenyl, and $C_{2-10}$ alkynyl, each of which is independently optionally substituted at each occurrence with one or more substituents selected from halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $=O$, $=S$, $=N(R^{52})$, $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^{50}$ is independently optionally substituted with one or more substituents selected from halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $=O$, $=S$, $=N(R^{52})$, $C_{1-6}$ alkyl, $C_{1-6}$ haloalkyl, $C_{2-6}$ alkenyl, and $C_{2-6}$ alkynyl;

$R^{51}$ is independently selected at each occurrence from:
hydrogen, $-C(O)R^{52}$, $-C(O)OR^{52}$, $-C(O)N(R^{52})_2$, $-C(O)NR^{53}R^{54}$;

$C_{1-6}$ alkyl, $C_{2-6}$ alkenyl, and $C_{2-6}$ alkynyl, each of which is independently optionally substituted at each occurrence with one or more substituents selected from halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $=O$, $=S$, $=N(R^{52})$, $C_{3-12}$ carbocycle and 3- to 12-membered heterocycle; and $C_{3-12}$ carbocycle and 3- to 12-membered heterocycle, wherein each $C_{3-12}$ carbocycle and 3- to 12-membered heterocycle in $R^{51}$ is independently optionally substituted with one or more substituents selected from halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $=O$, $=S$, $=N(R^{52})$, $C_{1-6}$ alkyl, $C_{1-6}$ haloalkyl, $C_{2-6}$ alkenyl, and $C_{2-6}$ alkynyl;

$R^{52}$ is independently selected at each occurrence from hydrogen; and $C_{1-20}$ alkyl, $C_{2-20}$ alkenyl, $C_{2-20}$ alkynyl, 2- to 6-membered heteroalkyl, $C_{3-12}$ carbocycle, and 3- to 12-membered heterocycle, each of which is optionally substituted by halogen, $-CN$, $-NO_2$, $-NH_2$, $-NHCH_3$, $-NHCH_2CH_3$, $=O$, $-OH$, $-OCH_3$, $-OCH_2CH_3$, $C_{3-12}$ carbocycle, or 3- to 6-membered heterocycle;

$R^{53}$ and $R^{54}$ are taken together with the nitrogen atom to which they are attached to form a heterocycle, optionally substituted with one or more $R^{50}$;

$R^{56}$ is independently selected at each occurrence from:
hydrogen;
$C_{1-10}$ alkyl, $C_{2-10}$ alkenyl, and $C_{2-10}$ alkynyl, each of which is independently optionally substituted at each occurrence with one or more substituents selected from halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $=O$, $=S$, $=N(R^{52})$, $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^{56}$ is independently optionally substituted with one or more substituents selected from halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $=O$, $=S$, $=N(R^{52})$, $C_{1-6}$ alkyl, $C_{1-6}$ haloalkyl, $C_{2-6}$ alkenyl, and $C_{2-6}$ alkynyl; and $R^{57}$ is independently selected at each occurrence from:
halogen, $-CN$, $-OH$, $-OMe$, $-NH_2$, $-NHC_{1-6}$ alkyl, $-N(C_{1-6}$ alkyl$)_2$, $-C(O)OH$, $-C(O)H$, $-C(O)C_{1-6}$ alkyl, $-NHC(O)C_{1-6}$ alkyl, $-N(C_{1-6}$ alkyl$)C(O)C_{1-6}$ alkyl, $-C(O)NH_2$, $-C(O)NH(C_{1-6}$ alkyl$)$, $-C(O)N(C_{1-6}$ alkyl$)_2$, $=O$, $=N(OH)$; and $C_{1-10}$ alkyl, optionally substituted at each occurrence with one or more substituents selected from $-CN$, $-OH$, $-NH_2$, $-OMe$, $-NH_2$, $-NHC_{1-6}$ alkyl, $-N(C_{1-6}$ alkyl$)_2$, $-C(O)OH$, $-C(O)H$, $-C(O)C_{1-6}$ alkyl, $-NHC(O)C_{1-6}$ alkyl, $-N(C_{1-6}$ alkyl$)C(O)C_{1-6}$ alkyl, $-C(O)NH_2$, $-C(O)NH(C_{1-6}$ alkyl$)$, $-C(O)N(C_{1-6}$ alkyl$)_2$, $=O$, and $=N(OH)$.

In certain aspects, a compound of Formula (II) is represented by Formula (II-B):

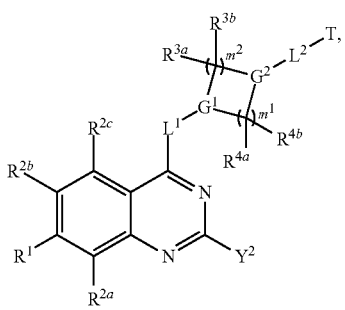

(II-B)

or a salt thereof, wherein:

$G^1$ and $G^2$ are each independently N or CH;

$R^{3a}$ and $R^{3b}$ are independently selected at each occurrence from H, —OH, —NH$_2$, —CO$_2$H, halo, cyano, $C_{1-6}$ alkyl, $C_{2-6}$ alkynyl, hydroxylalkyl, aminoalkyl, alkylaminoalkyl, cyanoalkyl, carboxyalkyl, aminocarbonylalkyl and aminocarbonyl; or $R^{3a}$ and $R^{3b}$ join to form oxo or a carbocyclic or heterocyclic ring; or $R^{3a}$ is independently selected at each occurrence from H, —OH, —NH$_2$, —CO$_2$H, halo, cyano, $C_{1-6}$ alkyl, $C_{2-6}$ alkynyl, hydroxylalkyl, aminoalkyl, alkylaminoalkyl, cyanoalkyl, carboxyalkyl, aminocarbonylalkyl and aminocarbonyl, and $R^{3b}$ joins with $R^{4b}$ to form a carbocyclic or heterocyclic ring;

$R^{4a}$ and $R^{4b}$ are independently selected at each occurrence from H, —OH, —NH$_2$, —CO$_2$H, halo, cyano, $C_{1-6}$ alkyl, $C_{2-6}$ alkynyl, hydroxylalkyl, aminoalkyl, alkylaminoalkyl, cyanoalkyl, carboxyalkyl, aminocarbonylalkyl and aminocarbonyl; or $R^{4a}$ and $R^{4b}$ join to form oxo or a carbocyclic or heterocyclic ring; or $R^{4a}$ is independently selected at each occurrence from H, —OH, —NH$_2$, —CO$_2$H, halo, cyano, $C_{1-6}$ alkyl, $C_{2-6}$ alkynyl, hydroxylalkyl, aminoalkyl, alkylaminoalkyl, cyanoalkyl, carboxyalkyl, aminocarbonylalkyl and aminocarbonyl, and $R^{4b}$ joins with $R^{3b}$ to form a carbocyclic or heterocyclic ring; and $m^1$ and $m^2$ are each independently 1, 2 or 3.

For a compound of Formula (II), (II-A) or (II-B), $Y^2$ may be $C_{1-4}$ alkyl substituted with —N(R$^{56}$)$_2$, wherein at least one $R^{56}$ is not hydrogen. In some embodiments, $R^{56}$ is independently selected at each occurrence from: hydrogen; $C_{1-10}$ alkyl, $C_{2-10}$ alkenyl, and $C_{2-10}$ alkynyl, each of which is independently optionally substituted at each occurrence with one or more substituents selected from halogen, —CN, —OR$^{52}$, —SR$^{52}$, —N(R$^{52}$)$_2$, —NR$^{53}$R$^{54}$, $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle is independently optionally substituted with one or more substituents selected from halogen, =O, $C_{1-6}$ alkyl, and $C_{1-6}$ haloalkyl. In some embodiments, $R^{56}$ is independently selected at each occurrence from hydrogen, $C_{1-4}$ alkyl, and $C_{1-4}$ alkyl substituted with one or more substituents selected from halogen, —CN, —N(R$^{52}$)$_2$, —NR$^{53}$R$^{54}$, $C_{3-12}$ carbocycle, and 3- to 12-membered heterocycle, wherein each $C_{3-12}$ carbocycle and 3- to 12-membered heterocycle is optionally substituted with one or more substituents selected from halogen, =O, $C_{1-6}$ alkyl, and $C_{1-6}$ haloalkyl. In some embodiments, $Y^2$ is selected from:

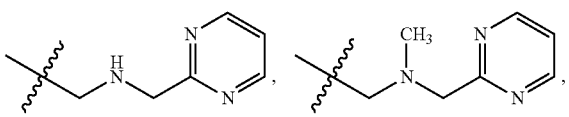

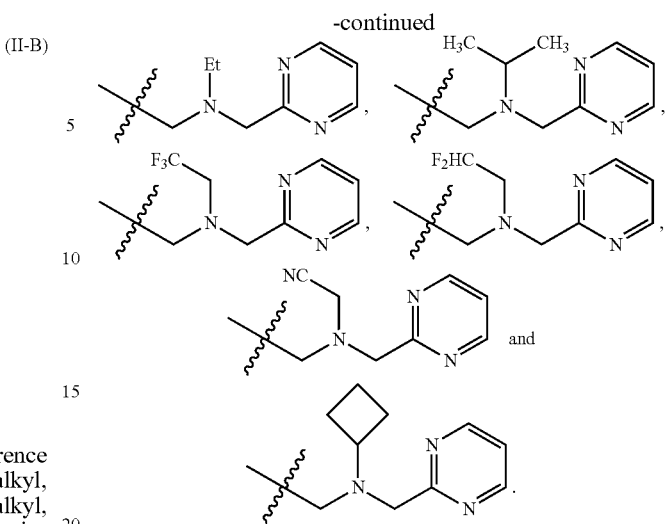

In some embodiments, $Y^2$ is —N(R$^{56}$)$_2$ and the two $R^{56}$ groups are taken together with the nitrogen atom to which they are attached to form a heterocycle, wherein the heterocycle is optionally substituted with one or more R$^{50}$. In some embodiments, $Y^2$ is —N(R$^{56}$)$_2$ and the two $R^{56}$ groups are taken together with the nitrogen atom to which they are attached to form a 3- to 6-membered heterocycle, wherein the heterocycle is substituted with —N(R$^{52}$)$_2$ or —NR$^{53}$R$^{54}$. In some embodiments, $Y^2$ is azetidinyl, optionally substituted with one or more R$^{50}$. In some embodiments, $Y^2$ is selected from

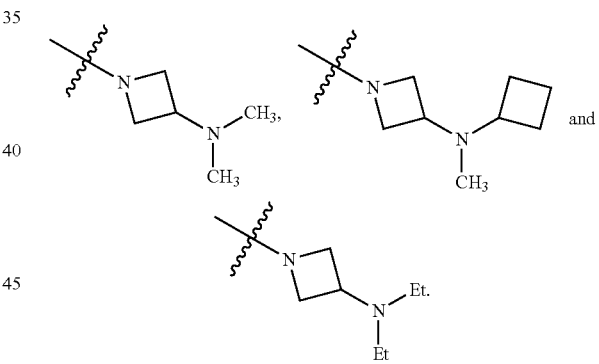

For a compound of Formula (I), (I-A), (I-B), (II), (II-A) or (II-B), $R^1$ may be selected from $C_{3-12}$ carbocycle and 3- to 12-membered heterocycle, each of which is optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), $C_{1-6}$ alkyl, $C_{1-6}$ haloalkyl, $C_{2-6}$ alkenyl, and $C_{2-6}$ alkynyl. In some embodiments, $R^1$ is selected from monocyclic aryl, bicyclic aryl, monocyclic heteroaryl, and bicyclic heteroaryl. In some embodiments, $R^1$ is selected from phenyl, naphthyl, indazolyl, and quinolinyl. In some embodiments, $R^1$ is substituted with one or more substituents selected from halogen, —OH, —OCH₃, C₁₋₄ alkyl, and C₁₋₄ haloalkyl. In some embodiments, R¹ is selected from:

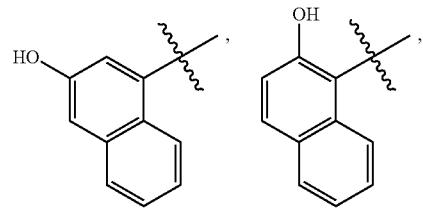

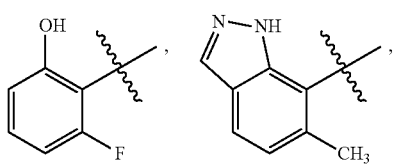

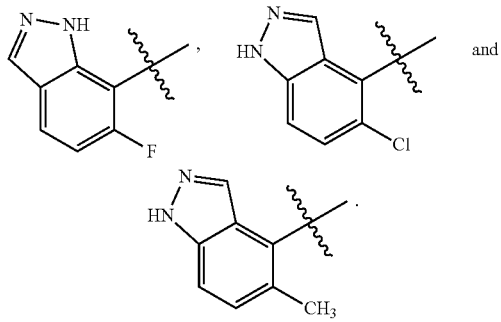

In some embodiments, R¹ is selected from:

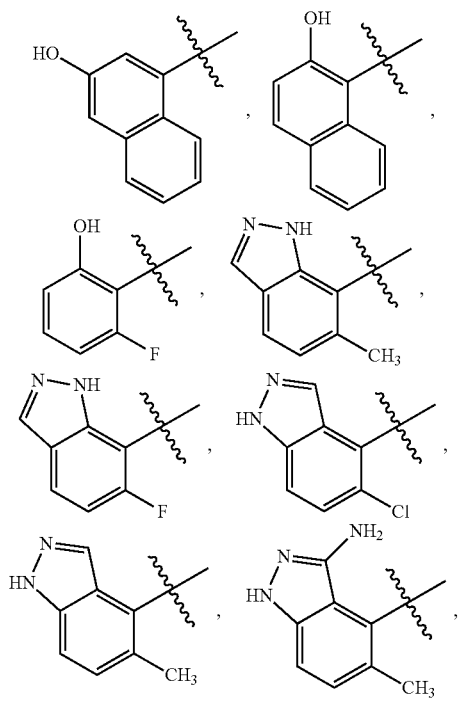

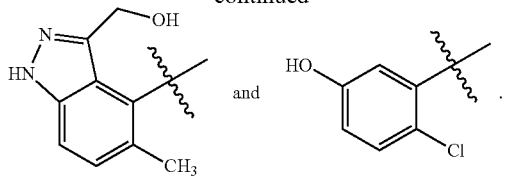

For a compound of Formula (I), (I-A), (I-B), (II), (II-A) or (II-B), $R^{2a}$, $R^{2b}$ and $R^{2c}$ may each be independently selected from hydrogen, halogen, —OH, —OCH₃, C₁₋₄ alkyl, and C₁₋₄ haloalkyl. In some embodiments, $R^{2a}$ and $R^{2b}$ are each independently selected from halogen. In some embodiments, $R^{2a}$ is fluorine. In some embodiments, $R^{2b}$ is chlorine. In some embodiments, $R^{2c}$ is hydrogen.

For a compound of Formula (I), (I-A), (I-B), (II), (II-A) or (II-B), C may be 5- to 8-membered heterocycle, optionally substituted with one or more $R^{57}$. In some embodiments, C is 6-membered monocyclic heterocycle, optionally substituted with one or more $R^{57}$. In some embodiments, the heterocycle comprises at least one nitrogen atom. In some embodiments, C is selected from piperidinylene and piperazinylene, optionally substituted with one or more $R^{57}$. In some embodiments, C is selected from morpholinyl, piperidinylene and piperazinylene, optionally substituted with one or more $R^{57}$. In some embodiments, C is selected from

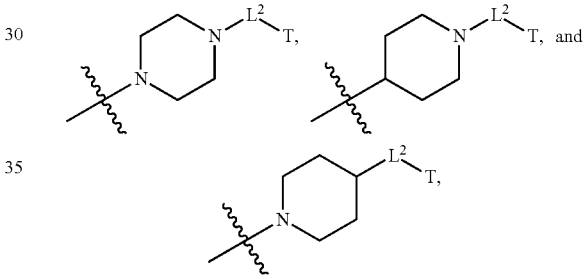

optionally substituted with one or more $R^{57}$. In some embodiments, C is selected from

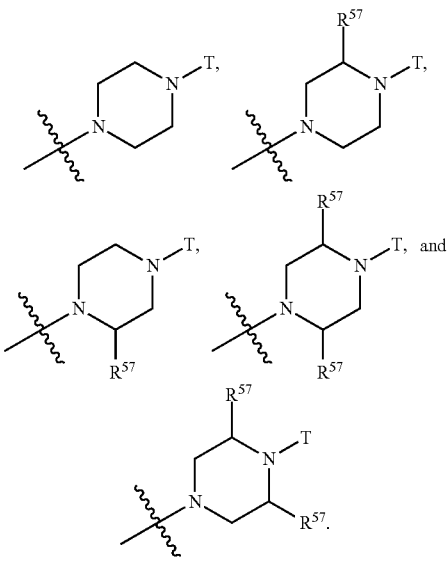

In some embodiments, $R^{57}$ is independently selected at each occurrence from $C_{1-6}$ alkyl, such as $CH_3$.

For a compound of Formula (I), (I-A), (I-B), (II), (II-A) or (II-B), T may be capable of forming a complex with a metal ion that is complexed with the Ras protein. In some embodiments, T is capable of forming an interaction with a mutation residue, such as G12D, in the Ras protein. In some embodiments, the mutation residue is selected from G12A, G12C, G12D, G12S and G12V. In some embodiments, T is selected from: —H, —$NH_2$, —OH, —NH($C_{1-6}$ alkyl),

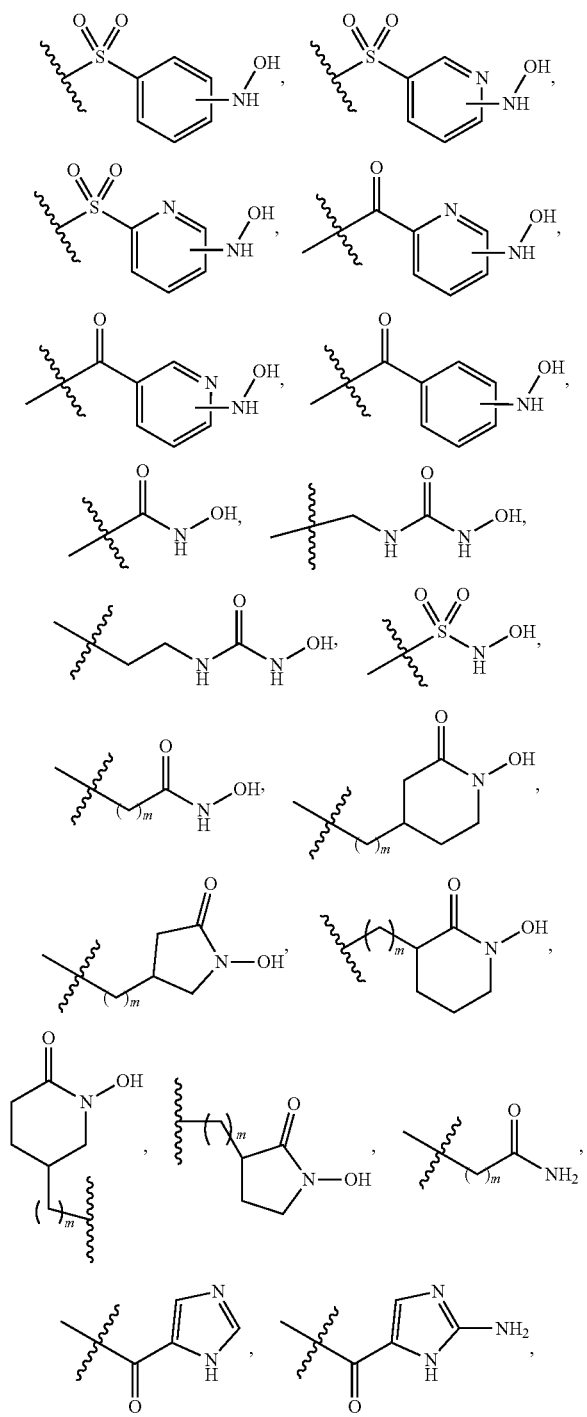

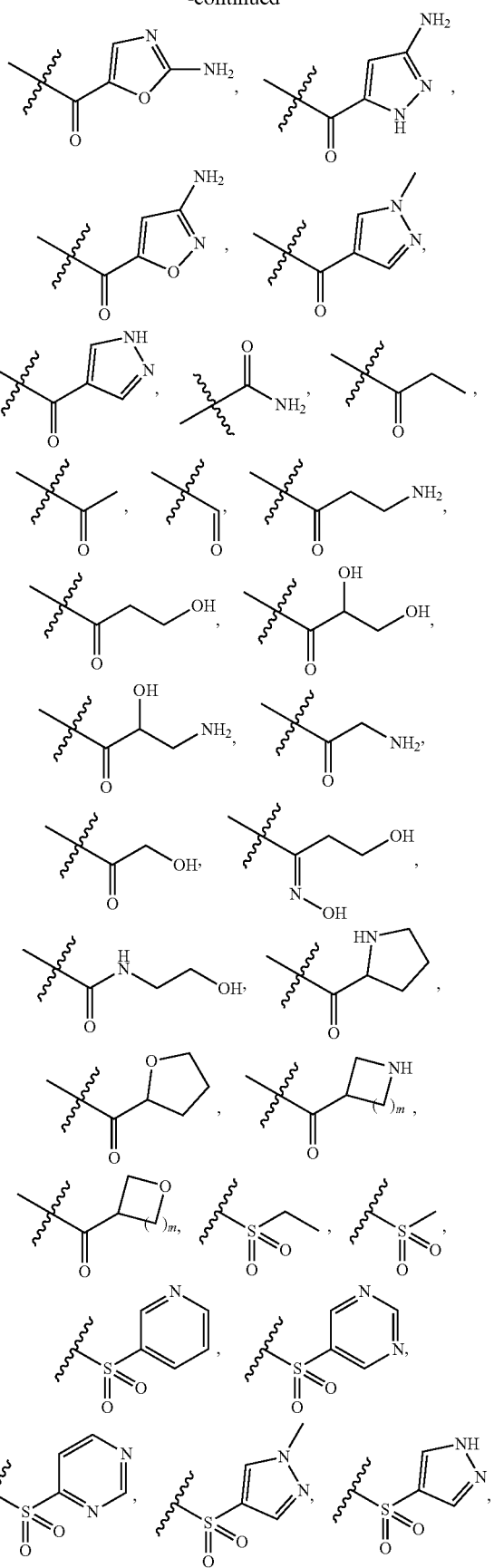

-continued

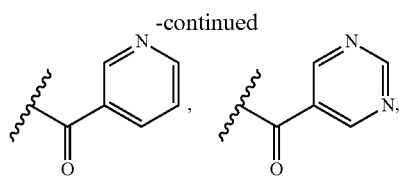

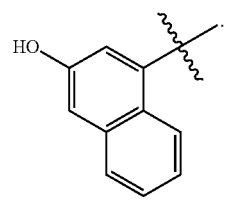 [SMILES: *c1cc(O)cc2ccccc12]

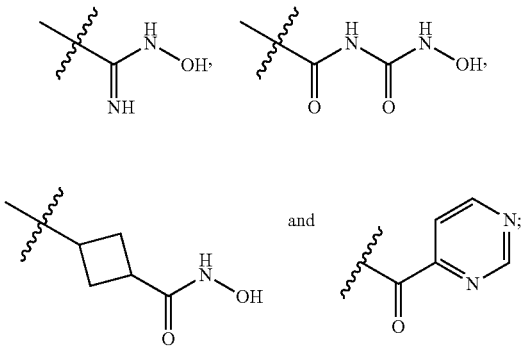

and and m, when present, is 0, 1, 2, or 3. In some embodiments, T is selected from $R^{57}$. In some embodiments, T is selected from hydrogen; and $C_{1-6}$ alkyl, optionally substituted with =O. In some embodiments, T is selected from hydrogen, —$CH_3$, —C(O)H, —C(O)$CH_3$, and —C(O)$CH_2CH_3$. In some embodiments, T is selected from hydrogen, $C_{1-10}$ alkyl, $C_{1-10}$ alkyl substituted with one or more $R^{52}$, —C(O)$R^{52}$, —C(O)N($R^{52}$)$_2$, —C(O)N$R^{53}R^{54}$, —N$R^{52}$C(O)$R^{52}$, —C(S)N($R^{52}$)$_2$, —C(S)N$R^{53}R^{54}$, —N$R^{52}$C(S)$R^{52}$, —S(O)$_2$N($R^{52}$)$_2$, —S(O)$_2$N$R^{53}R^{54}$, —N$R^{52}$S(O)$_2R^{52}$, —C(N$R^{52}$)N($R^{52}$)$_2$, —C(N$R^{52}$)N$R^{53}R^{54}$, and —N$R^{52}$C(N$R^{52}$)$R^{52}$; and $R^{52}$ is independently selected at each occurrence from: hydrogen; and $C_{1-20}$ alkyl, 2- to 6-membered heteroalkyl, $C_{3-12}$ carbocycle, and 3- to 12-membered heterocycle, each of which is optionally substituted by —CN, —$NO_2$, —$NH_2$, —$NHCH_3$, —$NHCH_2CH_3$, =O, —OH, —$OCH_3$, —$OCH_2CH_3$, $C_{3-12}$ carbocycle, or 3- to 6-membered heterocycle.

For a compound of Formula (I), (I-A), (I-B), (II), (II-A) or (II-B), $L^1$ may be selected from bond and —N($R^{51}$)—, such as $L^1$ is a bond. In some embodiments, $L^2$ is a bond.

For a compound of Formula (I), (I-A), (I-B), (II), (II-A) or (II-B), $R^1$ may be selected from phenyl, naphthyl, indazolyl, and quinolinyl, optionally substituted with one or more substituents selected from halogen, —OH, and —$CH_3$; $R^{2a}$ and $R^{2b}$ may each be independently selected from halogen; $R^{2c}$ may be hydrogen; C may be

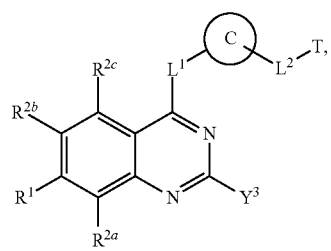

optionally substituted with one or more $R^{57}$; T may be selected from hydrogen; and $C_{1-6}$ alkyl, optionally substituted with =O; and $L^1$ and $L^2$ may each be a bond. In some embodiments, $R^1$ is

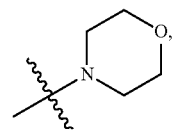 [SMILES: *N1CCOCC1]

In some embodiments, $R^{57}$ is —$CH_3$. In some embodiments, T is hydrogen.

For a compound of Formula (I), (I-A), (I-B), (II), (II-A) or (II-B), $R^1$ may be selected from phenyl, naphthyl, indazolyl, and quinolinyl, optionally substituted with one or more substituents selected from halogen, —OH, and —$CH_3$; $R^{2a}$ and $R^{2b}$ may each be independently selected from halogen; $R^{2c}$ may be hydrogen; C may be

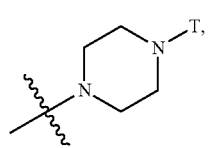

optionally substituted with one or more $R^{57}$; and $L^1$ may be a bond.

In certain aspects, the present disclosure provides a stereoisomer of a compound of Formula (III-A):

(III-A)

or a salt or prodrug thereof, wherein:

$R^1$ is selected from $C_{3-12}$ carbocycle and 3- to 12-membered heterocycle, each of which is substituted with one or more substituents independently selected from halogen, —OH, —$OR^{52}$, —$NH_2$, —NHMe, —$NMe_2$, $C_{1-3}$ alkyl, $C_{1-3}$ haloalkyl, $C_{3-12}$ carbocycle and 3- to 12-membered heterocycle;

$R^{2a}$ and $R^{2b}$ are each independently selected from hydrogen, halogen, —OH, —$OR^{52}$, $C_{1-4}$ alkyl, and $C_{1-4}$ haloalkyl, wherein at least one of $R^{2a}$ and $R^{2b}$ is not hydrogen;

$R^{2c}$ is selected from hydrogen, halogen, —OH, —$OR^{52}$, $C_{1-4}$ alkyl, and $C_{1-4}$ haloalkyl; and $Y^3$ is selected from —$OR^{55}$, —N($R^{56}$)$_2$; and $C_{1-10}$ alkyl, $C_{2-10}$ alkenyl and $C_{2-10}$ alkynyl, each of which is substituted with —$OR^{55}$ or —N($R^{56}$)$_2$ and optionally futher substituted with one or more $R^{50}$;

$L^1$ is selected from bond, —O—, —S—, —N($R^{51}$)—, —N($R^{51}$)$CH_2$—, —C(O)—, —C(O)O—, —OC(O)—, —OC(O)O—, —C(O)N($R^{51}$)—, —C(O)N($R^{51}$)C(O)—, —C(O)N($R^{51}$)C(O)N($R^{51}$)—, —N($R^{51}$)C(O)—, —N($R^{51}$)C(O)N($R^{51}$)—, —N($R^{51}$)C(O)O—, —OC(O)N($R^{51}$)—, —C(N$R^{51}$)—, —N($R^{51}$)C(N$R^{51}$)—, —C(N$R^{51}$)N($R^{51}$)—, —N($R^{51}$)C(N$R^{51}$)N($R^{51}$)—, —S(O)$_2$—, —OS(O)—, —S(O)O—, —S(O)—, —OS(O)$_2$—, —S(O)$_2$O—, —N(R$^{51}$)S(O)$_2$—, —S(O)$_2$N(R$^{51}$)—, —N(R$^{51}$)S(O)—, —S(O)N(R$^{51}$)—, —N(R$^{51}$)S(O)$_2$N(R$^{51}$)—, —N(R$^{51}$)S(O)N(R$^{51}$)—; alkylene, alkenylene, alkynylene, heteroalkylene, heteroalkenylene, and heteroalkynylene, each of which is optionally substituted with one or more R$^{50}$;

L$^2$ is selected from bond and alkylene;

C is selected from 3- to 12-membered heterocycle, optionally substituted with one or more R$^{57}$;

T is hydrogen or a polar group capable of forming a complex with a Ras protein via an interaction other than one resulting in a covalent bond with the cysteine residue at position 12 of a K-Ras, H-Ras or N-Ras G12C mutant protein;

R$^{50}$ is independently selected at each occurrence from:
halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$);

C$_{1-10}$ alkyl, C$_{2-10}$ alkenyl, and C$_{2-10}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{3-12}$ carbocycle, and 3- to 12-membered heterocycle; and C$_{3-12}$ carbocycle and 3- to 12-membered heterocycle, wherein each C$_{3-12}$ carbocycle and 3- to 12-membered heterocycle in R$^{50}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl;

R$^{51}$ is independently selected at each occurrence from: hydrogen, —C(O)R$^{52}$, —C(O)OR$^{52}$, —C(O)N(R$^{52}$)$_2$, —C(O)NR$^{53}$R$^{54}$; C$_{1-6}$ alkyl, C$_{2-6}$ alkenyl, and C$_{2-6}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{3-12}$ carbocycle and 3- to 12-membered heterocycle; and C$_{3-12}$ carbocycle and 3- to 12-membered heterocycle, wherein each C$_{3-12}$ carbocycle and 3- to 12-membered heterocycle in R$^{51}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl;

R$^{52}$ is independently selected at each occurrence from hydrogen; and C$_{1-20}$ alkyl, C$_{2-20}$ alkenyl, C$_{2-20}$ alkynyl, 2- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle;

R$^{53}$ and R$^{54}$ are taken together with the nitrogen atom to which they are attached to form a heterocycle, optionally substituted with one or more R$^{50}$;

R$^{55}$ is selected from:
C$_{1-10}$ alkyl, C$_{2-10}$ alkenyl, and C$_{2-10}$ alkynyl, each of which is independently optionally substituted at each occurrence with one or more, substituents selected from halogen, —NO$_2$, —CN, —OR$^{52}$, —SR$^{52}$, —N(R$^{52}$)$_2$, —NR$^{53}$R$^{54}$, —S(=O)$_2$N(R$^{52}$)$_2$, —S(=O)$_2$R$^{52}$, —S(=O)$_2$(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{3-12}$ carbocycle, and 3- to 12-membered heterocycle; and C$_{3-12}$ carbocycle and 3- to 12-membered heterocycle, wherein each C$_{3-12}$ carbocycle and 3- to 12-membered heterocycle in R$^{55}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl;

R$^{56}$ is independently selected at each occurrence from: hydrogen;
C$_{1-10}$ alkyl, C$_{2-10}$ alkenyl, and C$_{2-10}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in R$^{56}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), $C_{1-6}$ alkyl, $C_{1-6}$ haloalkyl, $C_{2-6}$ alkenyl, and $C_{2-6}$ alkynyl, or two R$^{56}$ groups are taken together with the nitrogen atom to which they are attached to form a heterocycle, optionally substituted with one or more R$^{50}$; and R$^{57}$ is independently selected at each occurrence from:

halogen, —CN, —OH, —OMe, —NH$_2$, —NHC$_{1-6}$ alkyl, —N(C$_{1-6}$ alkyl)$_2$, —C(O)OH, —C(O)H, —C(O)C$_{1-6}$ alkyl, —NHC(O)C$_{1-6}$ alkyl, —N(C$_{1-6}$ alkyl)C(O)C$_{1-6}$ alkyl, —C(O)NH$_2$, —C(O)NH(C$_{1-6}$ alkyl), —C(O)N(C$_{1-6}$ alkyl)$_2$, =O, =N(OH); and $C_{1-10}$ alkyl, optionally substituted at each occurrence with one or more substituents selected from —CN, —OH, —NH$_2$, —OMe, —NH$_2$, —NHC$_{1-6}$ alkyl, —N(C$_{1-6}$ alkyl)$_2$, —C(O)OH, —C(O)H, —C(O)C$_{1-6}$ alkyl, —NHC(O)C$_{1-6}$ alkyl, —N(C$_{1-6}$ alkyl)C(O)C$_{1-6}$ alkyl, —C(O)NH$_2$, —C(O)NH(C$_{1-6}$ alkyl), —C(O)N(C$_{1-6}$ alkyl)$_2$, =O, and =N(OH).

For a compound of Formula (I), (I-A), (I-B), (II), (II-A), (II-B) or (III-A), the compound may be provided as a substantially pure atropisomer. In some embodiments, the present disclosure provides a stereoisomer, such as an atropisomer, of a compound of Formula (I), (I-A), (I-B), (II), (II-A), (II-B) or (III-A). In some embodiments, the stereoisomer is provided in at least 90% enantiomeric excess. In some embodiments, the stereoisomer is provided in at least 90% diastereomeric excess. In some embodiments, R$^1$ is selected from:

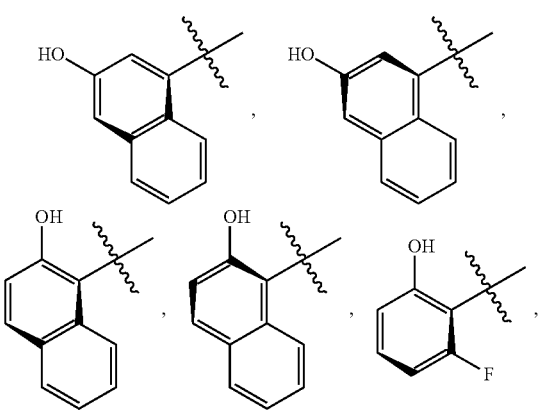

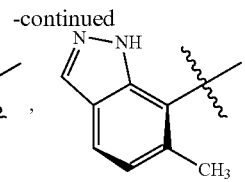

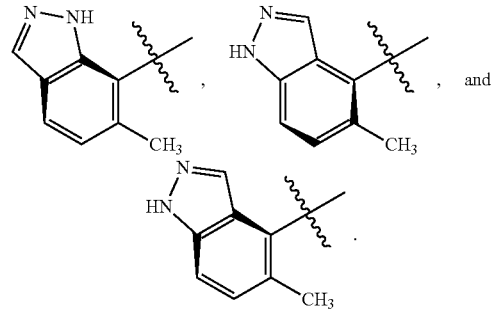

, and

In certain aspects, the present disclosure provides a compound selected from Table 1, Table 2 or Table 3.

In certain aspects, the present disclosure provides a pharmaceutical composition comprising a compound or salt of Formula (I), (I-A), (I-B), (II), (II-A), (II-B) or (III-A), and a pharmaceutically acceptable carrier. In some embodiments, the pharmaceutical composition is formulated for oral administration. In some embodiments, the pharmaceutical composition is formulated for injection.

In certain aspects, the present disclosure provides a method for treatment of cancer, the method comprising administering an effective amount of the pharmaceutical composition comprising a compound or salt of Formula (I), (I-A), (I-B), (II), (II-A), (II-B) or (III-A) to a subject in need thereof. In some embodiments, the cancer is mediated by a K-Ras, H-Ras, or N-Ras mutant protein. In some embodiments, the cancer is a hematological cancer, pancreatic cancer, MYH associated polyposis, colorectal cancer or lung cancer. In certain aspects, the present disclosure provides a method for regulating activity of a K-Ras, H-Ras or N-Ras mutant protein, the method comprising contacting the Ras mutant protein with a compound or salt of Formula (I), (I-A), (I-B), (II), (II-A), (II-B) or (III-A). In certain aspects, the present disclosure provides a method for inhibiting proliferation of a cell population, the method comprising contacting the cell population with a compound or salt of Formula (I), (I-A), (I-B), (II), (II-A), (II-B) or (III-A). In some embodiments, inhibition of proliferation is measured as a decrease in cell viability of the cell population. In certain aspects, the present disclosure provides a method for treating a disorder mediated by a K-Ras, H-Ras or N-Ras mutant protein in a subject in need thereof, the method comprising: determining if the subject has a K-Ras, H-Ras or N-Ras mutation; and if the subject is determined to have the K-Ras, H-Ras or N-Ras mutation, then administering to the subject a therapeutically effective amount of a pharmaceutical composition comprising a compound or salt of Formula (I), (I-A), (I-B), (II), (II-A), (II-B) or (III-A). In some embodiments, the disorder is a cancer, such as a hematological cancer, pancreatic cancer, MYH associated polyposis, colorectal cancer or lung cancer. In certain aspects, the present disclosure provides a method for inhibiting tumor metastasis, the method comprising administering an effective amount of a pharmaceutical composition comprising a compound or salt of Formula (I), (I-A), (I-B), (II), (II-A), (II-B) or (III-A) to a subject in need thereof. In some embodiments, the method further comprises administering a second anti-cancer agent.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE FIGURES

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3 shows some common oncogenes, their respective tumor type and cumulative mutation frequencies (all tumors).

DETAILED DESCRIPTION

Figure 2:
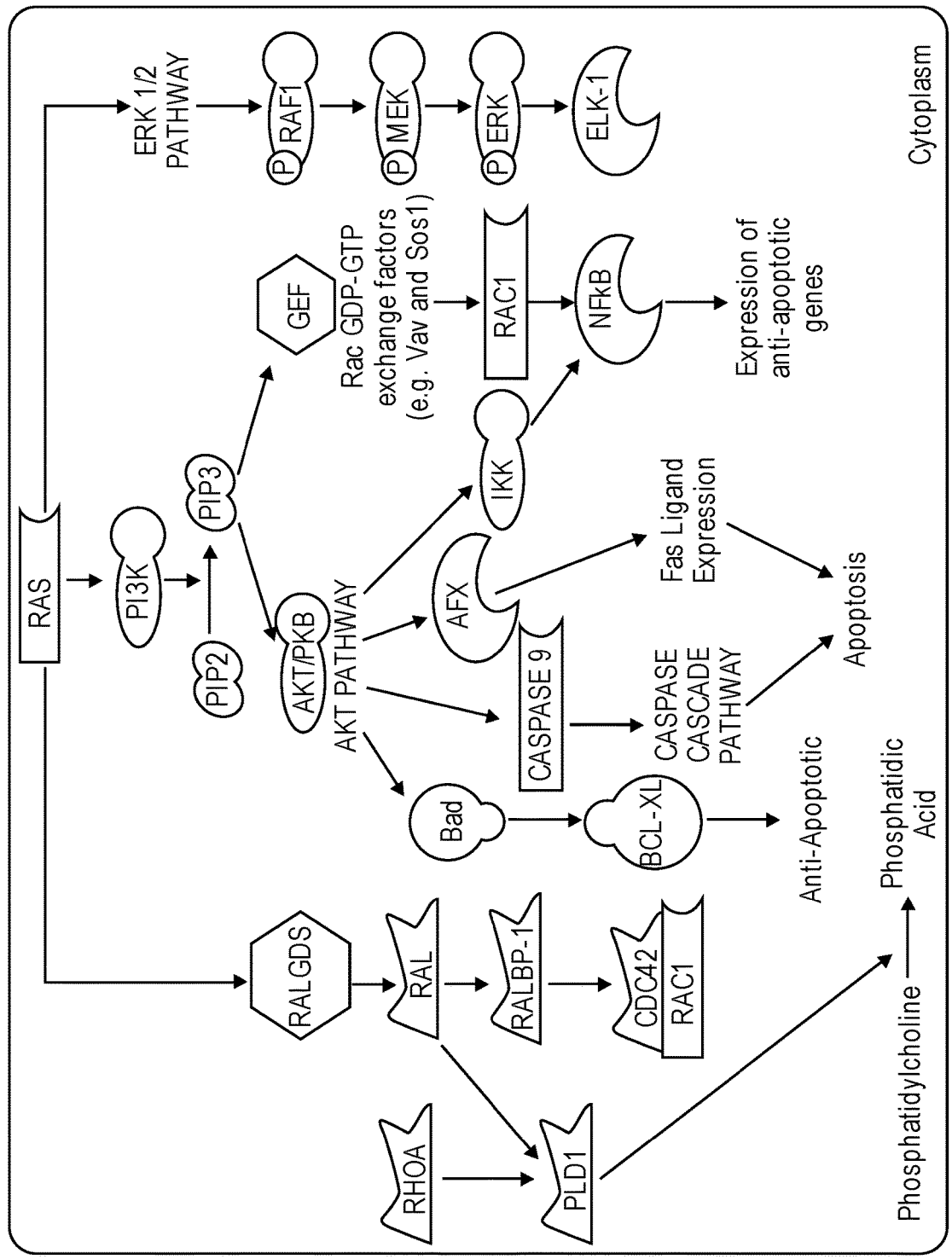
FIG. 2 depicts a signal transduction pathway for Ras.
Figure 1:
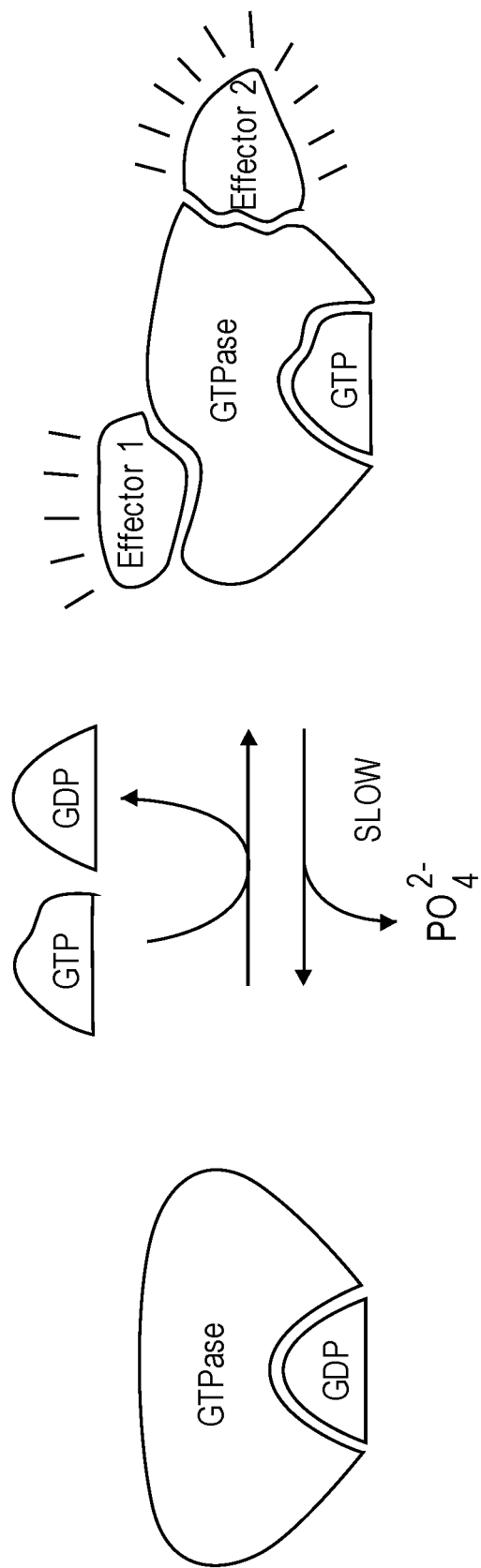
FIG. 1 illustrates the enzymatic activity of Ras.

Unless defined otherwise, all technical and scientific terms used herein have the same meaning as is commonly understood by one of skill in the art to which this invention belongs.

As used in the specification and claims, the singular form "a", "an" and "the" include plural references unless the context clearly dictates otherwise.

The term "$C_{x-y}$" or "$C_x$-$C_y$" when used in conjunction with a chemical moiety, such as alkyl, alkenyl, or alkynyl is meant to include groups that contain from x to y carbons in the chain. For example, the term "$C_3$, alkyl" refers to substituted or unsubstituted saturated hydrocarbon groups, including straight-chain alkyl and branched-chain alkyl groups that contain from x to y carbons in the chain.

"Alkyl" refers to substituted or unsubstituted saturated hydrocarbon groups, including straight-chain alkyl and branched-chain alkyl groups. An alkyl group may contain from one to twelve carbon atoms (e.g., $C_{1-12}$ alkyl), such as one to eight carbon atoms ($C_{1-8}$ alkyl) or one to six carbon atoms ($C_{1-6}$ alkyl). Exemplary alkyl groups include methyl, ethyl, n-propyl, isopropyl, n-butyl, isobutyl, sec-butyl, tert-butyl, pentyl, isopentyl, neopentyl, hexyl, septyl, octyl, nonyl, and decyl. An alkyl group is attached to the rest of the molecule by a single bond. Unless stated otherwise specifically in the specification, an alkyl group is optionally substituted by one or more substituents such as those substituents described herein.

"Haloalkyl" refers to an alkyl group that is substituted by one or more halogens. Exemplary haloalkyl groups include trifluoromethyl, difluoromethyl, trichloromethyl, 2,2,2-trifluoroethyl, 1,2-difluoroethyl, 3-bromo-2-fluoropropyl, and 1,2-dibromoethyl.

"Alkenyl" refers to substituted or unsubstituted hydrocarbon groups, including straight-chain or branched-chain alkenyl groups containing at least one double bond. An alkenyl group may contain from two to twelve carbon atoms (e.g., $C_{2-12}$ alkenyl). Exemplary alkenyl groups include ethenyl (i.e., vinyl), prop-1-enyl, but-1-enyl, pent-1-enyl, penta-1,4-dienyl, and the like. Unless stated otherwise specifically in the specification, an alkenyl group is optionally substituted by one or more substituents such as those substituents described herein.

"Alkynyl" refers to substituted or unsubstituted hydrocarbon groups, including straight-chain or branched-chain alkynyl groups containing at least one triple bond. An alkynyl group may contain from two to twelve carbon atoms (e.g., $C_{2-12}$ alkynyl). Exemplary alkynyl groups include ethynyl, propynyl, butynyl, pentynyl, hexynyl, and the like. Unless stated otherwise specifically in the specification, an alkynyl group is optionally substituted by one or more substituents such as those substituents described herein.

"Alkylene" or "alkylene chain" refers to substituted or unsubstituted divalent saturated hydrocarbon groups, including straight-chain alkylene and branched-chain alkylene groups that contain from one to twelve carbon atoms. Exemplary alkylene groups include methylene, ethylene, propylene, and n-butylene. Similarly, "alkenylene" and "alkynylene" refer to alkylene groups, as defined above, which comprise one or more carbon-carbon double or triple bonds, respectively. The points of attachment of the alkylene, alkenylene or alkynylene chain to the rest of the molecule can be through one carbon or any two carbons within the chain. Unless stated otherwise specifically in the specification, an alkylene, alkenylene, or alkynylene group is optionally substituted by one or more substituents such as those substituents described herein.

"Heteroalkyl", "heteroalkenyl" and "heteroalkynyl" refer to substituted or unsubstituted alkyl, alkenyl and alkynyl groups which respectively have one or more skeletal chain atoms selected from an atom other than carbon, e.g., O, N, P, Si, S or combinations thereof, and wherein the nitrogen, phosphorus, and sulfur atoms may optionally be oxidized and the nitrogen heteroatom may optionally be quaternized. If given, a numerical range refers to the chain length in total. For example, a 3- to 8-membered heteroalkyl has a chain length of 3 to 8 atoms. Connection to the rest of the molecule may be through either a heteroatom or a carbon in the heteroalkyl, heteroalkenyl or heteroalkynyl chain. Unless stated otherwise specifically in the specification, a heteroalkyl, heteroalkenyl, or heteroalkynyl group is optionally substituted by one or more substituents such as those substituents described herein.

"Heteroalkylene", "heteroalkenylene" and "heteroalkynylene" refer to substituted or unsubstituted alkylene, alkenylene and alkynylene groups which respectively have one or more skeletal chain atoms selected from an atom other than carbon, e.g., O, N, P, Si, S or combinations thereof, and wherein the nitrogen, phosphorus, and sulfur atoms may optionally be oxidized and the nitrogen heteroatom may optionally be quaternized. The points of attachment of the heteroalkylene, heteroalkenylene or heteroalkynylene chain to the rest of the molecule can be through either one heteroatom or one carbon, or any two heteroatoms, any two carbons, or any one heteroatom and any one carbon in the heteroalkyl, heteroalkenyl or heteroalkynyl chain. Unless stated otherwise specifically in the specification, a heteroalkylene, heteroalkenylene, or heteroalkynylene group is optionally substituted by one or more substituents such as those substituents described herein.

"Carbocycle" refers to a saturated, unsaturated or aromatic ring in which each atom of the ring is a carbon atom. Carbocycle may include 3- to 10-membered monocyclic rings, 6- to 12-membered bicyclic rings, and 6- to 12-membered bridged rings. Each ring of a bicyclic carbocycle may be selected from saturated, unsaturated, and aromatic rings.

In some embodiments, the carbocycle is an aryl. In some embodiments, the carbocycle is a cycloalkyl. In some embodiments, the carbocycle is a cycloalkenyl. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, are included in the definition of carbocyclic. Exemplary carbocycles include cyclopentyl, cyclohexyl, cyclohexenyl, adamantyl, phenyl, indanyl, and naphthyl. Unless stated otherwise specifically in the specification, a carbocycle is optionally substituted by one or more substituents such as those substituents described herein.

"Heterocycle" refers to a saturated, unsaturated or aromatic ring comprising one or more heteroatoms. Exemplary heteroatoms include N, O, Si, P, B, and S atoms. Heterocycles include 3- to 10-membered monocyclic rings, 6- to 12-membered bicyclic rings, and 6- to 12-membered bridged rings. Each ring of a bicyclic heterocycle may be selected from saturated, unsaturated, and aromatic rings. The heterocycle may be attached to the rest of the molecule through any atom of the heterocycle, valence permitting, such as a carbon or nitrogen atom of the heterocycle. In some embodiments, the heterocycle is a heteroaryl. In some embodiments, the heterocycle is a heterocycloalkyl. In an exemplary embodiment, a heterocycle, e.g., pyridyl, may be fused to a saturated or unsaturated ring, e.g., cyclohexane, cyclopentane, or cyclohexene. Exemplary heterocycles include pyrrolidinyl, pyrrolyl, imidazolyl, pyrazolyl, triazolyl, piperidinyl, pyridinyl, pyrimidinyl, pyridazinyl, pyrazinyl, thiophenyl, oxazolyl, thiazolyl, morpholinyl, indazolyl, indolyl, and quinolinyl. Unless stated otherwise specifically in the specification, a heterocycle is optionally substituted by one or more substituents such as those substituents described herein.

"Heteroaryl" refers to a 3- to 12-membered aromatic ring that comprises at least one heteroatom wherein each heteroatom may be independently selected from N, O, and S. As used herein, the heteroaryl ring may be selected from monocyclic or bicyclic and fused or bridged ring systems wherein at least one of the rings in the ring system is aromatic, i.e., it contains a cyclic, delocalized (4n+2) nelectron system in accordance with the Hückel theory. The heteroatom(s) in the heteroaryl may be optionally oxidized. One or more nitrogen atoms, if present, are optionally quaternized. The heteroaryl may be attached to the rest of the molecule through any atom of the heteroaryl, valence permitting, such as a carbon or nitrogen atom of the heteroaryl. Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, isoindolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, a heteroaryl is optionally substituted by one or more substituents such as those substituents described herein.

The term "substituted" refers to moieties having substituents replacing a hydrogen on one or more carbons or heteroatoms of the structure. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, a carbocycle, a heterocycle, a cycloalkyl, a heterocycloalkyl, an aromatic and heteroaromatic moiety. In some embodiments, substituents may include any substituents described herein, for example: halogen, hydroxy, oxo (=O), thioxo (=S), cyano (—CN), nitro (—NO$_2$), imino (=N—H), oximo (=N—OH), hydrazino (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2), and —R$^b$—S(O)$_t$N(R$^a$)$_2$ (where t is 1 or 2); and alkyl, alkenyl, alkynyl, aryl, aralkyl, aralkenyl, aralkynyl, cycloalkyl, cycloalkylalkyl, heterocycloalkyl, heterocycloalkylalkyl, heteroaryl, and heteroarylalkyl any of which may be optionally substituted by alkyl, alkenyl, alkynyl, halogen, hydroxy, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—

OR$^a$, —R$^b$—OC(O)—N(R$^a$)$_2$, —R$^b$—N(R$^a$)$_2$, —R$^b$—C(O) R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); wherein each R$^a$ is independently selected from hydrogen, alkyl, cycloalkyl, cycloalkylalkyl, aryl, aralkyl, heterocycloalkyl, heterocycloalkylalkyl, heteroaryl, or heteroarylalkyl, wherein each R$^a$, valence permitting, may be optionally substituted with alkyl, alkenyl, alkynyl, halogen, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); and wherein each R$^b$ is independently selected from a direct bond or a straight or branched alkylene, alkenylene, or alkynylene chain, and each R$^c$ is a straight or branched alkylene, alkenylene or alkynylene chain.

It will be understood by those skilled in the art that substituents can themselves be substituted, if appropriate. Unless specifically stated as "unsubstituted," references to chemical moieties herein are understood to include substituted variants. For example, reference to a "heteroaryl" group or moiety implicitly includes both substituted and unsubstituted variants.

Where substituent groups are specified by their conventional chemical formulae, written from left to right, they equally encompass the chemically identical substituents that would result from writing the structure from right to left, e.g., —CH$_2$O— is equivalent to —OCH$_2$—.

"Optional" or "optionally" means that the subsequently described event of circumstances may or may not occur, and that the description includes instances where the event or circumstance occurs and instances in which it does not. For example, "optionally substituted aryl" means that the aryl group may or may not be substituted and that the description includes both substituted aryl groups and aryl groups having no substitution.

"Electrophile" or "electrophilic moiety" is any moiety capable of reacting with a nucleophile (e.g., a moiety having a lone pair of electrons, a negative charge, a partial negative charge and/or an excess of electrons, for example an —SH group). Electrophiles typically are electron poor or comprise atoms which are electron poor. In certain embodiments, an electrophile contains a positive charge or partial positive charge, has a resonance structure which contains a positive charge or partial positive charge, or is a moiety in which delocalization or polarization of electrons results in one or more atoms which contains a positive charge or partial positive charge. In some embodiments, an electrophile comprises a conjugated double bond, for example an α,β-unsaturated carbonyl or α,β-unsaturated thiocarbonyl compound.

A "polar group" refers to a moiety with one or more dipoles as a result of opposing charges from one or more polar bonds arranged asymmetrically. A polar bond is any covalent bond between atoms of non-identical electronegativity. A polar group can be a group that is more hydrophilic than an alkyl group. In some embodiments, a polar group is a metal chelator or a metal chelator moiety. In some embodiments, a polar gorup comprises at least one heteroatom selected from S, O, and N. For example, a polar group can be an alkyl group that is substituted with one or more functional groups comprising a heteroatom. For example, a polar group can be an alkyl group substituted with one or more alcohol, ether, amine, hydroxyamine, aldehyde, ketone, ester, carboxylic acid, thiol, thioether, thiocarbonyl, sulfonate, sulfunite, phosphonate ester, amide, heterocycle and/or oxime.

The term "metal chelator" or "metal chelator moiety" is any moiety capable of forming two or more separate coordinate bonds between the metal chelator group and a single central metal atom or metal ion. Metal chelators typically have at least one pair of unbonded electrons which can bind to a metal atom or metal ion. In certain embodiments, a metal chelator moiety comprises at least two heteroatoms selected from S, O, and N. In some embodiments, the metal chelator moiety is a bidentate or tridenate functional group. In some embodiments, a metal chelator moiety comprises a bidentate functional group selected from the group consisting of hydroxyamine, hydroxyamide, sulfonamide, urea, amide and oxime. In some embodiments, a metal chelator moiety comprises two or more monodentate functional groups selected from the group consisting of hydroxy, amino, ether, aldehyde, ketone, amide, thiol, thioether, heterocycle (e.g. imidazole) or oxime.

Compounds of the present disclosure also include crystalline and amorphous forms of those compounds, pharmaceutically acceptable salts, and active metabolites of these compounds having the same type of activity, including, for example, polymorphs, pseudopolymorphs, solvates, hydrates, unsolvated polymorphs (including anhydrates), conformational polymorphs, and amorphous forms of the compounds, as well as mixtures thereof.

The compounds described herein may exhibit their natural isotopic abundance, or one or more of the atoms may be artificially enriched in a particular isotope having the same atomic number, but an atomic mass or mass number different from the atomic mass or mass number predominantly found in nature. All isotopic variations of the compounds of the present disclosure, whether radioactive or not, are encompassed within the scope of the present disclosure. For example, hydrogen has three naturally occurring isotopes, denoted $^1$H (protium), $^2$H (deuterium), and $^3$H (tritium). Protium is the most abundant isotope of hydrogen in nature. Enriching for deuterium may afford certain therapeutic advantages, such as increased in vivo half-life and/or exposure, or may provide a compound useful for investigating in vivo routes of drug elimination and metabolism. Isotopically-enriched compounds may be prepared by conventional techniques well known to those skilled in the art.

"Isomers" are different compounds that have the same molecular formula. "Stereoisomers" are isomers that differ only in the way the atoms are arranged in space. "Enantiomers" are a pair of stereoisomers that are non superimposable mirror images of each other. A 1:1 mixture of a pair of enantiomers is a "racemic" mixture. The term "(±)" is used to designate a racemic mixture where appropriate. "Diastereoisomers" or "diastereomers" are stereoisomers that have at least two asymmetric atoms but are not mirror images of each other. The absolute stereochemistry is specified according to the Cahn-Ingold-Prelog R-S system. When a compound is a pure enantiomer, the stereochemistry at each chiral carbon can be specified by either R or S. Resolved compounds whose absolute configuration is unknown can be designated (+) or (−) depending on the direction (dextro- or levorotatory) in which they rotate plane polarized light at the wavelength of the sodium D line. Certain compounds described herein contain one or more asymmetric centers and can thus give rise to enantiomers, diastereomers, and other stereoisomeric forms, the asymmetric centers of which can be defined, in terms of absolute stereochemistry, as (R)- or (S)-. The present chemical entities, pharmaceutical compositions and methods are meant to include all such possible stereoisomers, including racemic mixtures, optically pure forms, mixtures of diastereomers and intermediate mixtures. Optically active (R)- and (S)-isomers can be prepared using chiral synthons or chiral reagents, or resolved using conventional techniques. The optical activity of a compound can be analyzed via any suitable method, including but not limited to chiral chromatography and polarimetry, and the degree of predominance of one stereoisomer over the other isomer can be determined.

Chemical entities having carbon-carbon double bonds or carbon-nitrogen double bonds may exist in Z- or E-form (or cis- or trans-form). Furthermore, some chemical entities may exist in various tautomeric forms. Unless otherwise specified, chemical entities described herein are intended to include all Z-, E- and tautomeric forms as well.

The term "salt" or "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

"Pharmaceutically acceptable carrier, diluent or excipient" includes without limitation any adjuvant, carrier, excipient, glidant, sweetening agent, diluent, preservative, dye, colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

The term "effective amount" or "therapeutically effective amount" refers to that amount of a compound described herein that is sufficient to affect the intended application, including but not limited to disease treatment, as defined below. The therapeutically effective amount may vary depending upon the intended treatment application (in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment" or "treating" refers to an approach for obtaining beneficial or desired results with respect to a disease, disorder, or medical condition including but not limited to a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. In certain embodiments, for prophylactic benefit, the compositions are administered to a subject at risk of developing a particular disease, or to a subject reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "co-administration," "administered in combination with," and their grammatical equivalents, as used herein, encompass administration of two or more agents to an animal, including humans, so that both agents and/or their metabolites are present in the subject at the same time. Co-administration includes simultaneous administration in separate compositions, administration at different times in separate compositions, or administration in a composition in which both agents are present.

The terms "antagonist" and "inhibitor" are used interchangeably, and they refer to a compound having the ability to inhibit a biological function (e.g., activity, expression, binding, protein-protein interaction) of a target protein (e.g., K-Ras, H-Ras or N-Ras G12C). Accordingly, the terms "antagonist" and "inhibitor" are defined in the context of the biological role of the target protein. While preferred antagonists herein specifically interact with (e.g., bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor.

The term "agonist" as used herein refers to a compound having the ability to initiate or enhance a biological function of a target protein, whether by inhibiting the activity or expression of the target protein. Accordingly, the term "agonist" is defined in the context of the biological role of the target polypeptide. While preferred agonists herein specifically interact with (e.g., bind to) the target, compounds that initiate or enhance a biological activity of the target polypeptide by interacting with other members of the signal transduction pathway of which the target polypeptide is a member are also specifically included within this definition.

"Signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator may augment (agonist) or suppress (antagonist) the activity of a signaling molecule.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

The term "cell proliferation" refers to a phenomenon by which the cell number has changed as a result of division. This term also encompasses cell growth by which the cell morphology has changed (e.g., increased in size) consistent with a proliferative signal.

The term "selective inhibition" or "selectively inhibit" refers to a biologically active agent refers to the agent's ability to preferentially reduce the target signaling activity as compared to off-target signaling activity, via direct or indirect interaction with the target.

"Subject" refers to an animal, such as a mammal, for example a human. The methods described herein can be useful in both human therapeutics and veterinary applications. In some embodiments, the subject is a mammal, and in some embodiments, the subject is human. "Mammal" includes humans and both domestic animals such as laboratory animals and household pets (e.g., cats, dogs, swine, cattle, sheep, goats, horses, rabbits), and non-domestic animals such as wildlife and the like.

"Prodrug" is meant to indicate a compound that may be converted under physiological conditions or by solvolysis to a biologically active compound described herein (e.g., compound of Formula (I), (I-A), (I-B), (I-C), (II), (II-A), (II-B), or (II-C)). Thus, the term "prodrug" refers to a precursor of a biologically active compound that is pharmaceutically acceptable. In some aspects, a prodrug is inactive when administered to a subject but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam); Higuchi, T., et al., "Pro-drugs as Novel Delivery Systems," (1987) A.C.S. Symposium Series, Vol. 14; and Bioreversible Carriers in Drug Design, ed. Edward B. Roche, American Pharmaceutical Association and Pergamon Press) each of which is incorporated in full by reference herein. The term "prodrug" is also meant to include any covalently bonded carriers, which release the active compound in vivo when such prodrug is administered to a mammalian subject. Prodrugs of an active compound, as described herein, are typically prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of a hydroxy functional group, or acetamide, formamide and benzamide derivatives of an amine functional group in the active compound and the like.

The term "in vivo" refers to an event that takes place in a subject's body.

The term "in vitro" refers to an event that takes places outside of a subject's body. For example, an in vitro assay encompasses any assay run outside of a subject. In vitro assays encompass cell-based assays in which cells alive or dead are employed. In vitro assays also encompass a cell-free assay in which no intact cells are employed.

The disclosure is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the disclosure includes compounds produced by a process comprising administering a compound of this disclosure to a mammal for a period of time sufficient to yield a metabolic product thereof. Such products are typically identified by administering a radiolabelled compound of the disclosure in a detectable dose to an animal, such as rat, mouse, guinea pig, monkey, or to human, allowing sufficient time for metabolism to occur, and isolating its conversion products from the urine, blood or other biological samples.

The chemical naming protocol and structure diagrams used herein are a modified form of the I.U.P.A.C. nomenclature system, using the ACD/Name Version 9.07 software program and/or ChemDraw Ultra Version 11.0.1 software naming program (CambridgeSoft). For complex chemical names employed herein, a substituent group is typically named before the group to which it attaches. For example, cyclopropylethyl comprises an ethyl backbone with a cyclopropyl substituent. Except as described below, all bonds are identified in the chemical structure diagrams herein, except for all bonds on some carbon atoms, which are assumed to be bonded to sufficient hydrogen atoms to complete the valency.

The present disclosure provides compounds that are capable of selectively binding to and/or modulating a Ras protein. In some embodiments, the Ras protien includes but is not limited to a mutant K-Ras, H-Ras or N-Ras protein. In some embodiments, the compounds modulate the Ras protein by binding to or interacting with one or more amino acids and/or one or more metal ions. Some subject compounds may also perturb the switch I conformation. The binding of these compounds may disrupt Ras (non-limiting examples include, K-Ras, H-Ras or N-Ras) downstream signaling.

In certain aspects, the present disclosure provides a compound of Formula (I):

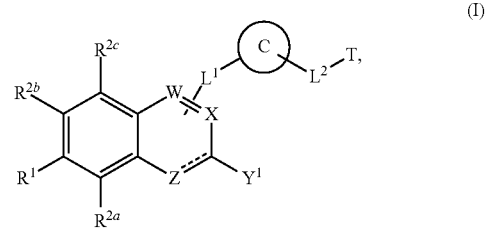

(I)

or a salt thereof, wherein:

$R^1$, $R^{2a}$, $R^{2b}$ and $R^{2c}$ are each independently selected from hydrogen and $R^{50}$;

W and X are each independently selected from N, $NR^5$ and $CR^6$;

Z is selected from bond, N, and $CR^6$;

$Y^1$ is selected from $-OR^{55}$; and alkyl, alkenyl, alkynyl, $C_{3-12}$ carbocycle and 3- to 12-membered heterocycle, each of which is substituted with $-OR^{55}$ and optionally futher substituted with one or more $R^{50}$;

$L^1$ is selected from bond, $-O-$, $-S-$, $-N(R^{51})-$, $-N(R^{51})CH_2-$, $-C(O)-$, $-C(O)O-$, $-OC(O)-$, $-OC(O)O-$, $-C(O)N(R^{51})-$, $-C(O)N(R^{51})C(O)-$, $-C(O)N(R^{51})C(O)N(R^{51})-$, $-N(R^{51})C(O)-$, $-N(R^{51})C(O)N(R^{51})-$, $-N(R^{51})C(O)O-$, $-OC(O)N(R^{51})-$, $-C(NR^{51})-$, $-N(R^{51})C(NR^{51})-$, $-C(NR^{51})N(R^{51})-$, $-N(R^{51})C(NR^{51})N(R^{51})-$, $-S(O)_2-$, $-OS(O)-$, $-S(O)O-$, $-S(O)-$, $-OS(O)_2-$, $-S(O)_2O-$, $-N(R^{51})S(O)_2-$, $-S(O)_2N(R^{51})-$, $-N(R^{51})S(O)-$, $-S(O)N(R^{51})-$, $-N(R^{51})S(O)_2N(R^{51})-$, $-N(R^{51})S(O)N(R^{51})-$; alkylene, alkenylene, alkynylene, heteroalkylene, heteroalkenylene, and heteroalkynylene, each of which is optionally substituted with one or more $R^{50}$;

$L^2$ is selected from bond and alkylene;

C is selected from 3- to 12-membered heterocycle, optionally substituted with one or more $R^{57}$;

T is hydrogen or a polar group capable of forming a complex with a Ras protein via an interaction other than one resulting in a covalent bond with the cysteine residue at position 12 of a K-Ras, H-Ras or N-Ras G12C mutant protein;

===== indicates a single or double bond such that all valences are satisfied;

$R^5$ is independently selected at each occurrence from $R^{51}$;

$R^6$ is independently selected at each occurrence from hydrogen, $R^{50}$, and a bond to $L^1$;

$R^{50}$ is independently selected at each occurrence from:
halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $=O$, $=S$, $=N(R^{52})$;

$C_{1-10}$ alkyl, $C_{2-10}$ alkenyl, and $C_{2-10}$ alkynyl, each of which is independently optionally substituted at each occurrence with one or more substituents selected from halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $=O$, $=S$, $=N(R^{52})$, $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^{50}$ is independently optionally substituted with one or more substituents selected from halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $=O$, $=S$, $=N(R^{52})$, $C_{1-6}$ alkyl, $C_{1-6}$ haloalkyl, $C_{2-6}$ alkenyl, and $C_{2-6}$ alkynyl;

$R^{51}$ is independently selected at each occurrence from:
hydrogen, $-C(O)R^{52}$, $-C(O)OR^{52}$, $-C(O)N(R^{52})_2$, $-C(O)NR^{53}R^{54}$;

$C_{1-6}$ alkyl, $C_{2-6}$ alkenyl, and $C_{2-6}$ alkynyl, each of which is independently optionally substituted at each occurrence with one or more substituents selected from halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $=O$, $=S$, $=N(R^{52})$, $C_{3-12}$ carbocycle and 3- to 12-membered heterocycle; and $C_{3-12}$ carbocycle and 3- to 12-membered heterocycle, wherein each $C_{3-12}$ carbocycle and 3- to 12-membered heterocycle in $R^{51}$ is independently optionally substituted with one or more substituents selected from halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $=O$, $=S$, $=N(R^{52})$, $C_{1-6}$ alkyl, $C_{1-6}$ haloalkyl, $C_{2-6}$ alkenyl, and $C_{2-6}$ alkynyl;

$R^{52}$ is independently selected at each occurrence from hydrogen; and $C_{1-20}$ alkyl, $C_{2-20}$ alkenyl, $C_{2-20}$ alkynyl, 2- to 6-membered heteroalkyl, $C_{3-12}$ carbocycle, and 3- to 12-membered heterocycle, each of which is optionally substituted by halogen, $-CN$, $-NO_2$, $-NH_2$, $-NHCH_3$, $-NHCH_2CH_3$, $=O$, $-OH$, $-OCH_3$, $-OCH_2CH_3$, $C_{3-12}$ carbocycle, or 3- to 6-membered heterocycle;

$R^{53}$ and $R^{54}$ are taken together with the nitrogen atom to which they are attached to form a heterocycle, optionally substituted with one or more $R^{50}$;

$R^{55}$ is selected from:
$C_{1-10}$ alkyl, $C_{2-10}$ alkenyl, and $C_{2-10}$ alkynyl, each of which is independently optionally substituted at each occurrence with one or more substituents selected from halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $=O$, $=S$, $=N(R^{52})$, $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^{55}$ is independently optionally substituted with one or more substituents selected from halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $=O$, $=S$, $=N(R^{52})$, $C_{1-6}$ alkyl, $C_{1-6}$ haloalkyl, $C_{2-6}$ alkenyl, and $C_{2-6}$ alkynyl; and $R^{57}$ is independently selected at each occurrence from:

halogen, $-CN$, $-OH$, $-OMe$, $-NH_2$, $-NHC_{1-6}$ alkyl, $-N(C_{1-6}$ alkyl$)_2$, $-C(O)OH$, $-C(O)H$, $-C(O)C_{1-6}$ alkyl, $-NHC(O)C_{1-6}$ alkyl, $-N(C_{1-6}$ alkyl$)C(O)C_{1-6}$ alkyl, $-C(O)NH_2$, $-C(O)NH(C_{1-6}$ alkyl$)$, $-C(O)N(C_{1-6}$ alkyl$)_2$, $=O$, $=N(OH)$; and $C_{1-10}$ alkyl, optionally substituted at each occurrence with one or more substituents selected from $-CN$, $-OH$, $-NH_2$, $-OMe$, $-NH_2$, $-NHC_{1-6}$ alkyl, $-N(C_{1-6}$ alkyl$)_2$, $-C(O)OH$, $-C(O)H$, $-C(O)C_{1-6}$ alkyl, $-NHC(O)C_{1-6}$ alkyl, $-N(C_{1-6}$ alkyl$)C(O)C_{1-6}$ alkyl, $-C(O)NH_2$, $-C(O)NH(C_{1-6}$ alkyl$)$, $-C(O)N(C_{1-6}$ alkyl$)_2$, $=O$, and $=N(OH)$;

wherein one of W, X and Z is $CR^6$ where $R^6$ is a bond to $L^1$; and wherein the compound of Formula (I) is not:

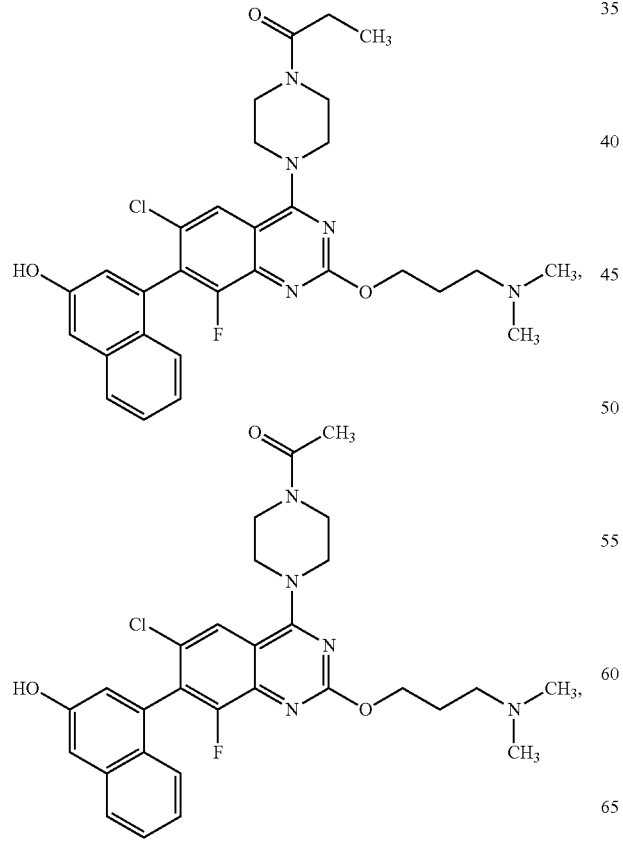

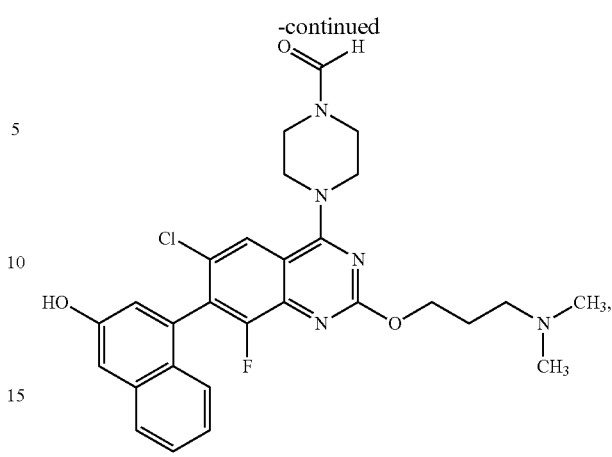

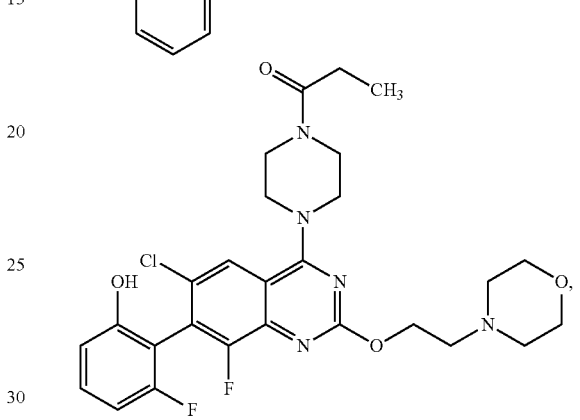

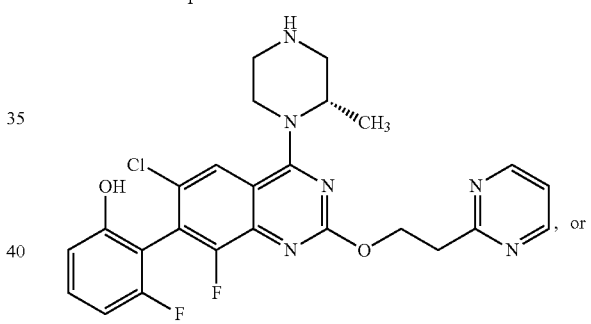

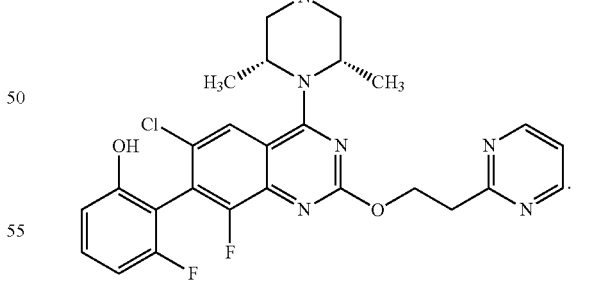

In some embodiments, for a compound of Formula (I), when $R^1$, $R^{2a}$, $R^{2b}$ and $R^{2c}$ are all independently selected from hydrogen and halo, then X and Z are both N and Ring C is substituted by at least one $R^{57}$. In some embodiments, for a compound of Formula (I), at least one of $R^{2a}$, $R^{2b}$ or $R^{2c}$ is not H when $R^1$ is pyridyl.

In some embodiments, a compound of Formula (I) is represented by Formula (I-A):

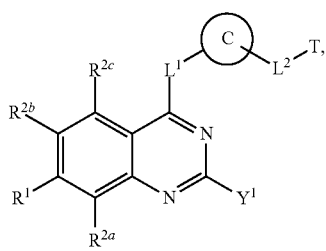

(I-A)

or a salt thereof.

In some embodiments, a compound of Formula (I) is represented by Formula (I-B):

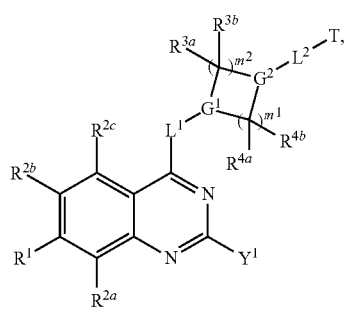

(I-B)

or a salt thereof, wherein:

$G^1$ and $G^2$ are each independently N or CH;

$R^{1a}$ and $R^{3b}$ are independently selected at each occurrence from H, —OH, —NH$_2$, —CO$_2$H, halo, cyano, C$_{1-6}$ alkyl, C$_{2-6}$ alkynyl, hydroxylalkyl, aminoalkyl, alkylaminoalkyl, cyanoalkyl, carboxyalkyl, aminocarbonylalkyl and aminocarbonyl; or $R^{3a}$ and $R^{3b}$ join to form oxo or a carbocyclic or heterocyclic ring; or $R^{3a}$ is independently selected at each occurrence from H, —OH, —NH$_2$, —CO$_2$H, halo, cyano, C$_{1-6}$ alkyl, C$_{2-6}$ alkynyl, hydroxylalkyl, aminoalkyl, alkylaminoalkyl, cyanoalkyl, carboxyalkyl, aminocarbonylalkyl and aminocarbonyl, and $R^{3b}$ joins with $R^{4b}$ to form a carbocyclic or heterocyclic ring;

$R^{4a}$ and $R^{4b}$ are independently selected at each occurrence from H, —OH, —NH$_2$, —CO$_2$H, halo, cyano, C$_{1-6}$ alkyl, C$_{2-6}$ alkynyl, hydroxylalkyl, aminoalkyl, alkylaminoalkyl, cyanoalkyl, carboxyalkyl, aminocarbonylalkyl and aminocarbonyl; or $R^{4a}$ and $R^{4b}$ join to form oxo or a carbocyclic or heterocyclic ring; or $R^{4a}$ is independently selected at each occurrence from H, —OH, —NH$_2$, —CO$_2$H, halo, cyano, C$_{1-6}$ alkyl, C$_{2-6}$ alkynyl, hydroxylalkyl, aminoalkyl, alkylaminoalkyl, cyanoalkyl, carboxyalkyl, aminocarbonylalkyl and aminocarbonyl, and $R^{4b}$ joins with $R^{3b}$ to form a carbocyclic or heterocyclic ring; and $m^1$ and $m^2$ are each independently 1, 2 or 3.

In some embodiments, for a compound of Formula (I-B), $m^1$ is 1. In some embodiments, $m^1$ is 2. In some embodiments, $m^2$ is 1. In some embodiments, $m^2$ is 2. In some embodiments, $m^1$ and $m^2$ are each 1. In some embodiments, $m^1$ and $m^2$ are each 2. In some embodiments, for a compound of Formula (I-B), at least one of $G^1$ or $G^2$ is N. In some embodiments, each of $G^1$ and $G^2$ is N. In some embodiments, each of $G^1$ and $G^2$ is N and $m^1$ and $m^2$ are each 2. In some embodiments, at least one of $G^1$ or $G^2$ is CH. In other embodiments, each of $G^1$ and $G^2$ is CH.

In some embodiments, for a compound of Formula (I-B), $R^{3a}$, $R^{3b}$, $R^{4a}$ and $R^{4b}$ are independently selected at each occurrence from H, —OH, —NH$_2$, —CO$_2$H, halo, cyano, C$_{1-6}$ alkyl, hydroxylalkyl, aminoalkyl, cyanoalkyl, carboxyalkyl and aminocarbonyl. In some embodiments, $R^{3a}$, $R^{3b}$, $R^{4a}$ and $R^{4b}$ are independently selected at each occurrence from hydrogen and C$_{1-6}$ alkyl, such as hydrogen and —CH$_3$. In some embodiments, $R^{3b}$ and $R^{4b}$ are each H and $R^{3a}$ and $R^{4a}$ are independently selected at each occurrence from H, —OH, C$_{1-6}$ alkyl, hydroxylalkyl, cyano, and aminocarbonyl. In some embodiments, $R^{3a}$ and $R^{4a}$ are each H and $R^{3b}$ and $R^{4b}$ are independently selected at each occurrence from H, —OH, —NH$_2$, —CO$_2$H, halo, cyano, C$_{1-6}$ alkyl, hydroxylalkyl, aminoalkyl, cyanoalkyl, carboxyalkyl and aminocarbonyl. In some embodiments, at least one of $R^{3a}$, $R^{3b}$, $R^{4a}$ or $R^{4b}$ is H. In some embodiments, each of $R^{3a}$, $R^{3b}$, $R^{4a}$ and $R^{4b}$ is H. In some embodiments, at least one $R^{3a}$, $R^{3b}$, $R^{4a}$ or $R^{4b}$ is —CH$_3$. In some embodiments, one or two $R^{3a}$, $R^{3b}$, $R^{4a}$ or $R^{4b}$ is —CH$_3$.

In some embodiments, for a compound of Formula (I-B), $R^{3a}$ and $R^{4a}$ are independently selected at each occurrence from H, —OH, —NH$_2$, —CO$_2$H, halo, C$_{1-6}$ alkyl, cyano, hydroxylalkyl, aminoalkyl, cyanoalkyl, carboxyalkyl and aminocarbonyl, and one $R^{3b}$ joins with one $R^{4b}$ to form a carbocyclic or heterocyclic ring. In some embodiments, one $R^{3a}$ and one $R^{3b}$ join to form a carbocyclic or heterocyclic ring. In some embodiments, one $R^{4a}$ and one $R^{4b}$ join to form a carbocyclic or heterocyclic ring. In some embodiments, $R^{3a}$ and $R^{3b}$ join to form oxo. In some embodiments, $R^{4a}$ and $R^{4b}$ join to form oxo.

In some embodiments, a compound of Formula (I-B) is represented by a structure selected from:

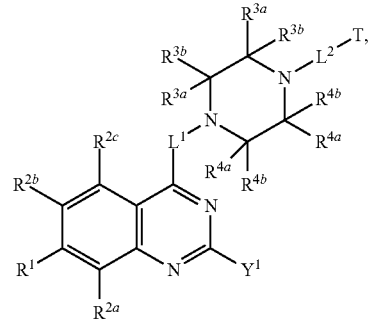

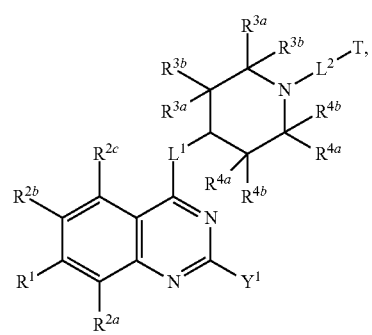

-continued

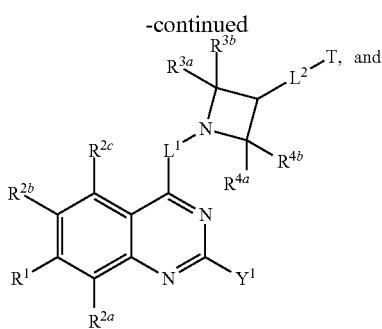

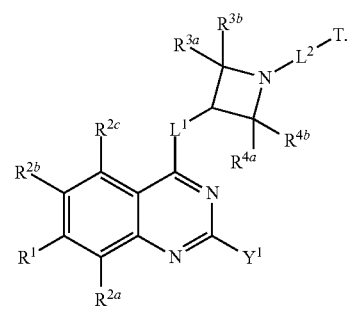

In certain aspects, the present disclosure provides a compound of Formula (I-C):

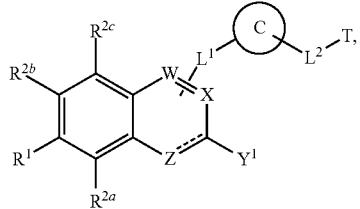

(I-C)

or a salt thereof, wherein:

$R^1$ is H, cyano, halo, $C_{1-6}$ alkyl, $C_{1-6}$ alkylamino, $C_{3-8}$ cycloalkyl, $C_{2-6}$ alkenyl, $C_{3-8}$ cycloalkenyl, heterocyclyl, heteroaryl, aryloxy or aryl;

$R^{2a}$, $R^{2b}$ and $R^{2c}$ are each independently H, halo, hydroxyl, $C_{1-6}$ alkyl, $C_{1-6}$ haloalkyl, $C_{3-8}$ cycloalkyl or aryl;

W and X are each independently N, $NR^5$ or $CR^6$;

Z is a bond, N or $CR^6$;

$Y^1$ is alkoxy, alkoxyalkyl, aminylalkoxy, arylalkoxy, heteroarylalkoxy, aryloxy or heteroaryloxy;

$L^1$ is a bond or $NR^7$;

$L^2$ is a bond or alkylene;

C is selected from 3- to 12-membered heterocycle, optionally substituted with one or more $R^{3a}$ or $R^{3b}$;

$R^{3a}$ and $R^{3b}$ are, at each occurrence, independently —H, —OH, —$NH_2$, —$CO_2H$, halo, cyano, $C_{1-6}$ alkyl, $C_{2-6}$ alkynyl, hydroxyalkyl, aminoalkyl, alkylamino alkyl, cyanoalkyl, carboxyalkyl, aminocarbonylalkyl or aminocarbonyl; or $R^{3a}$ and $R^{3b}$ attached to the same carbon atom join to form oxo; or $R^{3a}$ and $R^{3b}$ attached to the same carbon atom or different carbon atoms form a carbocyclic or heterocyclic ring;

$R^5$ and $R^7$ are each independently H or $C_{1-6}$ alkyl;

$R^6$ is, at each occurrence, independently H, oxo, cyano, cyanoalkyl, amino, aminylalkyl, aminylalkylaminyl, aminocarbonyl, alkylaminyl, haloalkylamino, hydroxylalkyamino, amindinylalkyl, amidinylalkoxy, amindinylalkylaminyl, guanidinylalkyl, guanidinylalkoxy, guanidinylalkylaminyl, $C_{1-6}$ alkoxy, aminylalkoxy, alkylcarbonylaminylalkoxy, $C_{1-6}$ alkyl, heterocyclyl, heterocyclyloxy, heterocyclylalkyloxy, heterocyclylamino, heterocyclylalkylamino, heteroaryl, heteroaryloxy, heteroarylalkyloxy, heteroarylamino, heteroarylalkylamino, aryl, aryloxy, arylamino, arylalkylamino, arylalkyloxy, or a bond to $L^1$;

═══ indicates a single or double bond such that all valences are satisfied; and

T is H or a polar group capable of forming a complex with a Ras protein via an interaction other than one resulting in a covalent bond with the cysteine residue at position 12 of a K-Ras, H-Ras or N-Ras G12C mutant protein;

wherein at least one of W, X or Z is $CR^6$ where $R^6$ is a bond to $L^1$, and provided that when $R^1$, $R^{2a}$, $R^{2b}$ and $R^{2c}$ are all independently selected from H and halo, then X and Z are both N and at least one of $R^{3a}$ and $R^{3b}$ is not H, and provided that at least one of $R^{2a}$, $R^{2b}$ or $R^{2c}$ is not H when $R^1$ is pyridyl.

In some embodiments, a compound of Formula (I), (I-A), (I-B) or (I-C) is not:

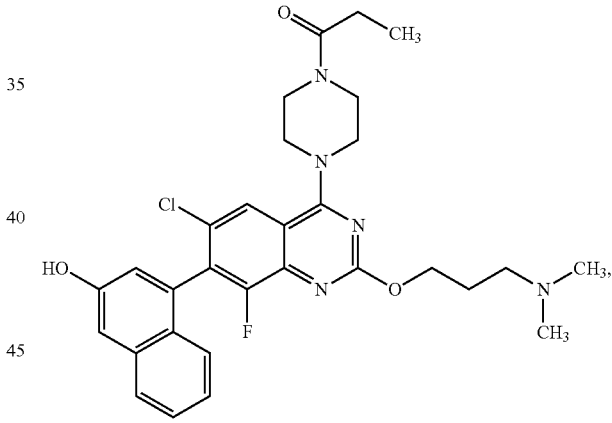

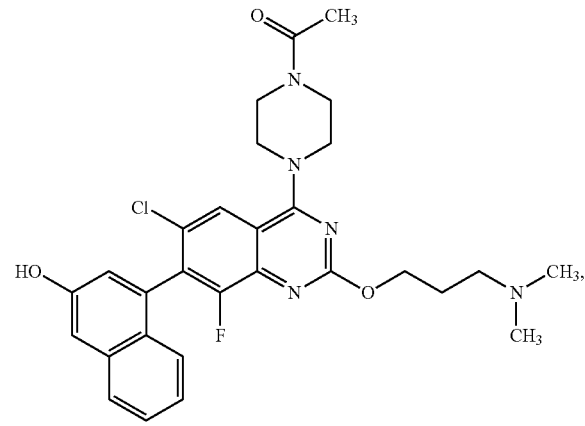

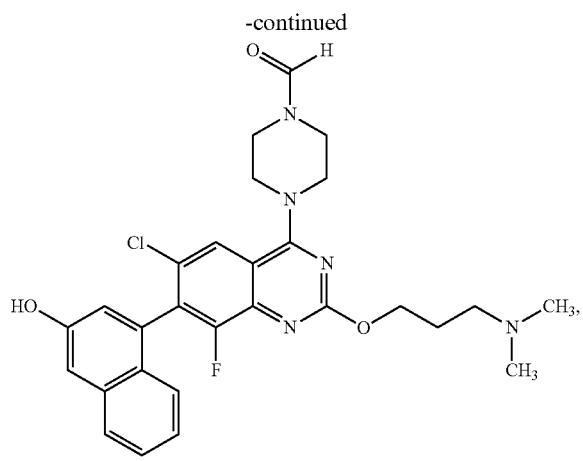

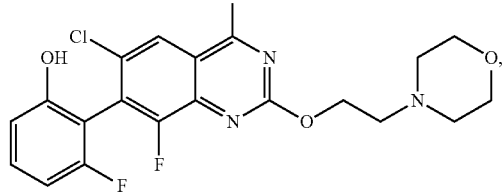

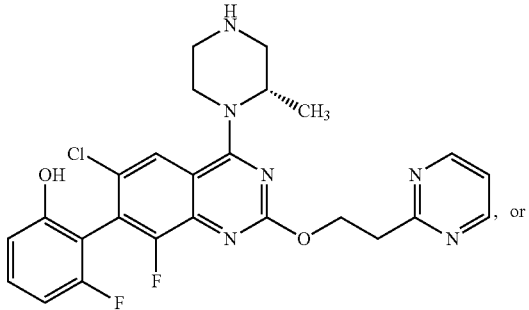

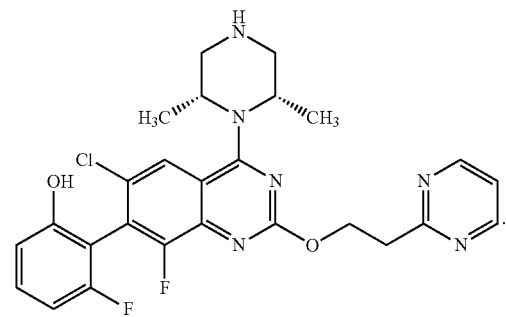

In some embodiments, for a compound of Formula (I), (I-A), (I-B) or (I-C), $Y^1$ is not

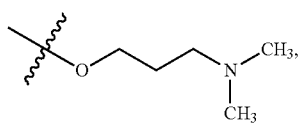

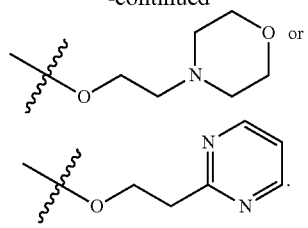

In some embodiments, when $R^1$ is 3-hydroxynaphthalenyl, T is —C(O)H, —C(O)CH$_3$, or —C(O)CH$_2$CH$_3$, and C is unsubstituted by $R^{57}$, then $Y^1$ is not

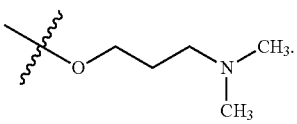

In some embodiments, $R^1$ is 3-hydroxynaphthalenyl, T is hydrogen, and $Y^1$ is

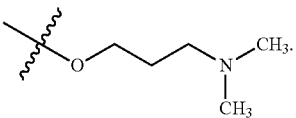

In some embodiments, for a compound of Formula (I), (I-A), (I-B) or (I-C), $Y^1$ is selected from —OR$^{55}$ and —CH$_2$OR$^{55}$. In some embodiments, $Y^1$ is OR$^{55}$. In some embodiments, $Y^1$ is

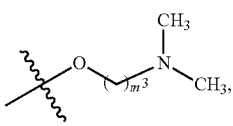

wherein m$^3$ is an integer from 1 to 6, such as m$^3$ is 2 or 3. In some embodiments, $Y^1$ is selected from

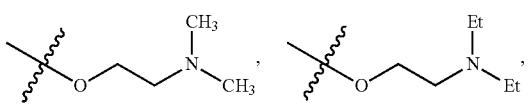

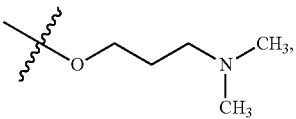

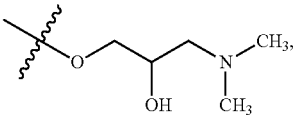

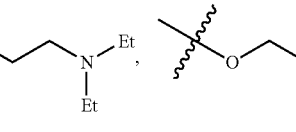

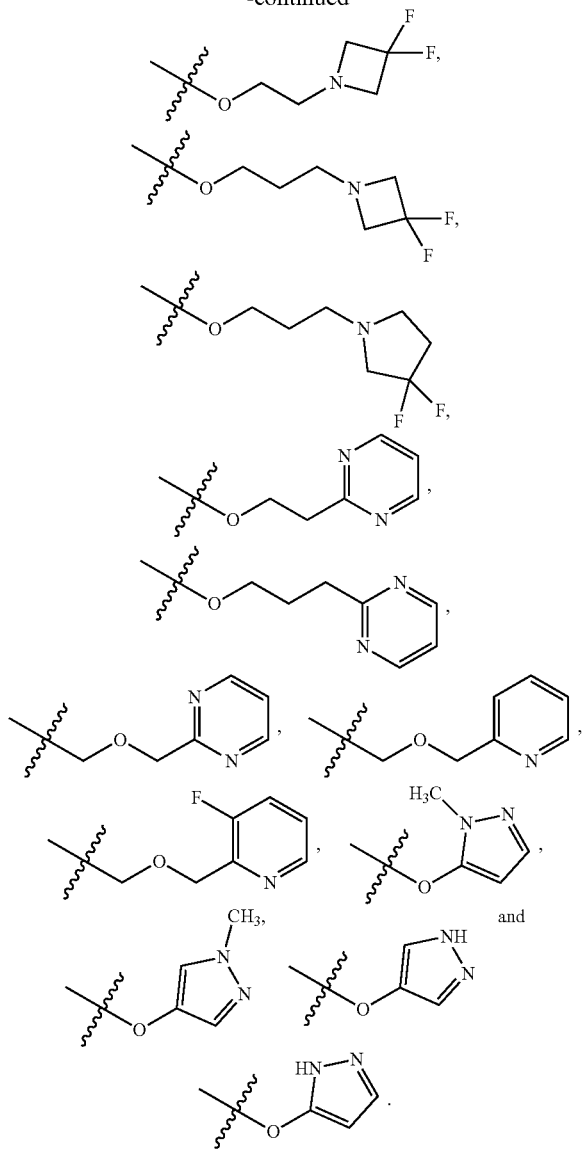

In some embodiments, $Y^1$ is selected from —$OR^{55}$; and $C_{1-10}$ alkyl, $C_{2-10}$ alkenyl and $C_{2-10}$ alkynyl, each of which is substituted with —$OR^{55}$ and optionally futher substituted with one or more $R^{50}$. In some embodiments, $Y^1$ is

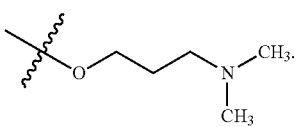

In some embodiments, for a compound of Formula (I), (I-A), (I-B) or (I-C), $R^{55}$ is selected from:
$C_{1-10}$ alkyl, $C_{2-10}$ alkenyl, and $C_{2-10}$ alkynyl, each of which is independently optionally substituted at each occurrence with one or more substituents selected from halogen, —$OR^{52}$, —$SR^{52}$, —$N(R^{52})_2$, —$NR^{53}R^{54}$, and 3- to 12-membered heterocycle; and
$C_{3-12}$ carbocycle and 3- to 12-membered heterocycle, wherein each $C_{3-12}$ carbocycle and 3- to 12-membered heterocycle is independently optionally substituted with one or more substituents selected from halogen, =O, $C_{1-6}$ alkyl, and $C_{1-6}$ haloalkyl.

In some embodiments, for a compound of Formula (I), (I-A), (I-B) or (I-C), $R^{55}$ is selected from $C_{1-4}$ alkyl substituted with —$N(R^{52})_2$, —$NR^{53}R^{54}$, or 3- to 12-membered heterocycle; and 3- to 12-membered heterocycle, wherein each 3- to 12-membered heterocycle is optionally substituted with one or more substituents selected from halogen, =O, $C_{1-6}$ alkyl, and $C_{1-6}$ haloalkyl.

In certain aspects, the present disclosure provides a compound of Formula (I):

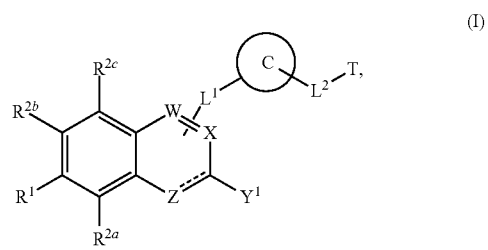

(I)

or a salt thereof, wherein:
$R^1$, $R^{2a}$, $R^{2b}$ and $R^{2c}$ are each independently selected from hydrogen and $R^{50}$;
W and X are each independently selected from N, $NR^5$ and $CR^6$;
Z is selected from bond, N, and $CR^6$;
$Y^1$ is selected from —$OR^{55}$, —$SR^{55}$ and $SO_2R^{55}$; and alkyl, alkenyl, alkynyl, $C_{3-12}$ carbocycle and 3- to 12-membered heterocycle, each of which is substituted with —$OR^{55}$, —$SR^{55}$ or $SO_2R^{55}$ and optionally futher substituted with one or more $R^{50}$;
$L^1$ is selected from bond, —O—, —S—, —N($R^{51}$)—, —N($R^{51}$)CH$_2$—, —C(O)—, —C(O)O—, —OC(O)—, —OC(O)O—, —C(O)N($R^{51}$)—, —C(O)N($R^{51}$)C(O)—, —C(O)N($R^{51}$)C(O)N($R^{51}$)—, —N($R^{51}$)C(O)—, —N($R^{51}$)C(O)N($R^{51}$)—, —N($R^{51}$)C(O)O—, —OC(O)N($R^{51}$)—, —C(N$R^{51}$)—, —N($R^{51}$)C(N$R^{51}$)—, —C(N$R^{51}$)N($R^{51}$)—, —N($R^{51}$)C(N$R^{51}$)N($R^{51}$), —S(O)$_2$—, —OS(O)—, —S(O)O—, —S(O)—, —OS(O)$_2$—, —S(O)$_2$O—, —N($R^{51}$)S(O)$_2$—, —S(O)$_2$N($R^{51}$)—, —N($R^{51}$)S(O)—, —S(O)N($R^{51}$)—, —N($R^{51}$)S(O)$_2$N($R^{51}$)—, —N($R^{51}$)S(O)N($R^{51}$)—; alkylene, alkenylene, alkynylene, heteroalkylene, heteroalkenylene, and heteroalkynylene, each of which is optionally substituted with one or more $R^{50}$;
$L^2$ is selected from bond and alkylene;
C is selected from 3- to 12-membered heterocycle, optionally substituted with one or more $R^{57}$;
T is hydrogen or a polar group capable of forming a complex with a Ras protein via an interaction other than one resulting in a covalent bond with the cysteine residue at position 12 of a K-Ras, H-Ras or N-Ras G12C mutant protein;
==== indicates a single or double bond such that all valences are satisfied;
$R^5$ is independently selected at each occurrence from $R^{51}$;
$R^6$ is independently selected at each occurrence from hydrogen, $R^{50}$, and a bond to $L^1$;
$R^{50}$ is independently selected at each occurrence from:
halogen, —$NO_2$, —CN, —$OR^{52}$, —$SR^{52}$, —$N(R^{52})_2$, —$NR^{53}R^{54}$, —S(=O)$R^{52}$, —S(=O)$_2R^{52}$, —S(=O)$_2$N($R^{52}$)$_2$, —S(=O)$_2$N$R^{53}R^{54}$, —$NR^{52}$S(=O)$_2R^{52}$, —$NR^{52}$S(=O)$_2$N($R^{52}$)$_2$, —$NR^{52}$S(=O)$_2$N$R^{53}R^{54}$, —C(O)$R^{52}$, —C(O)O$R^{52}$, —OC(O)$R^{52}$, —OC(O)

OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$);

C$_{1-10}$ alkyl, C$_{2-10}$ alkenyl, and C$_{2-10}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{3-12}$ carbocycle, and 3- to 12-membered heterocycle; and C$_{3-12}$ carbocycle and 3- to 12-membered heterocycle,
wherein each C$_{3-12}$ carbocycle and 3- to 12-membered heterocycle in R$^{50}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl;

R$^{51}$ is independently selected at each occurrence from:
hydrogen, —C(O)R$^{52}$, —C(O)OR$^{52}$, —C(O)N(R$^{52}$)$_2$, —C(O)NR$^{53}$R$^{54}$; C$_{1-6}$ alkyl, C$_{2-6}$ alkenyl, and C$_{2-6}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{3-12}$ carbocycle and 3- to 12-membered heterocycle; and C$_{3-12}$ carbocycle and 3- to 12-membered heterocycle,
wherein each C$_{3-12}$ carbocycle and 3- to 12-membered heterocycle in R$^{51}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl;

R$^{52}$ is independently selected at each occurrence from hydrogen; and C$_{1-20}$ alkyl, C$_{2-20}$ alkenyl, C$_{2-20}$ alkynyl, 2- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle;

R$^{53}$ and R$^{54}$ are taken together with the nitrogen atom to which they are attached to form a heterocycle, optionally substituted with one or more R$^{50}$;

R$^{55}$ is selected from:
C$_{1-10}$ alkyl, C$_{2-10}$ alkenyl, and C$_{2-10}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{3-12}$ carbocycle, and 3- to 12-membered heterocycle; and C$_{3-12}$ carbocycle and 3- to 12-membered heterocycle,
wherein each C$_{3-12}$ carbocycle and 3- to 12-membered heterocycle in R$^{55}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl; and R$^{57}$ is independently selected at each occurrence from:
halogen, —CN, —OH, —OMe, —NH$_2$, —NHC$_{1-6}$ alkyl, —N(C$_{1-6}$ alkyl)$_2$, —C(O)OH, —C(O)H, —C(O)C$_{1-6}$ alkyl, —NHC(O)C$_{1-6}$ alkyl, —N(C$_{1-6}$ alkyl)C(O)C$_{1-6}$ alkyl, —C(O)NH$_2$, —C(O)NH(C$_{1-6}$ alkyl), —C(O)N(C$_{1-6}$ alkyl)$_2$, =O, =N(OH); and C$_{1-10}$ alkyl, optionally substituted at each occurrence with one or more substituents selected from —CN, —OH, —NH$_2$, —OMe, —NH$_2$, —NHC$_{1-6}$ alkyl, —N(C$_{1-6}$ alkyl)$_2$, —C(O)OH, —C(O)H, —C(O)C$_{1-6}$ alkyl, —NHC(O)C$_{1-6}$ alkyl, —N(C$_{1-6}$ alkyl)C(O)C$_{1-6}$ alkyl, —C(O)NH$_2$, —C(O)NH(C$_{1-6}$ alkyl), —C(O)N(C$_{1-6}$ alkyl)$_2$, =O, and =N(OH);

wherein one of W, X and Z is CR$^6$ where R$^6$ is a bond to L$^1$; and wherein the compound of Formula (I) is not:

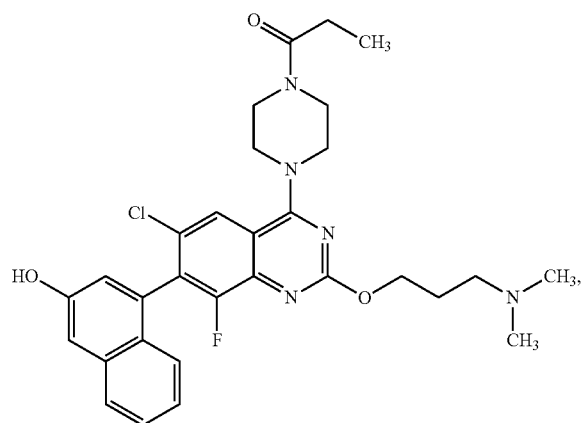

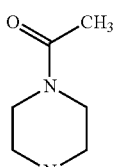

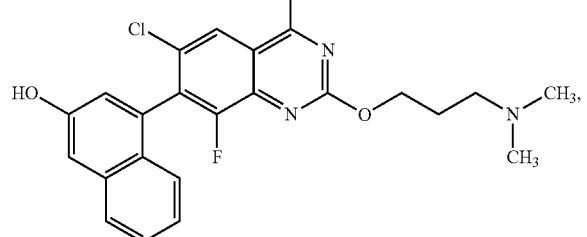

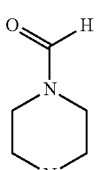

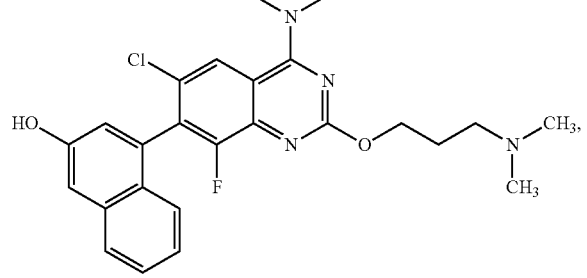

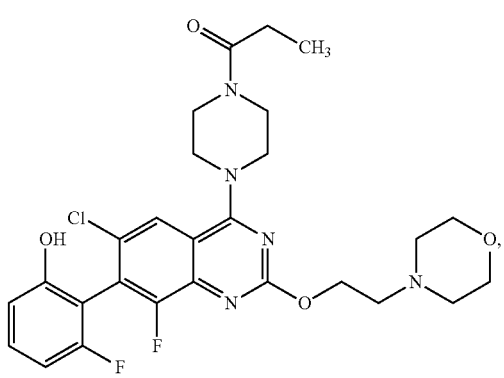

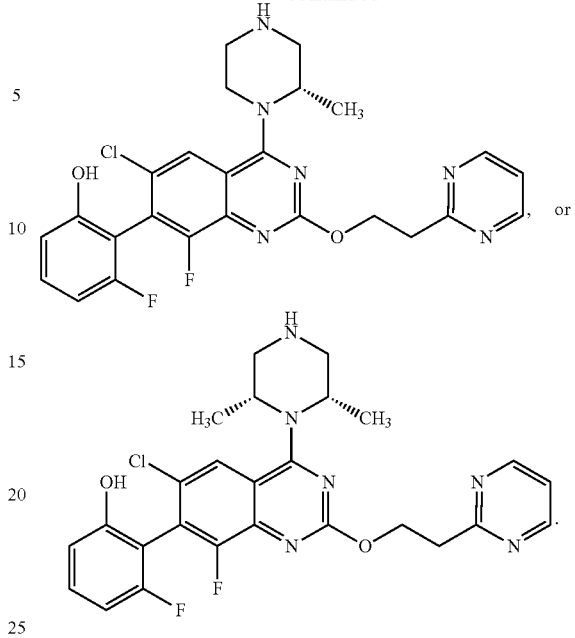

In certain aspects, the present disclosure provides a compound of Formula (II):

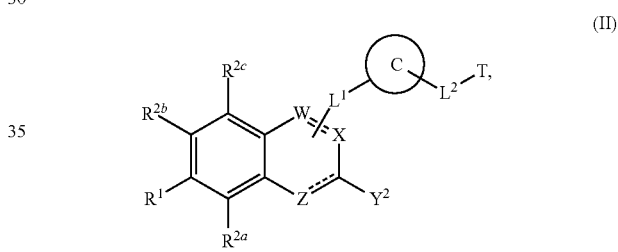

or a salt thereof, wherein:

$R^1$, $R^{2a}$, $R^{2b}$ and $R^{2c}$ are each independently selected from hydrogen and $R^{50}$;

W and X are each independently selected from N, $NR^5$ and $CR^6$;

Z is selected from bond, N, and $CR^6$;

$Y^2$ is selected from —$N(R^{56})_2$; and alkyl, alkenyl, alkynyl, $C_{3-12}$ carbocycle and 3- to 12-membered heterocycle, each of which is substituted with —$N(R^{56})_2$ and optionally futher substituted with one or more $R^{50}$;

$L^1$ is selected from bond, —O—, —S—, —$N(R^{51})$—, —$N(R^{51})CH_2$—, —C(O)—, —C(O)O—, —OC(O)—, —OC(O)O—, —$C(O)N(R^{51})$—, —$C(O)N(R^{51})C(O)$—, —$C(O)N(R^{51})C(O)N(R^{51})$—, —$N(R^{51})C(O)$—, —$N(R^{51})C(O)N(R^{51})$—, —$N(R^{51})C(O)O$—, —$OC(O)N(R^{51})$—, —$C(NR^{51})$—, —$N(R^{51})C(NR^{51})$—, —$C(NR^{51})N(R^{51})$—, —$N(R^{51})C(NR^{51})N(R^{51})$—, —$S(O)_2$—, —OS(O)—, —S(O)O—, —S(O)—, —$OS(O)_2$—, —$S(O)_2O$—, —$N(R^{51})S(O)_2$—, —$S(O)_2N(R^{51})$—, —$N(R^{51})S(O)$—, —$S(O)N(R^{51})$—, —$N(R^{51})S(O)_2N(R^{51})$—, —$N(R^{51})S(O)N(R^{51})$—; alkylene, alkenylene, alkynylene, heteroalkylene, heteroalkenylene, and heteroalkynylene, each of which is optionally substituted with one or more $R^{50}$;

$L^2$ is selected from bond and alkylene;

C is selected from 3- to 12-membered heterocycle, optionally substituted with one or more $R^{57}$;

T is hydrogen or a polar group capable of forming a complex with a Ras protein via an interaction other than one resulting in a covalent bond with the cysteine residue at position 12 of a K-Ras, H-Ras or N-Ras G12C mutant protein;

===== indicates a single or double bond such that all valences are satisfied;

$R^5$ is independently selected at each occurrence from $R^{51}$;

$R^6$ is independently selected at each occurrence from hydrogen, $R^{50}$, and a bond to $L^1$;

$R^{50}$ is independently selected at each occurrence from:
halogen, —$NO_2$, —CN, —$OR^{52}$, —$SR^{52}$, —$N(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, =O, =S, =$N(R^{52})$;

$C_{1-10}$ alkyl, $C_{2-10}$ alkenyl, and $C_{2-10}$ alkynyl, each of which is independently optionally substituted at each occurrence with one or more substituents selected from halogen, —$NO_2$, —CN, —$OR^{52}$, —$SR^{52}$, —$N(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, =O, =S, =$N(R^{52})$; $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^{50}$ is independently optionally substituted with one or more substituents selected from halogen, —$NO_2$, —CN, —$OR^{52}$, —$SR^5$, —$N(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, =O, =S, =$N(R^{52})$, $C_{1-6}$ alkyl, $C_{1-6}$ haloalkyl, $C_{2-6}$ alkenyl, and $C_{2-6}$ alkynyl;

$R^{51}$ is independently selected at each occurrence from:
hydrogen, —$C(O)R^{52}$, —$C(O)OR^{52}$, —$C(O)N(R^{52})_2$, —$C(O)NR^{53}R^{54}$;

$C_{1-6}$ alkyl, $C_{2-6}$ alkenyl, and $C_{2-6}$ alkynyl, each of which is independently optionally substituted at each occurrence with one or more substituents selected from halogen, —$NO_2$, —CN, —$OR^{52}$, —$SR^{52}$, —$N(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, =O, =S, =$N(R^{52})$, $C_{3-12}$ carbocycle and 3- to 12-membered heterocycle; and $C_{3-12}$ carbocycle and 3- to 12-membered heterocycle, wherein each $C_{3-12}$ carbocycle and 3- to 12-membered heterocycle in $R^{51}$ is independently optionally substituted with one or more substituents selected from halogen, —$NO_2$, —CN, —$OR^{52}$, —$SR^{52}$, —$N(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, =O, =S, =$N(R^{52})$, $C_{1-6}$ alkyl, $C_{1-6}$ haloalkyl, $C_{2-6}$ alkenyl, and $C_{2-6}$ alkynyl;

$R^{52}$ is independently selected at each occurrence from hydrogen; and $C_{1-20}$ alkyl, $C_{2-20}$ alkenyl, $C_{2-20}$ alkynyl, 2- to 6-membered heteroalkyl, $C_{3-12}$ carbocycle, and 3- to 12-membered heterocycle, each of which is optionally substituted by halogen, —CN, —$NO_2$, —$NH_2$, —$NHCH_3$, —$NHCH_2CH_3$, =O, —OH, —$OCH_3$, —$OCH_2CH_3$, $C_{3-12}$ carbocycle, or 3- to 6-membered heterocycle;

$R^{53}$ and $R^{54}$ are taken together with the nitrogen atom to which they are attached to form a heterocycle, optionally substituted with one or more $R^{50}$;

$R^{56}$ is independently selected at each occurrence from:
hydrogen;

$C_{1-10}$ alkyl, $C_{2-10}$ alkenyl, and $C_{2-10}$ alkynyl, each of which is independently optionally substituted at each occurrence with one or more substituents selected from halogen, —$NO_2$, —CN, —$OR^{52}$, —$SR^{52}$, —$N(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, =O, =S, =$N(R^{52})$, $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^{56}$ is independently optionally substituted with one or more substituents selected from halogen, —$NO_2$, —CN, —$OR^{52}$, —$SR^{52}$, —$N(R^{52})_2$, —$NR^{53}R^{54}$, —$S(=O)R^{52}$, —$S(=O)_2R^{52}$, —$S(=O)_2N(R^{52})_2$, —$S(=O)_2NR^{53}R^{54}$, —$NR^{52}S(=O)_2R^{52}$, —$NR^{52}S(=O)_2N(R^{52})_2$, —$NR^{52}S(=O)_2NR^{53}R^{54}$, —$C(O)R^{52}$, —$C(O)OR^{52}$, —$OC(O)R^{52}$, —$OC(O)OR^{52}$, —$OC(O)N(R^{52})_2$, —$OC(O)NR^{53}R^{54}$, —$NR^{52}C(O)R^{52}$, —$NR^{52}C(O)OR^{52}$, —$NR^{52}C(O)N(R^{52})_2$, —$NR^{52}C(O)NR^{53}R^{54}$, —$C(O)N(R^{52})_2$, —$C(O)NR^{53}R^{54}$, —$P(O)(OR^{52})_2$, —$P(O)(R^{52})_2$, =O, =S, =$N(R^{52})$, $C_{1-6}$ alkyl, $C_{1-6}$ haloalkyl, $C_{2-6}$ alkenyl, and $C_{2-6}$ alkynyl, or two $R^{56}$ groups are taken together with the nitrogen atom to which they are attached to form a heterocycle, optionally substituted with one or more $R^{50}$; and $R^{57}$ is independently selected at each occurrence from:
halogen, —CN, —OH, —OMe, —$NH_2$, —$NHC_{1-6}$ alkyl, —$N(C_{1-6}$ alkyl$)_2$, —C(O)OH, —C(O)H, —C(O)$C_{1-6}$ alkyl, —NHC(O)$C_{1-6}$ alkyl, —N($C_{1-6}$ alkyl)C(O)$C_{1-6}$ alkyl, —C(O)$NH_2$, —C(O)NH($C_{1-6}$ alkyl), —C(O)N($C_{1-6}$ alkyl$)_2$, =O, =N(OH); and $C_{1-10}$ alkyl, optionally substituted at each occurrence with one or more substituents selected from —CN, —OH, —$NH_2$, —OMe, —$NH_2$, —$NHC_{1-6}$ alkyl, —$N(C_{1-6}$ alkyl$)_2$, —C(O)OH, —C(O)H, —C(O)$C_{1-6}$ alkyl, —NHC(O)$C_{1-6}$ alkyl, —N($C_{1-6}$ alkyl)C(O)$C_{1-6}$ alkyl, —C(O)$NH_2$, —C(O)NH($C_{1-6}$ alkyl), —C(O)N($C_{1-6}$ alkyl$)_2$, =O, and =N(OH);

wherein one of W, X and Z is $CR^6$ where $R^6$ is a bond to $L^1$.

In some embodiments, for a compound of Formula (II), when $R^1$, $R^{2a}$, $R^{2b}$ and $R^{2c}$ are all independently selected from hydrogen and halo, then X and Z are both N and Ring C is substituted by at least one $R^{57}$. In some embodiments, for a compound of Formula (II), at least one of $R^{2a}$, $R^{2b}$ or $R^{2c}$ is not H when $R^1$ is pyridyl.

In some embodiments, a compound of Formula (II) is represented by Formula (II-A):

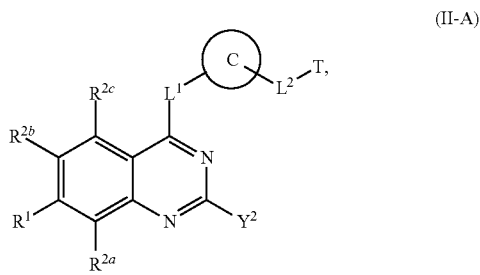

(II-A)

or a salt thereof.

In some embodiments, a compound of Formula (II) is represented by Formula (II-B):

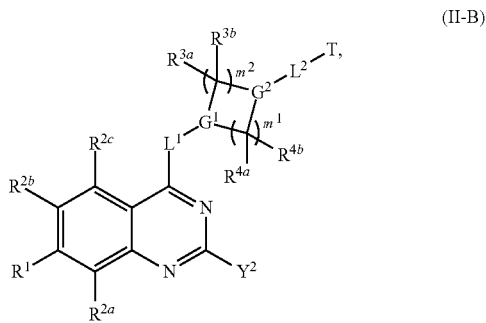

(II-B)

or a salt thereof, wherein:

$G^1$ and $G^2$ are each independently N or CH;

$R^{3a}$ and $R^{3b}$ are independently selected at each occurrence from H, —OH, —$NH_2$, —$CO_2H$, halo, cyano, $C_{1-6}$ alkyl, $C_{2-6}$ alkynyl, hydroxylalkyl, aminoalkyl, alkylaminoalkyl, cyanoalkyl, carboxyalkyl, aminocarbonylalkyl and aminocarbonyl; or $R^{3a}$ and $R^{3b}$ join to form oxo or a carbocyclic or heterocyclic ring; or $R^{3a}$ is independently selected at each occurrence from H, —OH, —$NH_2$, —$CO_2H$, halo, cyano, $C_{1-6}$ alkyl, $C_{2-6}$ alkynyl, hydroxylalkyl, aminoalkyl, alkylaminoalkyl, cyanoalkyl, carboxyalkyl, aminocarbonylalkyl and aminocarbonyl, and $R^{3b}$ joins with $R^{4b}$ to form a carbocyclic or heterocyclic ring;

$R^{4a}$ and $R^{4b}$ are independently selected at each occurrence from H, —OH, —$NH_2$, —$CO_2H$, halo, cyano, $C_{1-6}$ alkyl, $C_{2-6}$ alkynyl, hydroxylalkyl, aminoalkyl, alkylaminoalkyl, cyanoalkyl, carboxyalkyl, aminocarbonylalkyl and aminocarbonyl; or $R^{4a}$ and $R^{4b}$ join to form oxo or a carbocyclic or heterocyclic ring; or $R^{4a}$ is independently selected at each occurrence from H, —OH, —$NH_2$, —$CO_2H$, halo, cyano, $C_{1-6}$ alkyl, $C_{2-6}$ alkynyl, hydroxylalkyl, aminoalkyl, alkylaminoalkyl, cyanoalkyl, carboxyalkyl, aminocarbonylalkyl and aminocarbonyl, and $R^{4b}$ joins with $R^{3b}$ to form a carbocyclic or heterocyclic ring; and $m^1$ and $m^2$ are each independently 1, 2 or 3.

In some embodiments, for a compound of Formula (II-B), $m^1$ is 1. In some embodiments, $m^1$ is 2. In some embodiments, $m^2$ is 1. In some embodiments, $m^2$ is 2. In some embodiments, $m^1$ and $m^2$ are each 1. In some embodiments, $m^1$ and $m^2$ are each 2. In some embodiments, for a compound of Formula (II-B), at least one of $G^1$ or $G^2$ is N. In some embodiments, each of $G^1$ and $G^2$ is N. In some embodiments, each of $G^1$ and $G^2$ is N and $m^1$ and $m^2$ are each 2. In some embodiments, at least one of $G^1$ or $G^2$ is CH. In other embodiments, each of $G^1$ and $G^2$ is CH.

In some embodiments, for a compound of Formula (II-B), $R^{3a}$, $R^{3b}$, $R^{4a}$ and $R^{4b}$ are independently selected at each occurrence from H, —OH, —$NH_2$, —$CO_2H$, halo, cyano, $C_{1-6}$ alkyl, hydroxylalkyl, aminoalkyl, cyanoalkyl, carboxyalkyl and aminocarbonyl. In some embodiments, $R^{3a}$, $R^{3b}$, $R^{4a}$ and $R^{4b}$ are independently selected at each occurrence from hydrogen and $C_{1-6}$ alkyl, such as hydrogen and —$CH_3$. In some embodiments, $R^{3b}$ and $R^{4b}$ are each H and $R^{3a}$ and $R^{4a}$ are independently selected at each occurrence from H, —OH, $C_{1-6}$ alkyl, hydroxylalkyl, cyano, and aminocarbonyl. In some embodiments, $R^{3a}$ and $R^{4a}$ are each H and $R^{3b}$ and $R^{4b}$ are independently selected at each occurrence from H, —OH, —$NH_2$, —$CO_2H$, halo, cyano, $C_{1-6}$ alkyl, hydroxylalkyl, aminoalkyl, cyanoalkyl, carboxyalkyl and aminocarbonyl. In some embodiments, at least one of $R^{3a}$, $R^{3b}$, $R^{4a}$ or $R^{4b}$ is H. In some embodiments, each of $R^{3a}$, $R^{3b}$, $R^{4a}$ and $R^{4b}$ is H. In some embodiments, at least one $R^{3a}$, $R^{3b}$, $R^{4a}$ or $R^{4b}$ is —$CH_3$. In some embodiments, one or two $R^{3a}$, $R^{3b}$, $R^{4a}$ or $R^{4b}$ is —$CH_3$.

In some embodiments, for a compound of Formula (II-B), $R^{3a}$ and $R^{4a}$ are independently selected at each occurrence from H, —OH, —$NH_2$, —$CO_2H$, halo, $C_{1-6}$ alkyl, cyano, hydroxylalkyl, aminoalkyl, cyanoalkyl, carboxyalkyl and aminocarbonyl, and one $R^{3b}$ joins with one $R^{4b}$ to form a carbocyclic or heterocyclic ring. In some embodiments, one $R^{3a}$ and one $R^{3b}$ join to form a carbocyclic or heterocyclic ring. In some embodiments, one $R^{4a}$ and one $R^{4b}$ join to form a carbocyclic or heterocyclic ring. In some embodiments, $R^{3a}$ and $R^{3b}$ join to form oxo. In some embodiments, $R^{4a}$ and $R^{4b}$ join to form oxo.

In some embodiments, a compound of Formula (II-B) is represented by a structure selected from:

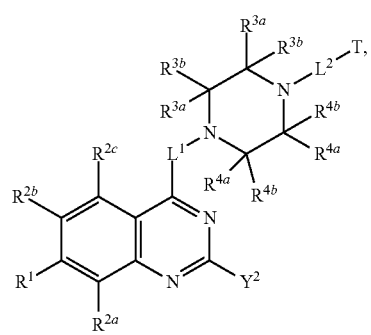

-continued

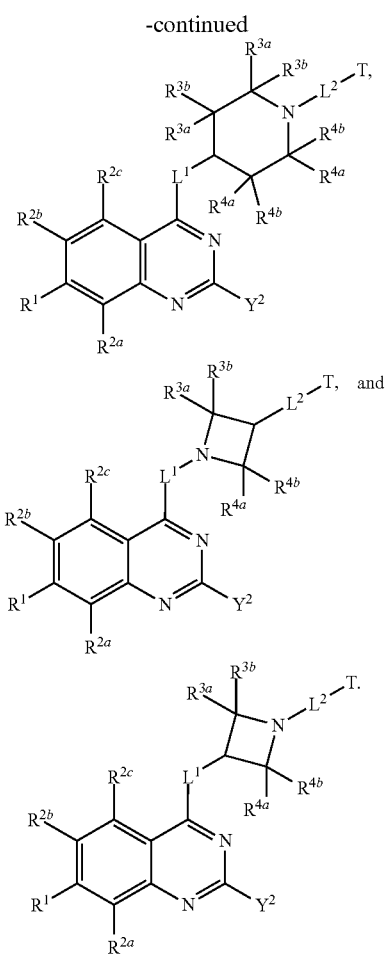

In certain aspects, the present disclosure provides a compound of Formula (II-C):

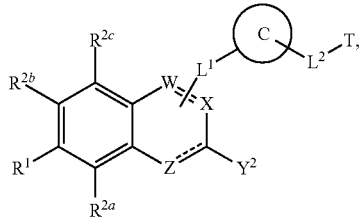

(II-C)

or a salt thereof, wherein:

R$^1$ is H, cyano, halo, C$_{1-6}$ alkyl, C$_{1-6}$ alkylamino, C$_{3-8}$ cycloalkyl, C$_{2-6}$ alkenyl, C$_{3-8}$ cycloalkenyl, heterocyclyl, heteroaryl, aryloxy or aryl;

R$^{2a}$, R$^{2b}$ and R$^{2c}$ are each independently H, halo, hydroxyl, C$_{1-6}$ alkyl, C$_{1-6}$haloalkyl, C$_{3-8}$ cycloalkyl or aryl;

W and X are each independently N, NR$^5$ or CR$^6$;

Z is a bond, N or CR$^6$;

Y$^2$ is alkylamino, alkylaminoalkyl, arylalkylamino, arylalkylaminoalkyl, heteroarylalkylamino or heteroarylalkylaminoalkyl;

L$^1$ is a bond or NR$^7$;

L$^2$ is a bond or alkylene;

C is selected from 3- to 12-membered heterocycle, optionally substituted with one or more R$^{3a}$ or R$^{3b}$;

R$^{3a}$ and R$^{3b}$ are, at each occurrence, independently —H, —OH, —NH$_2$, —CO$_2$H, halo, cyano, C$_{1-6}$ alkyl, C$_{2-6}$ alkynyl, hydroxyalkyl, aminoalkyl, alkylamino alkyl, cyanoalkyl, carboxyalkyl, aminocarbonylalkyl or aminocarbonyl; or R$^{3a}$ and R$^{3b}$ attached to the same carbon atom join to form oxo; or R$^{3a}$ and R$^{3b}$ attached to the same carbon atom or different carbon atoms form a carbocyclic or heterocyclic ring;

R$^5$ and R$^7$ are each independently H or C$_{1-6}$ alkyl;

R$^6$ is, at each occurrence, independently H, oxo, cyano, cyanoalkyl, amino, aminylalkyl, aminylalkylaminyl, aminocarbonyl, alkylaminyl, haloalkylamino, hydroxylalkyamino, amindinylalkyl, amidinylalkoxy, amindinylalkylaminyl, guanidinylalkyl, guanidinylalkoxy, guanidinylalkylaminyl, C$_{1-6}$ alkoxy, aminylalkoxy, alkylcarbonylaminylalkoxy, C$_{1-6}$ alkyl, heterocyclyl, heterocylyloxy, heterocyclylalkyloxy, heterocyclylamino, heterocylylalkylamino, heteroaryl, heteroaryloxy, heteroarylalkyloxy, heteroarylamino, heteroarylalkylamino, aryl, aryloxy, arylamino, arylalkylamino, arylalkyloxy, or a bond to L$^1$;

==== indicates a single or double bond such that all valences are satisfied; and T is H or a polar group capable of forming a complex with a Ras protein via an interaction other than one resulting in a covalent bond with the cysteine residue at position 12 of a K-Ras, H-Ras or N-Ras G12C mutant protein;

wherein at least one of W, X or Z is CR$^6$ where R$^6$ is a bond to L$^1$, and provided that when R$^1$, R$^{2a}$, R$^{2b}$ and R$^{2c}$ are all independently selected from H and halo, then X and Z are both N and at least one of R$^{3a}$ and R$^{3b}$ is not H, and provided that at least one of R$^{2a}$, R$^{2b}$ or R$^{2c}$ is not H when R$^1$ is pyridyl.

In some embodiments, for a compound of Formula (II), (II-A), (II-B) or (II-C), Y$^2$ is selected from —N(R$^{56}$)$_2$ and C$_{1-4}$ alkyl substituted with —N(R$^{56}$)$_2$, wherein at least one R$^{56}$ is not hydrogen. In some embodiments, Y$^2$ is C$_{1-4}$ alkyl substituted with —N(R$^{56}$)$_2$, wherein at least one R$^{56}$ is not hydrogen, such as —CH$_2$N(R$^{56}$)$_2$. In some embodiments, Y$^2$ is selected from

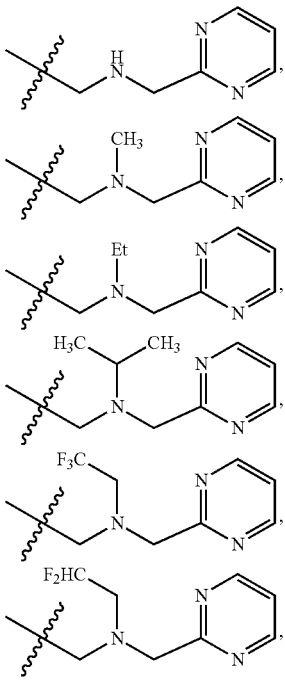

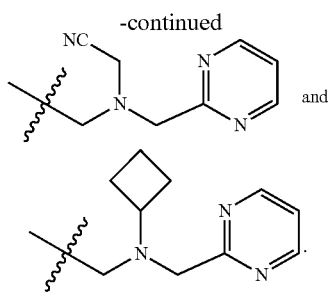

In some embodiments, $Y^2$ is $-CH_2N(R^{52})CH_2R^{52}$. In some embodiments, $Y^2$ is $-CH_2N(R^{58})CH_2R^{59}$, wherein $R^{58}$ is selected from hydrogen, $C_{1-4}$ alkyl, $C_{1-4}$ haloalkyl, $C_{1-4}$ alkyl substituted with halogen or $-CN$, $C_{3-6}$ carbocycle, and 3- to 6-membered heterocycle; and $R^{59}$ is selected from 3- to 8-membered heterocycle, optionally substituted with one or more halogens. In some embodiments, $Y^2$ is $-CH_2N(R^{58})CH_2R^{59}$, wherein $R^{58}$ is selected from hydrogen, $C_{1-4}$ alkyl, $C_{1-4}$ haloalkyl; and $R^{59}$ is pyrimidinyl. In some embodiments, $Y^2$ is

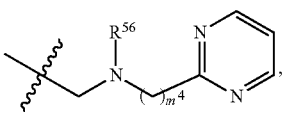

wherein $m^4$ is an integer from 1 to 6. In some embodiments, $m^4$ is 1 or 2. In some embodiments, $Y^2$ is selected from $-N(R^{56})_2$; and $C_{1-10}$ alkyl, $C_{2-10}$ alkenyl and $C_{2-10}$ alkynyl, each of which is substituted with $-N(R^{56})_2$ and optionally futher substituted with one or more $R^{50}$.

In some embodiments, for a compound of Formula (II), (II-A), (II-B) or (II-C), $R^{56}$ is independently selected at each occurrence from:
hydrogen;
$C_{1-10}$ alkyl, $C_{2-10}$ alkenyl, and $C_{2-10}$ alkynyl, each of which is independently optionally substituted at each occurrence with one or more substituents selected from halogen, $-CN$, $-OR^{52}$, $-SR^{52}$, $-N(R^{52})_2$, $-NR^{53}R^{54}$, $C_{3-12}$ carbocycle, and 3- to 12-membered heterocycle; and
$C_{3-12}$ carbocycle and 3- to 12-membered heterocycle, wherein each $C_{3-12}$ carbocycle and 3- to 12-membered heterocycle is independently optionally substituted with one or more substituents selected from halogen, $=O$, $C_{1-6}$ alkyl, and $C_{1-6}$ haloalkyl.

In some embodiments, for a compound of Formula (II), (II-A), (II-B) or (II-C), $R^{56}$ is independently selected at each occurrence from hydrogen, $C_{1-4}$ alkyl, and $C_{1-4}$ alkyl substituted with one or more substituents selected from halogen, $-CN$, $-N(R^{52})_2$, $-NR^{53}R^{54}$, $C_{3-12}$ carbocycle, and 3- to 12-membered heterocycle, wherein each $C_{3-12}$ carbocycle and 3- to 12-membered heterocycle is optionally substituted with one or more substituents selected from halogen, $=O$, $C_{1-6}$ alkyl, and $C_{1-6}$ haloalkyl.

In some embodiments, for a compound of Formula (II), (II-A) or (II-B), $Y^2$ is $-N(R^{56})_2$ and the two $R^{56}$ groups are taken together with the nitrogen atom to which they are attached to form a heterocycle, wherein the heterocycle is optionally substituted with one or more $R^{50}$. In some embodiments, $Y^2$ is $-N(R^{56})_2$ and the two $R^{56}$ groups are taken together with the nitrogen atom to which they are attached to form a 3- to 6-membered heterocycle, wherein the heterocycle is substituted with $-N(R^{52})_2$ or $-NR^{53}R^{54}$. In some embodiments, $Y^2$ is azetidinyl, optionally substituted with one or more $R^{50}$. In some embodiments, $Y^2$ is selected from

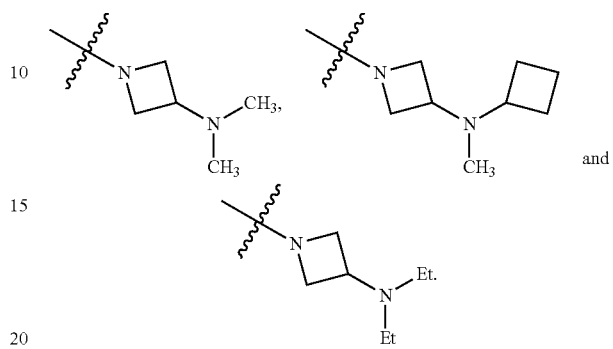

Without wishing to be bound by a theory, the correct selection of $R^1$ may contribute to the inhibitory activity of a compound of Formula (I), (I-A), (I-B), (I-C), (II), (II-A), (II-B) or (II-C) (e.g., against K-Ras, H-Ras or N-Ras G12C). In some embodiments, $R^1$ is capable of forming a reversible interaction with a K-Ras, H-Ras or N-Ras G12C mutant protein. In some embodiments, $R^1$ has a high affinity towards K-Ras, H-Ras or N-Ras and is highly specific towards G12C K-Ras, H-Ras or N-Ras. In some embodiments, $R^1$ is capable of forming a hydrophobic interaction with K-Ras, H-Ras or N-Ras G12C. In some embodiments, $R^1$ is capable of forming one or more hydrogen bonds to one or more residues of a G12C K-Ras, H-Ras or N-Ras protein.

In some embodiments, for a compound of Formula (I), (I-A), (I-B), (I-C), (II), (II-A), (II-B) or (II-C), $R^1$ is selected from $C_{3-12}$ carbocycle and 3- to 12-membered heterocycle, each of which is optionally substituted with one or more substituents selected from halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $=O$, $=S$, $=N(R^{52})$, $C_{1-6}$ alkyl, $C_{1-6}$ haloalkyl, $C_{2-6}$ alkenyl, and $C_{2-6}$ alkynyl. In some embodiments, $R^1$ is selected from monocyclic aryl, bicyclic aryl, monocyclic heteroaryl, and bicyclic heteroaryl. In some embodiments, $R^1$ is selected from phenyl, naphthyl, indazolyl, and quinolinyl. In some embodiments, $R^1$ is substituted with one or more substituents selected from halogen, $-OH$, $-OCH_3$, $C_{1-4}$ alkyl, and $C_{1-4}$ haloalkyl. In some embodiments, $R^1$ is selected from:

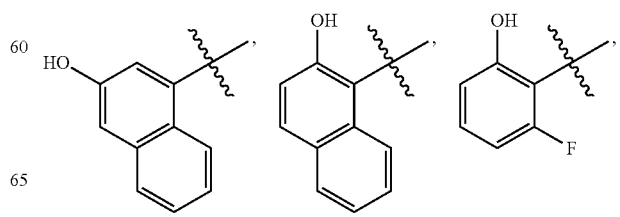

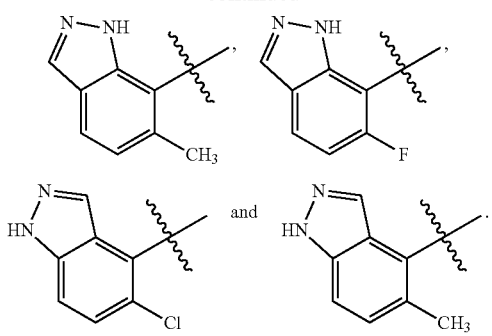

In some embodiments, R¹ is

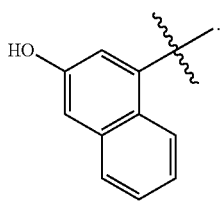

In some embodiments, R¹ is selected from phenyl, naphthyl, indazolyl, and quinolinyl, substituted with one or more substituents selected from halogen, —OH, —OCH₃, C₁₋₄ alkyl, and C₁₋₄ haloalkyl. In some embodiments, R¹ is selected from:

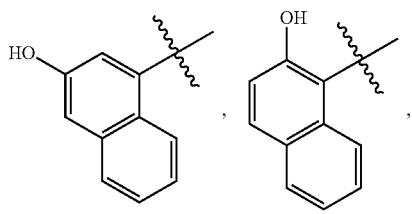

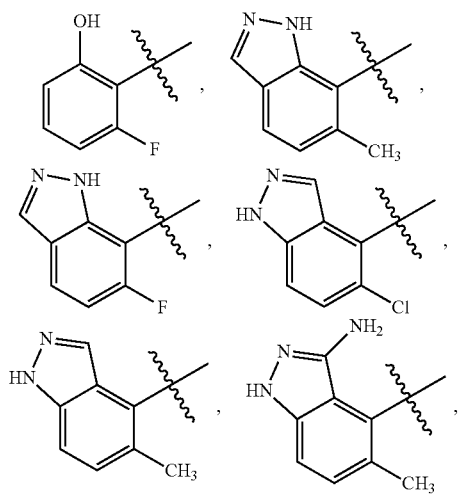

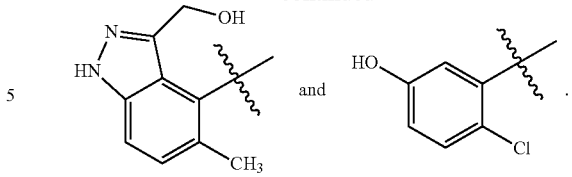

In some embodiments, R¹ is selected from phenyl, naphthyl, indazolyl, and quinolinyl, substituted with one or more substituents selected from —F, —OH, —OCH₃, —NH₂, —CH₂OH, C₁₋₄ alkyl, and C₁₋₄ haloalkyl.

In some embodiments, for a compound of Formula (I), (I-A), (I-B), (I-C), (II), (II-A), (II-B) or (II-C), R¹ is heterocyclyl, heteroaryl or aryl. In some embodiments, R¹ is aryl, such as phenyl or napthyl. In some embodiments, R¹ is unsubstituted aryl, such as unsubstituted phenyl or unsubstituted napthyl. In some embodiments, R¹ is substituted with one or more substituents. In some embodiments, the substituents are selected from halo, cyano, hydroxyl, C₁₋₆ alkyl, C₁₋₆ alkoxy and C₃₋₈ cycloalkyl. In some embodiments, the substituents are selected from fluoro, chloro, bromo, hydroxyl, methoxy and cyclopropyl. In some embodiments, the substituents are selected from —F, —OH, —OCH₃, —NH₂, —CH₂OH, C₁₋₄ alkyl, and C₁₋₄ haloalkyl.

In some embodiments, for a compound of Formula (I), (I-A), (I-B), (I-C), (II), (II-A), (II-B) or (II-C), R¹ is substituted with one or more substituents selected from halo, cyano, cyanoC₁₋₆alkyl, cyanoC₃₋₈cycloalkyl, hydroxyl, C₁₋₆alkyl, C₁₋₆alkylcycloalky, C₂₋₆alkynyl, C₁₋₆alkoxy, C₁₋₆haloalkoxy, C₁₋₆alkylaminyl, C₁₋₆alkylcarbonylaminyl, C₁₋₆hydroxylalkyl, C₁₋₆haloalkyl, C₁₋₆alkoxyalkyl, aminosulfone, aminocarbonyl, aminocarbonylC₁₋₆alkyl, aminocarbonylC₃₋₈cycloalkyl, C₁₋₆alkylaminocarbonyl, C₃₋₈cycloalkylaminocarbonyl, C₃₋₈cycloalkylalkyl, C₃₋₈cycloalkyl, C₃₋₈fusedcycloalkyl and heteroaryl. In some embodiments, R¹ is substituted with one or more substituents selected from fluoro, chloro, bromo, cyano, hydroxyl, hydroxylmethyl, methoxy, methoxymethyl, ethyl, isopropyl, trifluoromethyl, aminocarbonyl and cyclopropyl.

In some embodiments, for a compound of Formula (I), (I-A), (I-B), (I-C), (II), (II-A), (II-B) or (II-C), R¹ is selected from

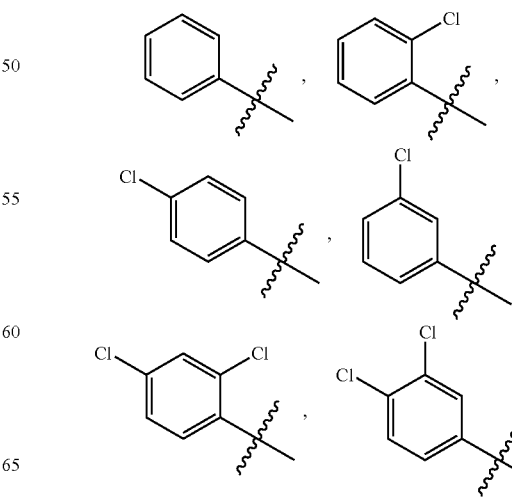

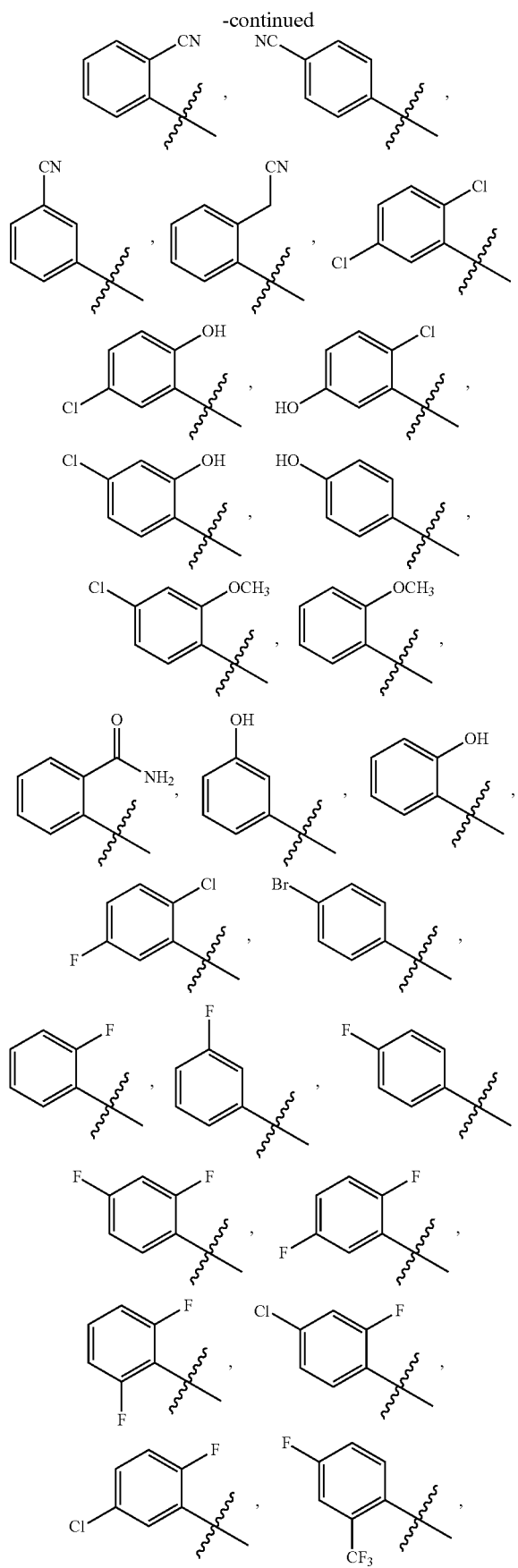
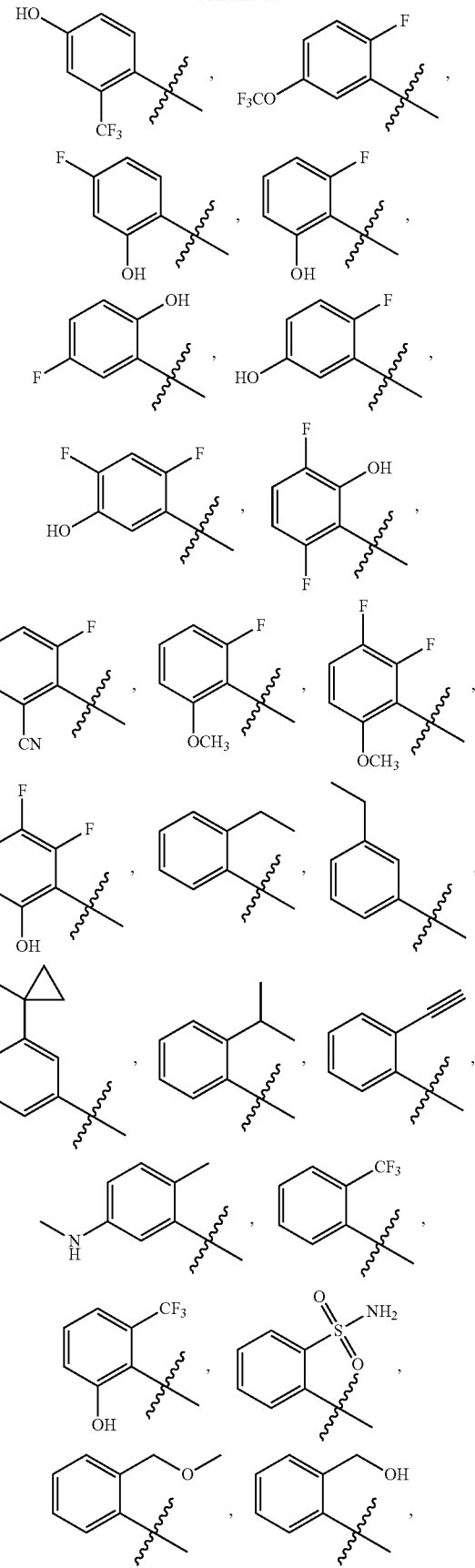

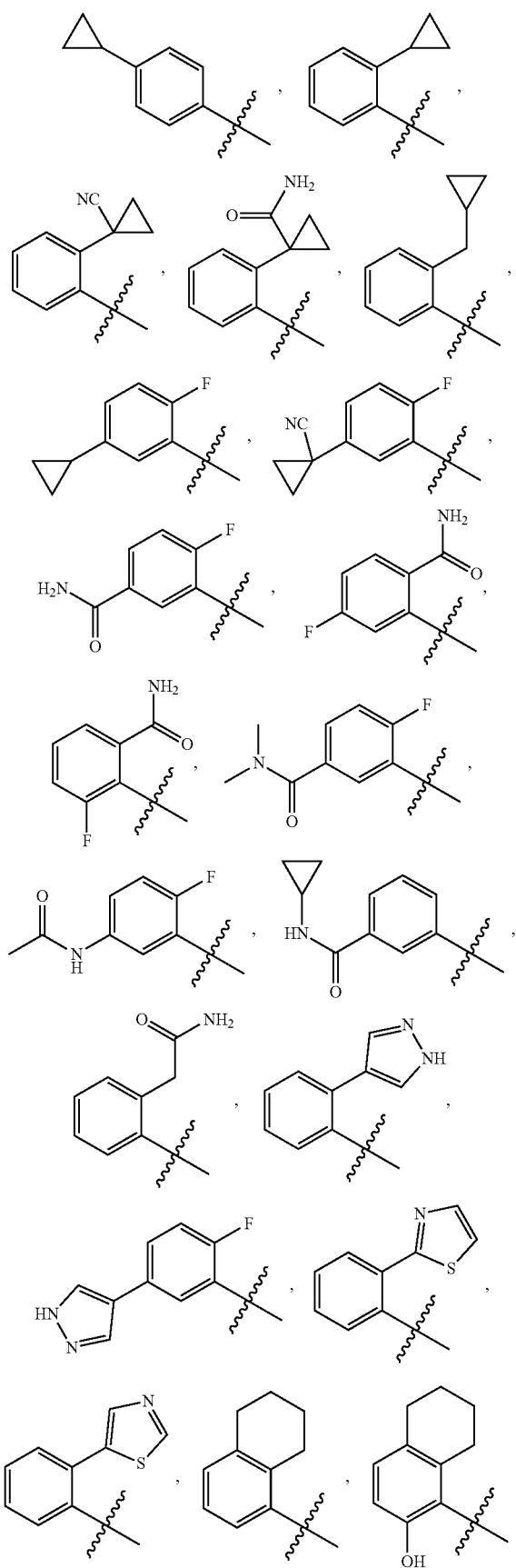

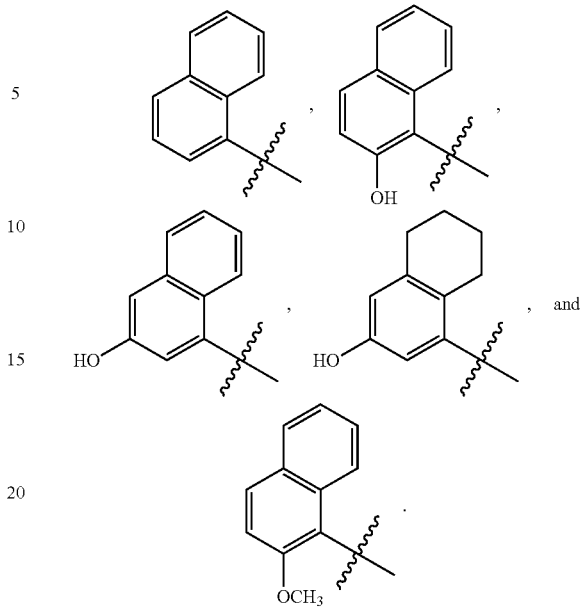

In some embodiments, for a compound of Formula (I), (I-A), (I-B), (I-C), (II), (II-A), (II-B) or (II-C), $R^1$ is heteroaryl. In some embodiments, $R^1$ comprises at least one ring heteroatom selected from oxygen, sulfur, nitrogen and combinations thereof. In some embodiments, $R^1$ comprises at least one ring heteroatom selected from sulfur and nitrogen. In some embodiments, $R^1$ is thiophenyl, pyridinyl, pyridinonyl, pyrimidinyl, benzooxazolyl, benzoisoxazolyl, benzodioxazolyl, benzoimidazolyl, quinolinyl, quinolinonyl, dihydroquinolinonyl, tetrahydroquinolinyl, quinazolinyl, indazolyl, indolinonyl, benzothiophenyl or dihydrobenzodioxinyl.

In some embodiments, for a compound of Formula (I), (I-A), (I-B), (I-C), (II), (II-A), (II-B) or (II-C), $R^1$ is substituted with one or more substituents. In some embodiments, $R^1$ is substituted with one or more substituents selected from halo, $C_{1-6}$ alkyl, $C_{1-6}$ alkoxy, and $C_{2-6}$ alkenylcarbonylaminyl. In some embodiments, $R^1$ is substituted with one or more substituents selected from halogen, hydroxy, and $C_{1-6}$ alkyl. In some embodiments, $R^1$ is substituted with one or more substituents selected from —F, —Cl, —OH, and —CH$_3$.

In some embodiments, for a compound of Formula (I), (I-A), (I-B), (I-C), (II), (II-A), (II-B) or (II-C), $R^1$ is selected from

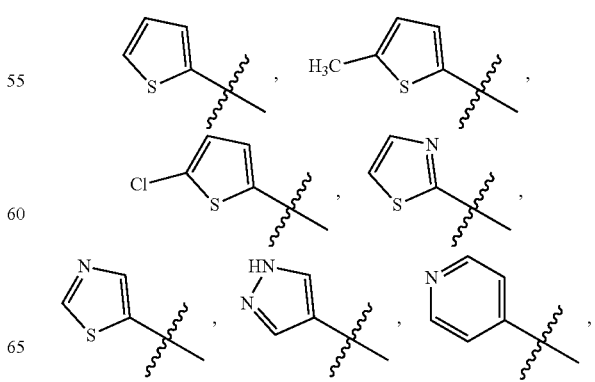

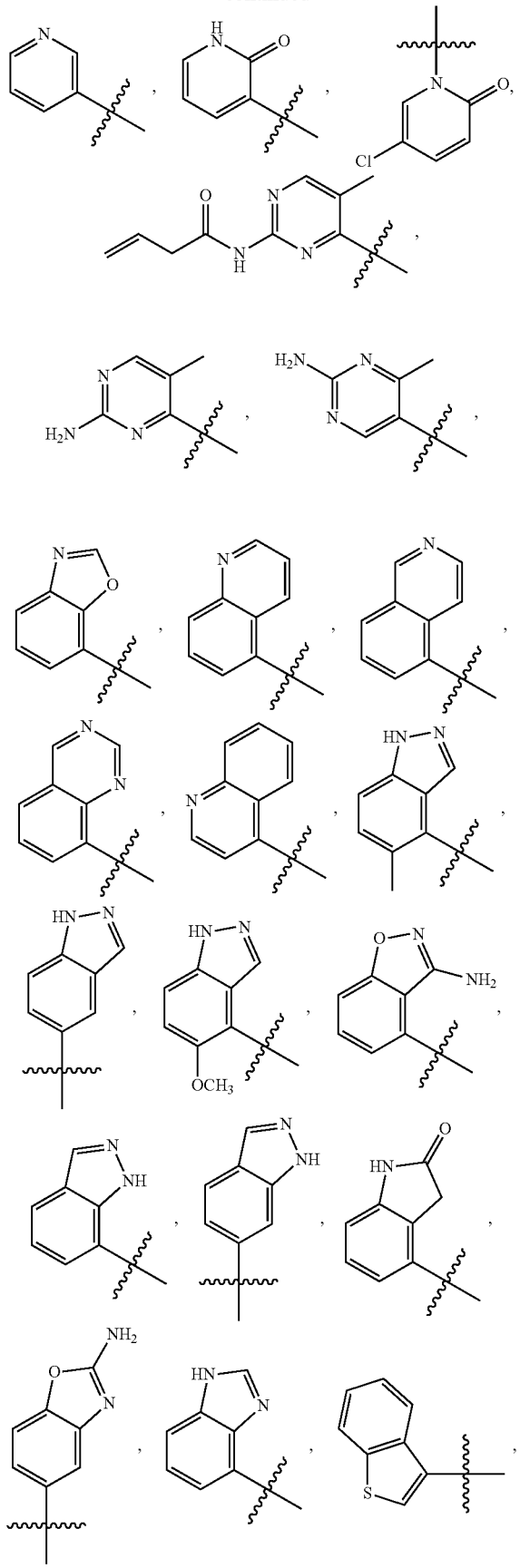

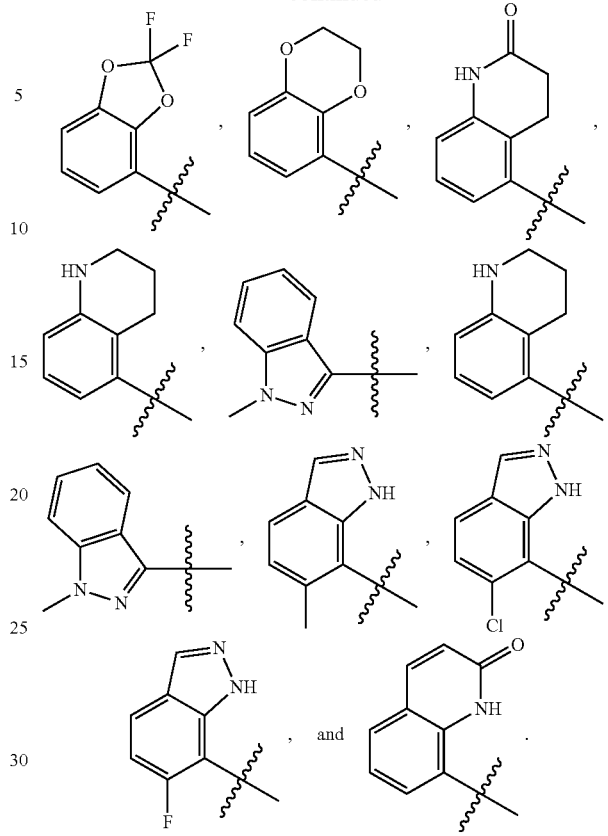

In some embodiments, $R^1$ is aliphatic heterocyclyl. In some embodiments, the aliphatic heterocyclyl comprises oxygen and/or nitrogen. In some embodiments, $R^1$ is morpholinyl, such as

In some embodiments, for a compound of Formula (I), (I-A), (I-B), (I-C), (II), (II-A), (II-B) or (II-C), $R^{2a}$, $R^{2b}$ and $R^{2c}$ are each independently selected from hydrogen, halogen, —OH, $C_{1-4}$ alkyl, and $C_{1-4}$ haloalkyl. In some embodiments, $R^{2a}$ and $R^{2b}$ are each independently selected from halogen. In some embodiments, $R^{2a}$ is fluorine. In some embodiments, $R^{2b}$ is chlorine. In some embodiments, $R^{2c}$ is hydrogen. In some embodiments, $R^{2a}$ is fluorine, $R^{2b}$ is chlorine, and $R^{2c}$ is hydrogen. In some embodiments, $R^{2a}$ and $R^{2b}$ are each independently selected from halogen, and $R^{2c}$ is hydrogen. In some embodiments, $R^{2a}$ and $R^{2b}$ are each independently selected from halogen, —OH, —OCH$_3$, $C_{1-4}$ alkyl, and $C_{1-4}$ haloalkyl, and $R^{2c}$ is hydrogen. In some embodiments, $R^{2a}$, $R^{2b}$ and $R^{2c}$ are each independently selected from hydrogen, halogen, and $C_{1-4}$ alkyl.

In some embodiments, for a compound of Formula (I), (I-A), (I-B), (I-C), (II), (II-A), (II-B) or (II-C), $R^{2a}$ is hydrogen. In some embodiments, $R^{2a}$ is halogen, such as chloro or fluoro. In some embodiments, $R^{2a}$ is $C_{1-6}$ alkyl. In some embodiments, $R^{2a}$ is $C_{3-8}$ cycloalkyl, such as cyclopropyl.

In some embodiments, for a compound of Formula (I), (I-A), (I-B), (I-C), (II), (II-A), (II-B) or (II-C), $R^{2b}$ and $R^{2c}$ are each hydrogen. In some embodiments, $R^{2b}$ and $R^{2c}$ are each independently selected from hydrogen and halogen. In some embodiments, $R^{2b}$ is halogen. In some embodiments, $R^{2c}$ is halogen. In some embodiments, said halogen is selected from fluorine and chlorine.

In some embodiments, for a compound of Formula (I), (I-A), (I-C), (II), (II-A) or (II-C), C is 5- to 8-membered heterocycle, optionally substituted with one or more $R^{57}$. In some embodiments, C is 6-membered monocyclic heterocycle, optionally substituted with one or more $R^{57}$. In some embodiments, said heterocycle comprises at least one ring nitrogen atom. In some embodiments, C is selected from piperidinylene and piperazinylene, optionally substituted with one or more $R^{57}$. In some embodiments, C is piperazinylene, optionally substituted with one or more $R^{57}$, such as piperazinylene substituted with 0, 1 or 2 $R^{57}$ substituents. In some embodiments, C is selected from

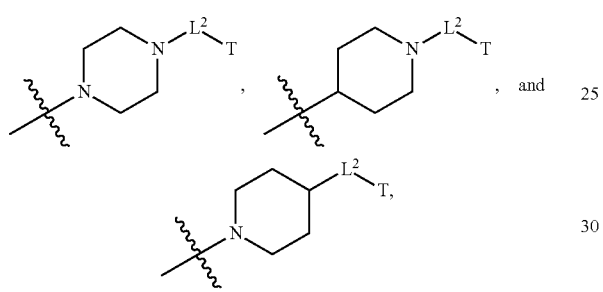

optionally substituted with one or more $R^{57}$. In some embodiments, C is selected from

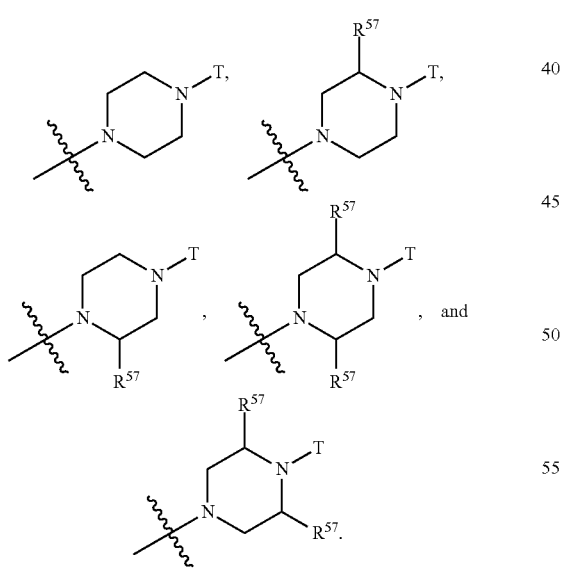

In some embodiments, $R^{57}$ is independently selected at each occurrence from $C_{1-6}$ alkyl, such as —$CH_3$.

In some embodiments, for a compound of Formula (I), (I-A), (I-C), (II), (II-A) or (II-C), C is selected from morpholinyl, piperidinylene and piperazinylene, optionally substituted with one or more $R^{57}$. In some embodiments, C is selected from

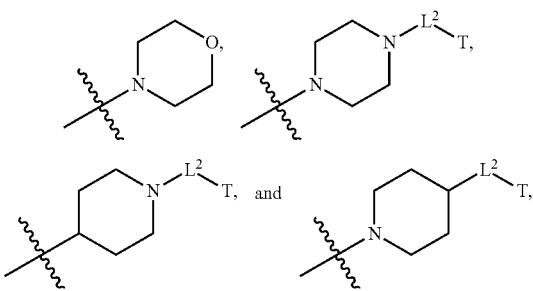

optionally substituted with one or more $R^{57}$.

In some embodiments, for a compound of Formula (I), (I-A), (I-C), (II), (II-A) or (II-C), C is selected from:

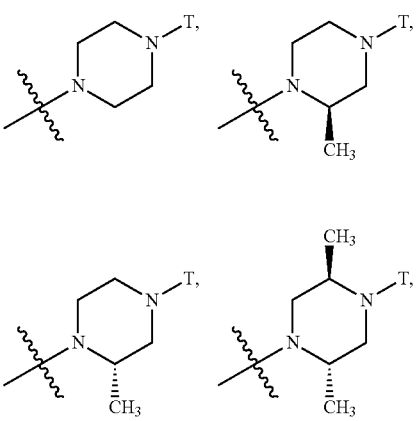

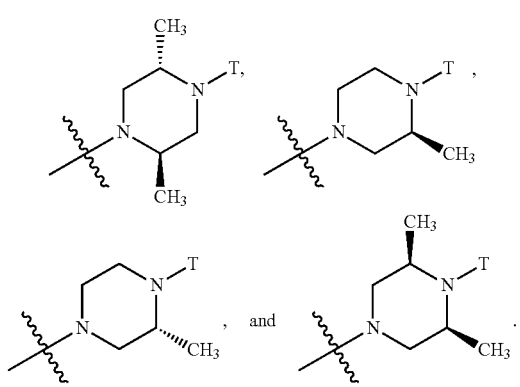

In some embodiments, T is selected from hydrogen; and $C_{1-6}$ alkyl, optionally substituted with =O. In some embodiments, T is selected from hydrogen, —$CH_3$, —C(O)H, —C(O)$CH_3$, and —C(O)$CH_2CH_3$. In some embodiments, T is hydrogen. In some embodiments, C is selected from:

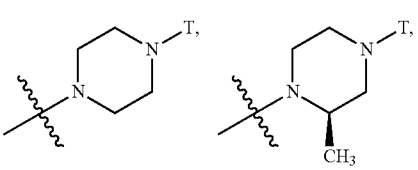

-continued

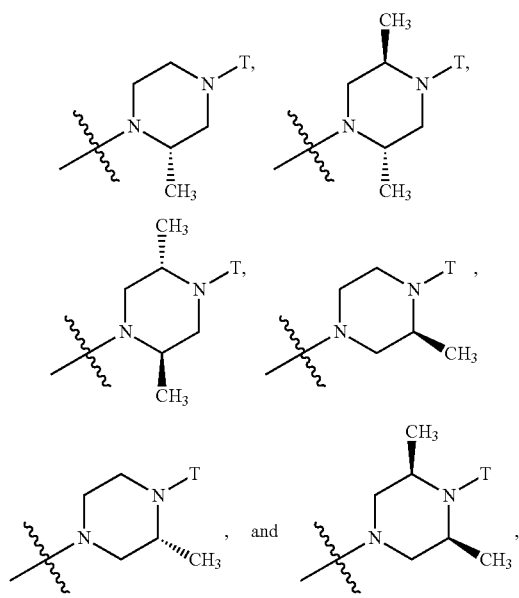

wherein T is selected from hydrogen, —CH$_3$, —C(O)H, —C(O)CH$_3$, and —C(O)CH$_2$CH$_3$. In some embodiments, C is selected from:

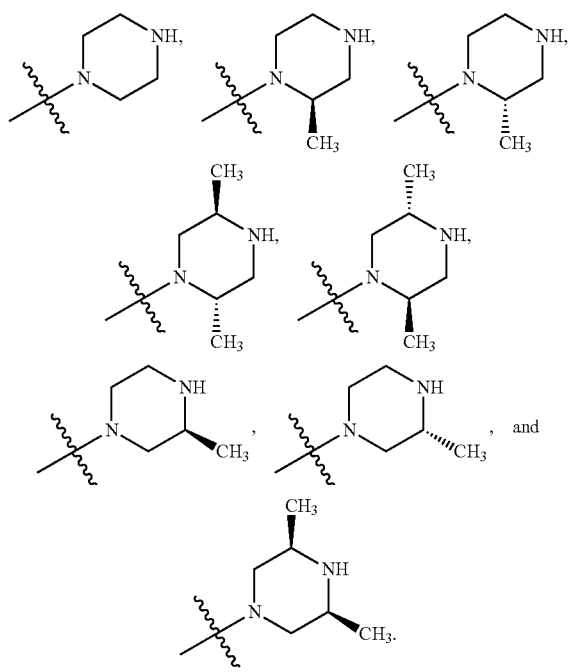

In some embodiments, C is selected from:

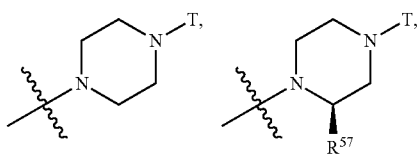

-continued

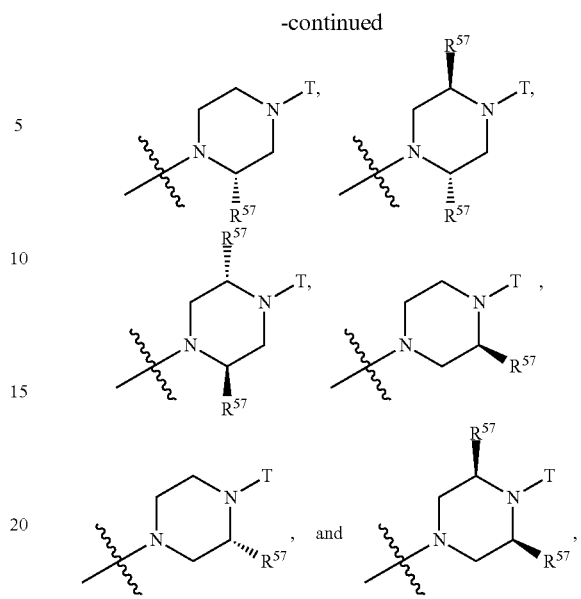

wherein T is selected from hydrogen; and C$_{1-6}$ alkyl, optionally substituted with =O; and R$^{57}$ is independently selected at each occurrence from C$_{1-6}$ alkyl, such as —CH$_3$.

In some embodiments, for a compound of Formula (I), (I-A), (I-B), (I-C), (II), (II-A), (II-B) or (II-C):

T is selected from hydrogen, C$_{1-10}$ alkyl, C$_{1-10}$ alkyl substituted with one or more R$^{52}$, —C(O)R$^{52}$, —C(O)N(R$^{52}$)$_2$, —C(O)NR$^{53}$R$^{54}$, —NR$^{52}$C(O)R$^{52}$, —C(S)N(R$^{52}$)$_2$, —C(S)NR$^{53}$R$^{54}$, —NR$^{52}$C(S)R$^{52}$, —S(O)$_2$N(R$^{52}$)$_2$, —S(O)$_2$ NR$^{53}$R$^{54}$, —NR$^{52}$S(O)$_2$R$^{52}$, —C(NR$^{52}$)N(R$^{52}$)$_2$, —C(NR$^{52}$)NR$^{53}$R$^{54}$, and —NR$^{52}$C(NR$^{52}$)R$^{52}$; wherein each R$^{52}$ in T is independently selected at each occurrence from:
hydrogen; and
C$_{1-20}$ alkyl, 2- to 6-membered heteroalkyl, C$_{3-12}$ carbocycle, and 3- to 12-membered heterocycle, each of which is optionally substituted by —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle.

In some embodiments, for a compound of Formula (I), (I-A), (I-B), (I-C), (II), (II-A), (II-B) or (II-C), T is not E, wherein E is an electrophile capable of bonding with a K-Ras, H-Ras or N-Ras protein comprising a G12C mutation. In some embodiments, T is not E, wherein the electrophile E is capable of forming an irreversible covalent bond with a G12C mutant K-Ras, H-Ras or N-Ras protein. In some embodiments, the electrophile E binds the cysteine residue at position 12 of a G12C mutant K-Ras, H-Ras or N-Ras protein. In some embodiments, T is not E, wherein E is selected from

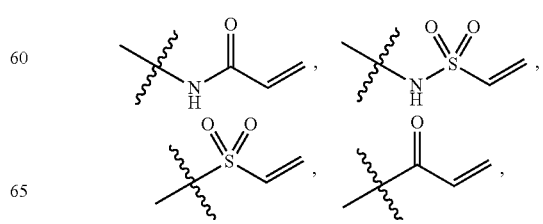

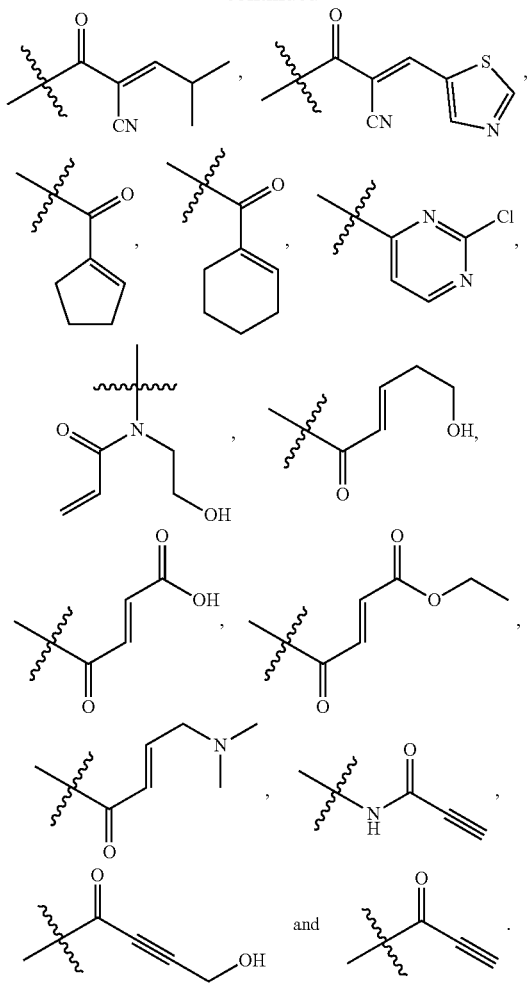

In some embodiments, T is not E, wherein E is selected from

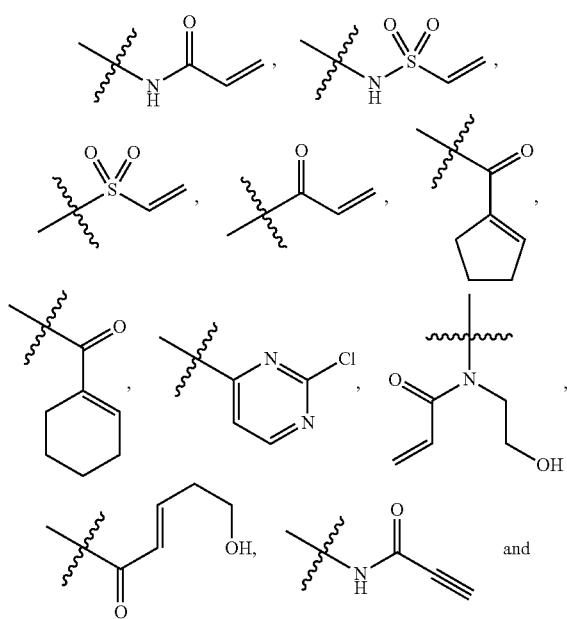

In some embodiments, T is not E, wherein E is selected from

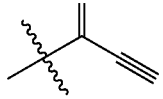

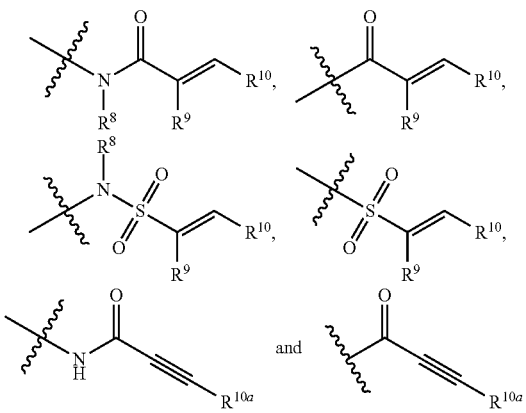

and wherein $R^8$ is H or $C_{1-6}$ alkyl; $R^9$ is H, cyano or $C_{1-6}$ alkyl, or $R^9$ joins with $R^{10}$ to form a carbocycle; $R^{10}$ is H or $C_{1-6}$ alkyl, or $R^{10}$ joins with $R^9$ to form a carbocycle; and $R^{10a}$ is H or $C_{1-6}$ alkyl. In some embodiments, E is

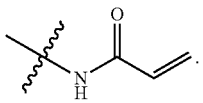

In some embodiments, E is

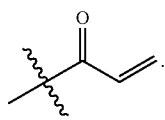 [SMILES: *C(=O)C=C]

In some embodiments, E is

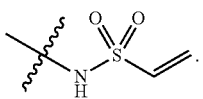

In some embodiments, for a compound of Formula (I), (I-A), (I-B), (I-C), (II), (II-A), (II-B) or (II-C), T is not E, and E has the following structure:

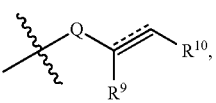

wherein:

≡ represents a double or triple bond;

Q is —C(O)—, —NR⁸C(O)—, —S(=O)₂— or —NR⁸S(=O)₂—; and

R⁸ is H, C₁₋₆ alkyl or hydroxylalkyl;

wherein when is ≡ a double bond, then R⁹ and R¹⁰ are each independently H, cyano, carboxyl, C₁₋₆ alkyl, alkoxycarbonyl, aminoalkyl, alkylaminoalkyl, or hydroxylalkyl, or R⁹ and R¹⁰ join to form a carbocyclic or heterocyclic ring; and wherein when ≡ is a triple bond; then R⁹ is absent and R¹⁰ is H, C₁₋₆ alkyl, aminoalkyl, alkylaminoalkyl or hydroxylalkyl. In some embodiments, when ≡ is a double bond, then R⁹ and R¹⁰ are each independently H, cyano, C₁₋₆ alkyl, aminoalkyl, alkylaminoalkyl, or hydroxylalkyl, or R⁹ and R¹⁰ join to form a carbocyclic or heterocyclic ring.

In some embodiments, for a compound of Formula (I), (I-A), (I-B), (I-C), (II), (II-A), (II-B) or (II-C), T is not E, and E has the following structure:

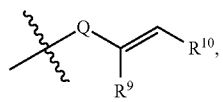

wherein:

Q is —C(O)—, —NR⁸C(O)—, —S(=O)₂— or —NR⁸S(=O)₂—;

R⁸ is H, C₁₋₆ alkyl or hydroxylalkyl; and

R⁹ and R¹⁰ are each independently H, cyano, C₁₋₆ alkyl, aminoalkyl, alkylaminoalkyl, or hydroxylalkyl, or R⁹ and R¹⁰ join to form a carbocyclic or heterocyclic ring.

In some embodiments, for a compound of Formula (I), (I-A), (I-B), (I-C), (II), (II-A), (II-B) or (II-C), T is not E, and E has the following structure:

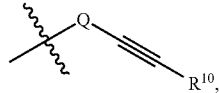

wherein:

Q is —C(O)—, —NR⁸C(O)—, —S(=O)₂— or —NR⁸S(=O)₂—;

R⁸ is H, C₁₋₆ alkyl or hydroxylalkyl; and

R¹⁰ is H, C₁₋₆ alkyl, aminoalkyl, alkylaminoalkyl or hydroxylalkyl.

In some embodiments, for a compound of Formula (I), (I-A), (I-B), (I-C), (II), (II-A), (II-B) or (II-C), T is hydrogen or a polar group capable of forming a complex with a Ras protein via an interaction other than one resulting in a covalent bond with the cysteine residue at position 12 of a K-Ras, H-Ras or N-Ras G12C mutant protein. In some embodiments, T is hydrogen or a group capable of forming a complex with a Ras protein via an interaction other than one resulting in an irreversible covalent bond with the cysteine residue at position 12 of a K-Ras, H-Ras or N-Ras G12C mutant protein. T can form a direct or indirect (e.g., through one or more water molecules) complex with a Ras protein. In some embodiments, T is a polar group capable of forming a bond with a metal ion, wherein the metal ion is complexed to a Ras protein. In some embodiments, T is a metal chelating moiety. In some embodiments, T is a polar group capable of directly or indirectly (e.g., through a water molecule) forming one or more interactions with a beta-phosphate of a nucleotide (GDP) or G12D residue of a Ras protein. In some embodiments, the Ras protein is a K-Ras, H-Ras or N-Ras wild-type protein. In other embodiments, the Ras protein is a K-Ras, H-Ras or N-Ras mutant protein. In some embodiments, the Ras protein is a K-Ras, H-Ras or N-Ras G12C mutant protein. In some embodiments, T is capable of forming an interaction with a mutation residue in the Ras protein. The mutation residue may be G12D. In some embodiments, the mutation residue is G12A, G12C, G12D, G12S or G12V.

In some embodiments, for a compound of Formula (I), (I-A), (I-B), (I-C), (II), (II-A), (II-B) or (II-C), T has a molecular weight less than 400, 350, 300, 250, 200, 190, 180, 170, 160, 150, 140, 130, 120, 110, 100, 90, 80, 70, 60, or 50 Daltons. T may have a molecular weight less than 200 daltons. In some embodiments, T has a molecular weight of greater than 40, 50, 60, 70, 80, 90, 100, or 110 Daltons. T may have a molecular weight of greater than 50 Daltons. In some embodiments, T has a molecular weight between about 50 and 300, 50 and 250, 50 and 200, 50 and 150, or 50 and 100 Daltons.

In some embodiments, for a compound of Formula (I), (I-A), (I-B), (I-C), (II), (II-A), (II-B) or (II-C), T is an optionally substituted alkyl group comprising at least 1, 2, 3, 4, 5, 6, 7, 8, or 9 heteroatoms selected from N, O, and S. In some embodiments, T is an optionally substituted alkyl group comprising at least 1, 2, 3, 4, or 5 nitrogen atoms. In some embodiments, T is an optionally substituted alkyl group comprising at least 1, 2, 3, 4, or 5 oxygen atoms. In some embodiments, T is an optionally substituted alkyl group comprising at least 1, 2, 3, 4, or 5 sulfur atoms. In some embodiments, T is an optionally substituted alkyl group comprising at least 1, 2, 3, 4, 5, 6, 7, 8, or 9 heteroatoms selected from N, O, and S, wherein T has a molecular weight between 50 and 300 Daltons, and wherein T does not comprise an electrophilic group capable of forming a covalent bond with a cysteine. In some embodiments, T does not comprise a Michael acceptor. In some embodiments, T does not comprise an alpha-beta unsaturated carbonyl group.

In some embodiments, for a compound of Formula (I), (I-A), (I-B), (I-C), (II), (II-A), (II-B) or (II-C), T is selected from —H, —NH₂, —OH, —NH(C₁₋₆ alkyl),

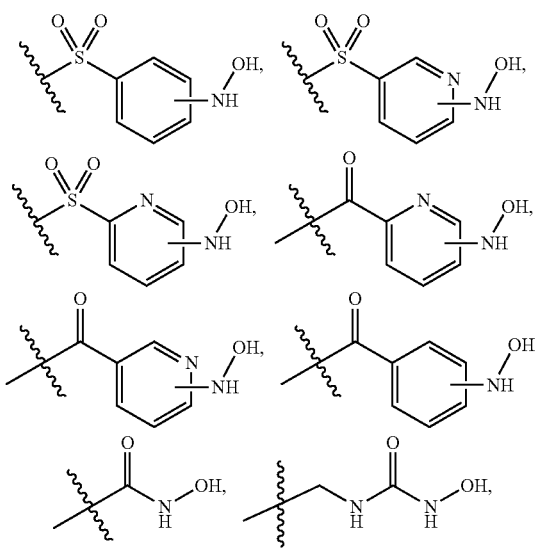

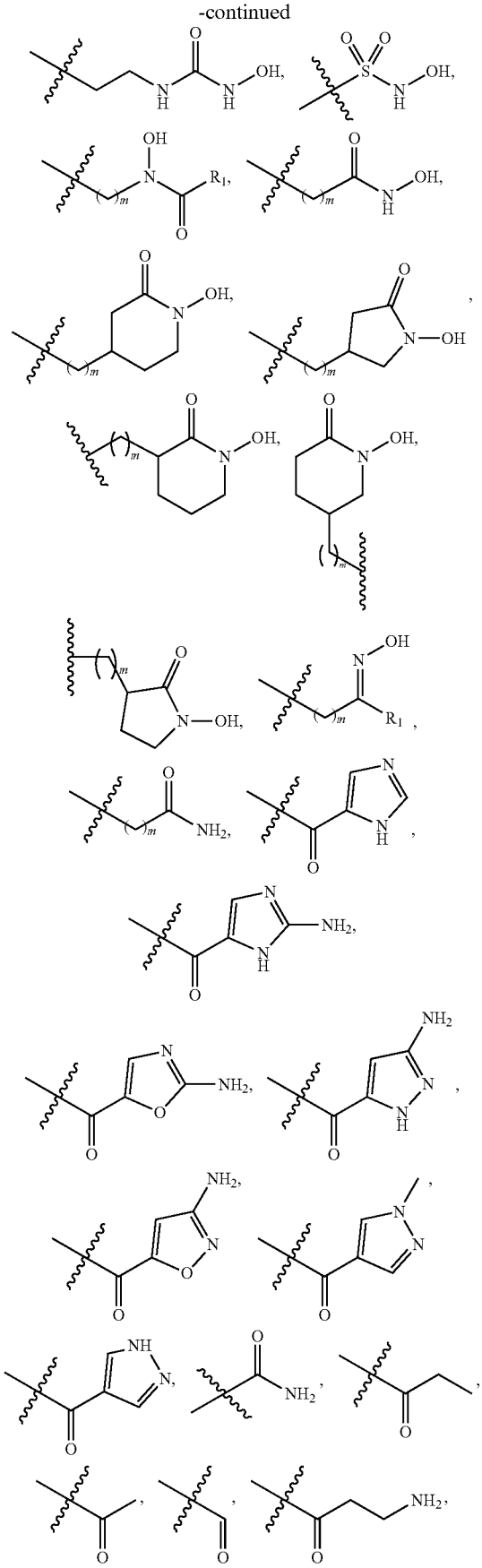
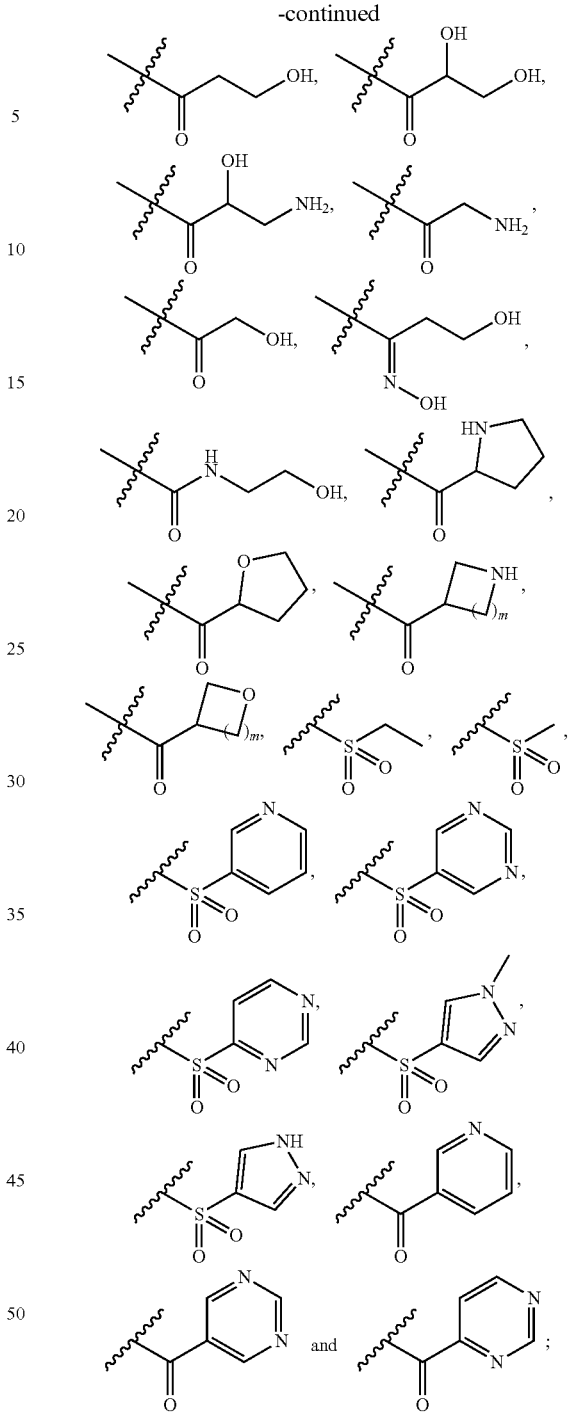

and m, when present, is 0, 1, 2, or 3. In some embodiments, m is 0. In some embodiments, m is 1. In some embodiments, m is 2. In some embodiments, m is 3. In some embodiments, m is 1, 2, or 3. In some embodiments, m is 1 or 2.

In some embodiments, for a compound of Formula (I), (I-A), (I-B), (I-C), (II), (II-A), (II-B) or (II-C), T is selected from $R^{57}$. In some embodiments, T is selected from hydrogen; and $C_{1-6}$ alkyl, optionally substituted with =O. In some embodiments, T is selected from hydrogen, —$CH_3$, —C(O)H, —C(O)$CH_3$, and —C(O)$CH_2CH_3$. In some embodiments, T is hydrogen.

In some embodiments, for a compound of Formula (I), (I-A), (I-B), (I-C), (II), (II-A), (II-B) or (II-C), $L^1$ is selected from bond and —N($R^{51}$)—. In some embodiments, $L^1$ is a bond.

In some embodiments, for a compound of Formula (I), (I-A), (I-B), (I-C), (II), (II-A), (II-B) or (II-C), $L^2$ is selected to provide proper spacing and/or orientation for the T group to form a complex with a K-Ras, H-Ras or N-Ras protein. In some embodiments, $L^2$ is a bond. In some embodiments, $L^2$ is alkylene. In some embodiments, the alkylene is substituted. In some embodiments, the alkylene is unsubstituted. In some embodiments, $L^2$ is $CH_2$ or $CH_2CH_2$.

In some embodiments, for a compound of Formula (I), (I-C), (II), or (II-C), X is N. In some embodiments, Z is N. In some embodiments, X is N and Z is N. In some embodiments, X is N, Z is N, and W is $CR^6$, wherein $R^6$ is a bond to $L^1$. In some embodiments, Z is N, W is $CR^6$, wherein $R^6$ is a bond to $L^1$, and X is $CR^6$, wherein $R^6$ is hydrogen, cyano, methoxy or amino. In some embodiments, Z is N, X is $CR^6$ and $R^6$ is hydrogen or cyano, and W is $CR^6$, wherein $R^6$ is a bond to $L^1$. In some embodiments, Z is N, W is $CR^6$, wherein $R^6$ is a bond to $L^1$, and X is $CR^6$, wherein $R^6$ is hydrogen. In some embodiments, Z is a bond.

In some embodiments, for a compound of Formula (I), (I-A), (I-B), (I-C), (II), (II-A), (II-B) or (II-C):
$R^1$ is selected from phenyl, naphthyl, indazolyl, and quinolinyl, optionally substituted with one or more substituents selected from halogen, —OH, —OCH$_3$, $C_{1-4}$ alkyl, and $C_{1-4}$ haloalkyl; and
$R^{2a}$, $R^{2b}$ and $R^{2c}$ are each independently selected from hydrogen, halogen, —OH, —OCH$_3$, $C_{1-4}$ alkyl, and $C_{1-4}$ haloalkyl.

In some embodiments, for a compound of Formula (I), (I-A), (I-B), (I-C), (II), (II-A), (II-B) or (II-C):
$R^1$ is selected from phenyl, naphthyl, indazolyl, and quinolinyl, optionally substituted with one or more substituents selected from halogen, —OH, —OCH$_3$, $C_{1-4}$ alkyl, and $C_{1-4}$ haloalkyl;
$R^{2a}$, $R^{2b}$ and $R^{2c}$ are each independently selected from hydrogen, halogen, —OH, —OCH$_3$, $C_{1-4}$ alkyl, and $C_{1-4}$ haloalkyl; and
T is selected from hydrogen; and $C_{1-6}$ alkyl, optionally substituted with =O.

In some embodiments, for a compound of Formula (I), (I-A), (I-B), (I-C), (II), (II-A), (II-B) or (II-C):
$R^1$ is selected from

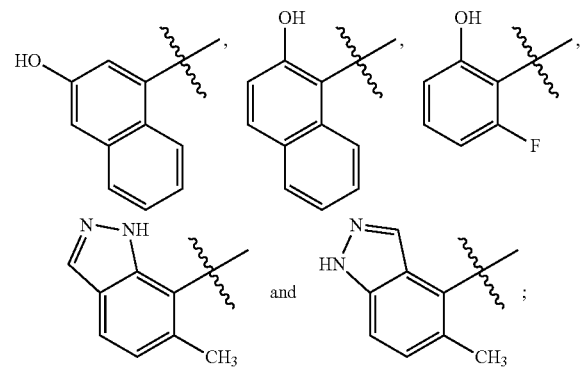

and
$R^{2a}$, $R^{2b}$ and $R^{2c}$ are each independently selected from hydrogen, halogen, $C_{1-4}$ alkyl, and $C_{1-4}$ halo alkyl.

In some embodiments, for a compound of Formula (I), (I-A), (I-B), (I-C), (II), (II-A), (II-B) or (II-C):
$R^1$ is selected from

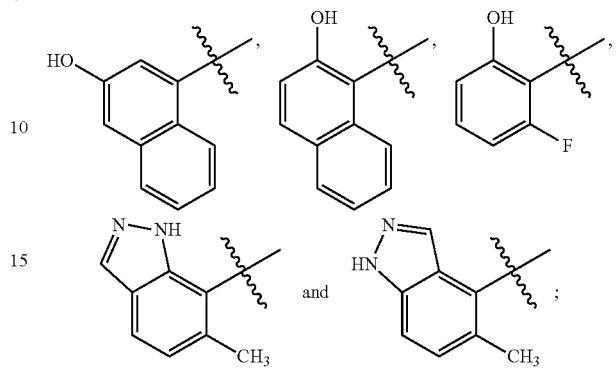

$R^{2a}$, $R^{2b}$ and $R^{2c}$ are each independently selected from hydrogen, halogen, $C_{1-4}$ alkyl, and $C_{1-4}$ haloalkyl; and
T is selected from hydrogen; and $C_{1-6}$ alkyl, optionally substituted with =O.

In some embodiments, for a compound of Formula (I), (I-A), (I-B), (I-C), (II), (II-A), (II-B) or (II-C):
$R^1$ is selected from $C_{3-12}$ carbocycle and 3- to 12-membered heterocycle, each of which is optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), $C_{1-6}$ alkyl, $C_{1-6}$ haloalkyl, $C_{2-6}$ alkenyl, and $C_{2-6}$ alkynyl; and
$R^{2a}$, $R^{2b}$ and $R^{2c}$ are each independently selected from hydrogen, halogen, —OH, —OCH$_3$, $C_{1-4}$ alkyl, and $C_{1-4}$ haloalkyl.

In some embodiments, for a compound of Formula (I), (I-A), (I-B), (I-C), (II), (II-A), (II-B) or (II-C):
$R^1$ is selected from $C_{3-12}$ carbocycle and 3- to 12-membered heterocycle, each of which is optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), $C_{1-6}$ alkyl, $C_{1-6}$ haloalkyl, $C_{2-6}$ alkenyl, and $C_{2-6}$ alkynyl;
$R^{2a}$ and $R^{2b}$ are each independently selected from halogen, —OH, —OCH$_3$, $C_{1-4}$ alkyl, and $C_{1-4}$ haloalkyl; and
$R^{2a}$ is hydrogen.

In some embodiments, for a compound of Formula (I), (I-A), (I-B), (I-C), (II), (II-A), (II-B) or (II-C):
$R^1$ is selected from $C_{3-12}$ carbocycle and 3- to 12-membered heterocycle, each of which is optionally substituted with one or more substituents selected from halogen, —OH, —OCH$_3$, $C_{1-4}$ alkyl, and $C_{1-4}$ haloalkyl;

$R^{2a}$ and $R^{2b}$ are each independently selected from halogen, —OH, —OCH$_3$, C$_{1-4}$ alkyl, and C$_{1-4}$ haloalkyl;

$R^{2c}$ is hydrogen; and

C is selected from:

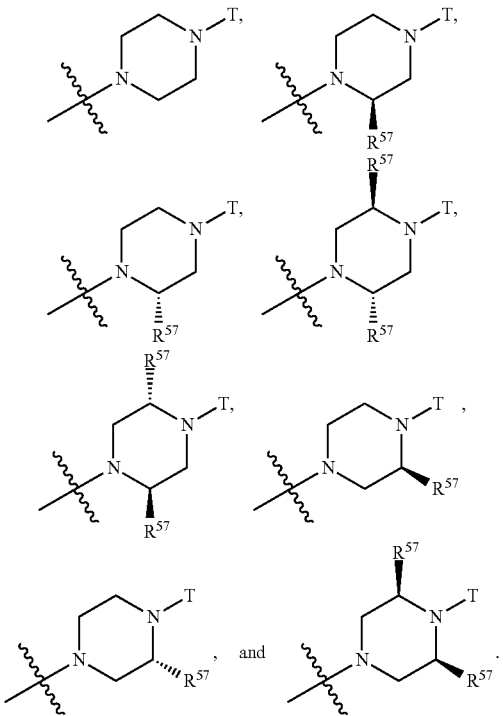

In some embodiments, for a compound of Formula (I), (I-A), (I-B), (I-C), (II), (II-A), (II-B) or (II-C):

$R^1$ is selected from C$_{3-12}$ carbocycle and 3- to 12-membered heterocycle, each of which is optionally substituted with one or more substituents selected from halogen, —OH, —OCH$_3$, C$_{1-4}$ alkyl, and C$_{1-4}$ haloalkyl;

$R^{2a}$ and $R^{2b}$ are each independently selected from halogen, —OH, —OCH$_3$, C$_{1-4}$ alkyl, and C$_{1-4}$ haloalkyl; and $R^{2c}$ is hydrogen.

In some embodiments, for a compound of Formula (I), (I-A), (II) or (II-A):

$R^1$ is selected from C$_{3-12}$ carbocycle and 3- to 12-membered heterocycle, each of which is optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$ N(R$^{52}$)$_2$, —NR$^{52}$S(=O)$_2$NR$^{53}$R$^{54}$, —C(O)R$^{52}$, —C(O) OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N (R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl;

$R^{2a}$, $R^{2b}$ and $R^{2c}$ are each independently selected from hydrogen, halogen, —OH, —OCH$_3$, C$_{1-4}$ alkyl, and C$_{1-4}$ haloalkyl; and C is piperazinylene, optionally substituted with one or more R$^{57}$.

In some embodiments, for a compound of Formula (I), (I-A), (II) or (II-A):

$R^1$ is selected from phenyl, naphthyl, indazolyl, and quinolinyl, optionally substituted with one or more substituents selected from halogen, —OH, —OCH$_3$, C$_{1-4}$ alkyl, and C$_{1-4}$ haloalkyl;

$R^{2a}$, $R^{2b}$ and $R^{2c}$ are each independently selected from hydrogen, halogen, —OH, —OCH$_3$, C$_{1-4}$ alkyl, and C$_{1-4}$ haloalkyl; and C is piperazinylene, optionally substituted with one or more R$^{57}$.

In some embodiments, for a compound of Formula (I), (I-A), (II) or (II-A):

$R^1$ is selected from phenyl, naphthyl, indazolyl, and quinolinyl, optionally substituted with one or more substituents selected from halogen, —OH, —OCH$_3$, C$_{1-4}$ alkyl, and C$_{1-4}$ haloalkyl;

$R^{2a}$, $R^{2b}$ and $R^{2c}$ are each independently selected from hydrogen, halogen, —OH, —OCH$_3$, C$_{1-4}$ alkyl, and C$_{1-4}$ haloalkyl;

C is selected from:

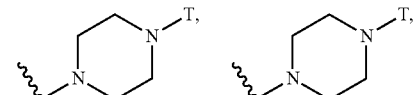

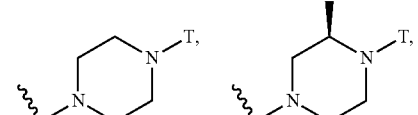

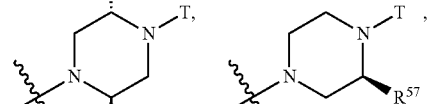

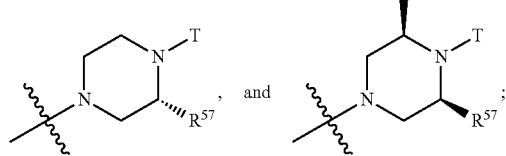

T is selected from hydrogen; and C$_{1-6}$ alkyl, optionally substituted with =O; and $R^{57}$ is independently selected at each occurrence from C$_{1-6}$ alkyl, such as —CH$_3$.

In some embodiments, for a compound of Formula (I), (I-A), (II) or (II-A):

$R^1$ is selected from

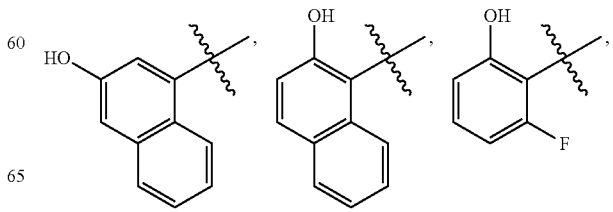

-continued

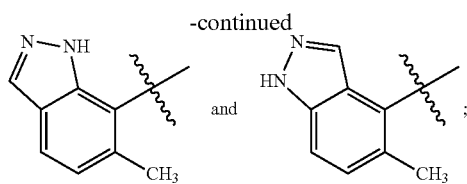

$R^{2a}$ and $R^{2b}$ are each independently selected from halogen;
$R^{2c}$ is hydrogen;
C is selected from:

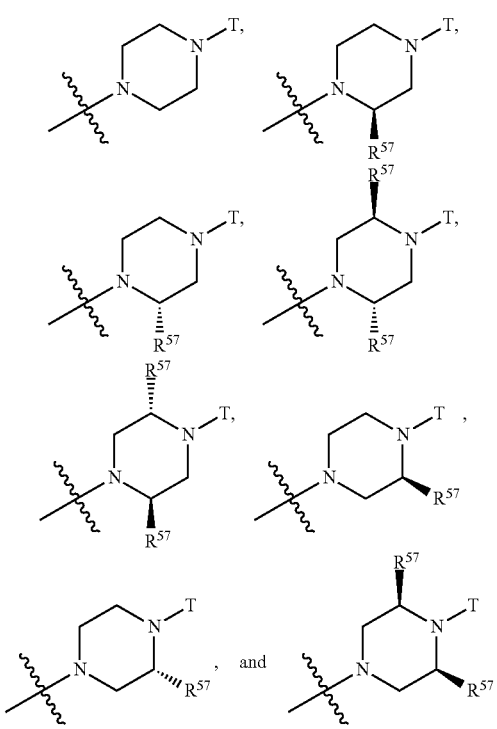

T is selected from hydrogen; and $C_{1-6}$ alkyl, optionally substituted with =O; and
$R^{57}$ is independently selected at each occurrence from $C_{1-6}$ alkyl, such as —$CH_3$.

In some embodiments, for a compound of Formula (I) or (I-A):
$R^{2a}$, $R^{2b}$ and $R^{2c}$ are each independently selected from hydrogen and halogen;
$Y^1$ is selected from —$OR^{55}$ and —$CH_2OR^{55}$;
C is selected from piperazinylene, optionally substituted with one or more $R^{57}$; and
T is selected from hydrogen; and $C_{1-6}$ alkyl, optionally substituted with =O.

In some embodiments, for a compound of Formula (I) or (I-A):
$R^1$ is selected from phenyl, naphthyl, indazolyl, and quinolinyl, optionally substituted with one or more substituents selected from halogen, —OH, —$OCH_3$, $C_{1-4}$ alkyl, and $C_{1-4}$ haloalkyl;
$R^{2a}$, $R^{2b}$ and $R^{2c}$ are each independently selected from hydrogen, halogen, $C_{1-4}$ alkyl, and $C_{1-4}$ halo alkyl;
$Y^1$ is selected from —$OR^{55}$ and —$CH_2OR^{55}$;
C is selected from piperidinylene and piperazinylene, optionally substituted with one or more $R^{57}$; and
T is selected from hydrogen; and $C_{1-6}$ alkyl, optionally substituted with =O.

In some embodiments, for a compound of Formula (I) or (I-A):
$R^1$ is selected from phenyl, naphthyl, indazolyl, and quinolinyl, optionally substituted with one or more substituents selected from halogen, —OH, —$OCH_3$, $C_{1-4}$ alkyl, and $C_{1-4}$ haloalkyl;
$R^{2a}$, $R^{2b}$ and $R^{2c}$ are each independently selected from hydrogen, halogen, $C_{1-4}$ alkyl, and $C_{1-4}$ haloalkyl;
$Y^1$ is

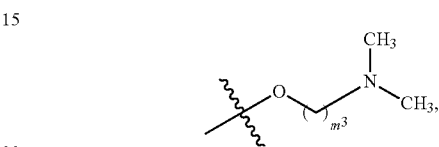

wherein $m^3$ is an integer from 1 to 6;
C is selected from piperidinylene and piperazinylene, optionally substituted with one or more $R^{57}$; and
T is selected from hydrogen; and $C_{1-6}$ alkyl, optionally substituted with =O.

In some embodiments, for a compound of Formula (I) or (I-A):
$R^1$ is selected from

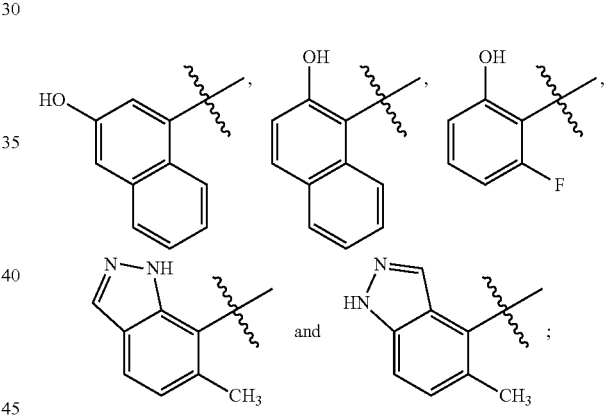

$R^{2a}$ and $R^{2b}$ are each independently selected from halogen;
$R^{2c}$ is hydrogen;
$Y^1$ is selected from —$OR^{55}$ and —$CH_2OR^{55}$;
C is selected from:

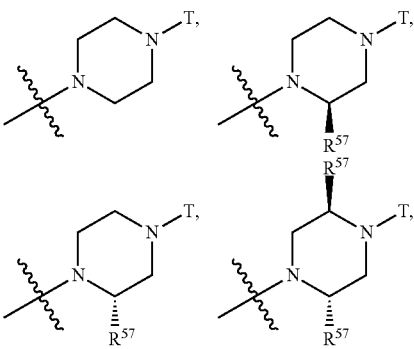

-continued

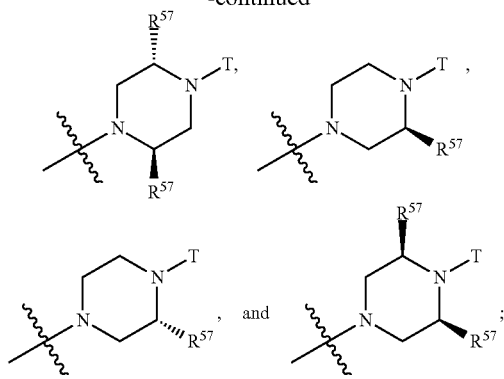

and

T is selected from hydrogen, —CH$_3$, —C(O)H, —C(O)CH$_3$, and —C(O)CH$_2$CH$_3$; and R$^{57}$ is independently selected at each occurrence from C$_{1-6}$ alkyl, such as —CH$_3$.

In some embodiments, for a compound of Formula (II) or (II-A):

R$^{2a}$, R$^{2b}$ and R$^{2c}$ are each independently selected from hydrogen and halogen;

Y$^2$ is selected from —N(R$^{56}$)$_2$ and —CH$_2$N(R$^{56}$)$_2$, wherein at least one R$^{56}$ is not hydrogen;

C is selected from piperazinylene, optionally substituted with one or more R$^{57}$; and T is selected from hydrogen; and C$_{1-6}$ alkyl, optionally substituted with =O.

In some embodiments, for a compound of Formula (II) or (II-A):

R$^1$ is selected from phenyl, naphthyl, indazolyl, and quinolinyl, optionally substituted with one or more substituents selected from halogen, —OH, —OCH$_3$, C$_{1-4}$ alkyl, and C$_{1-4}$ haloalkyl;

R$^{2a}$, R$^{2b}$ and R$^{2c}$ are each independently selected from hydrogen, halogen, C$_{1-4}$ alkyl, and C$_{1-4}$ haloalkyl;

Y$^2$ is selected from —N(R$^{56}$)$_2$ and —CH$_2$N(R$^{56}$)$_2$, wherein at least one R$^{56}$ is not hydrogen;

C is selected from piperidinylene and piperazinylene, optionally substituted with one or more R$^{57}$; and T is selected from hydrogen; and C$_{1-6}$ alkyl, optionally substituted with =O.

In some embodiments, for a compound of Formula (II) or (II-A):

R$^1$ is selected from

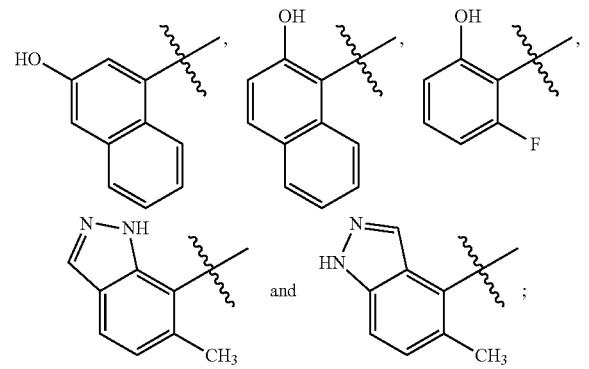

R$^{2a}$ and R$^{2b}$ are each independently selected from halogen;

R$^{2c}$ is hydrogen;

Y$^2$ is selected from —N(R$^{56}$)$_2$ and —CH$_2$N(R$^{56}$)$_2$, wherein at least one R$^{56}$ is not hydrogen;

C is selected from:

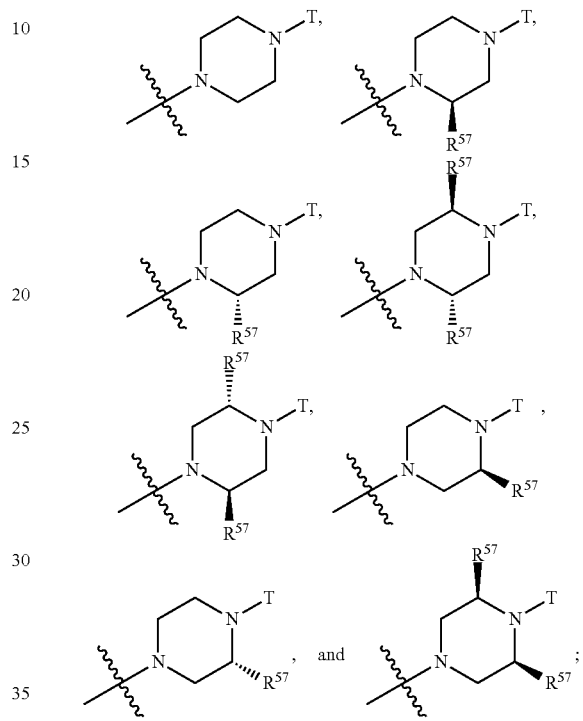

and

T is selected from hydrogen, —CH$_3$, —C(O)H, —C(O)CH$_3$, and —C(O)CH$_2$CH$_3$; and R$^{57}$ is independently selected at each occurrence from C$_{1-6}$ alkyl, such as —CH$_3$.

In certain aspects, the present disclosure provides a compound of Formula (I-A):

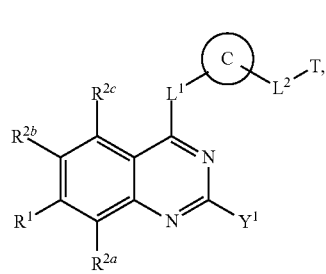

(I-A)

or a salt thereof, wherein:

R$^1$ is selected from C$_{5-12}$ carbocycle and 5- to 12-membered heterocycle;

R$^{2a}$ and R$^{2b}$ are each independently selected from halogen, —OH, —OCH$_3$, C$_{1-4}$ alkyl, and C$_{1-4}$ haloalkyl;

R$^{2c}$ is selected from hydrogen, halogen, —OH, C$_{1-4}$ alkyl, and C$_{1-4}$ haloalkyl;

$Y^1$ is selected from

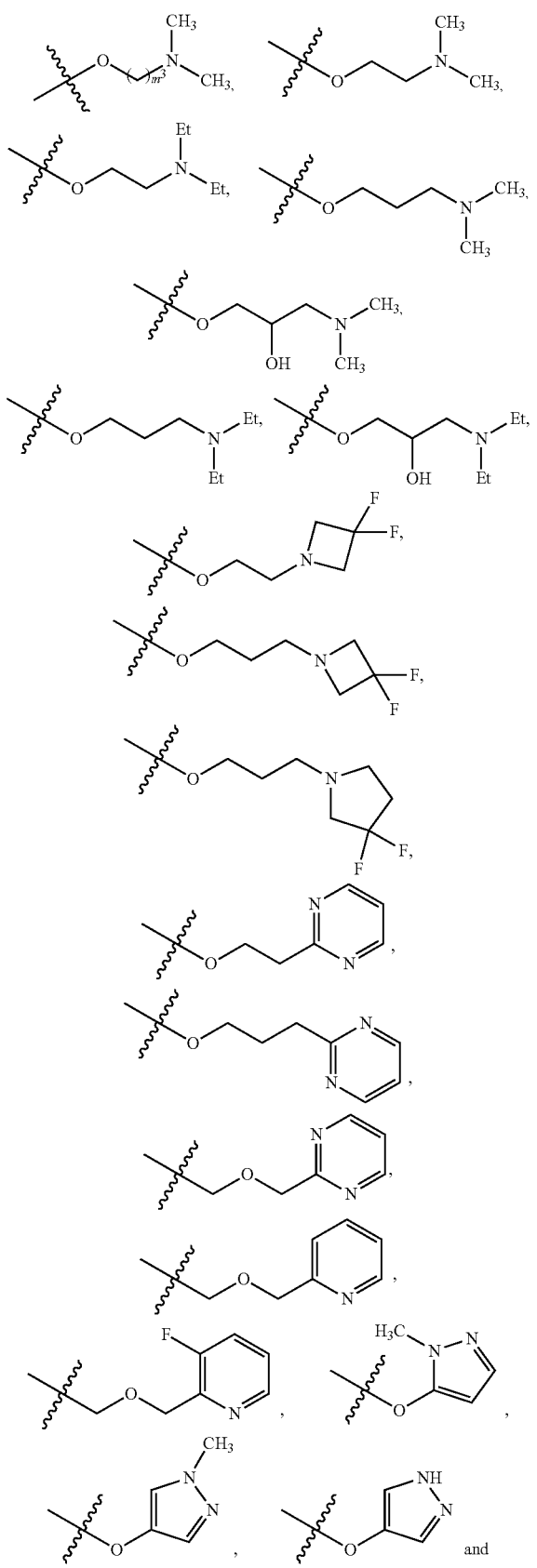

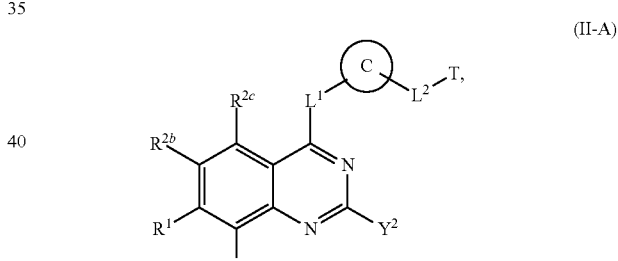

wherein $m^3$ is an integer from 1 to 6;

$L^1$ and $L^2$ are each independently selected from bond and $C_{1-3}$ alkylene;

C is selected from 3- to 12-membered heterocycle, optionally substituted with one or more $R^{57}$;

T is hydrogen or a polar group capable of forming a complex with a Ras protein via an interaction other than one resulting in a covalent bond with the cysteine residue at position 12 of a K-Ras, H-Ras or N-Ras G12C mutant protein;

$R^{57}$ is independently selected at each occurrence from:
halogen, —CN, —OH, —OMe, —$NH_2$, —$NHC_{1-6}$ alkyl, —$N(C_{1-6}$ alkyl$)_2$, —C(O)OH, —C(O)H, —C(O)$C_{1-6}$ alkyl, —NHC(O)$C_{1-6}$ alkyl, —N($C_{1-6}$ alkyl)C(O)$C_{1-6}$ alkyl, —C(O)$NH_2$, —C(O)NH($C_{1-6}$ alkyl), —C(O)N($C_{1-6}$ alkyl$)_2$, =O, =N(OH); and $C_{1-10}$ alkyl, optionally substituted at each occurrence with one or more substituents selected from —CN, —OH, —$NH_2$, —OMe, —$NH_2$, —$NHC_{1-6}$ alkyl, —$N(C_{1-6}$ alkyl$)_2$, —C(O)OH, —C(O)H, —C(O)$C_{1-6}$ alkyl, —NHC(O)$C_{1-6}$ alkyl, —N($C_{1-6}$ alkyl)C(O)$C_{1-6}$ alkyl, —C(O)$NH_2$, —C(O)NH($C_{1-6}$ alkyl), —C(O)N($C_{1-6}$ alkyl$)_2$, =O, and =N(OH).

In certain aspects, the present disclosure provides a compound of Formula (II-A):

(II-A)

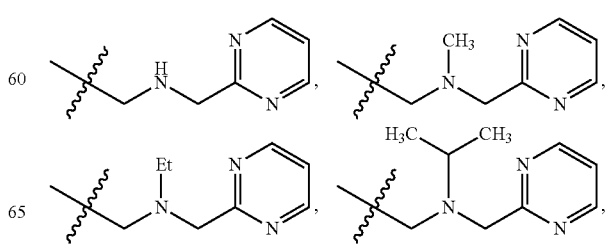

or a salt thereof, wherein:

$R^1$ is selected from $C_{5-12}$ carbocycle and 5- to 12-membered heterocycle;

$R^{2a}$ and $R^{2b}$ are each independently selected from halogen, —OH, —$OCH_3$, $C_{1-4}$ alkyl, and $C_{1-4}$ haloalkyl;

$R^{2c}$ is selected from hydrogen, halogen, —OH, $C_{1-4}$ alkyl, and $C_{1-4}$ haloalkyl;

$Y^2$ is selected from

-continued

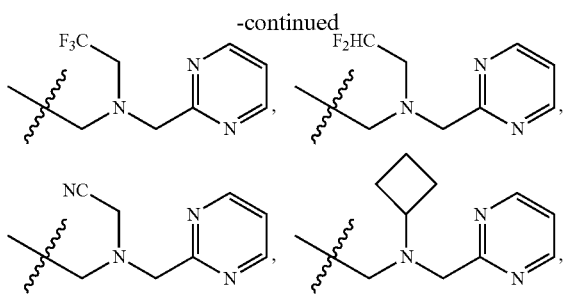

and —CH$_2$N(R$^{58}$)CH$_2$R$^{59}$, wherein R$^{58}$ is selected from hydrogen, C$_{1-4}$ alkyl, C$_{1-4}$ haloalkyl, C$_{1-4}$ alkyl substituted with halogen or —CN, C$_{3-6}$ carbocycle, and 3- to 6-membered heterocycle; and R$^{59}$ is selected from 3- to 8-membered heterocycle, optionally substituted with one or more halogens;

L$^1$ and L$^2$ are each independently selected from bond and C$_{1-3}$ alkylene;

C is selected from 3- to 12-membered heterocycle, optionally substituted with one or more R$^{57}$;

T is hydrogen or a polar group capable of forming a complex with a Ras protein via an interaction other than one resulting in a covalent bond with the cysteine residue at position 12 of a K-Ras, H-Ras or N-Ras G12C mutant protein;

R$^{57}$ is independently selected at each occurrence from:
halogen, —CN, —OH, —OMe, —NH$_2$, —NHC$_{1-6}$ alkyl, —N(C$_{1-6}$ alkyl)$_2$, —C(O)OH, —C(O)H, —C(O)C$_{1-6}$ alkyl, —NHC(O)C$_{1-6}$ alkyl, —N(C$_{1-6}$ alkyl)C(O)C$_{1-6}$ alkyl, —C(O)NH$_2$, —C(O)NH(C$_{1-6}$ alkyl), —C(O)N(C$_{1-6}$ alkyl)$_2$, =O, =N(OH); and C$_{1-10}$ alkyl, optionally substituted at each occurrence with one or more substituents selected from —CN, —OH, —NH$_2$, —OMe, —NH$_2$, —NHC$_{1-6}$ alkyl, —N(C$_{1-6}$ alkyl)$_2$, —C(O)OH, —C(O)H, —C(O)C$_{1-6}$ alkyl, —NHC(O)C$_{1-6}$ alkyl, —N(C$_{1-6}$ alkyl)C(O)C$_{1-6}$ alkyl, —C(O)NH$_2$, —C(O)NH(C$_{1-6}$ alkyl), —C(O)N(C$_{1-6}$ alkyl)$_2$, =O, and =N(OH).

In certain aspects, the present disclosure provides a compound of Formula (II-A):

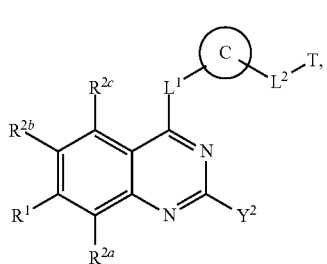

(II-A)

or a salt thereof, wherein:

R$^1$ is selected from C$_{5-12}$ carbocycle and 5- to 12-membered heterocycle;

R$^{2a}$ and R$^{2b}$ are each independently selected from halogen, —OH, —OCH$_3$, C$_{1-4}$ alkyl, and C$_{1-4}$ haloalkyl;

R$^{2c}$ is selected from hydrogen, halogen, —OH, C$_{1-4}$ alkyl, and C$_{1-4}$ haloalkyl;

Y$^2$ is selected from

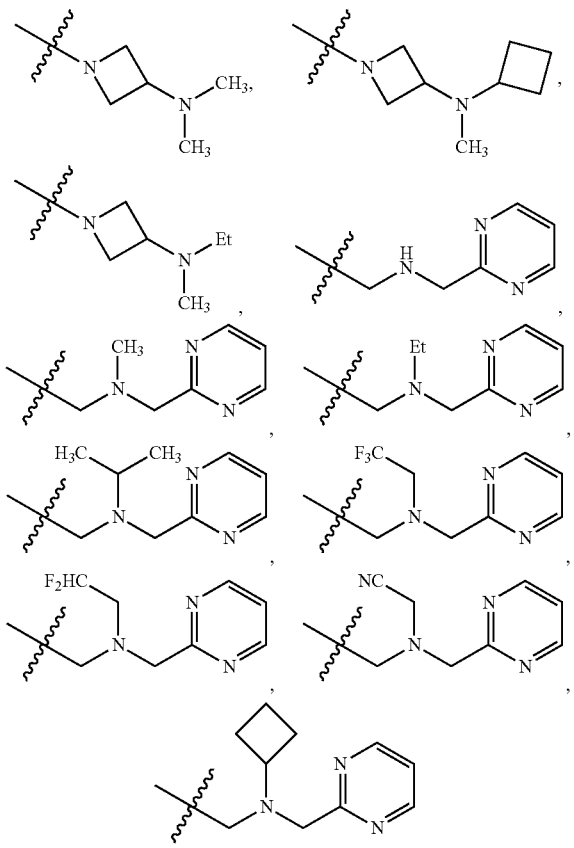

and —CH$_2$N(R$^{58}$)CH$_2$R$^{59}$, wherein R$^{58}$ is selected from hydrogen, C$_{1-4}$ alkyl, C$_{1-4}$ haloalkyl, C$_{1-4}$ alkyl substituted with halogen or —CN, C$_{3-6}$ carbocycle, and 3- to 6-membered heterocycle; and R$^{59}$ is selected from 3- to 8-membered heterocycle, optionally substituted with one or more halogens;

L$^1$ and L$^2$ are each independently selected from bond and C$_{1-3}$ alkylene;

C is selected from 3- to 12-membered heterocycle, optionally substituted with one or more R$^{57}$;

T is hydrogen or a polar group capable of forming a complex with a Ras protein via an interaction other than one resulting in a covalent bond with the cysteine residue at position 12 of a K-Ras, H-Ras or N-Ras G12C mutant protein;

R$^{57}$ is independently selected at each occurrence from:
halogen, —CN, —OH, —OMe, —NH$_2$, —NHC$_{1-6}$ alkyl, —N(C$_{1-6}$ alkyl)$_2$, —C(O)OH, —C(O)H, —C(O)C$_{1-6}$ alkyl, —NHC(O)C$_{1-6}$ alkyl, —N(C$_{1-6}$ alkyl)C(O)C$_{1-6}$ alkyl, —C(O)NH$_2$, —C(O)NH(C$_{1-6}$ alkyl), —C(O)N(C$_{1-6}$ alkyl)$_2$, =O, =N(OH); and C$_{1-10}$ alkyl, optionally substituted at each occurrence with one or more substituents selected from —CN, —OH, —NH$_2$, —OMe, —NH$_2$, —NHC$_{1-6}$ alkyl, —N(C$_{1-6}$ alkyl)$_2$, —C(O)OH, —C(O)H, —C(O)C$_{1-6}$ alkyl, —NHC(O)C$_{1-6}$ alkyl, —N(C$_{1-6}$ alkyl)C(O)C$_{1-6}$ alkyl, —C(O)NH$_2$, —C(O)NH(C$_{1-6}$ alkyl), —C(O)N(C$_{1-6}$ alkyl)$_2$, =O, and =N(OH).

Any combination of the groups described above for the various variables is contemplated herein. Throughout the specification, groups and substituents thereof can be chosen to provide stable moieties and compounds.

In certain embodiments, the present disclosure provides a stereoisomer of a compound of Formula (I), (I-A), (I-B), (I-C), (II), (II-A), (II-B) or (II-C). In some embodiments, the stereoisomer is in enantiomeric excess. In some embodiments, the stereoisomer is provided in at least 20%, 30%, 40%, 50%, 55%, 60%, 65%, 70%, 75%, 80%, 85%, 88%, 90%, 91%, 92%, 93%, 94%, 95%, 96%, 97%, 98%, 99%, 99.5%, or 99.9%, enantiomeric excess. In some embodiments, the stereoisomer is provided in greater than 20%, 30%, 40%, 50%, 55%, 60%, 65%, 70%, 75%, 80%, 85%, 88%, 90%, 91%, 92%, 93%, 94%, 95%, 96%, 97%, 98%, 99%, 99.5%, or 99.9%, enantiomeric excess. In some embodiments, the stereoisomer is in greater than 95% enantiomeric excess, such as greater than 99% enantiomeric excess.

In certain embodiments, the present disclosure provides a stereoisomer of a compound of Formula (I), (I-A), (I-B), (I-C), (II), (II-A), (II-B) or (II-C). In some embodiments, the stereoisomer is in diastereomeric excess. In some embodiments, the stereoisomer is provided in at least 20%, 30%, 40%, 50%, 55%, 60%, 65%, 70%, 75%, 80%, 85%, 88%, 90%, 91%, 92%, 93%, 94%, 95%, 96%, 97%, 98%, 99%, 99.5%, or 99.9%, diastereomeric excess. In some embodiments, the stereoisomer is provided in greater than 20%, 30%, 40%, 50%, 55%, 60%, 65%, 70%, 75%, 80%, 85%, 88%, 90%, 91%, 92%, 93%, 94%, 95%, 96%, 97%, 98%, 99%, 99.5%, or 99.9%, diastereomeric excess. In some embodiments, the stereoisomer is in greater than 95% diastereomeric excess, such as greater than 99% diastereomeric excess.

In certain embodiments, the present disclosure provides an atropisomer of a compound of Formula (I), (I-A), (I-B), (I-C), (II), (II-A), (II-B) or (II-C). In some embodiments, the atropisomer is in enantiomeric excess. In some embodiments, the atropisomer is provided in at least 20%, 30%, 40%, 50%, 55%, 60%, 65%, 70%, 75%, 80%, 85%, 88%, 90%, 91%, 92%, 93%, 94%, 95%, 96%, 97%, 98%, 99%, 99.5%, or 99.9%, enantiomeric excess. In some embodiments, the atropisomer is provided in greater than 20%, 30%, 40%, 50%, 55%, 60%, 65%, 70%, 75%, 80%, 85%, 88%, 90%, 91%, 92%, 93%, 94%, 95%, 96%, 97%, 98%, 99%, 99.5%, or 99.9%, enantiomeric excess. In some embodiments, the atropisomer is in greater than 95% enantiomeric excess, such as greater than 99% enantiomeric excess.

In certain embodiments, the compound of Formula (I), (I-A), (I-B), (I-C), (II), (II-A), (II-B) or (II-C) is preferably used as a non-racemic mixture, wherein one atropisomer is present in excess of its corresponding enantiomer or epimer. Typically, such mixture will contain a mixture of the two isomers in a ratio of at least about 9:1, preferably at least 19:1. In some embodiments, the atropisomer is provided in at least 96% enantiomeric excess, meaning the compound has less than 2% of the corresponding enantiomer. In some embodiments, the atropisomer is provided in at least 96% diastereomeric excess, meaning the compound has less than 2% of the corresponding diastereomer.

In certain embodiments, the compound of Formula (I), (I-A), (I-B), (I-C), (II), (II-A), (II-B) or (II-C) is preferably used as a non-racemic mixture wherein the (+)-isomer is the major component of the mixture. Typically, such mixture will contain no more than about 10% of the (−)-isomer, meaning the ratio of (+)- to (−)-isomers is at least about 9:1, and preferably less than 5% of the (−)-isomer, meaning the ratio of (+)- to (−)-isomers is at least about 19:1. In some embodiments, the compound used has less than 2% of the (−)-isomer, meaning it has an enantiomeric excess of at least about 96%. In some embodiments, the compound has an enantiomeric excess of at least 98%. In some embodiments, the compound has an enantiomeric excess of at least 99%.

In certain embodiments, the compound of Formula (I), (I-A), (I-B), (I-C), (II), (II-A), (II-B) or (II-C) is preferably used as a non-racemic mixture wherein the (−)-isomer is the major component of the mixture. Typically, such mixture will contain no more than about 10% of the (+)-isomer, meaning the ratio of (−)- to (+)-isomers is at least about 9:1, and preferably less than 5% of the (+)-isomer, meaning the ratio of (−)- to (+)-isomers is at least about 19:1. In some embodiments, the compound used has less than 2% of the (+)-isomer, meaning it has an enantiomeric excess of at least about 96%. In some embodiments, the compound has an enantiomeric excess of at least 98%. In some embodiments, the compound has an enantiomeric excess of at least 99%.

The term "atropisomers" refers to conformational stereoisomers which occur when rotation about a single bond in the molecule is prevented, or greatly slowed, as a result of steric interactions with other parts of the molecule and the substituents at both ends of the single bond are asymmetrical (i.e., optical activity arises without requiring an asymmetric carbon center or stereocenter). Where the rotational barrier about the single bond is high enough, and interconversion between conformations is slow enough, separation and isolation of the isomeric species may be permitted. Atropisomers are enantiomers (or epimers) without a single asymmetric atom. By one definition, atropisomerism is defined to exist where the isomers have a half-life ($t_{1/2}$) of at least 1000 seconds, which is a free energy barrier of 22.3 kcal mol$^{-1}$ (93.3 kJ mol$^{-1}$) at 300 K (Oki, M., "Recent Advances in Atropisomerism," Topics in Stereochemistry (1983) 14:1). The atropisomers are considered stable if the barrier to interconversion is high enough to permit the atropisomers to undergo little or no interconversion at room temperature for at least a week, preferably at least a year. In some embodiments, an atropisomeric compound of the disclosure does not undergo more than about 5% interconversion to its opposite atropisomer at room temperature during one week when the atropisomeric compound is in substantially pure form, which is generally a solid state. In some embodiments, an atropisomeric compound of the disclosure does not undergo more than about 5% interconversion to its opposite atropisomer at room temperature (approximately 25° C.) during one year. Preferably, the atropisomeric compounds of the disclosure are stable enough to undergo no more than about 5% interconversion in an aqueous pharmaceutical formulation held at 0° C. for at least one week. The present chemical entities, pharmaceutical compositions and methods are meant to include all such possible atropisomers, including racemic mixtures, diastereomeric mixtures, epimeric mixtures, optically pure forms of single atropisomers, and intermediate mixtures.

The energy barrier to thermal racemization of atropisomers may be determined by the steric hindrance to free rotation of one or more bonds forming a chiral axis. Certain biaryl compounds exhibit atropisomerism where rotation around an interannular bond lacking C2 symmetry is restricted. The free energy barrier for isomerization (enantiomerization) is a measure of the stability of the interannular bond with respect to rotation. Optical and thermal excitation can promote racemization of such isomers, dependent on electronic and steric factors.

Ortho-substituted biaryl compounds may exhibit this type of conformational, rotational isomerism. Such biaryls are enantiomeric, chiral atropisomers where the sp$^2$-sp$^2$ carbon-carbon, interannular bond between the aryl rings has a sufficiently high energy barrier to prevent free rotation, and where substituents $W^1 \neq W^2$ and $W^3 \neq W^4$ render the molecule asymmetric.

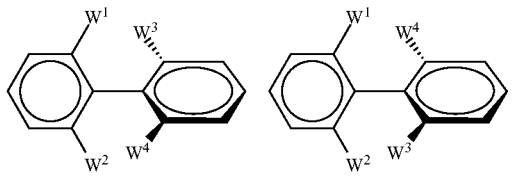

The steric interaction between $W^1:W^3$, $W^1:W^4$, and/or $W^2:W^4$, $W^2:W^3$ is large enough to make the planar conformation an energy maximum. Two non-planar, axially chiral enantiomers then exist as atropisomers when their interconversion is slow enough such that they can be isolated free of each other. Bold lines and dashed lines in the figures shown above indicate those moieties, or portions of the molecule, which are sterically restricted due to a rotational energy barrier. Bolded moieties exist orthogonally above the plane of the page, and dashed moieties exist orthogonally below the plane of the page. The 'flat' part of the molecule (the left ring in each of the two depicted biaryls) is in the plane of the page.

In certain aspects, the present disclosure provides at least 90% epimeric excess of an atropisomer selected from:

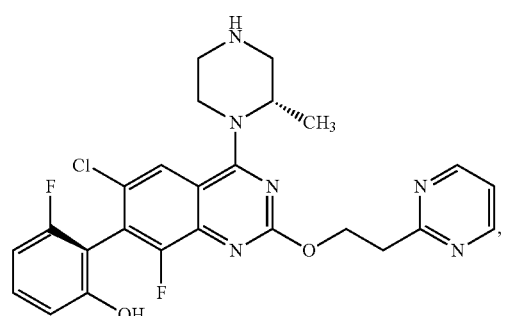

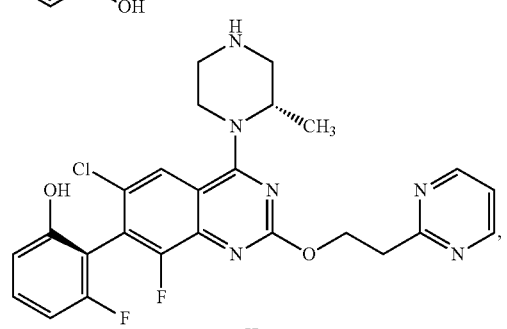

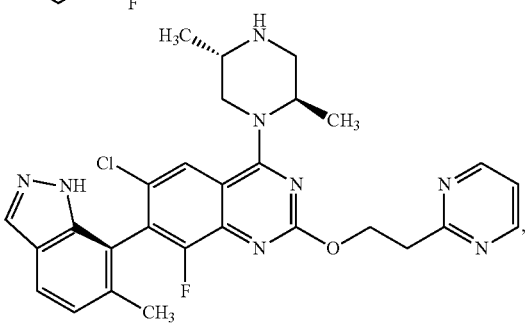

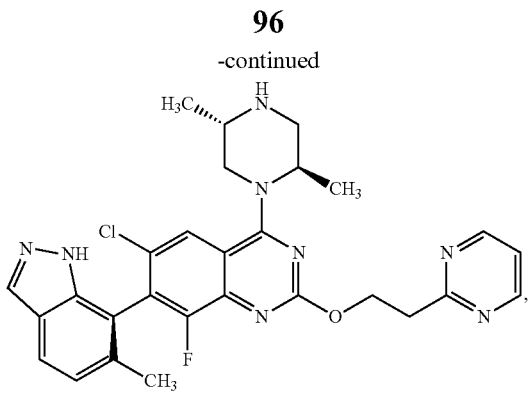

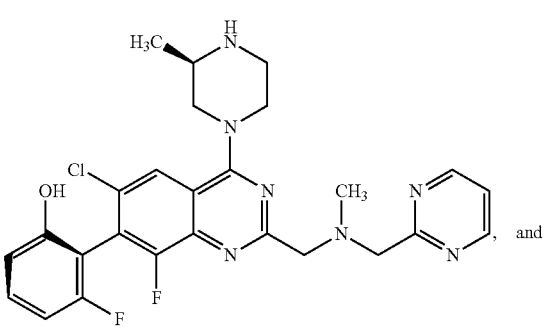

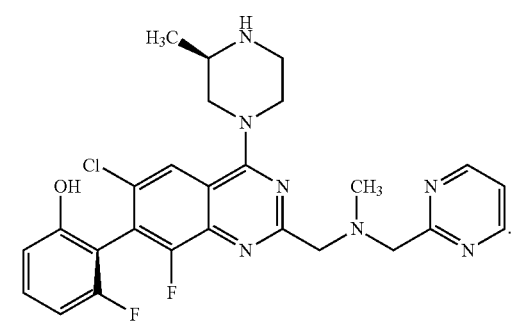

In certain aspects, the present disclosure provides at least 90% enantiomeric excess of an atropisomer selected from:

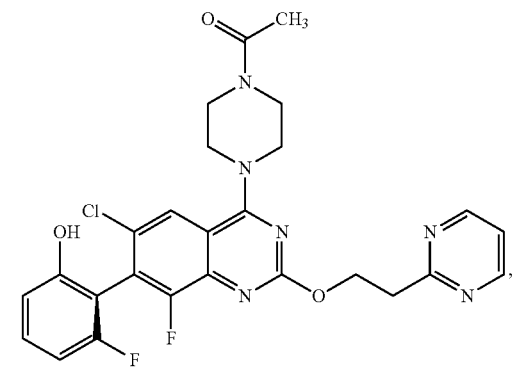

97

-continued

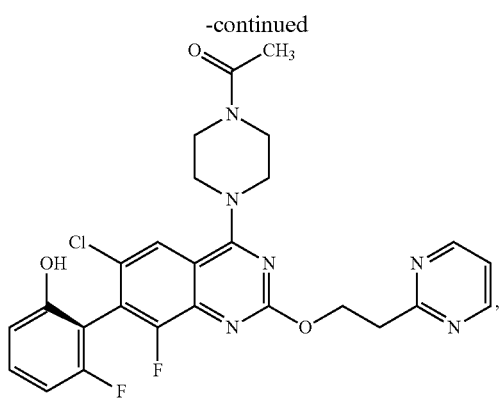

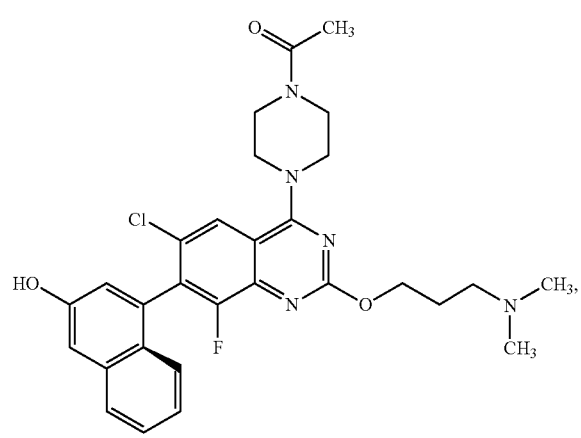

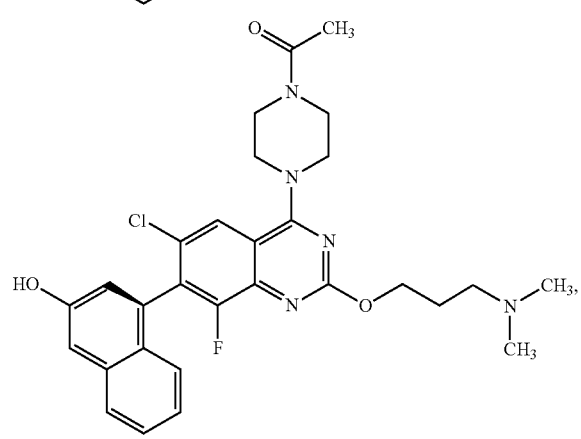

98

-continued

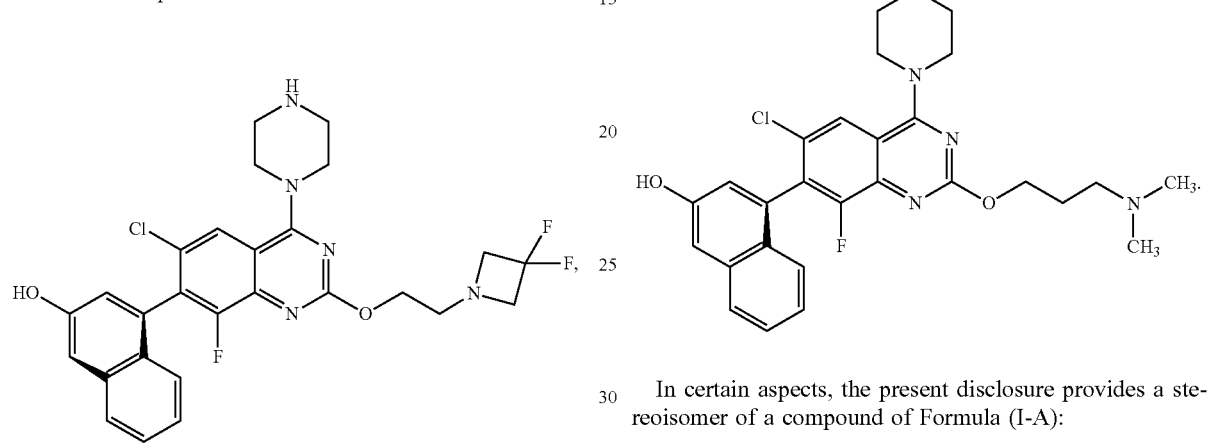

In certain aspects, the present disclosure provides a stereoisomer of a compound of Formula (I-A):

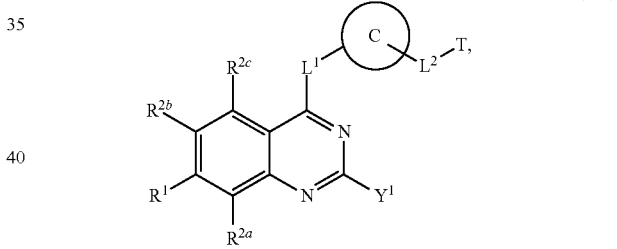

(I-A)

or a salt thereof, wherein:

$R^1$ is selected from $C_{3-12}$ carbocycle and 3- to 12-membered heterocycle, each of which is substituted with one or more substituents independently selected from halogen, —OH, —OR$^{52}$, —NH$_2$, —NHMe, —NMe$_2$, $C_{1-3}$ alkyl, $C_{1-3}$ haloalkyl, $C_{3-12}$ carbocycle and 3- to 12-membered heterocycle;

$R^{2a}$ and $R^{2b}$ are each independently selected from hydrogen, halogen, —OH, —OR$^{52}$, $C_{1-4}$ alkyl, and $C_{1-4}$ haloalkyl, wherein at least one of $R^{2a}$ and $R^{2b}$ is not hydrogen;

$R^{2c}$ is selected from hydrogen, halogen, —OH, —OR$^{52}$, $C_{1-4}$ alkyl, and $C_{1-4}$ haloalkyl; and $Y^1$ is selected from —OR$^{55}$; and $C_{1-10}$ alkyl, $C_{2-10}$ alkenyl and $C_{2-10}$ alkynyl, each of which is substituted with —OR$^{55}$ and optionally futher substituted with one or more R$^{50}$;

$L^1$ is selected from bond, —O—, —S—, —N(R$^{51}$)—, —N(R$^{51}$)CH$_2$—, —C(O)—, —C(O)O—, —OC(O)—, —OC(O)O—, —C(O)N(R$^{51}$)—, —C(O)N(R$^{51}$)C(O)—, —C(O)N(R$^{51}$)C(O)N(R$^{51}$)—, —N(R$^{51}$)C(O)—, —N(R$^{51}$)C(O)N(R$^{51}$)—, —N(R$^{51}$)C(O)O—, —OC(O)N(R$^{51}$)—, —C(NR$^{51}$)—, —N(R$^{51}$)C(NR$^{51}$)—, —C(NR$^{51}$)N(R$^{51}$)—, —N(R$^{51}$)C(NR$^{51}$)N(R$^{51}$)—, —S(O)$_2$—, —OS(O)—, —S(O)O—, —S(O)—, —OS(O)$_2$—, —S(O)$_2$O—, —N(R$^{51}$)S(O)$_2$—, —S(O)$_2$N(R$^{51}$)—, —N(R$^{51}$)S(O)—, —S(O)N(R$^{51}$)—, —N(R$^{51}$)S(O)$_2$N(R$^{51}$)—, —N(R$^{51}$)S(O)N(R$^{51}$)—; alkylene, alkenylene, alkynylene, heteroalkylene, heteroalkenylene, and heteroalkynylene, each of which is optionally substituted with one or more R$^{50}$;

L$^2$ is selected from bond and alkylene;

C is selected from 3- to 12-membered heterocycle, optionally substituted with one or more R$^{57}$;

T is hydrogen or a polar group capable of forming a complex with a Ras protein via an interaction other than one resulting in a covalent bond with the cysteine residue at position 12 of a K-Ras, H-Ras or N-Ras G12C mutant protein;

R$^{50}$ is independently selected at each occurrence from: halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$);

C$_{1-10}$ alkyl, C$_{2-10}$ alkenyl, and C$_{2-10}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{3-12}$ carbocycle, and 3- to 12-membered heterocycle; and C$_{3-12}$ carbocycle and 3- to 12-membered heterocycle, wherein each C$_{3-12}$ carbocycle and 3- to 12-membered heterocycle in R$^{50}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl;

R$^{51}$ is independently selected at each occurrence from: hydrogen, —C(O)R$^{52}$, —C(O)OR$^{52}$, —C(O)N(R$^{52}$)$_2$, —C(O)NR$^{53}$R$^{54}$;

C$_{1-6}$ alkyl, C$_{2-6}$ alkenyl, and C$_{2-6}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{3-12}$ carbocycle and 3- to 12-membered heterocycle; and C$_{3-12}$ carbocycle and 3- to 12-membered heterocycle, wherein each C$_{3-12}$ carbocycle and 3- to 12-membered heterocycle in R$^{51}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl;

R$^{52}$ is independently selected at each occurrence from hydrogen; and C$_{1-20}$ alkyl, C$_{2-20}$ alkenyl, C$_{2-20}$ alkynyl, 2- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle;

R$^{53}$ and R$^{54}$ are taken together with the nitrogen atom to which they are attached to form a heterocycle, optionally substituted with one or more R$^{50}$;

R$^{55}$ is selected from:

C$_{1-10}$ alkyl, C$_{2-10}$ alkenyl, and C$_{2-10}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{3-12}$ carbocycle, and 3- to 12-membered heterocycle; and C$_{3-12}$ carbocycle and 3- to 12-membered heterocycle, wherein each C$_{3-12}$ carbocycle and 3- to 12-membered heterocycle in R$^{55}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl; and R$^{57}$ is independently selected at each occurrence from: halogen, —CN, —OH, —OMe, —NH$_2$, —NHC$_{1-6}$ alkyl, —N(C$_{1-6}$ alkyl)$_2$, —C(O)OH, —C(O)H, —C(O)C$_{1-6}$ alkyl, —NHC(O)C$_{1-6}$ alkyl, —N(C$_{1-6}$ alkyl)C(O)C$_{1-6}$ alkyl, —C(O)NH$_2$, —C(O)NH(C$_{1-6}$ alkyl), —C(O)N(C$_{1-6}$ alkyl)$_2$, =O, =N(OH); and C$_{1-10}$ alkyl, optionally substituted at each occurrence with one or more substituents selected from —CN, —OH, —NH$_2$, —OMe, —NH$_2$, —NHC$_{1-6}$ alkyl, —N(C$_{1-6}$ alkyl)$_2$, —C(O)OH, —C(O)H, —C(O)C$_{1-6}$ alkyl, —NHC(O)C$_{1-6}$ alkyl, —N(C$_{1-6}$ alkyl)C(O)C$_{1-6}$ alkyl, —C(O)NH$_2$, —C(O)NH(C$_{1-6}$ alkyl), —C(O)N(C$_{1-6}$ alkyl)$_2$, =O, and =N(OH).

In some embodiments, the stereoisomer of a compound of Formula (I-A) is provided in at least 20%, 30%, 40%, 50%, 55%, 60%, 65%, 70%, 75%, 80%, 85%, 88%, 90%, 91%, 92%, 93%, 94%, 95%, 96%, 97%, 98%, 99%, 99.5%, or 99.9%, enantiomeric excess. In some embodiments, the stereoisomer is provided in greater than 20%, 30%, 40%, 50%, 55%, 60%, 65%, 70%, 75%, 80%, 85%, 88%, 90%, 91%, 92%, 93%, 94%, 95%, 96%, 97%, 98%, 99%, 99.5%, or 99.9%, enantiomeric excess. In some embodiments, the stereoisomer is in greater than 95% enantiomeric excess, such as greater than 99% enantiomeric excess. In some embodiments, the stereoisomer of a compound of Formula (I-A) is an atropisomer.

In some embodiments, the stereoisomer of a compound of Formula (I-A) is provided in at least 20%, 30%, 40%, 50%, 55%, 60%, 65%, 70%, 75%, 80%, 85%, 88%, 90%, 91%, 92%, 93%, 94%, 95%, 96%, 97%, 98%, 99%, 99.5%, or 99.9%, diastereomeric excess. In some embodiments, the stereoisomer is provided in greater than 20%, 30%, 40%, 50%, 55%, 60%, 65%, 70%, 75%, 80%, 85%, 88%, 90%, 91%, 92%, 93%, 94%, 95%, 96%, 97%, 98%, 99%, 99.5%, or 99.9%, diastereomeric excess. In some embodiments, the stereoisomer is in greater than 95% diastereomeric excess, such as greater than 99% diastereomeric excess. In some embodiments, the stereoisomer of a compound of Formula (I-A) comprises an atropisomer.

In some embodiments, for a stereoisomer of a compound of Formula (I-A), R$^1$ is selected from:

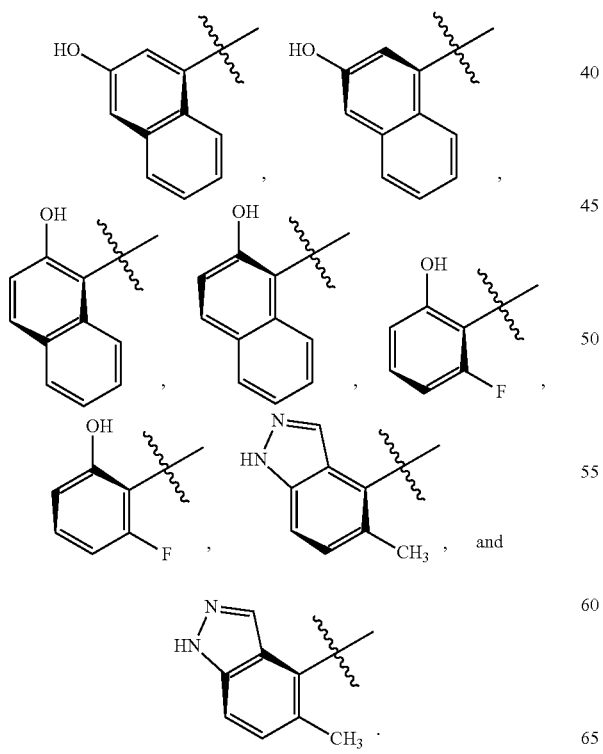

In some embodiments, R$^1$ is selected from:

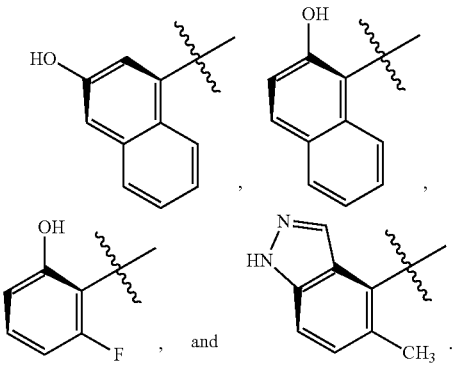

In some embodiments, R$^{2a}$ and R$^{2b}$ are each independently selected from halogen. In some embodiments, R$^1$, R$^{2a}$ and R$^{2b}$ are selected to produce an atropisomer.

In some embodiments, for a stereoisomer of a compound of Formula (I-A), R$^1$ is selected from:

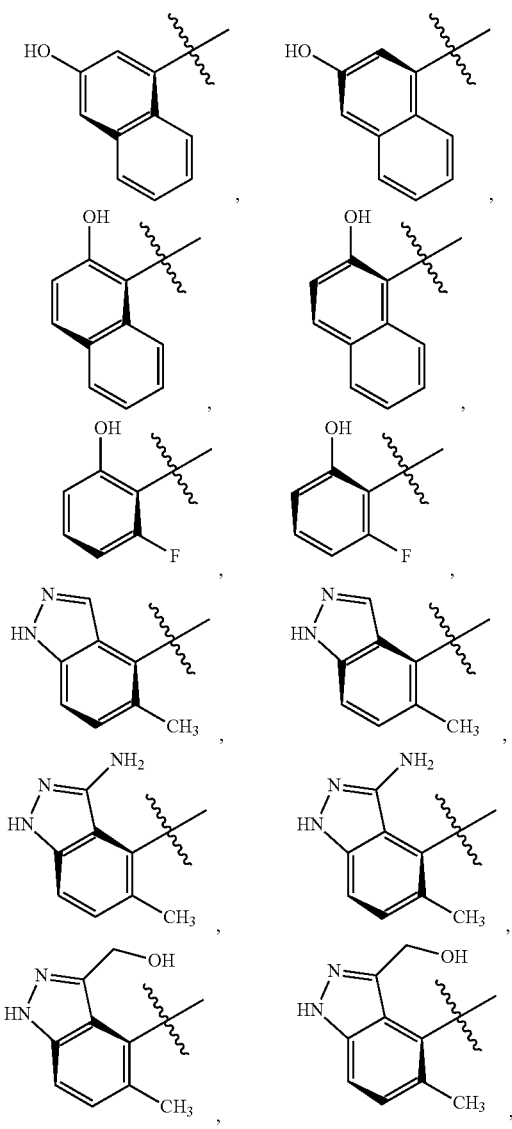

-continued

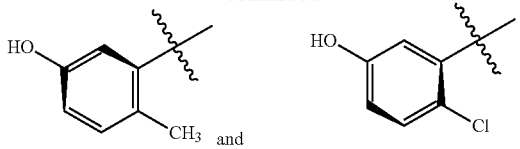
and

Any combination of the groups described above for the various variables of a compound of Formula (I-A) is contemplated herein for the stereoisomer of a compound of Formula (I-A).

In certain aspects, the present disclosure provides a stereoisomer of a compound of Formula (II-A):

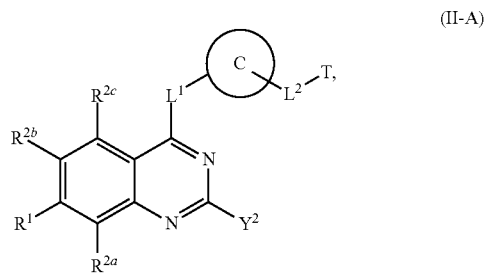

(II-A)

or a salt thereof, wherein:

$R^1$ is selected from $C_{3-12}$ carbocycle and 3- to 12-membered heterocycle, each of which is substituted with one or more substituents independently selected from halogen, —OH, —OR$^{52}$, —NH$_2$, —NHMe, —NMe$_2$, $C_{1-3}$ haloalkyl, $C_{3-12}$ carbocycle and 3- to 12-membered heterocycle;

$R^{2a}$ and $R^{2b}$ are each independently selected from hydrogen, halogen, —OH, —OR$^{52}$, $C_{1-4}$ alkyl, and $C_{1-4}$ haloalkyl, wherein at least one of $R^{2a}$ and $R^{2b}$ is not hydrogen;

$R^{2c}$ is selected from hydrogen, halogen, —OH, —OR$^{52}$, $C_{1-4}$ alkyl, and $C_{1-4}$ haloalkyl; and $Y^2$ is selected from —N(R$^{56}$)$_2$; and $C_{1-10}$ alkyl, $C_{2-10}$ alkenyl and $C_{2-10}$ alkynyl, each of which is substituted with —N(R$^{56}$)$_2$ and optionally futher substituted with one or more R$^{50}$;

$L^1$ is selected from bond, —O—, —S—, —N(R$^{51}$)—, —N(R$^{51}$)CH$_2$—, —C(O)—, —C(O)O—, —OC(O)—, —OC(O)O—, —C(O)N(R$^{51}$)—, —C(O)N(R$^{51}$)C(O)—, —C(O)N(R$^{51}$)C(O)N(R$^{51}$)—, —N(R$^{51}$)C(O)—, —N(R$^{51}$)C(O)N(R$^{51}$)—, —N(R$^{51}$)C(O)O—, —OC(O)N(R$^{51}$)—, —C(NR$^{51}$)—, —N(R$^{51}$)C(NR$^{51}$)—, —C(NR$^{51}$)N(R$^{51}$)—, —N(R$^{51}$)C(NR$^{51}$)N(R$^{51}$)—, —S(O)$_2$—, —OS(O)—, —S(O)O—, —S(O)—, —OS(O)$_2$—, —S(O)$_2$O—, —N(R$^{51}$)S(O)$_2$—, —S(O)$_2$N(R$^{51}$)—, —N(R$^{51}$)S(O)—, —S(O)N(R$^{51}$)—, —N(R$^{51}$)S(O)$_2$N(R$^{51}$)—, —N(R$^{51}$)S(O)N(R$^{51}$)—; alkylene, alkenylene, alkynylene, heteroalkylene, heteroalkenylene, and heteroalkynylene, each of which is optionally substituted with one or more R$^{50}$;

$L^2$ is selected from bond and alkylene;

C is selected from 3- to 12-membered heterocycle, optionally substituted with one or more R$^{57}$;

T is hydrogen or a polar group capable of forming a complex with a Ras protein via an interaction other than one resulting in a covalent bond with the cysteine residue at position 12 of a K-Ras, H-Ras or N-Ras G12C mutant protein;

$R^{50}$ is independently selected at each occurrence from: halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$);

$C_{1-10}$ alkyl, $C_{2-10}$ alkenyl, and $C_{2-10}$ alkynyl, each of which is independently optionally substituted at each occurrence with one or more substituents selected from halogen, —NO$_2$, —CN, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in R$^{50}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), $C_{1-6}$ alkyl, $C_{1-6}$ haloalkyl, $C_{2-6}$ alkenyl, and $C_{2-6}$ alkynyl;

$R^{51}$ is independently selected at each occurrence from: hydrogen, —C(O)R$^{52}$, —C(O)OR$^{52}$, —C(O)N(R$^{52}$)$_2$, —C(O)NR$^{53}$R$^{54}$;

$C_{1-6}$ alkyl, $C_{2-6}$ alkenyl, and $C_{2-6}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), $C_{3-12}$ carbocycle and 3- to 12-membered heterocycle; and $C_{3-12}$ carbocycle and 3- to 12-membered heterocycle, wherein each $C_{3-12}$ carbocycle and 3- to 12-membered heterocycle in R$^{51}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)

$NR^{53}R^{54}$, $-P(O)(OR^{52})_2$, $-P(O)(R^{52})_2$, =O, =S, =N($R^{52}$), $C_{1-6}$ alkyl, $C_{1-6}$ haloalkyl, $C_{2-6}$ alkenyl, and $C_{2-6}$ alkynyl;

$R^{52}$ is independently selected at each occurrence from hydrogen; and $C_{1-20}$ alkyl, $C_{2-20}$ alkenyl, $C_{2-20}$ alkynyl, 2- to 6-membered heteroalkyl, $C_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, $C_{3-12}$ carbocycle, or 3- to 6-membered heterocycle;

$R^{53}$ and $R^{54}$ are taken together with the nitrogen atom to which they are attached to form a heterocycle, optionally substituted with one or more $R^{50}$;

$R^{56}$ is independently selected at each occurrence from: hydrogen;

$C_{1-10}$ alkyl, $C_{2-10}$ alkenyl, and $C_{2-10}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^{56}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), $C_{1-6}$ alkyl, $C_{1-6}$ haloalkyl, $C_{2-6}$ alkenyl, and $C_{2-6}$ alkynyl; and $R^{57}$ is independently selected at each occurrence from: halogen, —CN, —OH, —OMe, —NH$_2$, —NHC$_{1-6}$ alkyl, —N(C$_{1-6}$ alkyl)$_2$, —C(O)OH, —C(O)H, —C(O)C$_{1-6}$ alkyl, —NHC(O)C$_{1-6}$ alkyl, —N(C$_{1-6}$ alkyl)C(O)C$_{1-6}$ alkyl, —C(O)NH$_2$, —C(O)NH(C$_{1-6}$ alkyl), —C(O)N(C$_{1-6}$ alkyl)$_2$, =O, =N(OH); and $C_{1-10}$ alkyl, optionally substituted at each occurrence with one or more substituents selected from —CN, —OH, —NH$_2$, —OMe, —NH$_2$, —NHC$_{1-6}$ alkyl, —N(C$_{1-6}$ alkyl)$_2$, —C(O)OH, —C(O)H, —C(O)C$_{1-6}$ alkyl, —NHC(O)C$_{1-6}$ alkyl, —N(C$_{1-6}$ alkyl)C(O)C$_{1-6}$ alkyl, —C(O)NH$_2$, —C(O)NH(C$_{1-6}$ alkyl), —C(O)N(C$_{1-6}$ alkyl)$_2$, =O, and =N(OH).

In some embodiments, the stereoisomer of a compound of Formula (II-A) is provided in at least 20%, 30%, 40%, 50%, 55%, 60%, 65%, 70%, 75%, 80%, 85%, 88%, 90%, 91%, 92%, 93%, 94%, 95%, 96%, 97%, 98%, 99%, 99.5%, or 99.9%, enantiomeric excess. In some embodiments, the stereoisomer is provided in greater than 20%, 30%, 40%, 50%, 55%, 60%, 65%, 70%, 75%, 80%, 85%, 88%, 90%, 91%, 92%, 93%, 94%, 95%, 96%, 97%, 98%, 99%, 99.5%, or 99.9%, enantiomeric excess. In some embodiments, the stereoisomer is in greater than 95% enantiomeric excess, such as greater than 99% enantiomeric excess. In some embodiments, the stereoisomer of a compound of Formula (II-A) is an atropisomer.

In some embodiments, the stereoisomer of a compound of Formula (II-A) is provided in at least 20%, 30%, 40%, 50%, 55%, 60%, 65%, 70%, 75%, 80%, 85%, 88%, 90%, 91%, 92%, 93%, 94%, 95%, 96%, 97%, 98%, 99%, 99.5%, or 99.9%, diastereomeric excess. In some embodiments, the stereoisomer is provided in greater than 20%, 30%, 40%, 50%, 55%, 60%, 65%, 70%, 75%, 80%, 85%, 88%, 90%, 91%, 92%, 93%, 94%, 95%, 96%, 97%, 98%, 99%, 99.5%, or 99.9%, diastereomeric excess. In some embodiments, the stereoisomer is in greater than 95% diastereomeric excess, such as greater than 99% diastereomeric excess. In some embodiments, the stereoisomer of a compound of Formula (II-A) comprises an atropisomer.

In some embodiments, for a stereoisomer of a compound of Formula (II-A), $R^1$ is selected from:

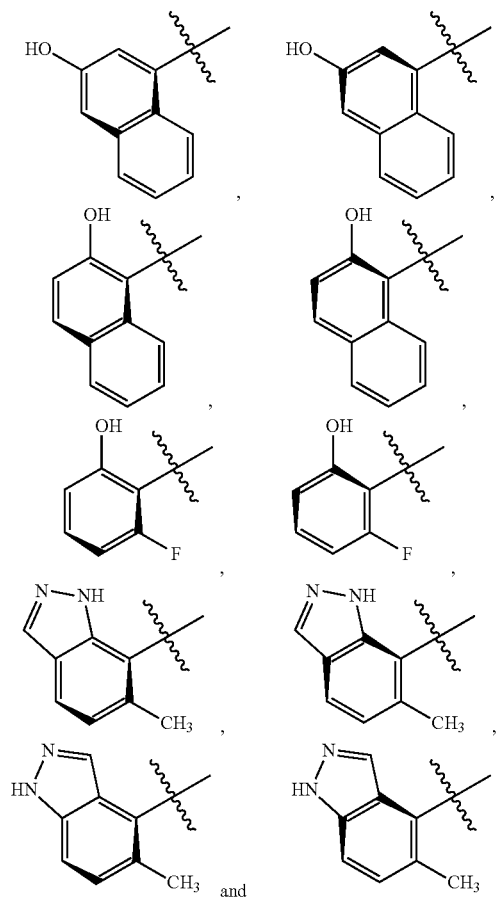

In some embodiments, $R^1$ is selected from:

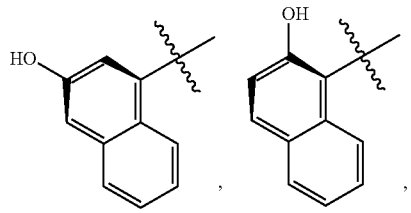

107

-continued

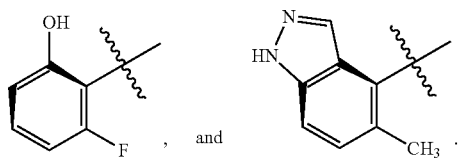

In some embodiments, $R^{2a}$ and $R^{2b}$ are each independently selected from halogen. In some embodiments, $R^1$, $R^{2a}$ and $R^{2b}$ are selected to produce an atropisomer.

In some embodiments, for a stereoisomer of a compound of Formula (II-A), $R^1$ is selected from:

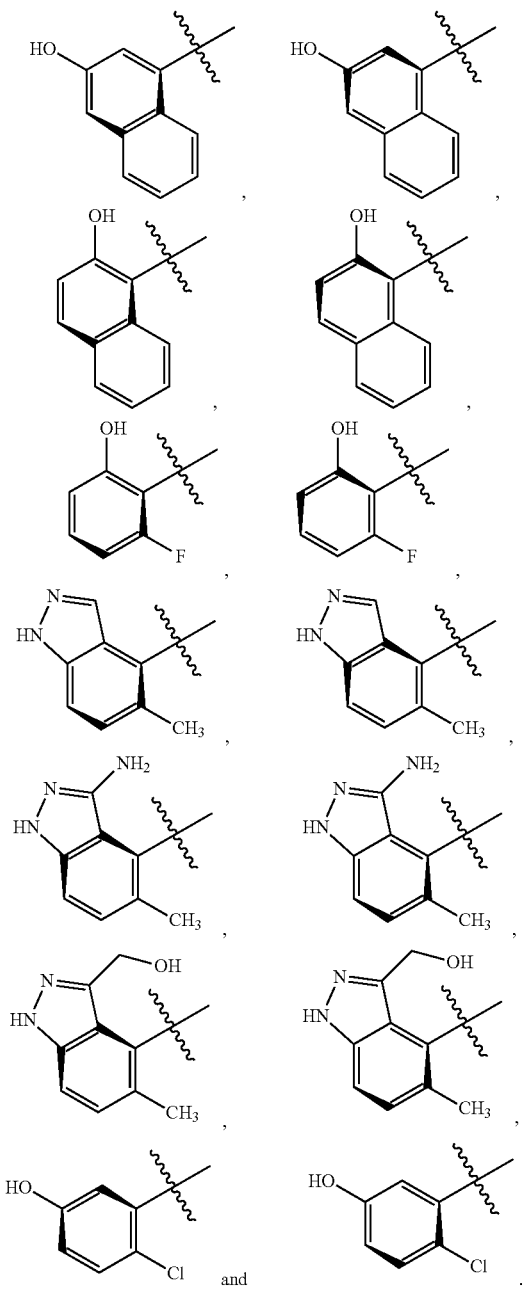

108

Any combination of the groups described above for the various variables of a compound of Formula (II-A) is contemplated herein for the stereoisomer of a compound of Formula (II-A).

In certain aspects, the present disclosure provides a stereoisomer of a compound of Formula (III-A):

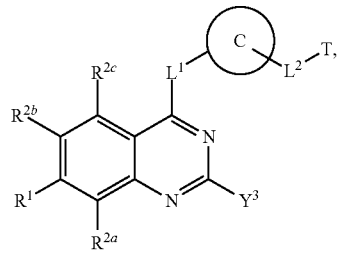

(III-A)

or a salt or prodrug thereof, wherein:

$R^1$ is selected from $C_{3-12}$ carbocycle and 3- to 12-membered heterocycle, each of which is substituted with one or more substituents independently selected from halogen, —OH, —OR$^{52}$, —NH$_2$, —NHMe, —NMe$_2$, $C_{1-3}$ alkyl, $C_{1-3}$ haloalkyl, $C_{3-12}$ carbocycle and 3- to 12-membered heterocycle;

$R^{2a}$ and $R^{2b}$ are each independently selected from hydrogen, halogen, —OH, —OR$^{52}$, $C_{1-4}$ alkyl, and $C_{1-4}$ haloalkyl, wherein at least one of $R^{2a}$ and $R^{2b}$ is not hydrogen;

$R^{2c}$ is selected from hydrogen, halogen, —OH, —OR$^{52}$, $C_{1-4}$ alkyl, and $C_{1-4}$ haloalkyl; and $Y^3$ is selected from —OR$^{55}$, —N(R$^{56}$)$_2$; and $C_{1-10}$ alkyl, $C_{2-10}$ alkenyl and $C_{2-10}$ alkynyl, each of which is substituted with —OR$^{55}$ or —N(R$^{56}$)$_2$ and optionally futher substituted with one or more R$^{50}$;

$L^1$ is selected from bond, —O—, —S—, —N(R$^{51}$)—, —N(R$^{51}$)CH$_2$—, —C(O)—, —C(O)O—, —OC(O)—, —OC(O)O—, —C(O)N(R$^{51}$)—, —C(O)N(R$^{51}$)C(O)—, —C(O)N(R$^{51}$)C(O)N(R$^{51}$)—, —N(R$^{51}$)C(O)—, —N(R$^{51}$)C(O)N(R$^{51}$)—, —N(R$^{51}$)C(O)O—, —OC(O)N(R$^{51}$)—, —C(NR$^{51}$)—, —N(R$^{51}$)C(NR$^{51}$)—, —C(NR$^{51}$)N(R$^{51}$)—, —N(R$^{51}$)C(NR$^{51}$)N(R$^{51}$)—, —S(O)$_2$—, —OS(O)—, —S(O)O—, —S(O)—, —OS(O)$_2$—, —S(O)$_2$O—, —N(R$^{51}$)S(O)$_2$—, —S(O)$_2$N(R$^{51}$)—, —N(R$^{51}$)S(O)—, —S(O)N(R$^{51}$)—, —N(R$^{51}$)S(O)$_2$N(R$^{51}$)—, —N(R$^{51}$)S(O)N(R$^{51}$)—; alkylene, alkenylene, alkynylene, heteroalkylene, heteroalkenylene, and heteroalkynylene, each of which is optionally substituted with one or more R$^{50}$;

$L^2$ is selected from bond and alkylene;

C is selected from 3- to 12-membered heterocycle, optionally substituted with one or more R$^{57}$;

T is hydrogen or a polar group capable of forming a complex with a Ras protein via an interaction other than one resulting in a covalent bond with the cysteine residue at position 12 of a K-Ras, H-Ras or N-Ras G12C mutant protein;

$R^{50}$ is independently selected at each occurrence from: halogen, —NO$_2$, —CN, —OR$^{52}$, —SR$^{52}$, —N(R$^{52}$)$_2$, —NR$^{53}$R$^{54}$, —S(═O)R$^{52}$, —S(═O)$_2$R$^{52}$, —S(═O)$_2$N(R$^{52}$)$_2$, —S(═O)$_2$NR$^{53}$R$^{54}$, —NR$^{52}$S(═O)$_2$R$^{52}$, —NR$^{52}$S(═O)$_2$N(R$^{52}$)$_2$, —NR$^{52}$S(═O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$);

C$_{1-10}$ alkyl, C$_{2-10}$ alkenyl, and C$_{2-10}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{3-12}$ carbocycle, and 3- to 12-membered heterocycle; and C$_{3-12}$ carbocycle and 3- to 12-membered heterocycle, wherein each C$_{3-12}$ carbocycle and 3- to 12-membered heterocycle in R$^{50}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl;

R$^{51}$ is independently selected at each occurrence from: hydrogen, —C(O)R$^{52}$, —C(O)OR$^{52}$, —C(O)N(R$^{52}$)$_2$, —C(O)NR$^{53}$R$^{54}$;

C$_{1-6}$ alkyl, C$_{2-6}$ alkenyl, and C$_{2-6}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{3-12}$ carbocycle and 3- to 12-membered heterocycle; and C$_{3-12}$ carbocycle and 3- to 12-membered heterocycle, wherein each C$_{3-12}$ carbocycle and 3- to 12-membered heterocycle in R$^{51}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl;

R$^{52}$ is independently selected at each occurrence from hydrogen; and C$_{1-20}$ alkyl, C$_{2-20}$ alkenyl, C$_{2-20}$ alkynyl, 2- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle;

R$^{53}$ and R$^{54}$ are taken together with the nitrogen atom to which they are attached to form a heterocycle, optionally substituted with one or more R$^{50}$;

R$^{55}$ is selected from:

C$_{1-10}$ alkyl, C$_{2-10}$ alkenyl, and C$_{2-10}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{3-12}$ carbocycle, and 3- to 12-membered heterocycle; and C$_{3-12}$ carbocycle and 3- to 12-membered heterocycle, wherein each C$_{3-12}$ carbocycle and 3- to 12-membered heterocycle in R$^{55}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl;

R$^{56}$ is independently selected at each occurrence from: hydrogen;

C$_{1-10}$ alkyl, C$_{2-10}$ alkenyl, and C$_{2-10}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{3-12}$ carbocycle, and 3- to 12-membered heterocycle; and C$_{3-12}$ carbocycle and 3- to 12-membered heterocycle, wherein each C$_{3-12}$ carbocycle and 3- to 12-membered heterocycle in R$^{56}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)

$NR^{53}R^{54}$, $-P(O)(OR^{52})_2$, $-P(O)(R^{52})_2$, $=O$, $=S$, $=N(R^{52})$, $C_{1-6}$ alkyl, $C_{1-6}$ haloalkyl, $C_{2-6}$ alkenyl, and $C_{2-6}$ alkynyl, or two $R^{56}$ groups are taken together with the nitrogen atom to which they are attached to form a heterocycle, optionally substituted with one or more $R^{50}$; and $R^{57}$ is independently selected at each occurrence from:
halogen, $-CN$, $-OH$, $-OMe$, $-NH_2$, $-NHC_{1-6}$ alkyl, $-N(C_{1-6}$ alkyl$)_2$, $-C(O)OH$, $-C(O)H$, $-C(O)C_{1-6}$ alkyl, $-NHC(O)C_{1-6}$ alkyl, $-N(C_{1-6}$ alkyl$)C(O)C_{1-6}$ alkyl, $-C(O)NH_2$, $-C(O)NH(C_{1-6}$ alkyl), $-C(O)N(C_{1-6}$ alkyl$)_2$, $=O$, $=N(OH)$; and $C_{1-10}$ alkyl, optionally substituted at each occurrence with one or more substituents selected from $-CN$, $-OH$, $-NH_2$, $-OMe$, $-NH_2$, $-NHC_{1-6}$ alkyl, $-N(C_{1-6}$ alkyl$)_2$, $-C(O)OH$, $-C(O)H$, $-C(O)C_{1-6}$ alkyl, $-NHC(O)C_{1-6}$ alkyl, $-N(C_{1-6}$ alkyl$)C(O)C_{1-6}$ alkyl, $-C(O)NH_2$, $-C(O)NH(C_{1-6}$ alkyl), $-C(O)N(C_{1-6}$ alkyl$)_2$, $=O$, and $=N(OH)$.

In some embodiments, the stereoisomer of a compound of Formula (III-A) is provided in at least 20%, 30%, 40%, 50%, 55%, 60%, 65%, 70%, 75%, 80%, 85%, 88%, 90%, 91%, 92%, 93%, 94%, 95%, 96%, 97%, 98%, 99%, 99.5%, or 99.9%, enantiomeric excess. In some embodiments, the stereoisomer is provided in greater than 20%, 30%, 40%, 50%, 55%, 60%, 65%, 70%, 75%, 80%, 85%, 88%, 90%, 91%, 92%, 93%, 94%, 95%, 96%, 97%, 98%, 99%, 99.5%, or 99.9%, enantiomeric excess. In some embodiments, the stereoisomer is in greater than 95% enantiomeric excess, such as greater than 99% enantiomeric excess. In some embodiments, the stereoisomer of a compound of Formula (III-A) is an atropisomer.

In some embodiments, the stereoisomer of a compound of Formula (III-A) is provided in at least 20%, 30%, 40%, 50%, 55%, 60%, 65%, 70%, 75%, 80%, 85%, 88%, 90%, 91%, 92%, 93%, 94%, 95%, 96%, 97%, 98%, 99%, 99.5%, or 99.9%, diastereomeric excess. In some embodiments, the stereoisomer is provided in greater than 20%, 30%, 40%, 50%, 55%, 60%, 65%, 70%, 75%, 80%, 85%, 88%, 90%, 91%, 92%, 93%, 94%, 95%, 96%, 97%, 98%, 99%, 99.5%, or 99.9%, diastereomeric excess. In some embodiments, the stereoisomer is in greater than 95% diastereomeric excess, such as greater than 99% diastereomeric excess. In some embodiments, the stereoisomer of a compound of Formula (III-A) comprises an atropisomer.

In some embodiments, for a stereoisomer of a compound of Formula (III-A), $R^1$ is selected from:

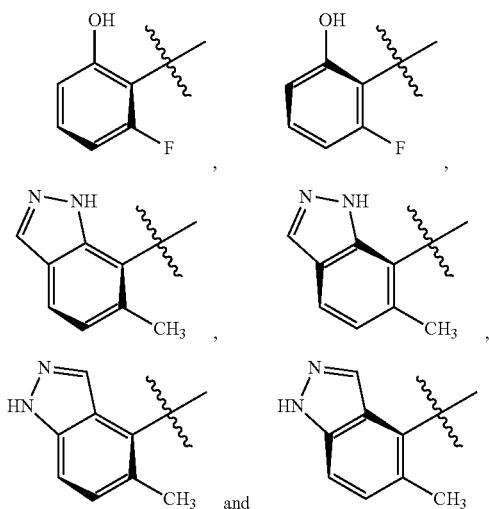

In some embodiments, $R^1$ is selected from:

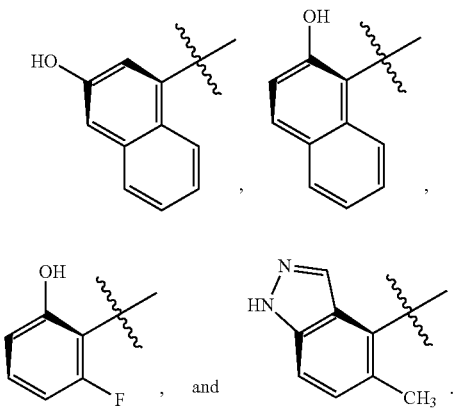

In some embodiments, $R^{2a}$ and $R^{2b}$ are each independently selected from halogen. In some embodiments, $R^1$, $R^{2a}$ and $R^{2b}$ are selected to produce an atropisomer.

In some embodiments, for a stereoisomer of a compound of Formula (III-A), $R^1$ is selected from:

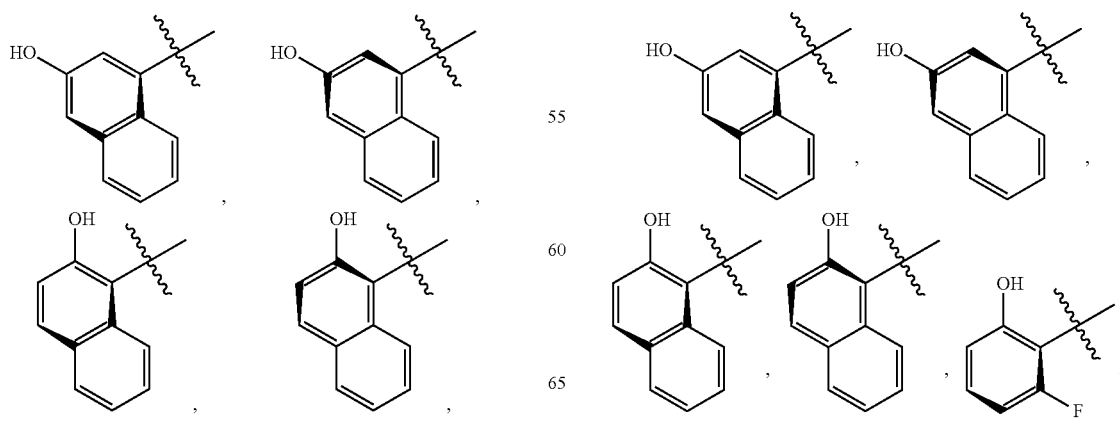

-continued

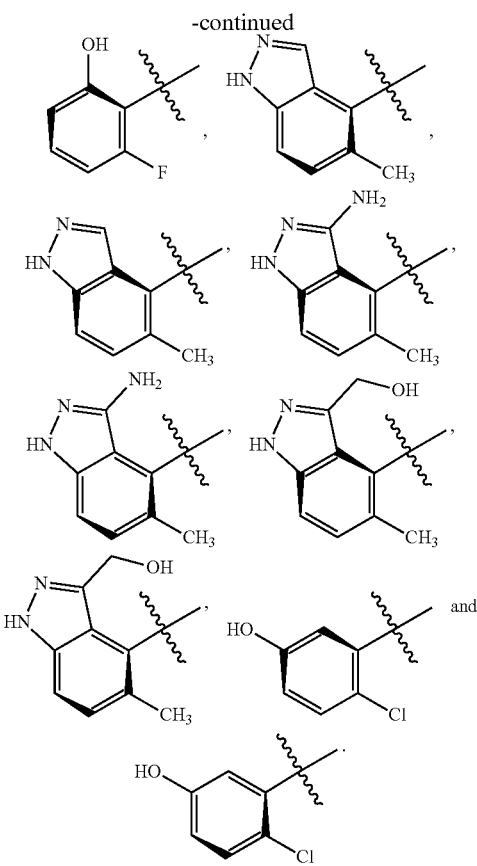

Any combination of the groups described above for the various variables of a compound of Formulas (I-A) or (II-A) is contemplated herein for the stereoisomer of a compound of Formula (III-A).

In certain aspects, the present disclosure provides a stereoisomer of a compound or salt of Formula (III-A), wherein:

$R^1$ is

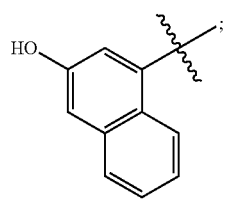 [SMILES: *c1cc(O)cc2ccccc12]

$R^{2a}$ and $R^{2b}$ are each independently selected from halogen; $R^{2c}$ is hydrogen;

$Y^3$ is selected from —OR$^{55}$ and

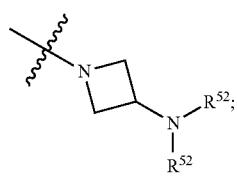

$L^1$ is a bond; $L^2$ is a bond;
C is selected from

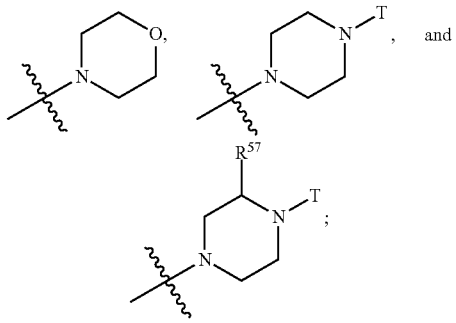

T is selected from hydrogen; and $C_{1-6}$ alkyl, optionally substituted with =O;

$R^{52}$ is independently selected at each occurrence from hydrogen and halogen; and $C_{1-20}$ alkyl, $C_{2-20}$ alkenyl, $C_{2-20}$ alkynyl, 2- to 6-membered heteroalkyl, $C_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, $C_{3-12}$ carbocycle, or 3- to 6-membered heterocycle; and $R^{57}$ is independently selected at each occurrence from: halogen, —CN, —OH, —OMe, —NH$_2$, —NHC$_{1-6}$ alkyl, —N(C$_{1-6}$ alkyl)$_2$, —C(O)OH, —C(O)H, —C(O)C$_{1-6}$ alkyl, —NHC(O)C$_{1-6}$ alkyl, —N(C$_{1-6}$ alkyl)C(O)C$_{1-6}$ alkyl, —C(O)NH$_2$, —C(O)NH(C$_{1-6}$ alkyl), —C(O)N(C$_{1-6}$ alkyl)$_2$, =O, =N(OH); and $C_{1-10}$ alkyl, optionally substituted at each occurrence with one or more substituents selected from —CN, —OH, —NH$_2$, —OMe, —NH$_2$, —NHC$_{1-6}$ alkyl, —N(C$_{1-6}$ alkyl)$_2$, —C(O)OH, —C(O)H, —C(O)C$_{1-6}$ alkyl, —NHC(O)C$_{1-6}$ alkyl, —N(C$_{1-6}$ alkyl)C(O)C$_{1-6}$ alkyl, —C(O)NH$_2$, —C(O)NH(C$_{1-6}$ alkyl), —C(O)N(C$_{1-6}$ alkyl)$_2$, =O, and =N(OH).

In certain aspects, the present disclosure provides a stereoisomer of a compound of Formula (III-A):

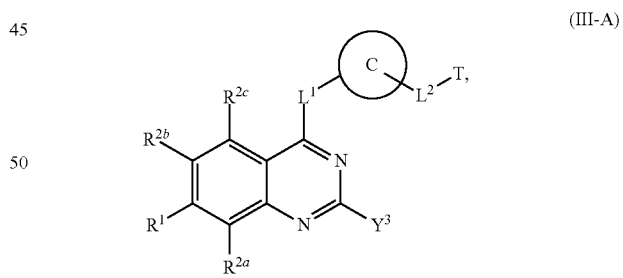

(III-A)

or a salt or prodrug thereof, wherein:

$R^1$ is selected from $C_{3-12}$ carbocycle and 3- to 12-membered heterocycle, each of which is substituted with one or more substituents independently selected from halogen, —OH, —OR$^{52}$, —NH$_2$, —NHMe, —NMe$_2$, $C_{1-3}$ alkyl, $C_{1-3}$ haloalkyl, $C_{3-12}$ carbocycle and 3- to 12-membered heterocycle;

$R^{2a}$ and $R^{2b}$ are each independently selected from hydrogen, halogen, —OH, —OR$^{52}$, $C_{1-4}$ alkyl, and $C_{1-4}$ haloalkyl, wherein at least one of $R^{2a}$ and $R^{2b}$ is not hydrogen;

$R^{2c}$ is selected from hydrogen, halogen, —OH, —OR$^{52}$, $C_{1-4}$ alkyl, and $C_{1-4}$ haloalkyl; and $Y^3$ is selected from $-OR^{55}$, $-N(R^{56})_2$, $-SR^{55}$ and $SO_2R^{55}$; and $C_{1-10}$ alkyl, $C_{2-10}$ alkenyl and $C_{2-10}$ alkynyl, each of which is substituted with $-OR^{55}$, $-N(R^{56})_2$, $-SR^{55}$ or $SO_2R^{55}$ and optionally futher substituted with one or more $R^{50}$;

$L^1$ is selected from bond, $-O-$, $-S-$, $-N(R^{51})-$, $-N(R^{51})CH_2-$, $-C(O)-$, $-C(O)O-$, $-OC(O)-$, $-OC(O)O-$, $-C(O)N(R^{51})-$, $-C(O)N(R^{51})C(O)-$, $-C(O)N(R^{51})C(O)N(R^{51})-$, $-N(R^{51})C(O)-$, $-N(R^{51})C(O)N(R^{51})-$, $-N(R^{51})C(O)O-$, $-OC(O)N(R^{51})-$, $-C(NR^{51})-$, $-N(R^{51})C(NR^{51})-$, $-C(NR^{51})N(R^{51})-$, $-N(R^{51})C(NR^{51})N(R^{51})-$, $-S(O)_2-$, $-OS(O)-$, $-S(O)O-$, $-S(O)-$, $-OS(O)_2-$, $-S(O)_2O-$, $-N(R^{51})S(O)_2-$, $-S(O)_2N(R^{51})-$, $-N(R^{51})S(O)-$, $-S(O)N(R^{51})-$, $-N(R^{51})S(O)_2N(R^{51})-$, $-N(R^{51})S(O)N(R^{51})-$; alkylene, alkenylene, alkynylene, heteroalkylene, heteroalkenylene, and heteroalkynylene, each of which is optionally substituted with one or more $R^{50}$;

$L^2$ is selected from bond and alkylene;

C is selected from 3- to 12-membered heterocycle, optionally substituted with one or more $R^{57}$;

T is hydrogen or a polar group capable of forming a complex with a Ras protein via an interaction other than one resulting in a covalent bond with the cysteine residue at position 12 of a K-Ras, H-Ras or N-Ras G12C mutant protein;

$R^{50}$ is independently selected at each occurrence from: halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $=O$, $=S$, $=N(R^{52})$;

$C_{1-10}$ alkyl, $C_{2-10}$ alkenyl, and $C_{2-10}$ alkynyl, each of which is independently optionally substituted at each occurrence with one or more substituents selected from halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $=O$, $=S$, $=N(R^{52})$, $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^{50}$ is independently optionally substituted with one or more substituents selected from halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $=O$, $=S$, $=N(R^{52})$, $C_{1-6}$ alkyl, $C_{1-6}$ haloalkyl, $C_{2-6}$ alkenyl, and $C_{2-6}$ alkynyl;

$R^{51}$ is independently selected at each occurrence from: hydrogen, $-C(O)R^{52}$, $-C(O)OR^{52}$, $-C(O)N(R^{52})_2$, $-C(O)NR^{53}R^{54}$;

$C_{1-6}$ alkyl, $C_{2-6}$ alkenyl, and $C_{2-6}$ alkynyl, each of which is independently optionally substituted at each occurrence with one or more substituents selected from halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $=O$, $=S$, $=N(R^{52})$, $C_{3-12}$ carbocycle and 3- to 12-membered heterocycle; and $C_{3-12}$ carbocycle and 3- to 12-membered heterocycle, wherein each $C_{3-12}$ carbocycle and 3- to 12-membered heterocycle in $R^{51}$ is independently optionally substituted with one or more substituents selected from halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $=O$, $=S$, $=N(R^{52})$, $C_{1-6}$ alkyl, $C_{1-6}$ haloalkyl, $C_{2-6}$ alkenyl, and $C_{2-6}$ alkynyl;

$R^{52}$ is independently selected at each occurrence from hydrogen; and $C_{1-20}$ alkyl, $C_{2-20}$ alkenyl, $C_{2-20}$ alkynyl, 2- to 6-membered heteroalkyl, $C_{3-12}$ carbocycle, and 3- to 12-membered heterocycle, each of which is optionally substituted by halogen, $-CN$, $-NO_2$, $-NH_2$, $-NHCH_3$, $-NHCH_2CH_3$, $=O$, $-OH$, $-OCH_3$, $-OCH_2CH_3$, $C_{3-12}$ carbocycle, or 3- to 6-membered heterocycle;

$R^{53}$ and $R^{54}$ are taken together with the nitrogen atom to which they are attached to form a heterocycle, optionally substituted with one or more $R^{50}$;

$R^{55}$ is selected from:

$C_{1-10}$ alkyl, $C_{2-10}$ alkenyl, and $C_{2-10}$ alkynyl, each of which is independently optionally substituted at each occurrence with one or more substituents selected from halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, $-NR^{52}C(O)NR^{53}R^{54}$, $-C(O)N(R^{52})_2$, $-C(O)NR^{53}R^{54}$, $-P(O)(OR^{52})_2$, $-P(O)(R^{52})_2$, $=O$, $=S$, $=N(R^{52})$, $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^{55}$ is independently optionally substituted with one or more substituents selected from halogen, $-NO_2$, $-CN$, $-OR^{52}$, $-SR^{52}$, $-N(R^{52})_2$, $-NR^{53}R^{54}$, $-S(=O)R^{52}$, $-S(=O)_2R^{52}$, $-S(=O)_2N(R^{52})_2$, $-S(=O)_2NR^{53}R^{54}$, $-NR^{52}S(=O)_2R^{52}$, $-NR^{52}S(=O)_2N(R^{52})_2$, $-NR^{52}S(=O)_2NR^{53}R^{54}$, $-C(O)R^{52}$, $-C(O)OR^{52}$, $-OC(O)R^{52}$, $-OC(O)OR^{52}$, $-OC(O)N(R^{52})_2$, $-OC(O)NR^{53}R^{54}$, $-NR^{52}C(O)R^{52}$, $-NR^{52}C(O)OR^{52}$, $-NR^{52}C(O)N(R^{52})_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl;

R$^{56}$ is independently selected at each occurrence from: hydrogen;

C$_{1-10}$ alkyl, C$_{2-10}$ alkenyl, and C$_{2-10}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{3-12}$ carbocycle, and 3- to 12-membered heterocycle; and C$_{3-12}$ carbocycle and 3- to 12-membered heterocycle, wherein each C$_{3-12}$ carbocycle and 3- to 12-membered heterocycle in R$^{56}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), C$_{1-6}$ alkyl, C$_{1-6}$ haloalkyl, C$_{2-6}$ alkenyl, and C$_{2-6}$ alkynyl, or two R$^{56}$ groups are taken together with the nitrogen atom to which they are attached to form a heterocycle, optionally substituted with one or more R$^{50}$; and R$^{57}$ is independently selected at each occurrence from: halogen, —CN, —OH, —OMe, —NH$_2$, —NHC$_{1-6}$ alkyl, —N(C$_{1-6}$ alkyl)$_2$, —C(O)OH, —C(O)H, —C(O)C$_{1-6}$ alkyl, —NHC(O)C$_{1-6}$ alkyl, —N(C$_{1-6}$ alkyl)C(O)C$_{1-6}$ alkyl, —C(O)NH$_2$, —C(O)NH(C$_{1-6}$ alkyl), —C(O)N(C$_{1-6}$ alkyl)$_2$, =O, =N(OH); and C$_{1-10}$ alkyl, optionally substituted at each occurrence with one or more substituents selected from —CN, —OH, —NH$_2$, —OMe, —NH$_2$, —NHC$_{1-6}$ alkyl, —N(C$_{1-6}$ alkyl)$_2$, —C(O)OH, —C(O)H, —C(O)C$_{1-6}$ alkyl, —NHC(O)C$_{1-6}$ alkyl, —N(C$_{1-6}$ alkyl)C(O)C$_{1-6}$ alkyl, —C(O)NH$_2$, —C(O)NH(C$_{1-6}$ alkyl), —C(O)N(C$_{1-6}$ alkyl)$_2$, =O, and =N(OH).

In some embodiments, for a compound of Formula (I), (I-A), (I-B), (I-C), (II), (II-A), (II-B), (II-C) or (III-A), R$^{52}$ is further selected at each occurrence from halogen. For example, Y$^1$ may be OR$^{55}$, wherein R$^{55}$ is C$_{1-10}$ alkyl substituted with S(=O)$_2$R$^{52}$, wherein R$^{52}$ is halogen, such as fluorine.

In some embodiments, for a compound of Formula (I), (I-A), (I-B) or (I-C), Y$^1$ is selected from —OR$^{55}$, —SR$^{55}$ and SO$_2$R$^{55}$; and alkyl, alkenyl, alkynyl, C$_{3-12}$ carbocycle and 3- to 12-membered heterocycle, each of which is substituted with —OR$^{55}$, —SR$^{55}$ or SO$_2$R$^{55}$ and optionally futher substituted with one or more R$^{50}$. In some embodiments, for a compound of Formula (M-A), Y$^3$ is selected from —OR$^{55}$, —N(R$^{56}$)$_2$, —SR$^{55}$ and SO$_2$R$^{55}$; and C$_{1-10}$ alkyl, C$_{2-10}$ alkenyl and C$_{2-10}$ alkynyl, each of which is substituted with —OR$^{55}$, —N(R$^{56}$)$_2$, —SR$^{55}$ or SO$_2$R$^{55}$ and optionally futher substituted with one or more R$^{50}$.

The chemical entities described herein can be synthesized according to one or more illustrative schemes herein and/or techniques known in the art. Materials used herein are either commercially available or prepared by synthetic methods generally known in the art. These schemes are not limited to the compounds listed in the examples or by any particular substituents, which are employed for illustrative purposes. Although various steps are described and depicted in Schemes 1-3 and Examples 1-4, the steps in some cases may be performed in a different order than the order shown in Schemes 1-3 and Examples 1-4. Various modifications to these synthetic reaction schemes may be made and will be suggested to one skilled in the art having referred to the disclosure contained in this application. Numberings or R groups in each scheme do not necessarily correspond to that of the claims or other schemes or tables herein.

Unless specified to the contrary, the reactions described herein take place at atmospheric pressure, generally within a temperature range from –10° C. to 200° C. Further, except as otherwise specified, reaction times and conditions are intended to be approximate, e.g., taking place at about atmospheric pressure within a temperature range of about –10° C. to about 110° C. over a period of about 1 to about 24 hours; reactions left to run overnight average a period of about 16 hours.

In general, compounds of the disclosure may be prepared by the following reaction schemes:

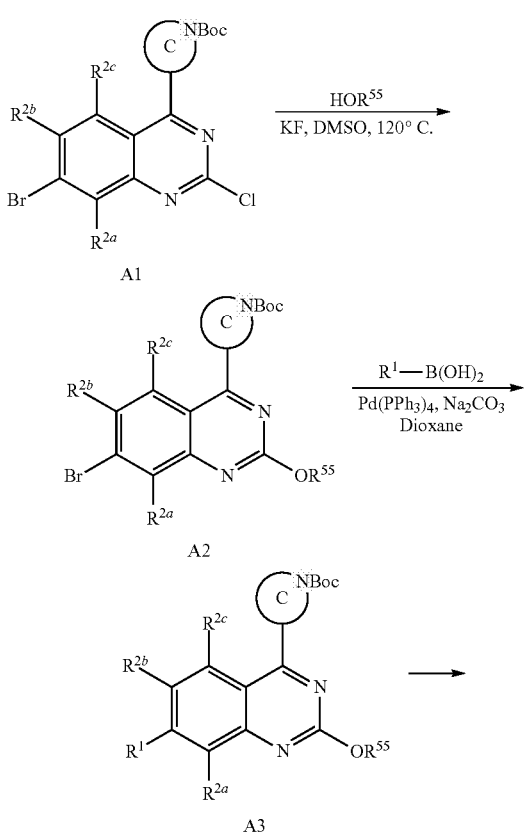

-continued

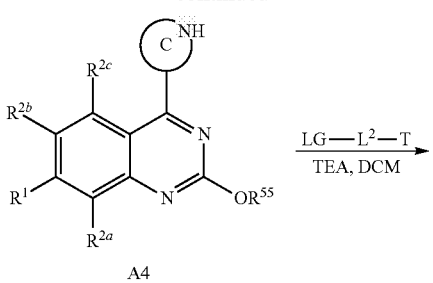

A4

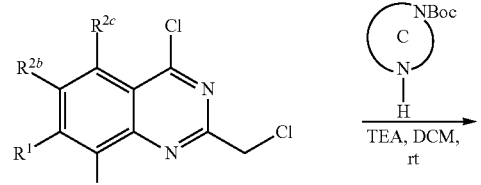

B4

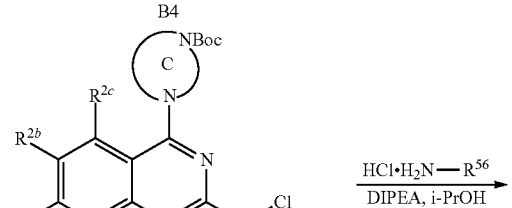

B5

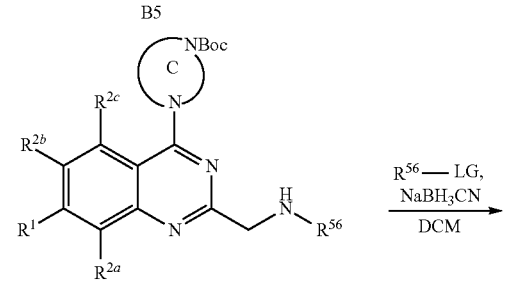

B6

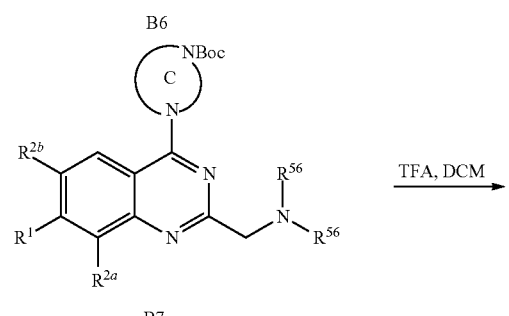

B7

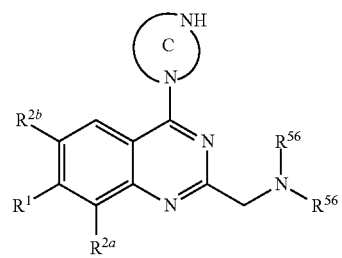

B8

A5

In some embodiments, a compound of Formula A5 may be prepared according to Scheme 1. For example, 2-chloroquinazoline A1 can be reacted with an appropriately substituted alcohol to provide ether A2. Installation of a desired $R^1$ substituent may proceed via a Suzuki reaction to give compound A3. Boc deprotection provides free amine A4, which can optionally be coupled to LG-$L^2$-T, where LG is a leaving group, to provide a compound of Formula A5. In some examples, T is an acyl group, and LG-$L^2$-T is an acyl chloride group.

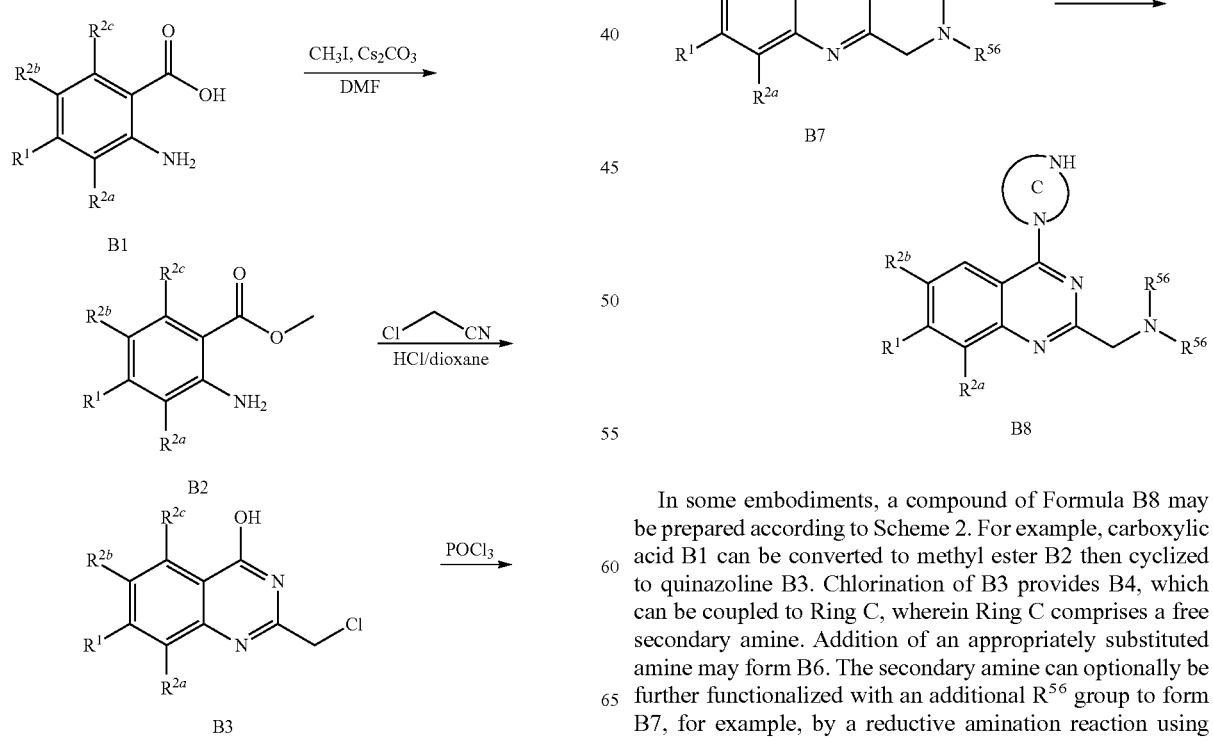

In some embodiments, a compound of Formula B8 may be prepared according to Scheme 2. For example, carboxylic acid B1 can be converted to methyl ester B2 then cyclized to quinazoline B3. Chlorination of B3 provides B4, which can be coupled to Ring C, wherein Ring C comprises a free secondary amine. Addition of an appropriately substituted amine may form B6. The secondary amine can optionally be further functionalized with an additional $R^{56}$ group to form B7, for example, by a reductive amination reaction using formaldehyde or acetaldehyde. Deprotection of the Boc group affords a compound of Formula B8, which can optionally be further substituted with a T group as shown in Scheme 1.

Scheme 3

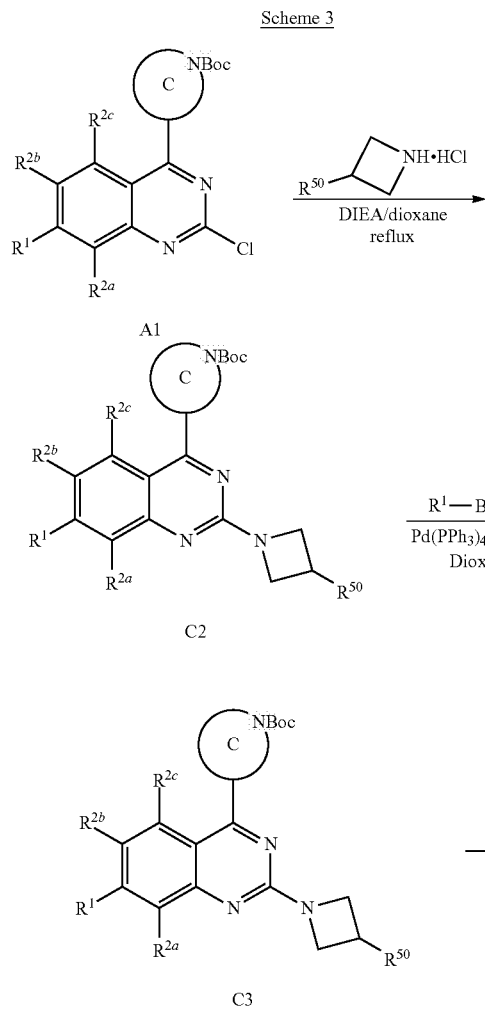

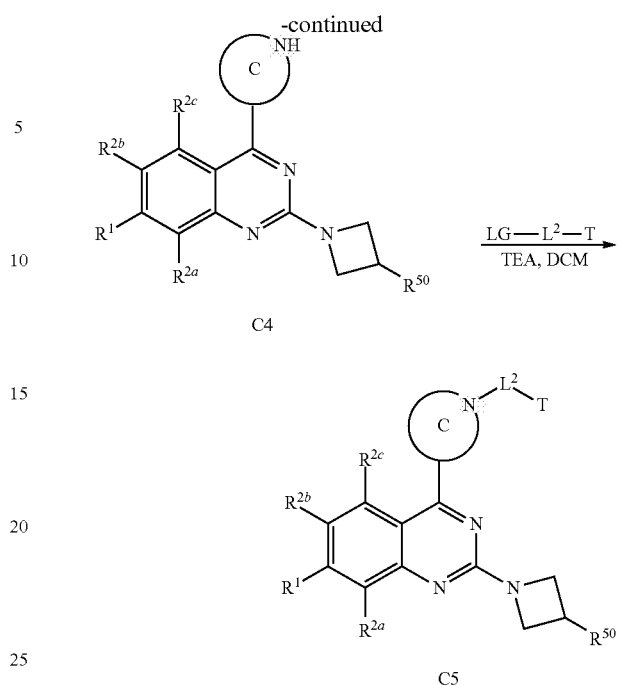

In some embodiments, a compound of Formula C5 may be prepared according to Scheme 3. For example, 2-chloroquinazoline A1 can be reacted with an appropriately substituted azetidine to provide C2. Installation of a desired R[1] substituent may proceed via a Suzuki reaction to give compound C3. Boc deprotection provides free amine C4, which can optionally be coupled to LG-L[2]-T, where LG is a leaving group, to provide a compound of Formula C5. In some examples, T is an acyl group, and LG-L[2]-T is an acyl chloride group.

In some embodiments, a compound of the present disclosure, for example, a compound of a formula given in Table 1, Table 2 or Table 3 is synthesized according to one of the general routes outlined in Schemes 1-3, Examples 1-4, or by methods generally known in the art. In some embodiments, exemplary compounds may include, but are not limited to, a compound or salt therof selected from Table 1, Table 2, or Table 3.

TABLE 1

| No. | Structure | [M + H]+ |
| --- | --- | --- |
| 1 | 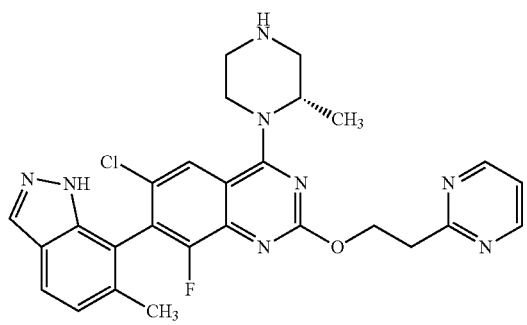 [SMILES: Cc1ccc2cn[nH]c2c1-c1c(Cl)cc2c(N3CCNC[C@@H]3C)nc(OCCc3ncccn3)nc2c1F] | 533.2 |

TABLE 1-continued

| No. | Structure | [M + H]+ |
|---|---|---|
| 2 | 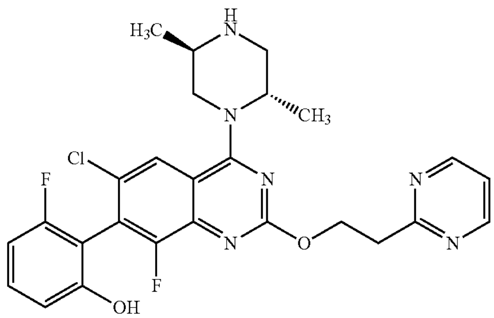 [SMILES: C[C@@H]1CN(c2nc(OCCc3ncccn3)nc3c(F)c(-c4c(O)cccc4F)c(Cl)cc23)[C@@H](C)CN1] | 527.2 |
| 3 | 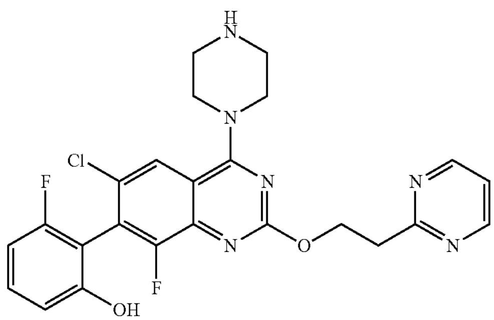 [SMILES: Oc1cccc(F)c1-c1c(Cl)cc2c(N3CCNCC3)nc(OCCc3ncccn3)nc2c1F] | 499.1 |
| 4 | 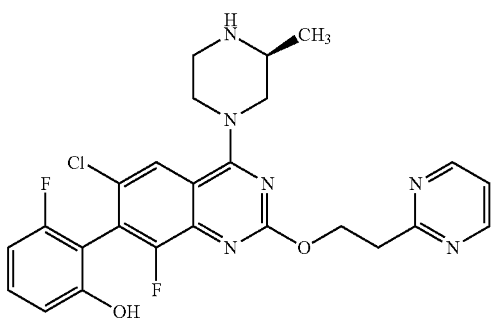 [SMILES: C[C@H]1CN(c2nc(OCCc3ncccn3)nc3c(F)c(-c4c(O)cccc4F)c(Cl)cc23)CCN1] | 513.2 |
| 5 | 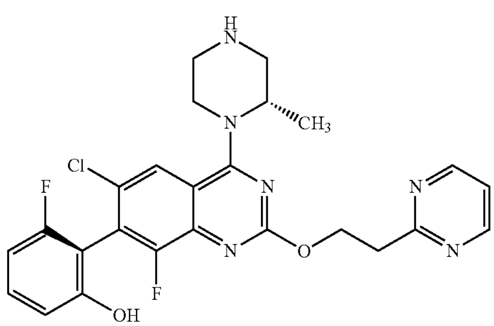 | 513.2 |
| 6 | 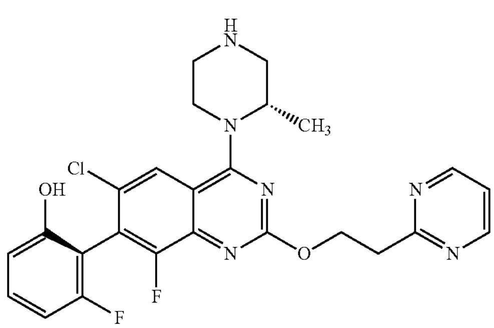 | 513.2 |

TABLE 1-continued

| No. | Structure | [M + H]+ |
|---|---|---|
| 7 | 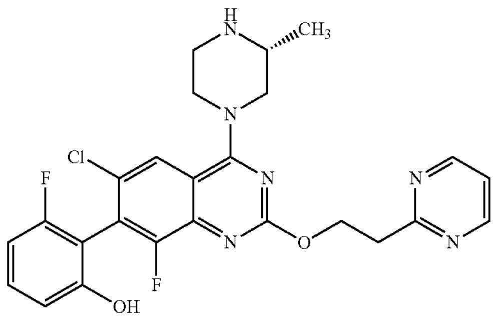 [SMILES: C[C@@H]1CN(c2nc(OCCc3ncccn3)nc3c(F)c(-c4c(O)cccc4F)c(Cl)cc23)CCN1] | 513.2 |
| 8 | 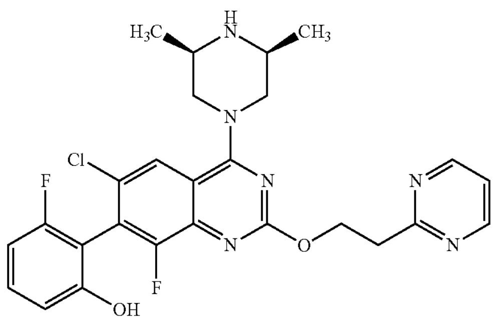 [SMILES: C[C@@H]1CN(c2nc(OCCc3ncccn3)nc3c(F)c(-c4c(O)cccc4F)c(Cl)cc23)C[C@H](C)N1] | 527.2 |
| 9 | 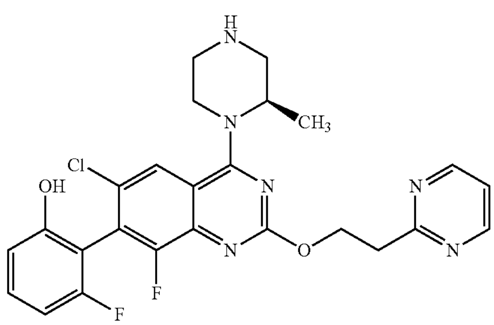 [SMILES: C[C@@H]1CNCCN1c1nc(OCCc2ncccn2)nc2c(F)c(-c3c(O)cccc3F)c(Cl)cc12] | 513.1 |
| 10 | 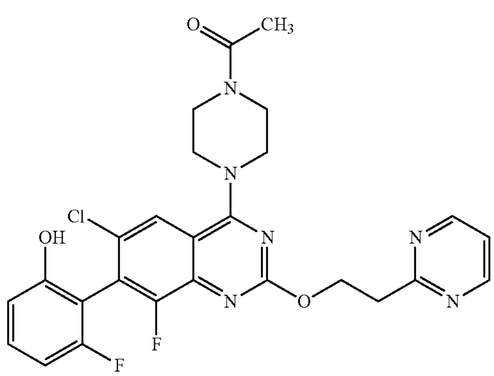 [SMILES: CC(=O)N1CCN(c2nc(OCCc3ncccn3)nc3c(F)c(-c4c(O)cccc4F)c(Cl)cc23)CC1] | 541.2 |

TABLE 1-continued
| No. | Structure | [M + H]+ |
|---|---|---|
| 11 | 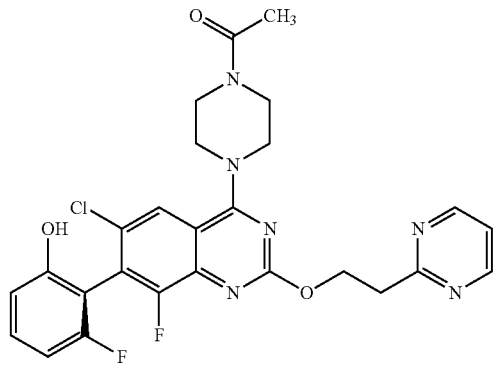 | 541.1 |
| 12 | 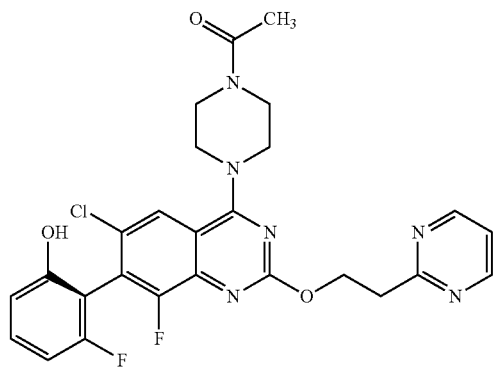 | 541.1 |
| 13 | 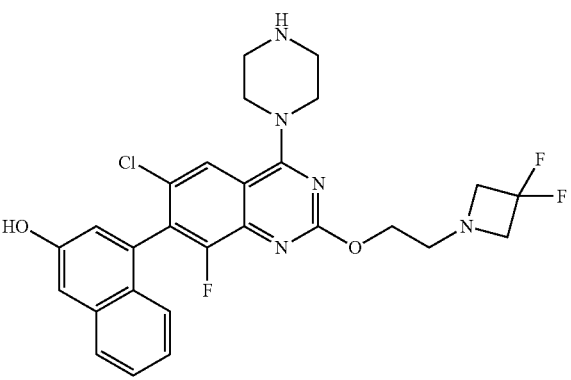 [SMILES: Oc1cc(-c2c(Cl)cc3c(N4CCNCC4)nc(OCCN4CC(F)(F)C4)nc3c2F)c2ccccc2c1] | 544.2 |
| 14 | 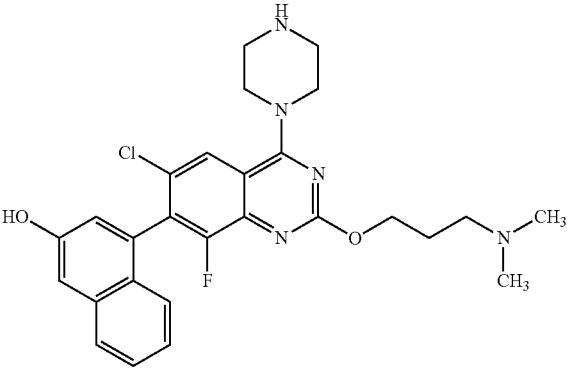 [SMILES: CN(C)CCCOc1nc(N2CCNCC2)c2cc(Cl)c(-c3cc(O)cc4ccccc34)c(F)c2n1] | 510.2 |

TABLE 1-continued
| No. | Structure | [M + H]+ |
|---|---|---|
| 15 | 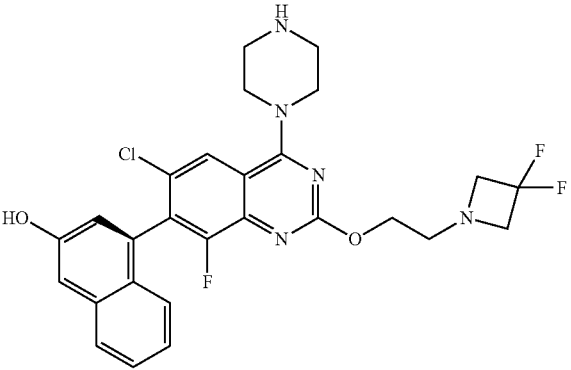 | 544.1 |
| 16 | 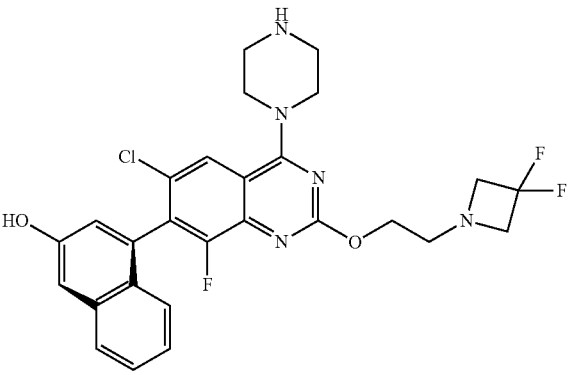 | 544.2 |
| 17 | 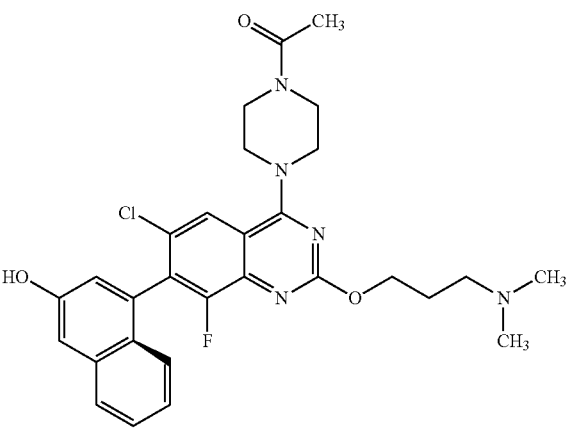 | 552.2 |
| 18 | 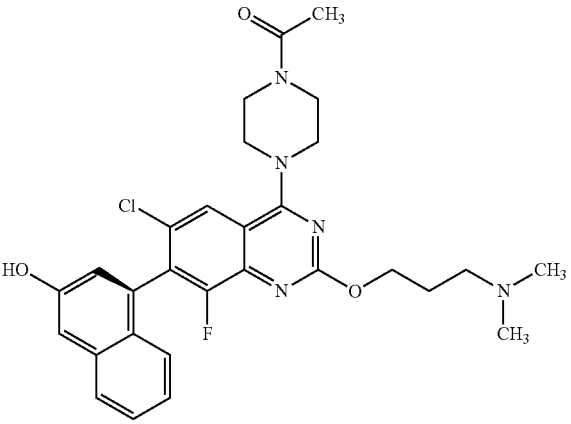 | 552.2 |

TABLE 1-continued
| No. | Structure | [M + H]+ |
|---|---|---|
| 19 | 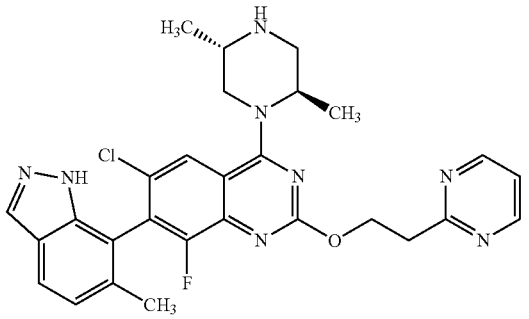 [SMILES: Cc1ccc2cn[nH]c2c1-c1c(Cl)cc2c(N3C[C@H](C)NC[C@H]3C)nc(OCCc3ncccn3)nc2c1F] | 547.2 |
| 20 | 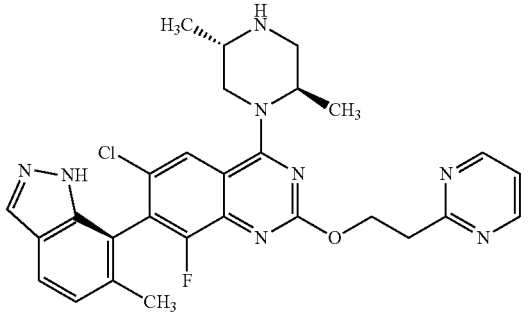 | 547.2 |
| 21 | 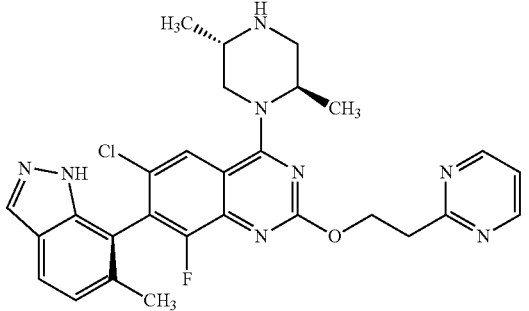 | 547.2 |
| 22 | 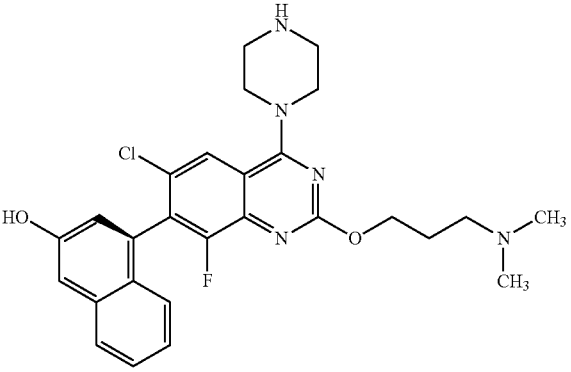 | 510.2 |

TABLE 1-continued

| No. | Structure | [M + H]+ |
|---|---|---|
| 23 | 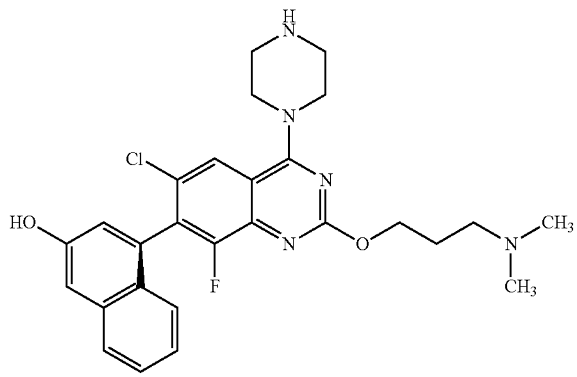 | 510.2 |
| 24 | 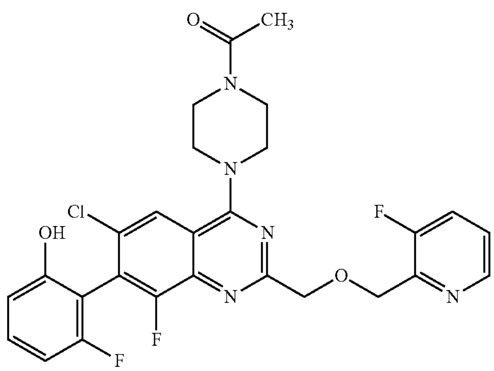 [SMILES: CC(=O)N1CCN(c2nc(COCc3ncccc3F)nc3c(F)c(-c4c(O)cccc4F)c(Cl)cc23)CC1] | 558.2 |
| 25 | 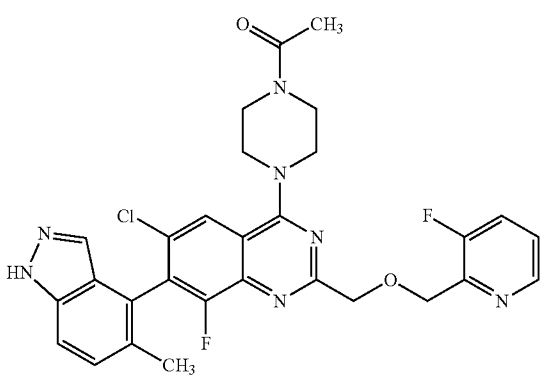 [SMILES: CC(=O)N1CCN(c2nc(COCc3ncccc3F)nc3c(F)c(-c4c(C)ccc5[nH]ncc45)c(Cl)cc23)CC1] | 578.1 |
| 26 | 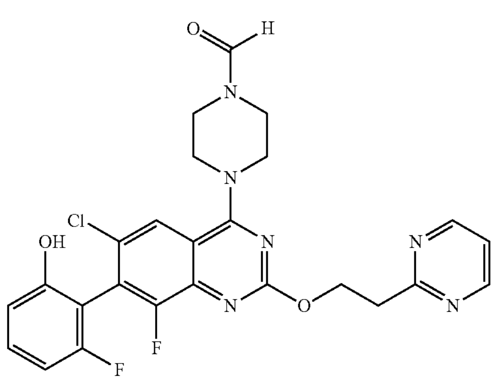 [SMILES: O=CN1CCN(c2nc(OCCc3ncccn3)nc3c(F)c(-c4c(O)cccc4F)c(Cl)cc23)CC1] | 527.1 |

TABLE 1-continued
| No. | Structure | [M + H]+ |
|---|---|---|
| 27 | 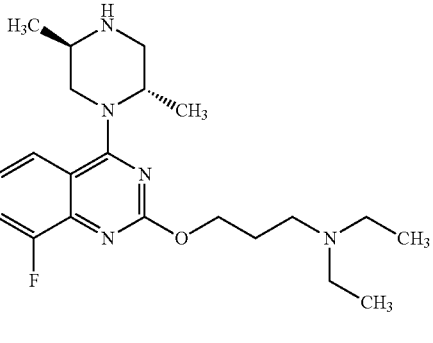 | |
| 28 | 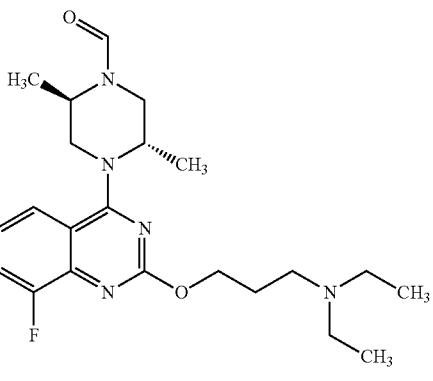 | |
| 29 | 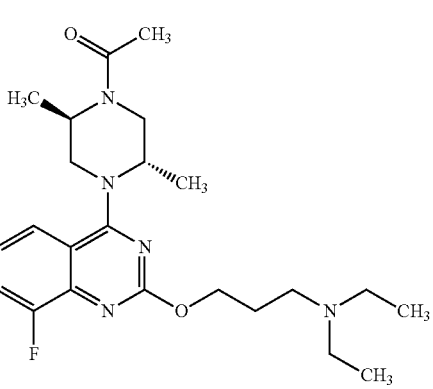 | |
| 30 | 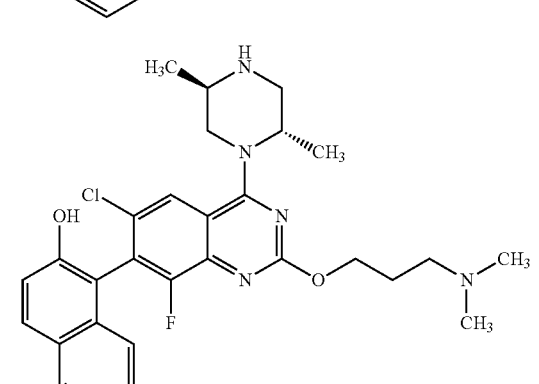 | 538.3 |

TABLE 1-continued
| No. | Structure | [M + H]+ |
|---|---|---|
| 31 | 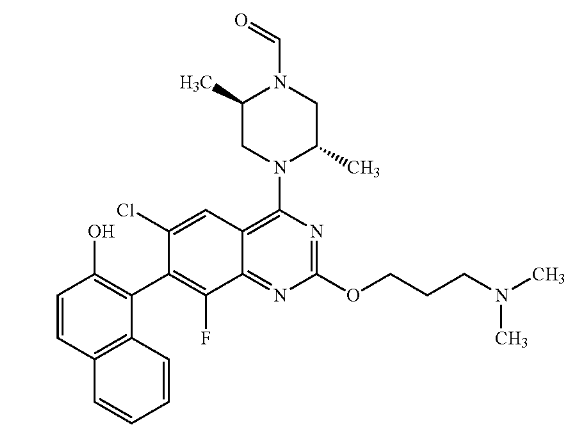 [SMILES: C[C@@H]1CN(c2nc(OCCCN(C)C)nc3c(F)c(-c4c(O)ccc5ccccc45)c(Cl)cc23)[C@@H](C)CN1C=O] | 566.3 |
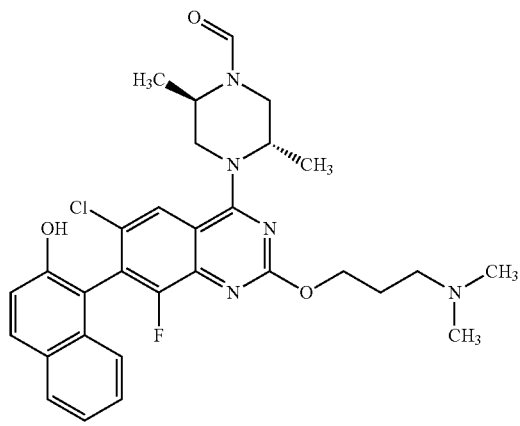
| 32 | | 580.4 |
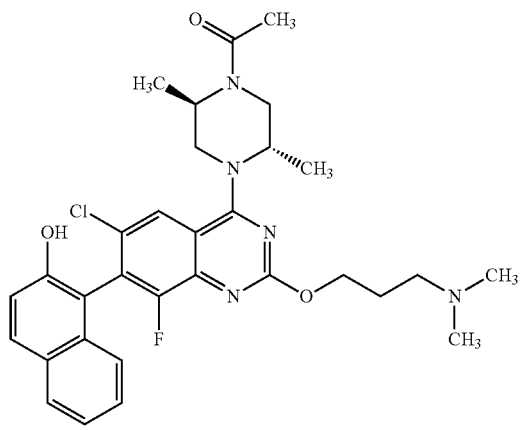 [SMILES: CC(=O)N1C[C@H](C)N(c2nc(OCCCN(C)C)nc3c(F)c(-c4c(O)ccc5ccccc45)c(Cl)cc23)C[C@H]1C]
| 33 | | |
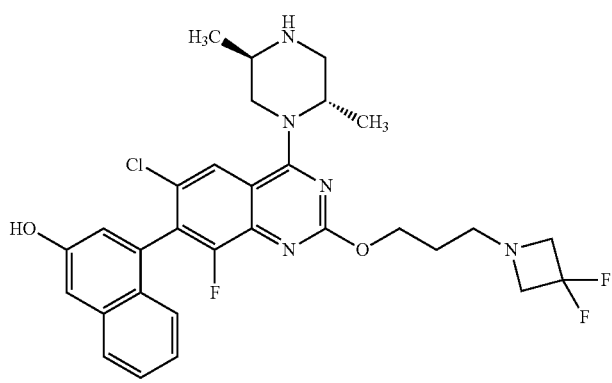 [SMILES: C[C@@H]1CN(c2nc(OCCCN3CC(F)(F)C3)nc3c(F)c(-c4cc(O)cc5ccccc45)c(Cl)cc23)[C@@H](C)CN1]

TABLE 1-continued
| No. | Structure | [M + H]+ |
|---|---|---|
| 34 | 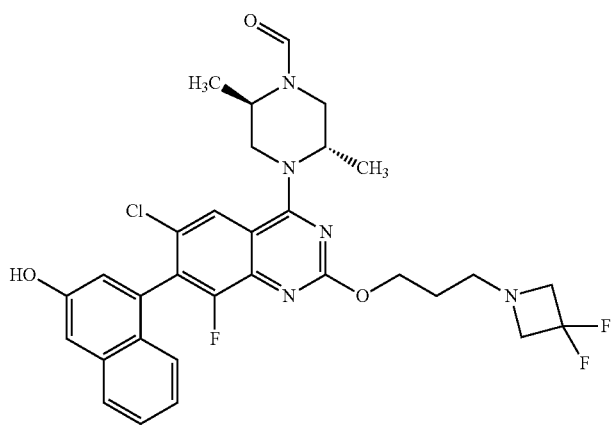 [SMILES: C[C@@H]1CN(c2nc(OCCCN3CC(F)(F)C3)nc3c(F)c(-c4cc(O)cc5ccccc45)c(Cl)cc23)[C@@H](C)CN1C=O] | |
| 35 | 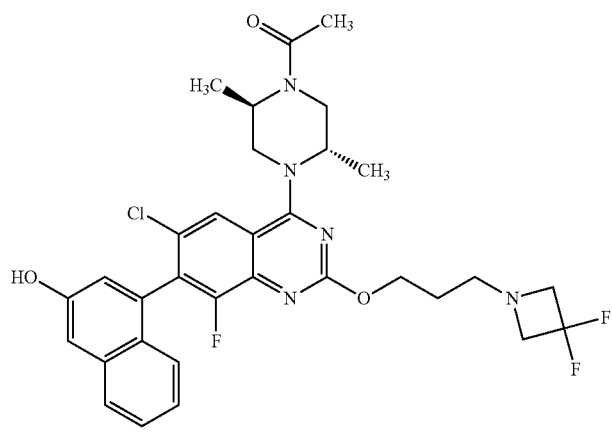 [SMILES: CC(=O)N1C[C@H](C)N(c2nc(OCCCN3CC(F)(F)C3)nc3c(F)c(-c4cc(O)cc5ccccc45)c(Cl)cc23)C[C@H]1C] | |
| 36 | 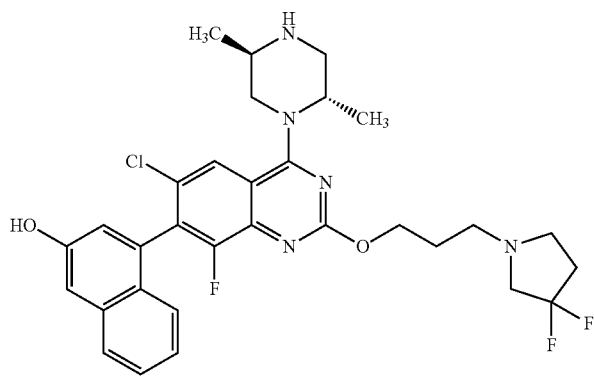 [SMILES: C[C@@H]1CN(c2nc(OCCCN3CCC(F)(F)C3)nc3c(F)c(-c4cc(O)cc5ccccc45)c(Cl)cc23)[C@@H](C)CN1] | 600.4 |

TABLE 1-continued

| No. | Structure | [M + H]+ |
|---|---|---|
| 37 | 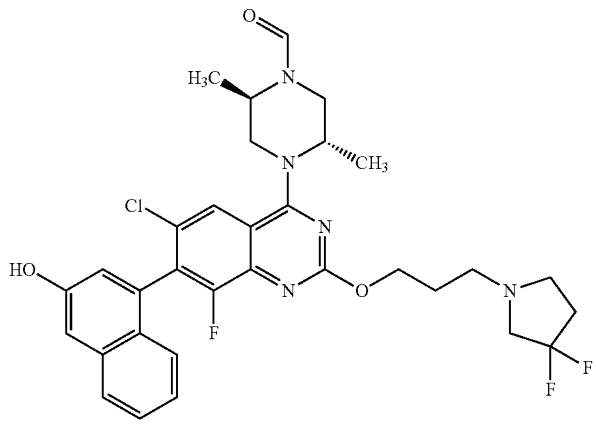 [SMILES: C[C@@H]1CN(c2nc(OCCCN3CCC(F)(F)C3)nc3c(F)c(-c4cc(O)cc5ccccc45)c(Cl)cc23)[C@@H](C)CN1C=O] | |
| 38 | 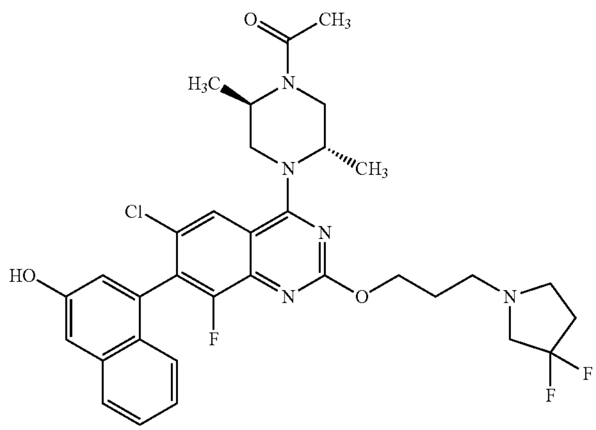 [SMILES: CC(=O)N1C[C@H](C)N(c2nc(OCCCN3CCC(F)(F)C3)nc3c(F)c(-c4cc(O)cc5ccccc45)c(Cl)cc23)C[C@H]1C] | 642.4 |
| 39 | 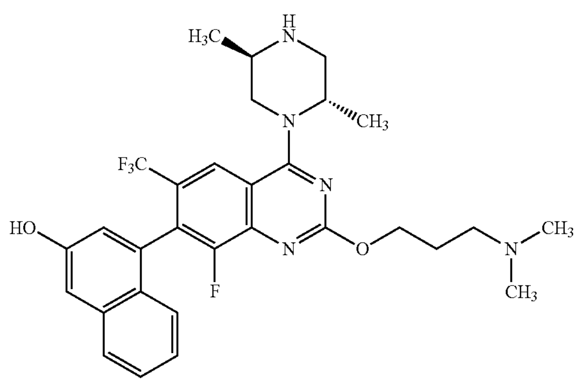 [SMILES: C[C@@H]1CN(c2nc(OCCCN(C)C)nc3c(F)c(-c4cc(O)cc5ccccc45)c(C(F)(F)F)cc23)[C@@H](C)CN1] | |
| 40 | 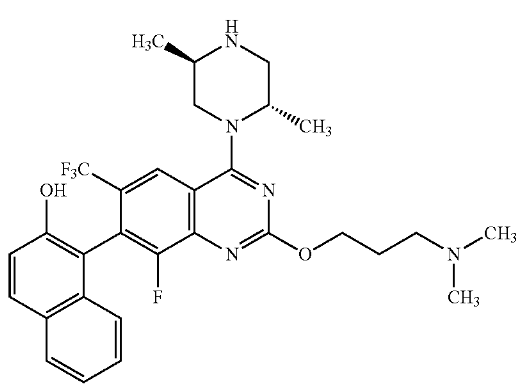 [SMILES: C[C@@H]1CN(c2nc(OCCCN(C)C)nc3c(F)c(-c4c(O)ccc5ccccc45)c(C(F)(F)F)cc23)[C@@H](C)CN1] | |

TABLE 1-continued
| No. | Structure | [M + H]+ |
|---|---|---|
| 41 | 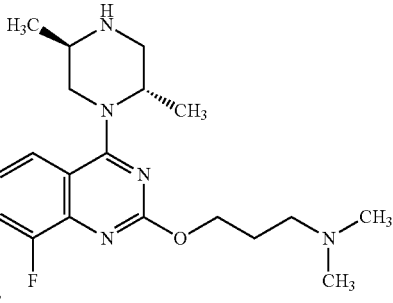 | |
| 42 | 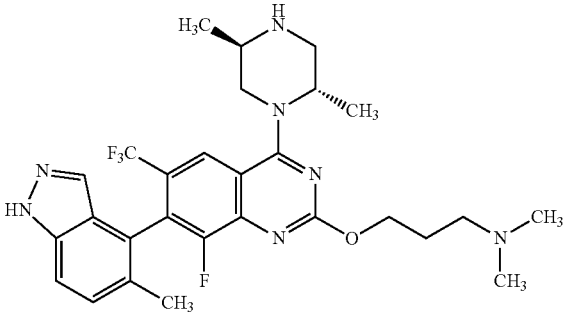 [SMILES: Cc1ccc2[nH]ncc2c1-c1c(C(F)(F)F)cc2c(N3C[C@@H](C)NC[C@@H]3C)nc(OCCCN(C)C)nc2c1F] | |
| 43 | 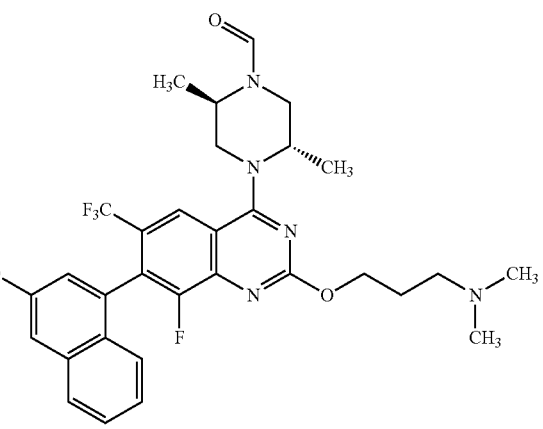 | |
| 44 | 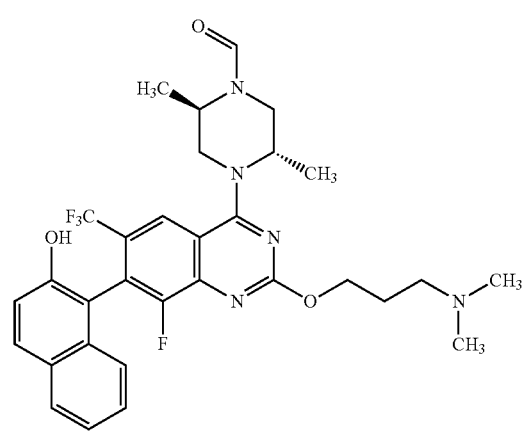 [SMILES: C[C@@H]1CN(c2nc(OCCCN(C)C)nc3c(F)c(-c4c(O)ccc5ccccc45)c(C(F)(F)F)cc23)[C@@H](C)CN1C=O] | |

TABLE 1-continued

| No. | Structure | [M + H]+ |
|---|---|---|
| 45 | 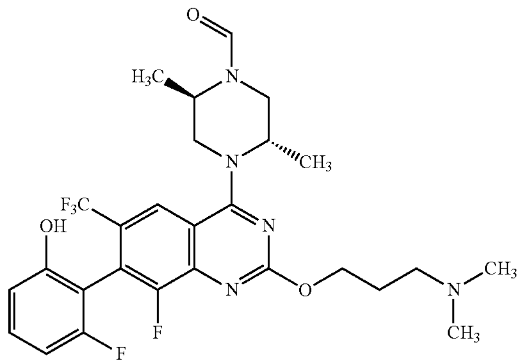 [SMILES: C[C@@H]1CN(c2nc(OCCCN(C)C)nc3c(F)c(-c4c(O)cccc4F)c(C(F)(F)F)cc23)[C@@H](C)CN1C=O] | |
| 46 | 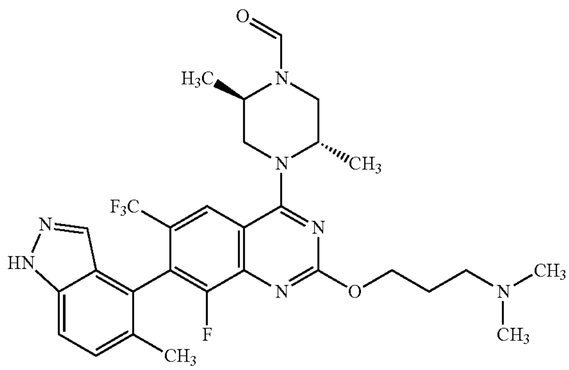 [SMILES: Cc1ccc2[nH]ncc2c1-c1c(C(F)(F)F)cc2c(N3C[C@@H](C)N(C=O)C[C@@H]3C)nc(OCCCN(C)C)nc2c1F] | |
| 47 | 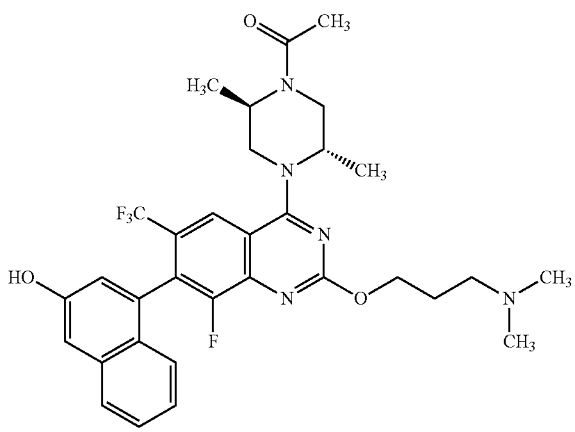 [SMILES: CC(=O)N1C[C@H](C)N(c2nc(OCCCN(C)C)nc3c(F)c(-c4cc(O)cc5ccccc45)c(C(F)(F)F)cc23)C[C@H]1C] | 614.4 |
| 48 | 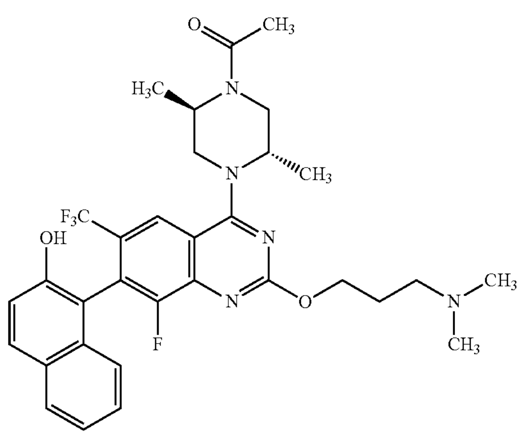 [SMILES: CC(=O)N1C[C@H](C)N(c2nc(OCCCN(C)C)nc3c(F)c(-c4c(O)ccc5ccccc45)c(C(F)(F)F)cc23)C[C@H]1C] | |

TABLE 1-continued
| No. | Structure | [M + H]+ |
|---|---|---|
| 49 | 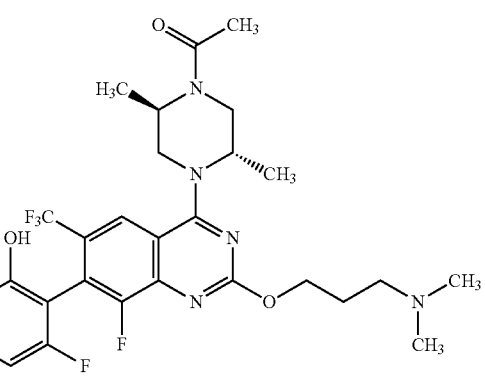 | |
| 50 | 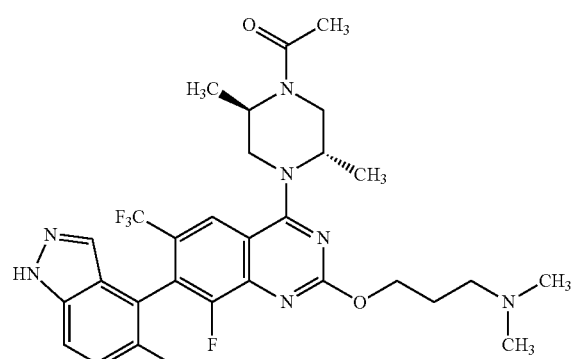 | |
| 51 | 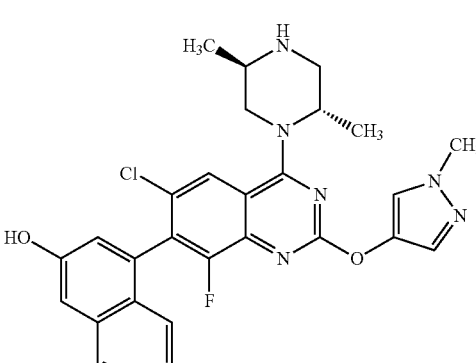 | 533.3 |
| 52 | 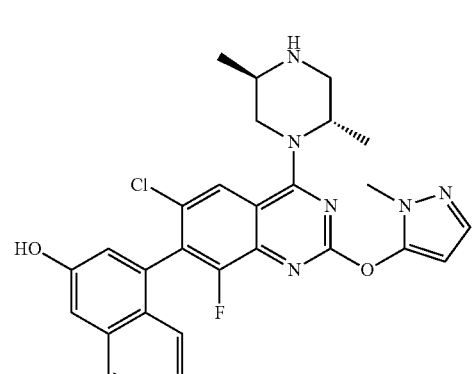 | 533.3 |

TABLE 1-continued
| No. | Structure | [M + H]+ |
|---|---|---|
| 53 | 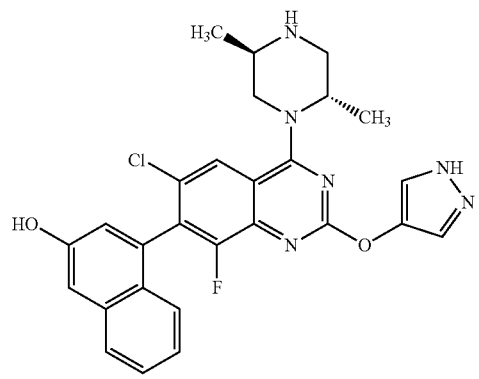 [SMILES: C[C@@H]1CN(c2nc(Oc3cn[nH]c3)nc3c(F)c(-c4cc(O)cc5ccccc45)c(Cl)cc23)[C@@H](C)CN1] | 519.2 |
| 54 | 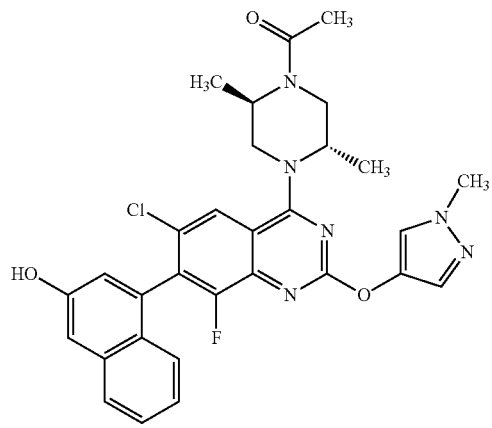 [SMILES: CC(=O)N1C[C@H](C)N(c2nc(Oc3cnn(C)c3)nc3c(F)c(-c4cc(O)cc5ccccc45)c(Cl)cc23)C[C@H]1C] | 575.4 |
| 55 | 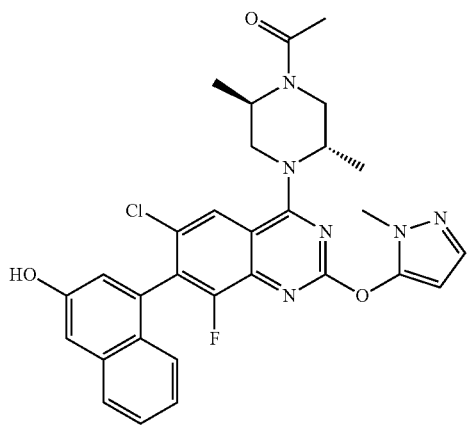 [SMILES: CC(=O)N1C[C@H](C)N(c2nc(Oc3ccnn3C)nc3c(F)c(-c4cc(O)cc5ccccc45)c(Cl)cc23)C[C@H]1C] | 575.2 |

TABLE 1-continued
| No. | Structure | [M + H]+ |
|---|---|---|
| 56 | 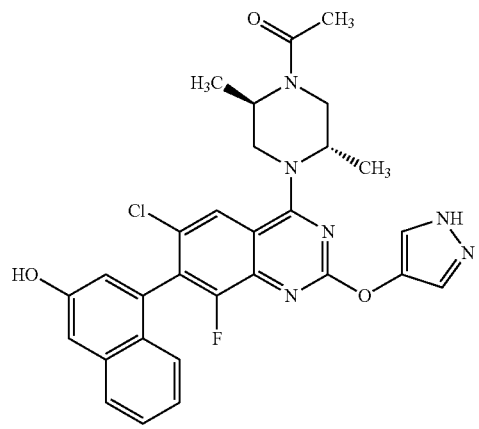 [SMILES: CC(=O)N1C[C@H](C)N(c2nc(Oc3cn[nH]c3)nc3c(F)c(-c4cc(O)cc5ccccc45)c(Cl)cc23)C[C@H]1C] | 561.3 |
| 57 | 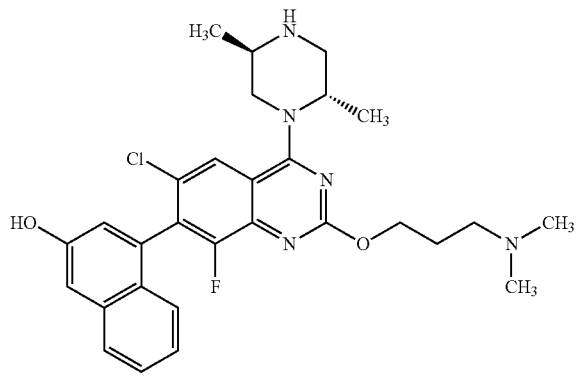 [SMILES: C[C@@H]1CN(c2nc(OCCCN(C)C)nc3c(F)c(-c4cc(O)cc5ccccc45)c(Cl)cc23)[C@@H](C)CN1] | 538.4 |
| 58 | 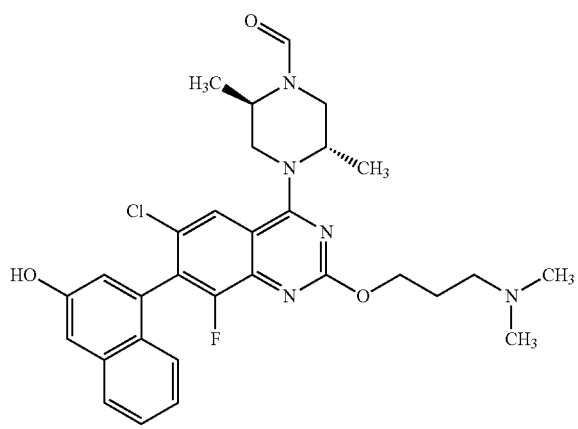 [SMILES: C[C@@H]1CN(c2nc(OCCCN(C)C)nc3c(F)c(-c4cc(O)cc5ccccc45)c(Cl)cc23)[C@@H](C)CN1C=O] | 566.4 |

TABLE 1-continued
| No. | Structure | [M + H]+ |
|---|---|---|
| 59 | 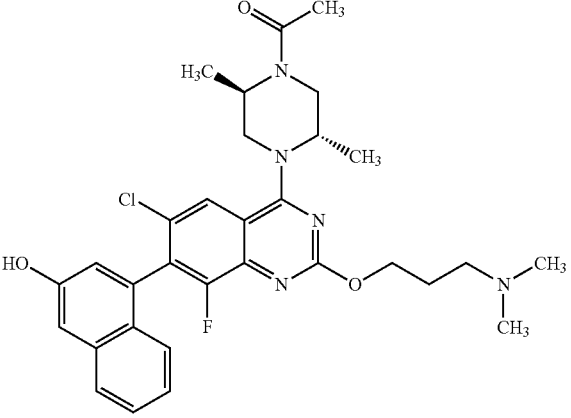 [SMILES: CC(=O)N1C[C@H](C)N(c2nc(OCCCN(C)C)nc3c(F)c(-c4cc(O)cc5ccccc45)c(Cl)cc23)C[C@H]1C] | 580.4 |
| 60 | 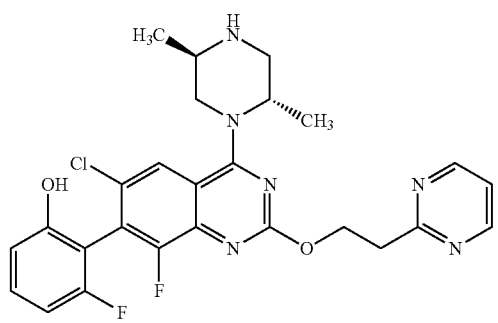 [SMILES: C[C@@H]1CN(c2nc(OCCc3ncccn3)nc3c(F)c(-c4c(O)cccc4F)c(Cl)cc23)[C@@H](C)CN1] | |
| 61 | 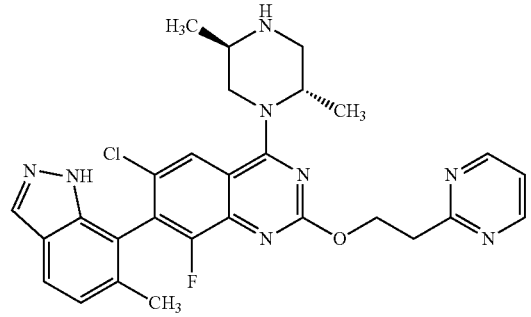 [SMILES: Cc1ccc2cn[nH]c2c1-c1c(Cl)cc2c(N3C[C@@H](C)NC[C@@H]3C)nc(OCCc3ncccn3)nc2c1F] | 547.3 |
| 62 | 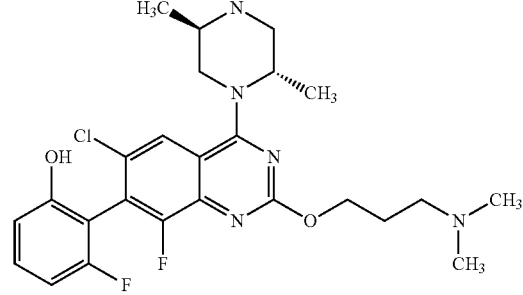 | 506.3 |

TABLE 1-continued
| No. | Structure | [M + H]+ |
|---|---|---|
| 63 | 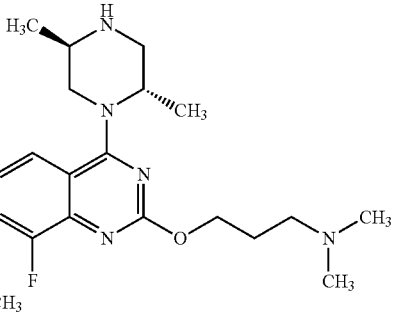 | 526.4 |
| 64 | 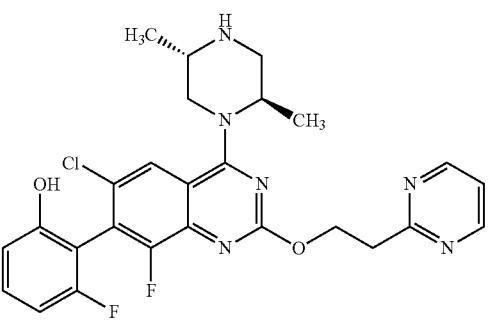 [SMILES: C[C@@H]1CN[C@@H](C)CN1c1nc(OCCc2ncccn2)nc2c(F)c(-c3c(O)cccc3F)c(Cl)cc12] | |
| 65 | 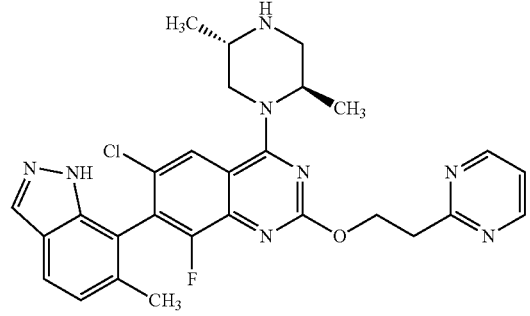 [SMILES: Cc1ccc2cn[nH]c2c1-c1c(Cl)cc2c(N3C[C@H](C)NC[C@H]3C)nc(OCCc3ncccn3)nc2c1F] | |
| 66 | 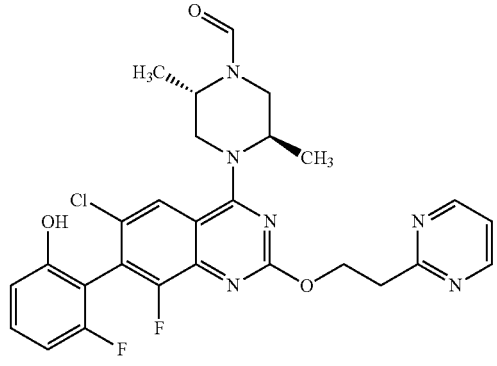 [SMILES: C[C@@H]1CN(C=O)[C@@H](C)CN1c1nc(OCCc2ncccn2)nc2c(F)c(-c3c(O)cccc3F)c(Cl)cc12] | |

TABLE 1-continued

| No. | Structure | [M + H]+ |
|---|---|---|
| 67 | 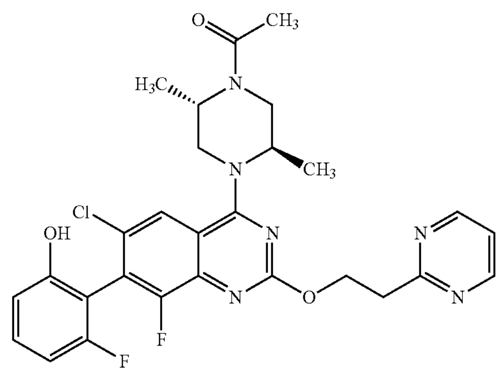 [SMILES: CC(=O)N1C[C@@H](C)N(c2nc(OCCc3ncccn3)nc3c(F)c(-c4c(O)cccc4F)c(Cl)cc23)C[C@@H]1C] | |
| 85 | 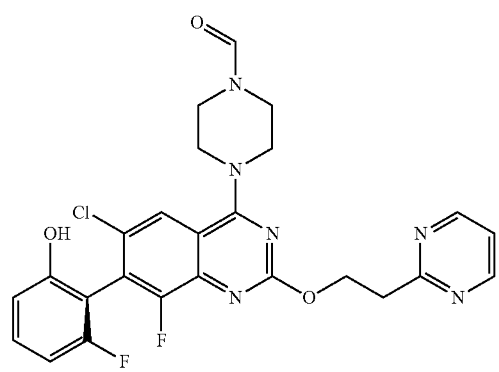 | 527.2 |
| 86 | 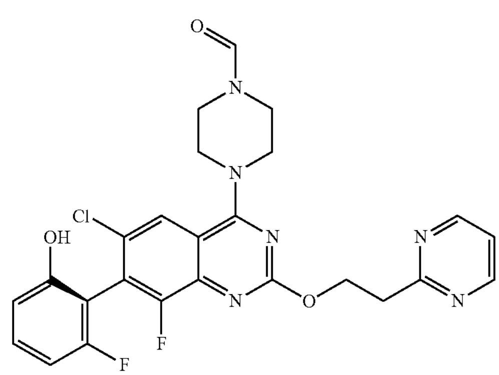 | 527.2 |
| 87 | 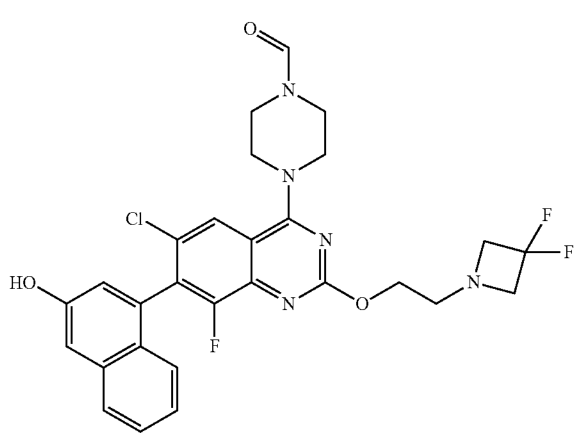 [SMILES: O=CN1CCN(c2nc(OCCN3CC(F)(F)C3)nc3c(F)c(-c4cc(O)cc5ccccc45)c(Cl)cc23)CC1] | 572.2 |

TABLE 1-continued
| No. | Structure | [M + H]+ |
|---|---|---|
| 88 | 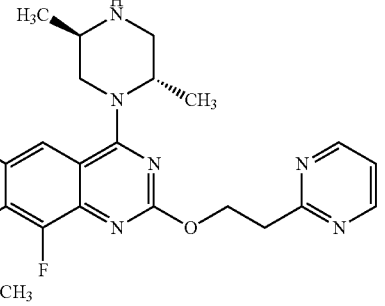 | 547.4 |
| 89 | 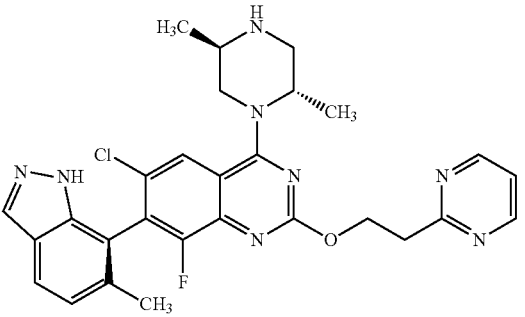 | 547.4 |
| 90 | 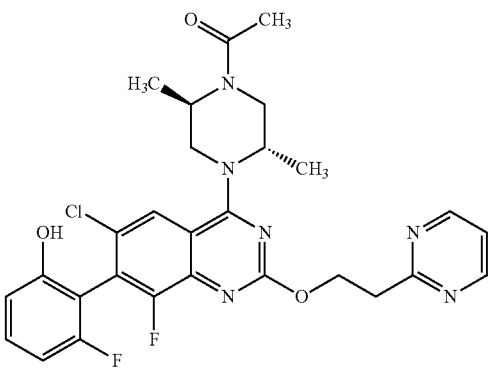 [SMILES: CC(=O)N1C[C@H](C)N(c2nc(OCCc3ncccn3)nc3c(F)c(-c4c(O)cccc4F)c(Cl)cc23)C[C@H]1C] | 569.3 |
| 91 | 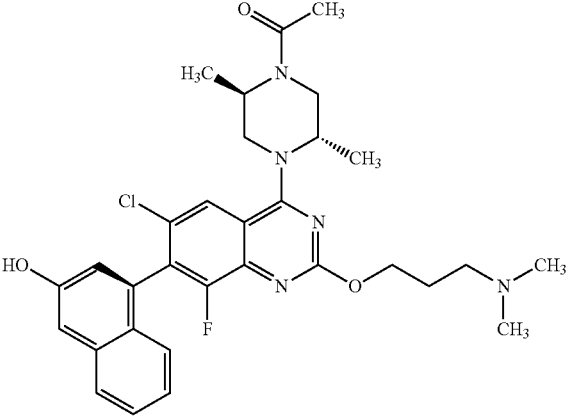 | 580.4 |

TABLE 1-continued

| No. | Structure | [M + H]+ |
|---|---|---|
| 92 | 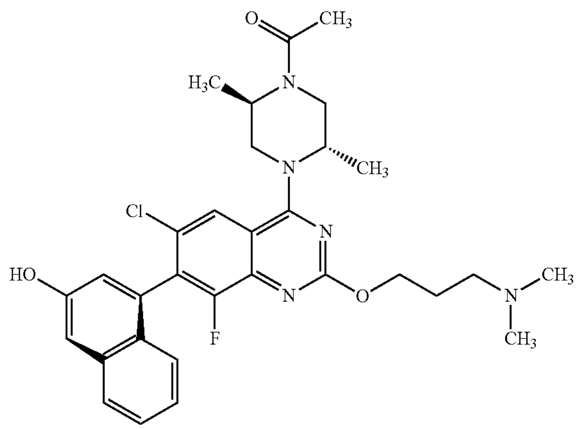 | 580.3 |
| 93 | 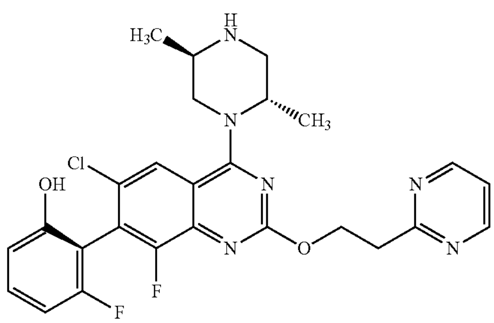 | 527.3 |
| 94 | 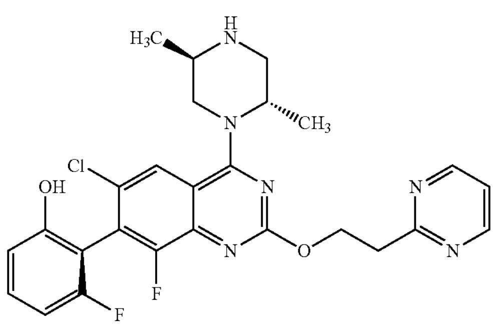 | 527.3 |
| 95 | 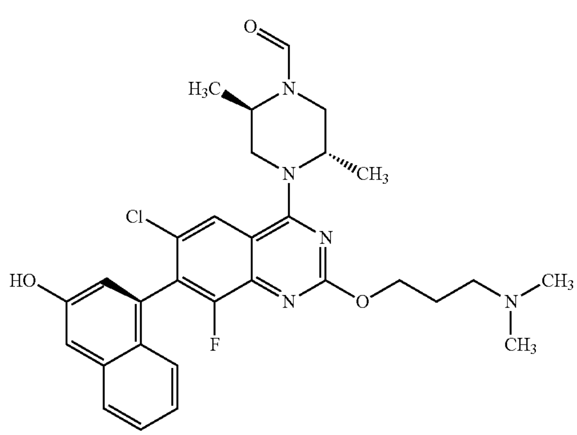 | 566.3 |

TABLE 1-continued

| No. | Structure | [M + H]+ |
|---|---|---|
| 96 | 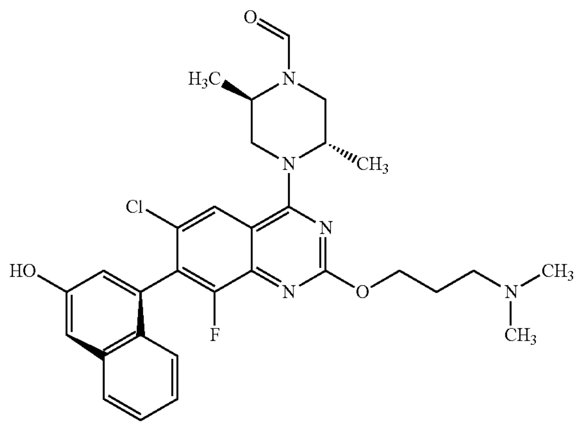 | 566.3 |
| 97 | 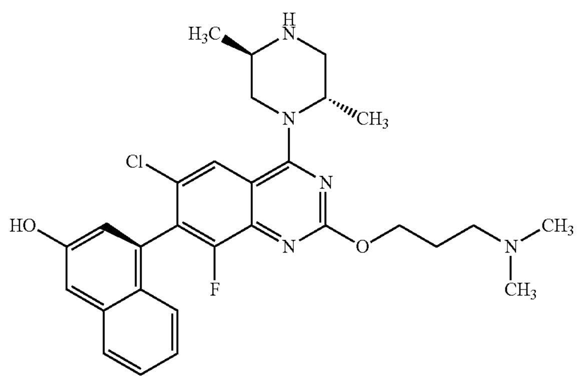 | 538.4 |
| 98 | 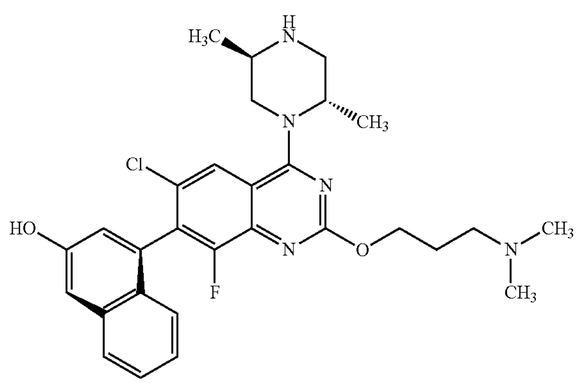 | 538.4 |
| 99 | 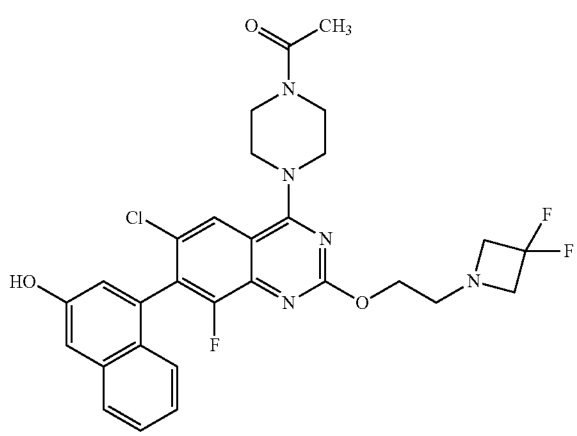 [SMILES: CC(=O)N1CCN(c2nc(OCCN3CC(F)(F)C3)nc3c(F)c(-c4cc(O)cc5ccccc45)c(Cl)cc23)CC1] | 586.3 |

TABLE 1-continued
| No. | Structure | [M + H]+ |
|---|---|---|
| 100 | 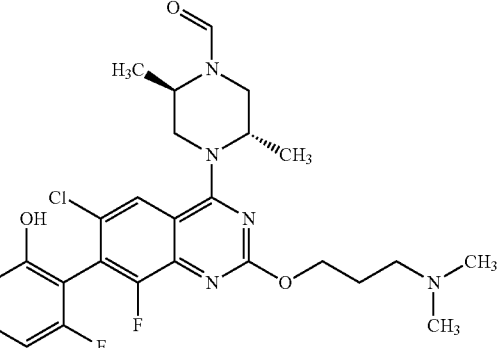 | 534.4 |
| 101 | 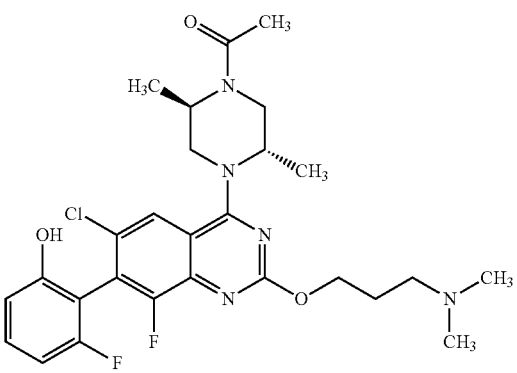 [SMILES: CC(=O)N1C[C@H](C)N(c2nc(OCCCN(C)C)nc3c(F)c(-c4c(O)cccc4F)c(Cl)cc23)C[C@H]1C] | 548.4 |
| 102 | 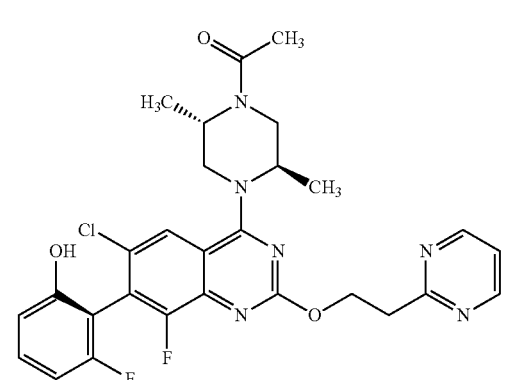 | 569.3 |
| 103 | 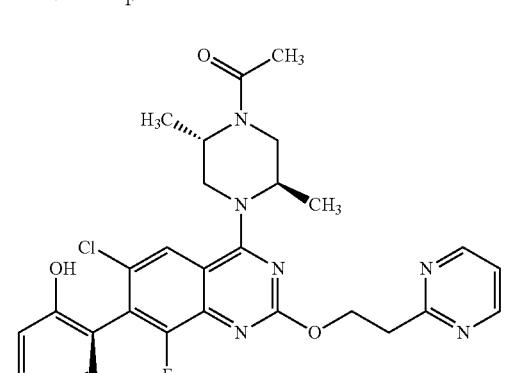 | 569.3 |

TABLE 1-continued
| No. | Structure | [M + H]+ |
|---|---|---|
| 104 | 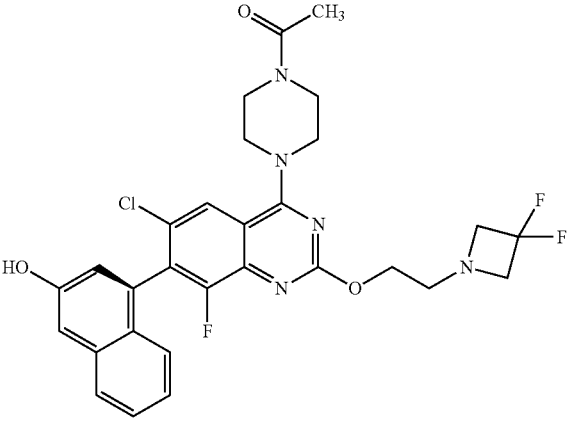 | 586.3 |
| 105 | 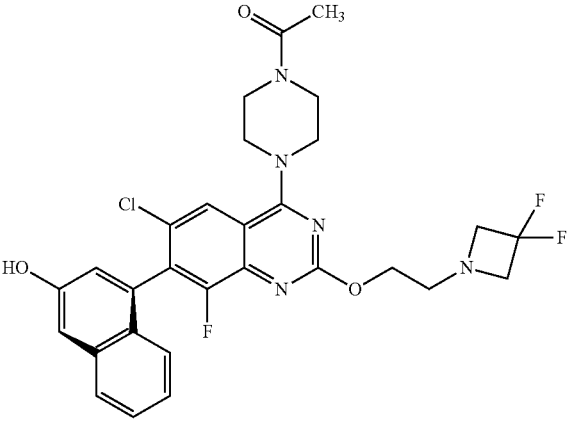 | 586.3 |
| 106 | 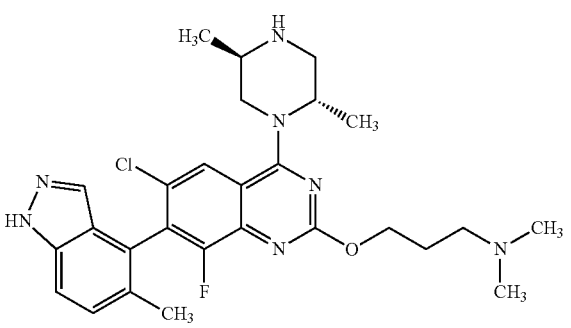 [SMILES: Cc1ccc2[nH]ncc2c1-c1c(Cl)cc2c(N3C[C@@H](C)NC[C@@H]3C)nc(OCCCN(C)C)nc2c1F] | 526.4 |
| 107 | 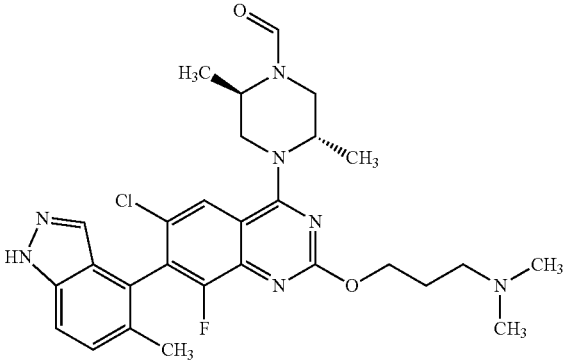 [SMILES: Cc1ccc2[nH]ncc2c1-c1c(Cl)cc2c(N3C[C@@H](C)N(C=O)C[C@@H]3C)nc(OCCCN(C)C)nc2c1F] | 554.4 |

TABLE 1-continued

| No. | Structure | [M + H]+ |
|---|---|---|
| 108 | 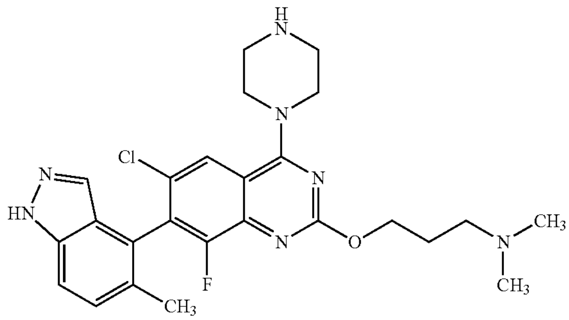 [SMILES: Cc1ccc2[nH]ncc2c1-c1c(Cl)cc2c(N3CCNCC3)nc(OCCCN(C)C)nc2c1F] | 498.3 |
| 109 | 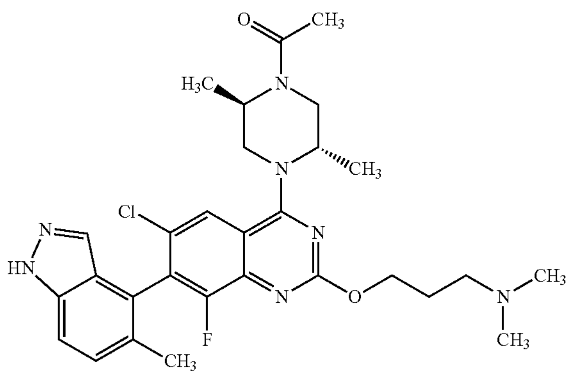 [SMILES: CC(=O)N1C[C@H](C)N(c2nc(OCCCN(C)C)nc3c(F)c(-c4c(C)ccc5[nH]ncc45)c(Cl)cc23)C[C@H]1C] | 568.4 |
| 110 | 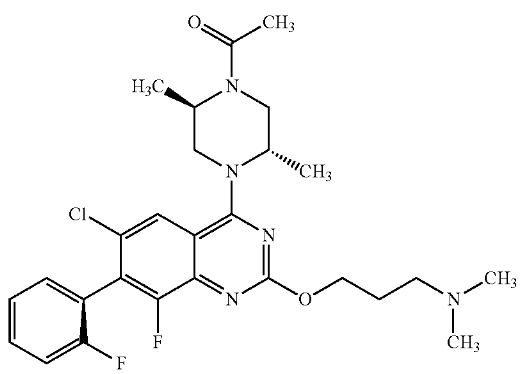 | 548.3 |
| 111 | 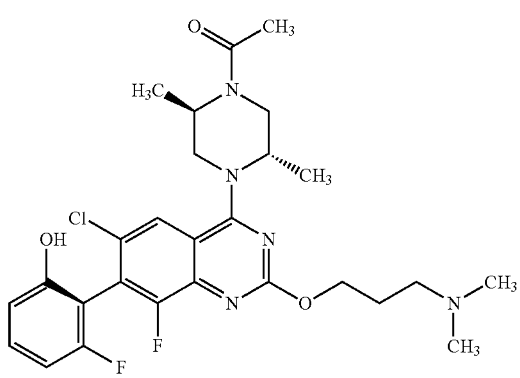 | 548.3 |

TABLE 1-continued
| No. | Structure | [M + H]+ |
|---|---|---|
| 112 | 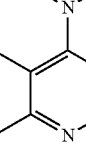 | 478.2 |
| 113 | 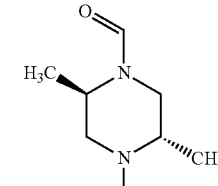 | 534.3 |
| 114 | 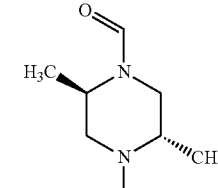 | 534.3 |
| 115 | 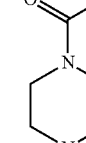 | 520.2 |

TABLE 1-continued

| No. | Structure | [M + H]+ |
|-----|-----------|----------|
| 116 | 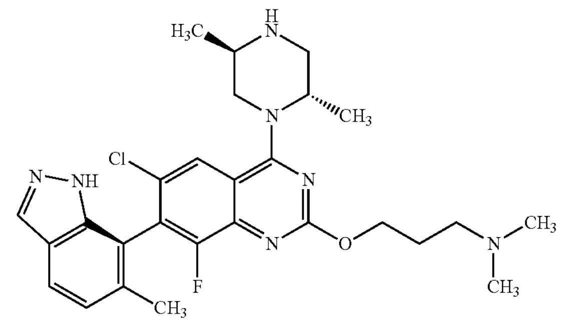 | 526.3 |
| 117 | 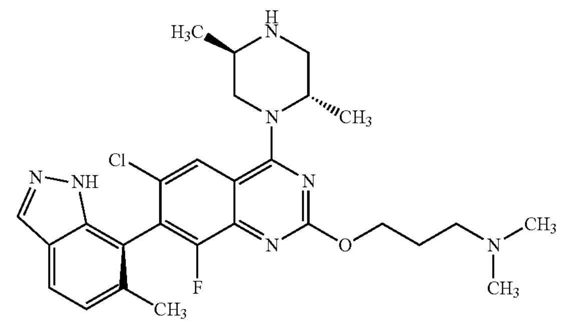 | 526.3 |
| 118 | 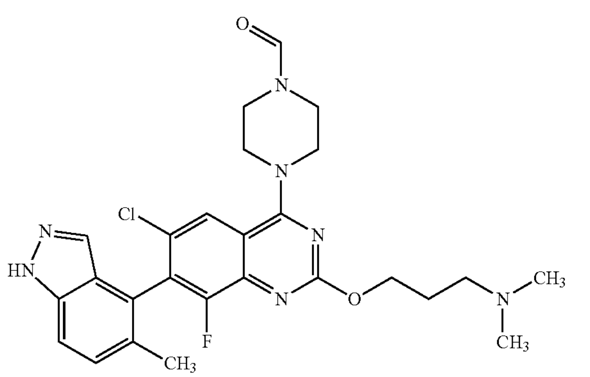 [SMILES: Cc1ccc2[nH]ncc2c1-c1c(Cl)cc2c(N3CCN(C=O)CC3)nc(OCCCN(C)C)nc2c1F] | 526.3 |
| 119 | 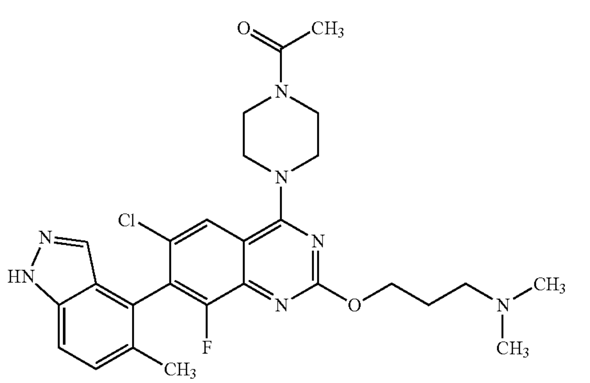 [SMILES: CC(=O)N1CCN(c2nc(OCCCN(C)C)nc3c(F)c(-c4c(C)ccc5[nH]ncc45)c(Cl)cc23)CC1] | 540.4 |

TABLE 1-continued

| No. | Structure | [M + H]+ |
|---|---|---|
| 120 | 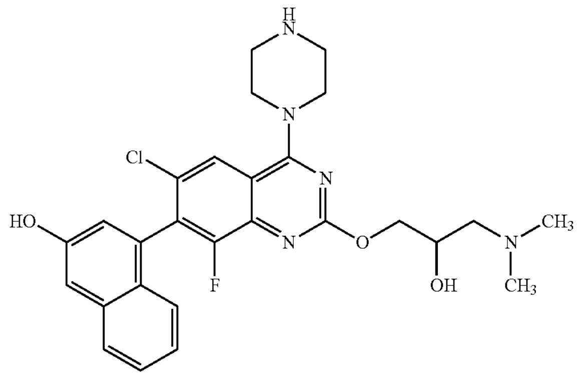 [SMILES: CN(C)CC(O)COc1nc(N2CCNCC2)c2cc(Cl)c(-c3cc(O)cc4ccccc34)c(F)c2n1] | 526.2 |
| 121 | 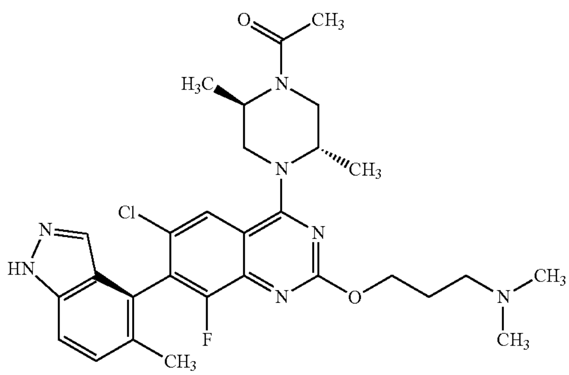 | 568.3 |
| 122 | 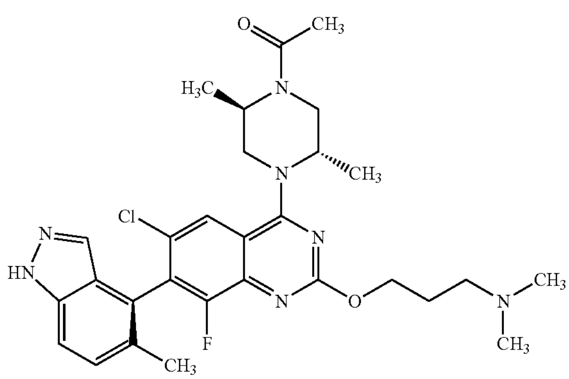 | 568.3 |
| 123 | 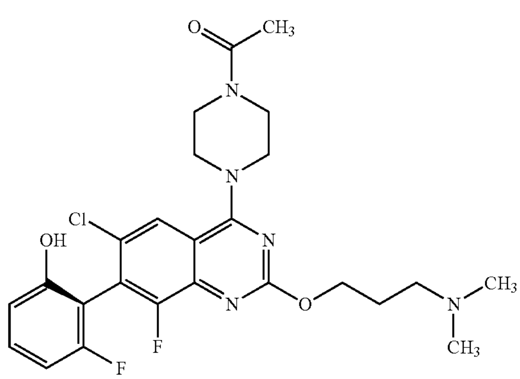 | 520.3 |

TABLE 1-continued
| No. | Structure | [M + H]+ |
|---|---|---|
| 124 | 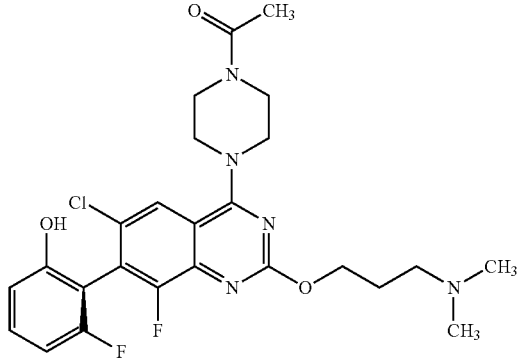 | 520.3 |
| 125 | 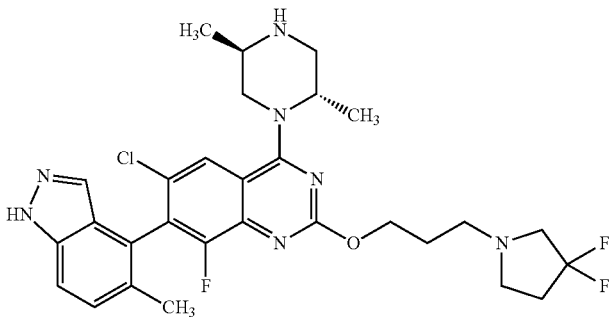 [SMILES: Cc1ccc2[nH]ncc2c1-c1c(Cl)cc2c(N3C[C@@H](C)NC[C@@H]3C)nc(OCCCN3CCC(F)(F)C3)nc2c1F] | 588.4 |
| 126 | 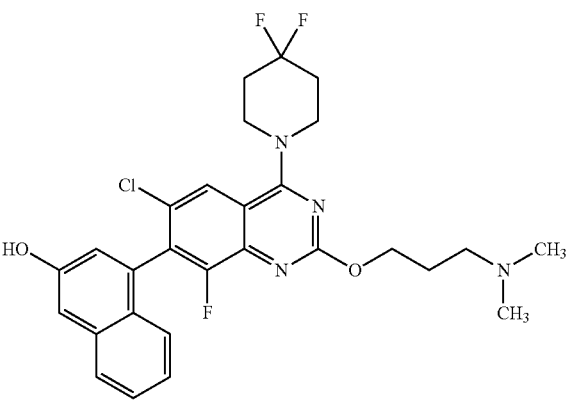 [SMILES: CN(C)CCCOc1nc(N2CCC(F)(F)CC2)c2cc(Cl)c(-c3cc(O)cc4ccccc34)c(F)c2n1] | 545.3 |
| 127 | 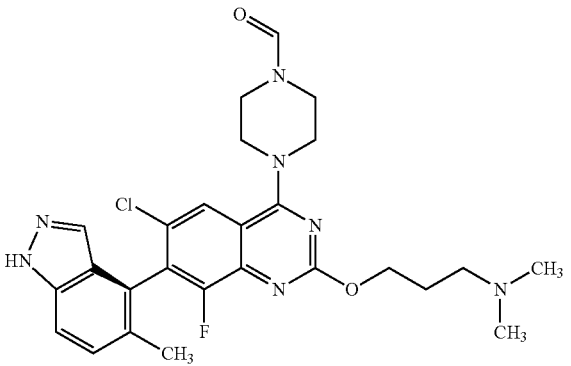 | 526.3 | ns
TABLE 1-continued
| No. | Structure | [M + H]+ |
|---|---|---|
| 128 | 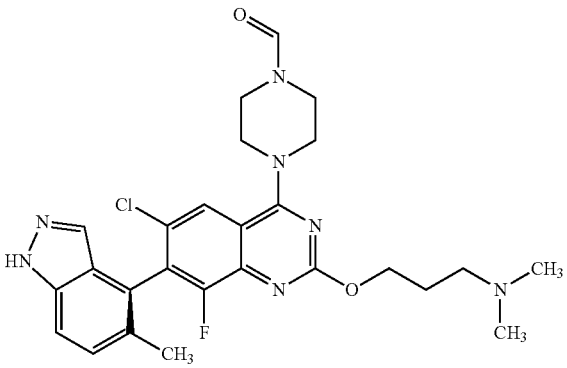 | 526.3 |
| 129 | 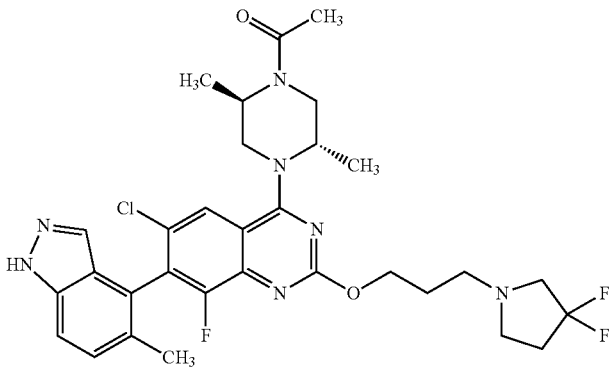 [SMILES: CC(=O)N1C[C@H](C)N(c2nc(OCCCN3CCC(F)(F)C3)nc3c(F)c(-c4c(C)ccc5[nH]ncc45)c(Cl)cc23)C[C@H]1C] | 630.4 |
| 130 | 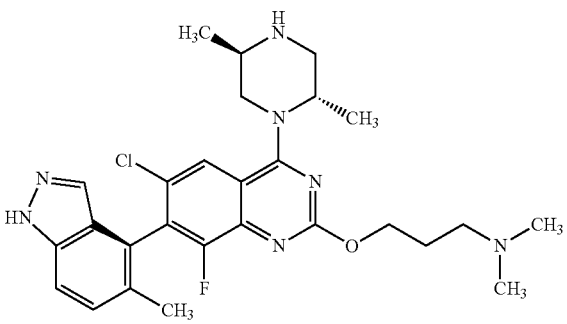 | 526.3 |
| 131 | 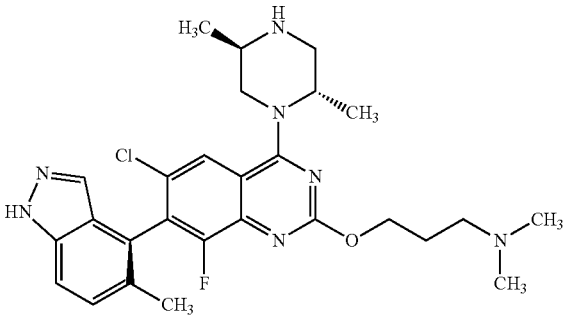 | 526.3 |

TABLE 1-continued

| No. | Structure | [M + H]+ |
|-----|-----------|----------|
| 132 | 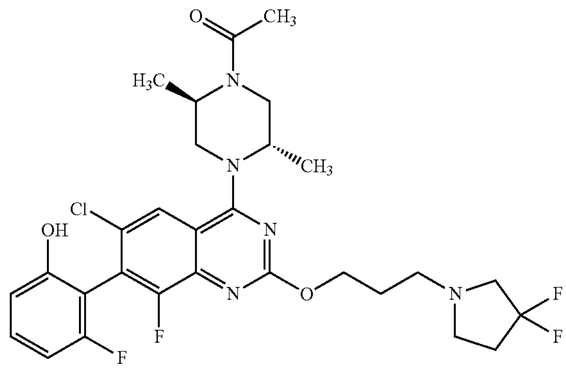 [SMILES: CC(=O)N1C[C@H](C)N(c2nc(OCCCN3CCC(F)(F)C3)nc3c(F)c(-c4c(O)cccc4F)c(Cl)cc23)C[C@H]1C] | 610.3 |
| 133 | 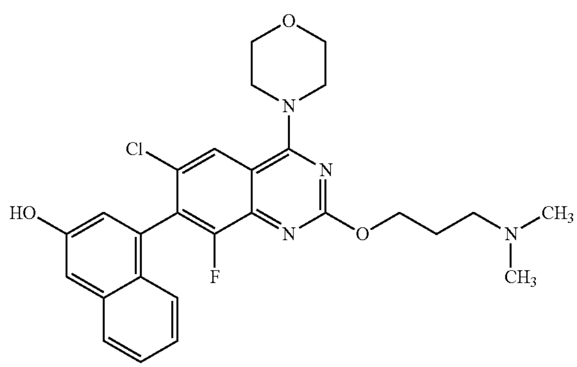 [SMILES: CN(C)CCCOc1nc(N2CCOCC2)c2cc(Cl)c(-c3cc(O)cc4ccccc34)c(F)c2n1] | 511.3 |
| 134 | 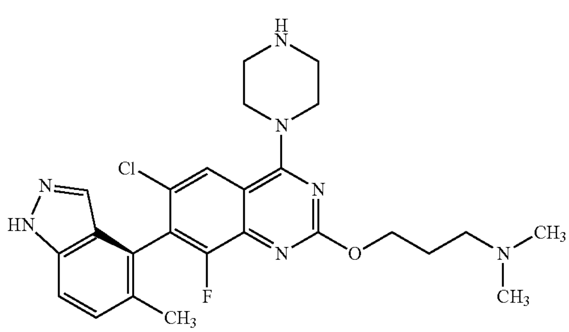 | 498.4 |
| 135 | 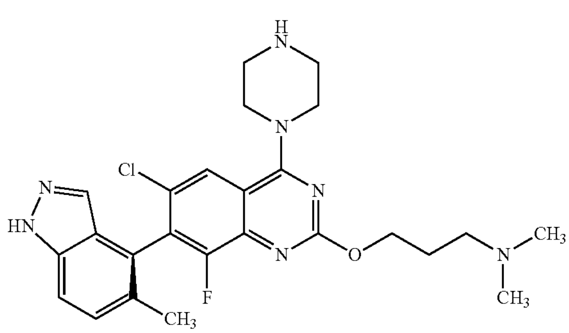 | 498.4 |

TABLE 1-continued

| No. | Structure | [M + H]+ |
|---|---|---|
| 136 | 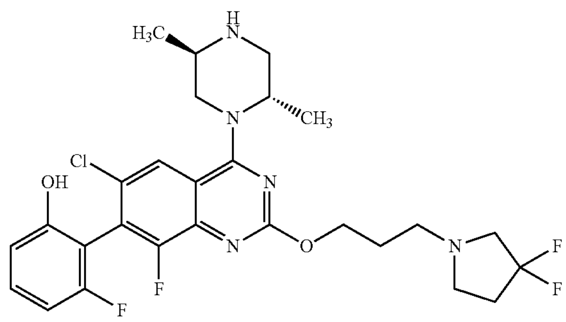 [SMILES: C[C@@H]1CN(c2nc(OCCCN3CCC(F)(F)C3)nc3c(F)c(-c4c(O)cccc4F)c(Cl)cc23)[C@@H](C)CN1] | 568.4 |
| 137 | 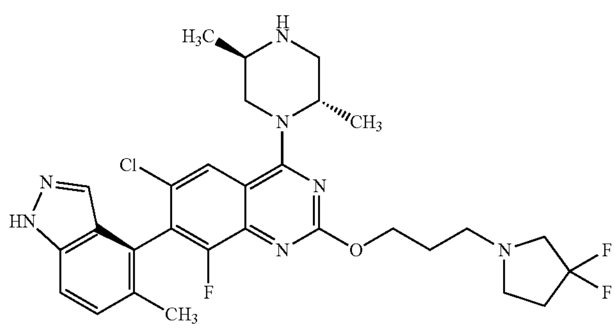 | 588.4 |
| 138 | 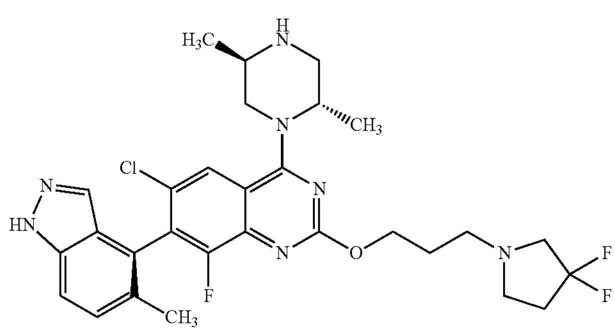 | 588.4 |
| 139 | 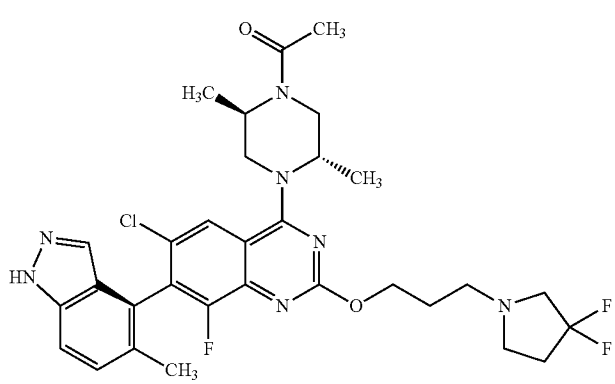 | 630.4 |

TABLE 1-continued

| No. | Structure | [M + H]+ |
|---|---|---|
| 140 | 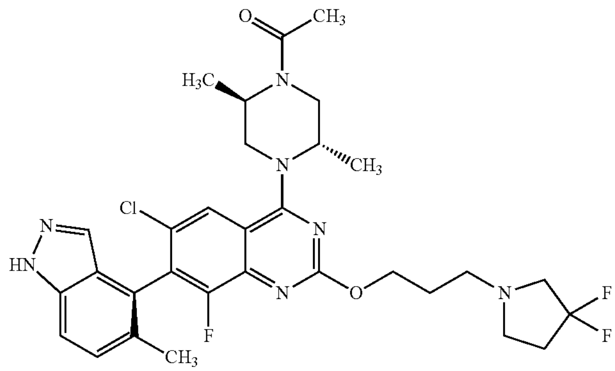 | 630.4 |
| 141 | 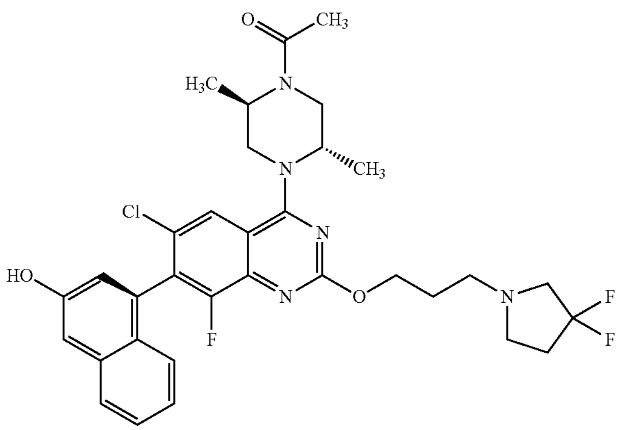 | 642.3 |
| 142 | 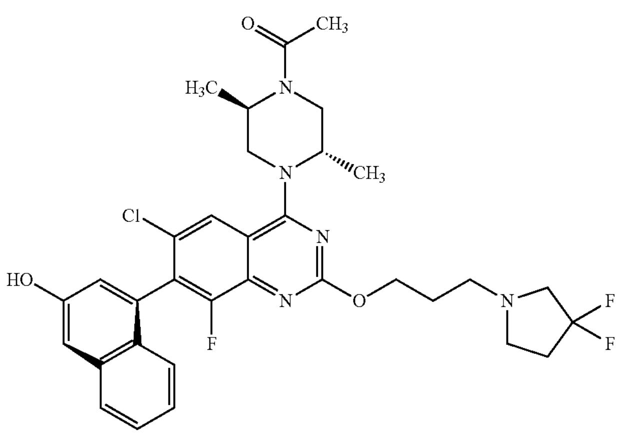 | 642.3 |
| 143 | 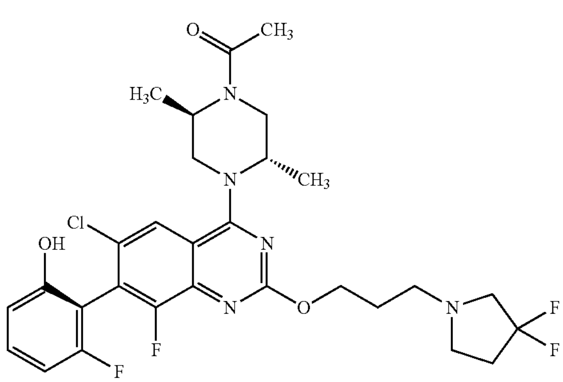 | 610.4 |

TABLE 1-continued

| No. | Structure | [M + H]+ |
|---|---|---|
| 144 | 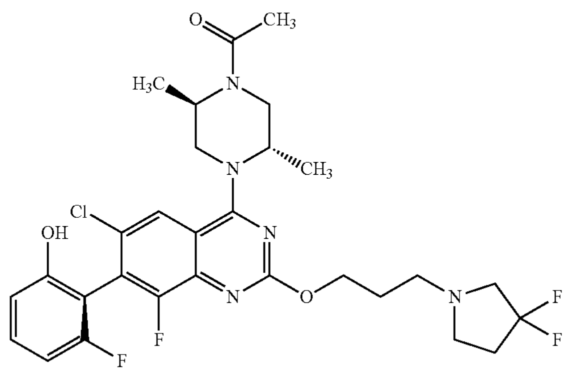 | 610.4 |
| 145 | 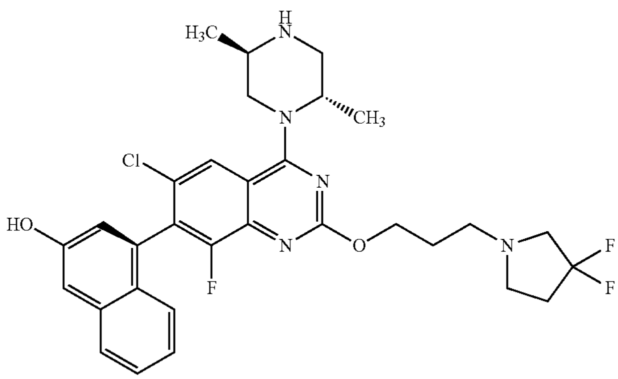 | 600.4 |
| 146 | 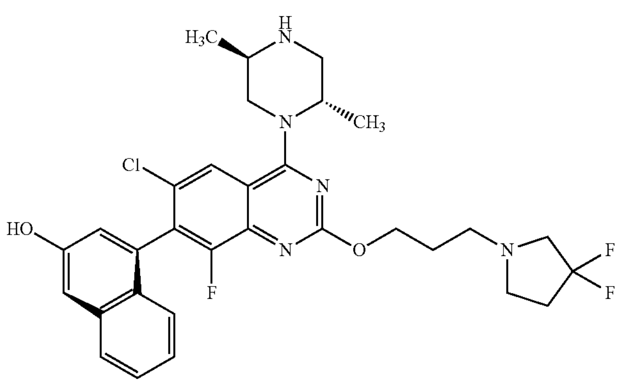 | 600.4 |
| 147 | 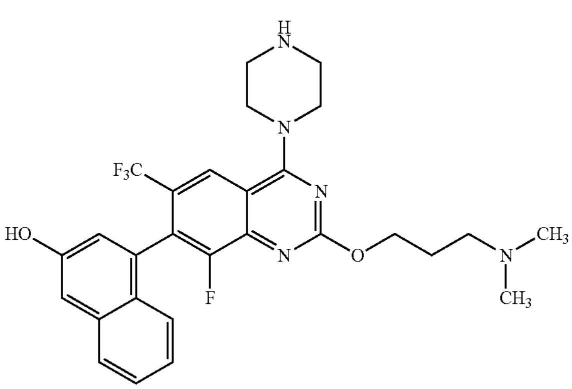 [SMILES: CN(C)CCCOc1nc(N2CCNCC2)c2cc(C(F)(F)F)c(-c3cc(O)cc4ccccc34)c(F)c2n1] | 544.3 |

TABLE 1-continued

| No. | Structure | [M + H]+ |
|---|---|---|
| 148 | 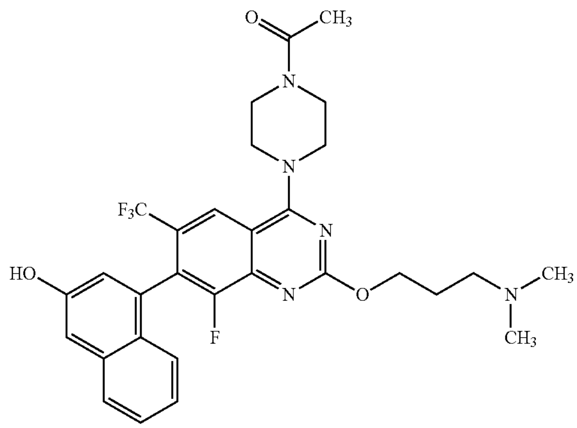 [SMILES: CC(=O)N1CCN(c2nc(OCCCN(C)C)nc3c(F)c(-c4cc(O)cc5ccccc45)c(C(F)(F)F)cc23)CC1] | 86.4 |
| 149 | 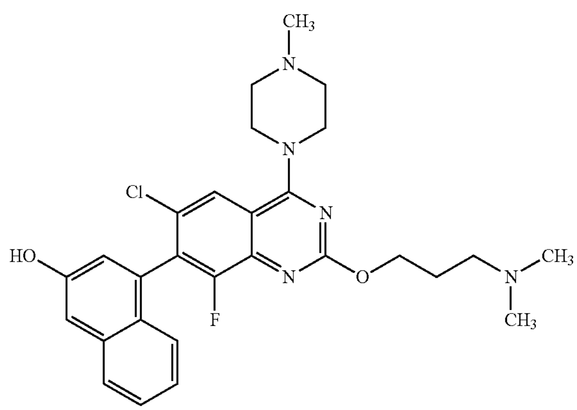 [SMILES: CN(C)CCCOc1nc(N2CCN(C)CC2)c2cc(Cl)c(-c3cc(O)cc4ccccc34)c(F)c2n1] | 524.3 |
| 150 | 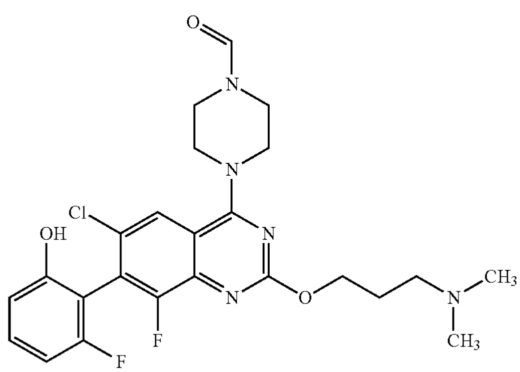 [SMILES: CN(C)CCCOc1nc(N2CCN(C=O)CC2)c2cc(Cl)c(-c3c(O)cccc3F)c(F)c2n1] | 506.3 |
| 151 | 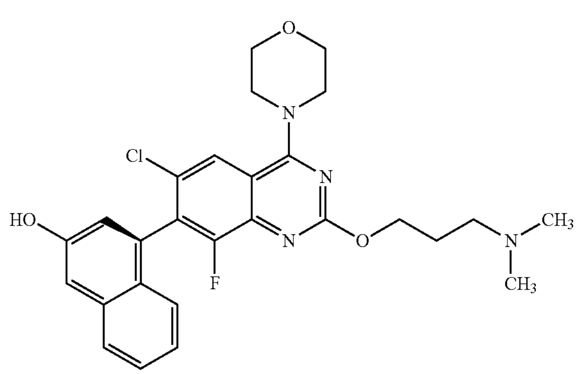 | 511.3 |

TABLE 1-continued

| No. | Structure | [M + H]+ |
|---|---|---|
| 152 | 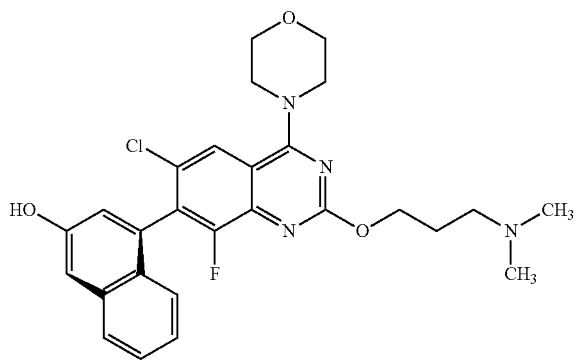 | 511.3 |
| 153 | 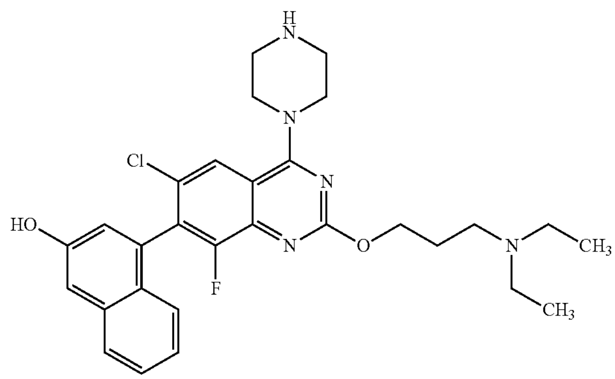 [SMILES: CCN(CC)CCCOc1nc(N2CCNCC2)c2cc(Cl)c(-c3cc(O)cc4ccccc34)c(F)c2n1] | 538.3 |
| 154 | 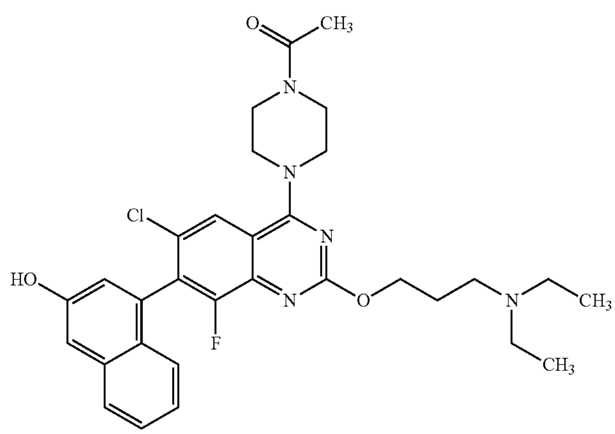 [SMILES: CCN(CC)CCCOc1nc(N2CCN(C(C)=O)CC2)c2cc(Cl)c(-c3cc(O)cc4ccccc34)c(F)c2n1] | 580.3 |
| 155 | 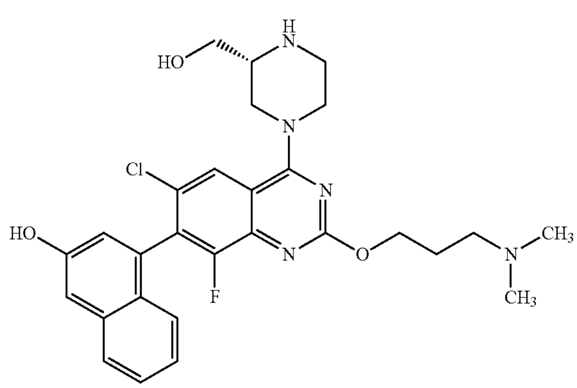 [SMILES: CN(C)CCCOc1nc(N2CCN[C@@H](CO)C2)c2cc(Cl)c(-c3cc(O)cc4ccccc34)c(F)c2n1] | 542.3 |

TABLE 1-continued

| No. | Structure | [M + H]+ |
|---|---|---|
| 156 | 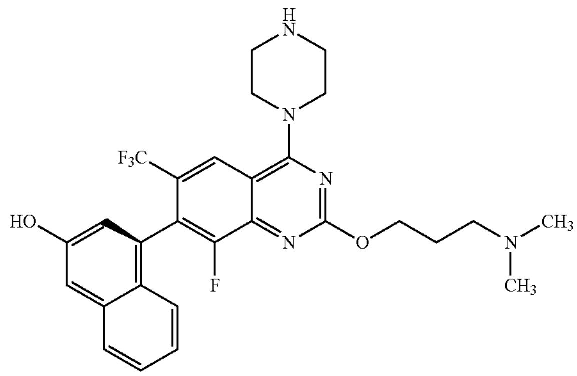 | 544.3 |
| 157 | 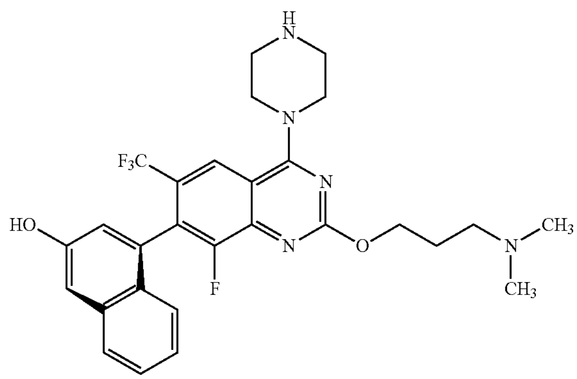 | 544.3 |
| 158 | 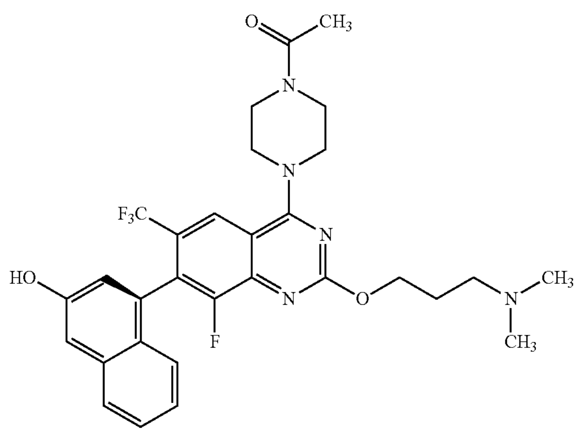 | 586.4 |
| 159 | 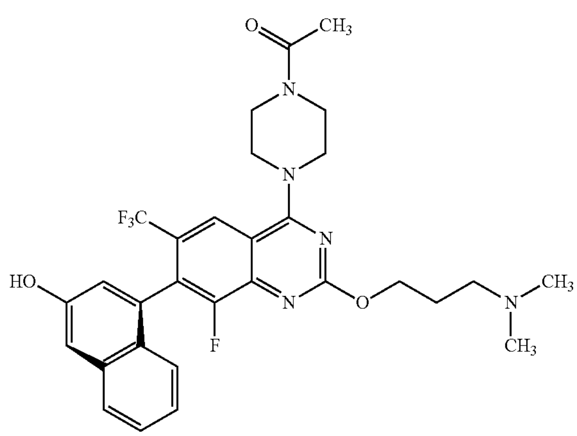 | 586.4 |

TABLE 1-continued

| No. | Structure | [M + H]⁺ |
|---|---|---|
| 160 | (structure) | 548.3 |
| 161 | (structure) | 545.3 |
| 162 | (structure) | 545.3 |
| 163 | (structure) | 545.3 |

TABLE 1-continued
| No. | Structure | [M + H]+ |
|---|---|---|
| 164 | 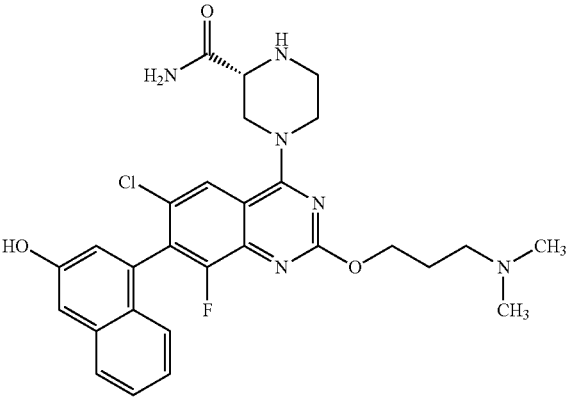 [SMILES: CN(C)CCCOc1nc(N2CCN[C@@H](C(N)=O)C2)c2cc(Cl)c(-c3cc(O)cc4ccccc34)c(F)c2n1] | 553.3 |
| 165 | 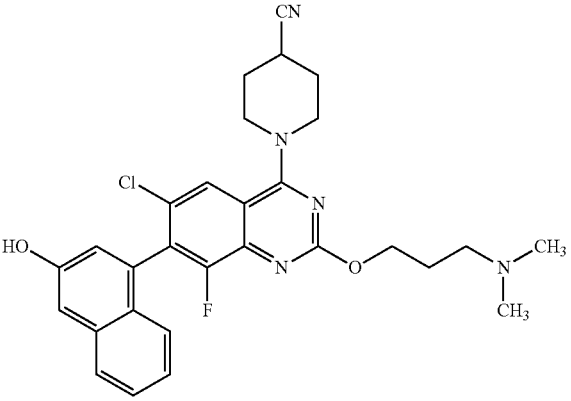 [SMILES: CN(C)CCCOc1nc(N2CCC(C#N)CC2)c2cc(Cl)c(-c3cc(O)cc4ccccc34)c(F)c2n1] | 534.4 |
| 166 | 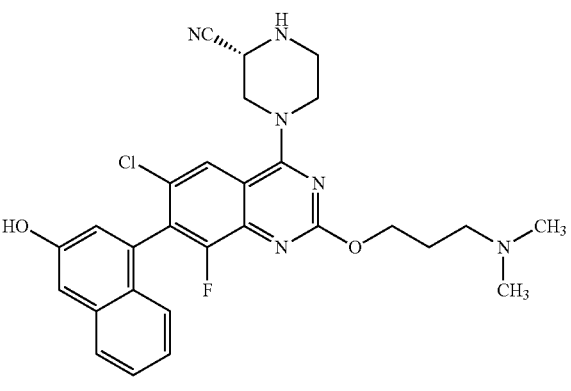 [SMILES: CN(C)CCCOc1nc(N2CCN[C@@H](C#N)C2)c2cc(Cl)c(-c3cc(O)cc4ccccc34)c(F)c2n1] | 535.4 |
| 167 | 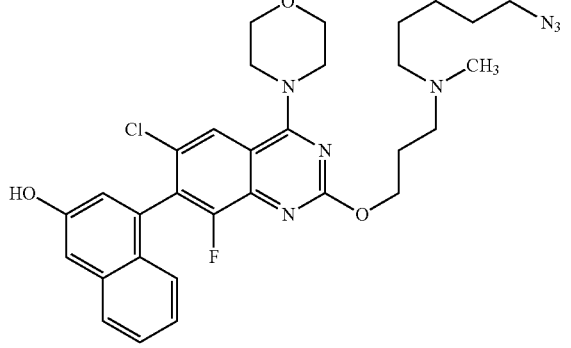 | 608.4 |

TABLE 1-continued
| No. | Structure | [M + H]+ |
|---|---|---|
| 168 | 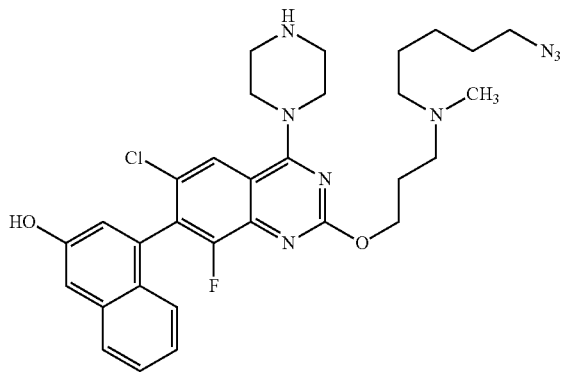 [SMILES: CN(CCCCCN=[N+]=[N-])CCCOc1nc(N2CCNCC2)c2cc(Cl)c(-c3cc(O)cc4ccccc34)c(F)c2n1] | 607.4 |
| 169 | 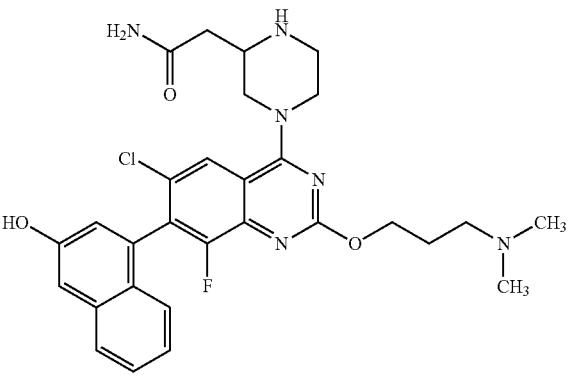 [SMILES: CN(C)CCCOc1nc(N2CCNC(CC(N)=O)C2)c2cc(Cl)c(-c3cc(O)cc4ccccc34)c(F)c2n1] | 567.4 |
| 170 | 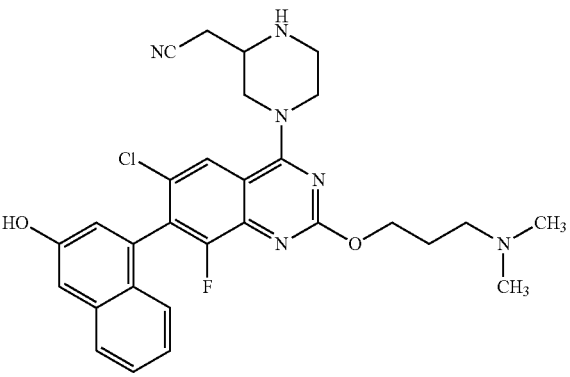 [SMILES: CN(C)CCCOc1nc(N2CCNC(CC#N)C2)c2cc(Cl)c(-c3cc(O)cc4ccccc34)c(F)c2n1] | 549.4 |
| 171 | 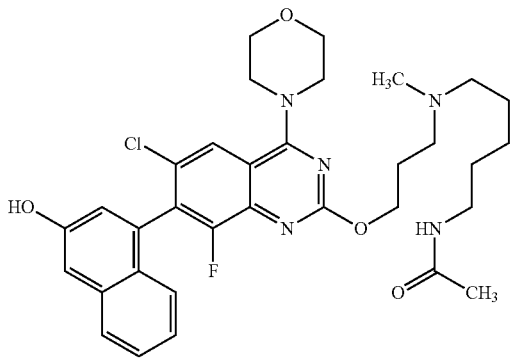 [SMILES: CC(=O)NCCCCCN(C)CCCOc1nc(N2CCOCC2)c2cc(Cl)c(-c3cc(O)cc4ccccc34)c(F)c2n1] | 624.3 |

TABLE 1-continued

| No. | Structure | [M + H]+ |
|---|---|---|
| 172 | 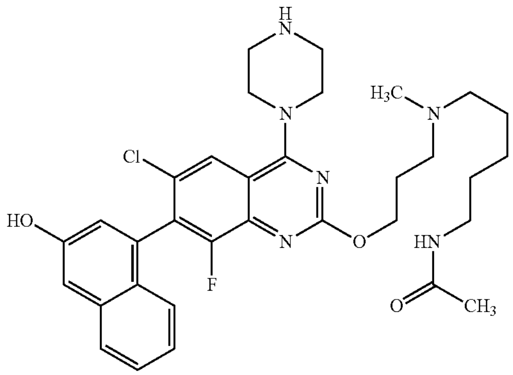 [SMILES: CC(=O)NCCCCCN(C)CCCOc1nc(N2CCNCC2)c2cc(Cl)c(-c3cc(O)cc4ccccc34)c(F)c2n1] | 623.3 |
| 173 | 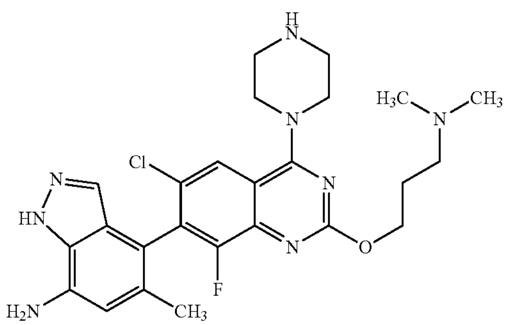 [SMILES: Cc1cc(N)c2[nH]ncc2c1-c1c(Cl)cc2c(N3CCNCC3)nc(OCCCN(C)C)nc2c1F] | 513.3 |
| 174 | 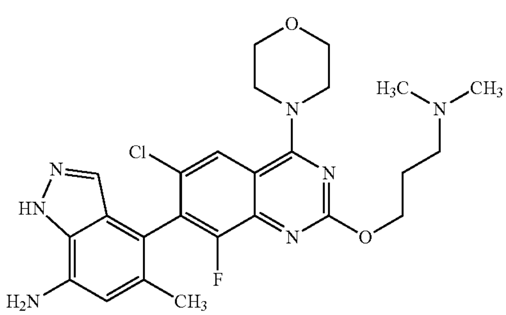 [SMILES: Cc1cc(N)c2[nH]ncc2c1-c1c(Cl)cc2c(N3CCOCC3)nc(OCCCN(C)C)nc2c1F] | 514.3 |
| 175 | 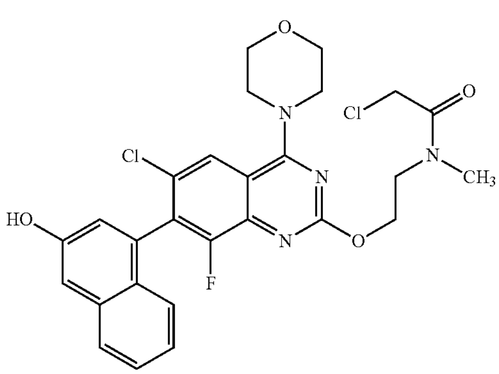 [SMILES: CN(CCOc1nc(N2CCOCC2)c2cc(Cl)c(-c3cc(O)cc4ccccc34)c(F)c2n1)C(=O)CCl] | 559.2 |

TABLE 1-continued

| No. | Structure | [M + H]+ |
|---|---|---|
| 176 | 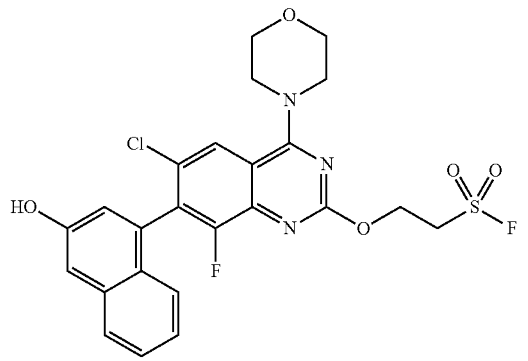 [SMILES: O=S(=O)(F)CCOc1nc(N2CCOCC2)c2cc(Cl)c(-c3cc(O)cc4ccccc34)c(F)c2n1] | 536.3 |

TABLE 2

| No. | Structure | [M + H]+ |
|---|---|---|
| 68 | 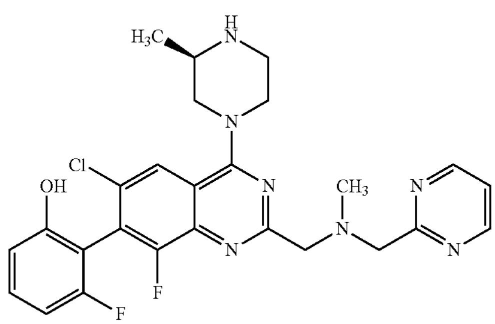 [SMILES: C[C@@H]1CN(c2nc(CN(C)Cc3ncccn3)nc3c(F)c(-c4c(O)cccc4F)c(Cl)cc23)CCN1] | 525.6 |
| 69 | 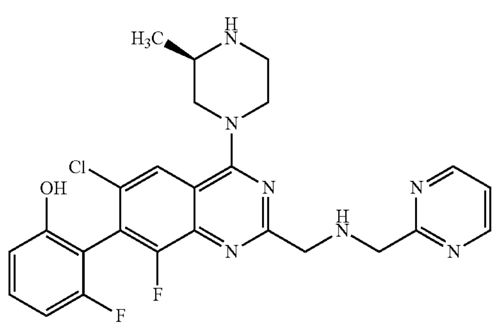 [SMILES: C[C@@H]1CN(c2nc(CNCc3ncccn3)nc3c(F)c(-c4c(O)cccc4F)c(Cl)cc23)CCN1] | 512.2 |
| 70 | 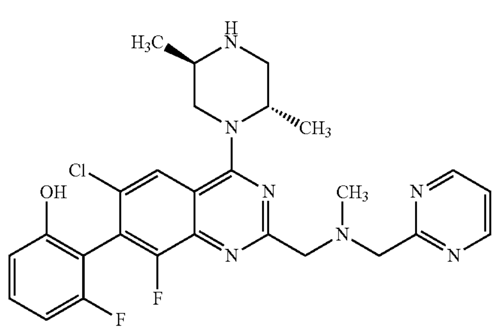 [SMILES: C[C@@H]1CN(c2nc(CN(C)Cc3ncccn3)nc3c(F)c(-c4c(O)cccc4F)c(Cl)cc23)[C@@H](C)CN1] | 540.2 |

TABLE 2-continued

| No. | Structure | [M + H]+ |
|---|---|---|
| 71 | 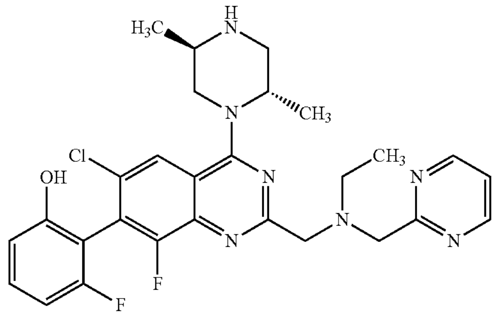 [SMILES: CCN(Cc1ncccn1)Cc1nc(N2C[C@@H](C)NC[C@@H]2C)c2cc(Cl)c(-c3c(O)cccc3F)c(F)c2n1] | 554.2 |
| 72 | 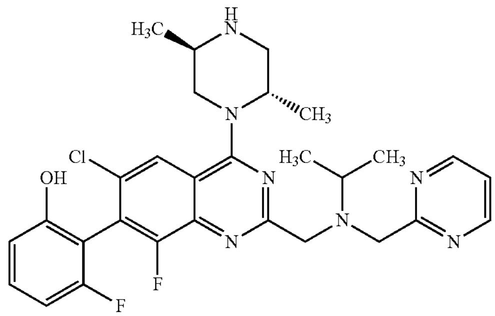 [SMILES: CC(C)N(Cc1ncccn1)Cc1nc(N2C[C@@H](C)NC[C@@H]2C)c2cc(Cl)c(-c3c(O)cccc3F)c(F)c2n1] | 568.2 |
| 73 | 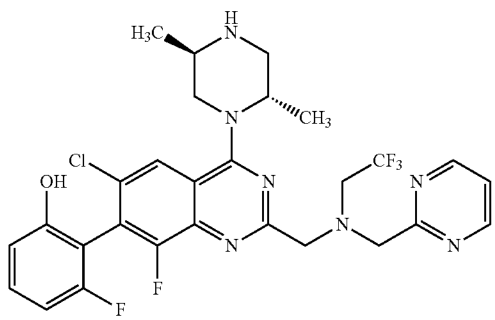 | 608.2 |
| 74 | 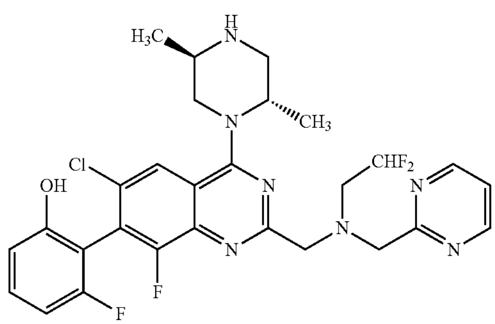 [SMILES: C[C@@H]1CN(c2nc(CN(Cc3ncccn3)CC(F)F)nc3c(F)c(-c4c(O)cccc4F)c(Cl)cc23)[C@@H](C)CN1] | 590.2 |
| 75 | 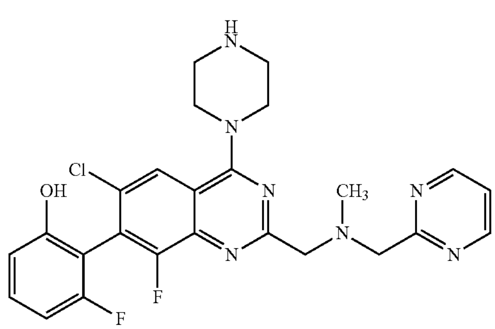 [SMILES: CN(Cc1ncccn1)Cc1nc(N2CCNCC2)c2cc(Cl)c(-c3c(O)cccc3F)c(F)c2n1] | 512.2 |

TABLE 2-continued
| No. | Structure | [M + H]+ |
|---|---|---|
| 76 | 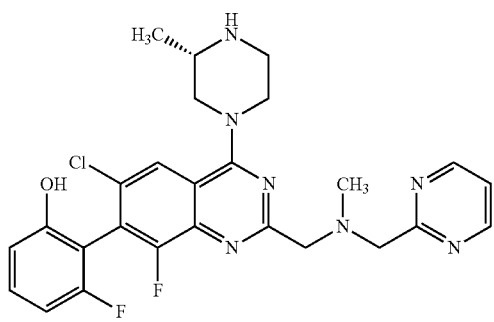 [SMILES: C[C@H]1CN(c2nc(CN(C)Cc3ncccn3)nc3c(F)c(-c4c(O)cccc4F)c(Cl)cc23)CCN1] | 526.1 |
| 77 | 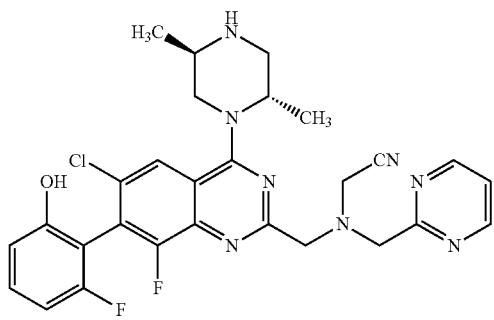 [SMILES: C[C@@H]1CN(c2nc(CN(CC#N)Cc3ncccn3)nc3c(F)c(-c4c(O)cccc4F)c(Cl)cc23)[C@@H](C)CN1] | 565.1 |
| 78 | 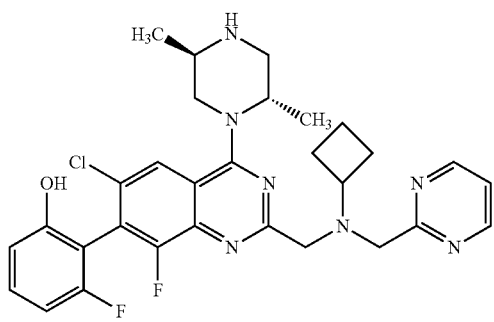 [SMILES: C[C@@H]1CN(c2nc(CN(Cc3ncccn3)C3CCC3)nc3c(F)c(-c4c(O)cccc4F)c(Cl)cc23)[C@@H](C)CN1] | 580.2 |
| 79 | 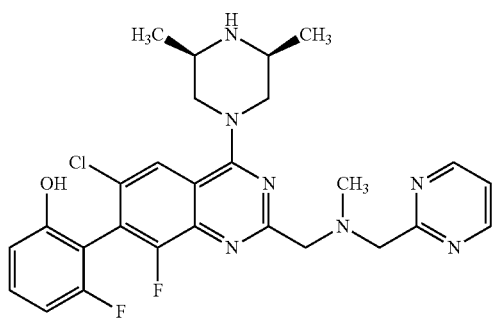 [SMILES: C[C@@H]1CN(c2nc(CN(C)Cc3ncccn3)nc3c(F)c(-c4c(O)cccc4F)c(Cl)cc23)C[C@H](C)N1] | 539.7 |

TABLE 2-continued

| No. | Structure | [M + H]+ |
|---|---|---|
| 80 | 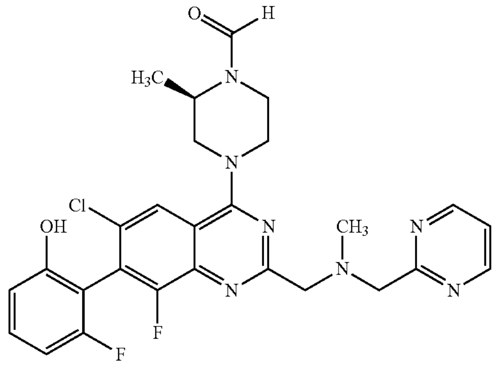 [SMILES: C[C@@H]1CN(c2nc(CN(C)Cc3ncccn3)nc3c(F)c(-c4c(O)cccc4F)c(Cl)cc23)CCN1C=O] | 553.7 |
| 81 | 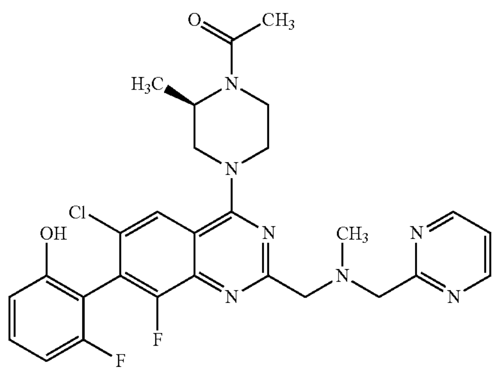 | 567.7 |
| 82 | 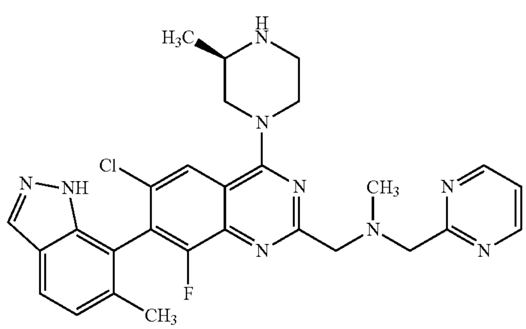 [SMILES: Cc1ccc2cn[nH]c2c1-c1c(Cl)cc2c(N3CCN[C@H](C)C3)nc(CN(C)Cc3ncccn3)nc2c1F] | 545.4 |
| 83 | 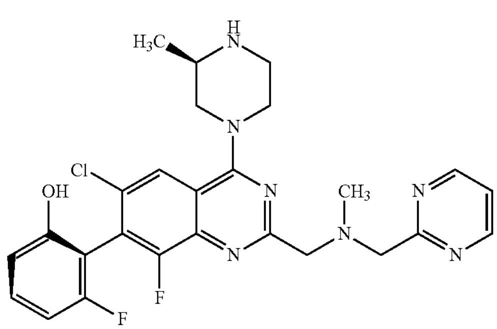 | 525.7 |

TABLE 2-continued

| No. | Structure | [M + H]+ |
|---|---|---|
| 84 | 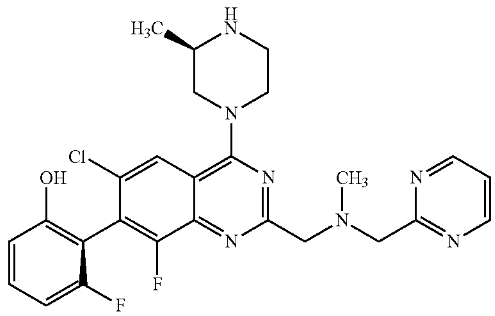 | 525.7 |

TABLE 3

| No. | Structure | [M + H]+ |
|---|---|---|
| 300 | 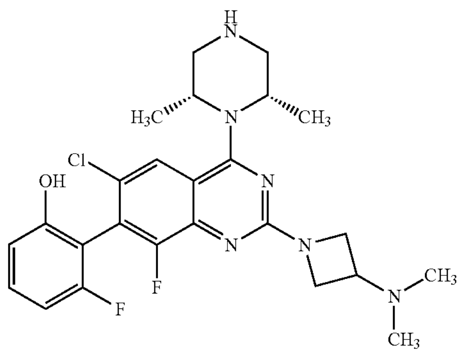 [SMILES: C[C@@H]1CNC[C@H](C)N1c1nc(N2CC(N(C)C)C2)nc2c(F)c(-c3c(O)cccc3F)c(Cl)cc12] | 503.25 |
| 301 | 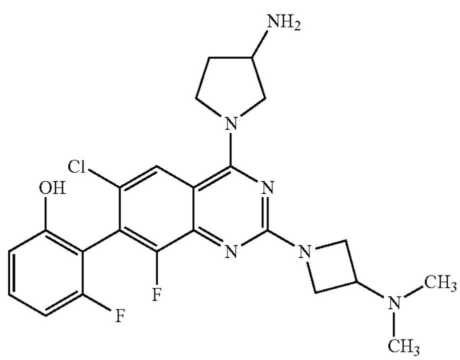 [SMILES: CN(C)C1CN(c2nc(N3CCC(N)C3)c3cc(Cl)c(-c4c(O)cccc4F)c(F)c3n2)C1] | 475.30 |
| 302 | 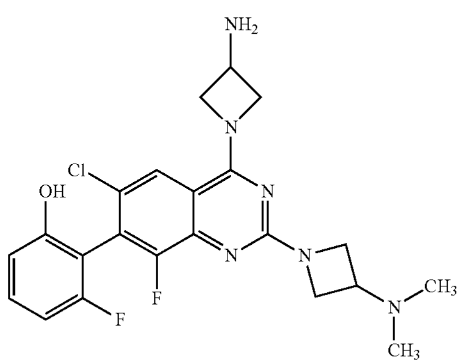 [SMILES: CN(C)C1CN(c2nc(N3CC(N)C3)c3cc(Cl)c(-c4c(O)cccc4F)c(F)c3n2)C1] | 461.20 |

TABLE 3-continued

| No. | Structure | [M + H]+ |
|---|---|---|
| 303 | 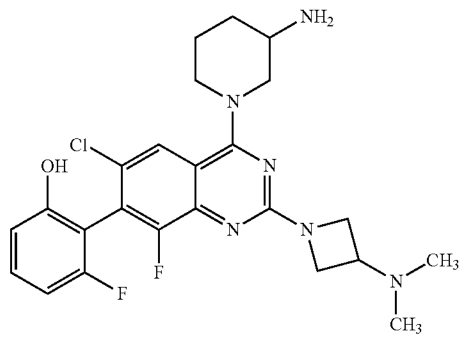 [SMILES: CN(C)C1CN(c2nc(N3CCCC(N)C3)c3cc(Cl)c(-c4c(O)cccc4F)c(F)c3n2)C1] | 489.30 |
| 304 | 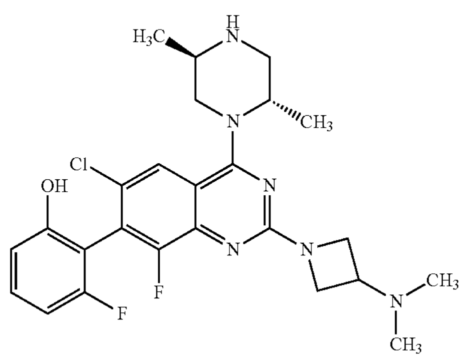 [SMILES: C[C@@H]1CN(c2nc(N3CC(N(C)C)C3)nc3c(F)c(-c4c(O)cccc4F)c(Cl)cc23)[C@@H](C)CN1] | 503.25 |
| 305 | 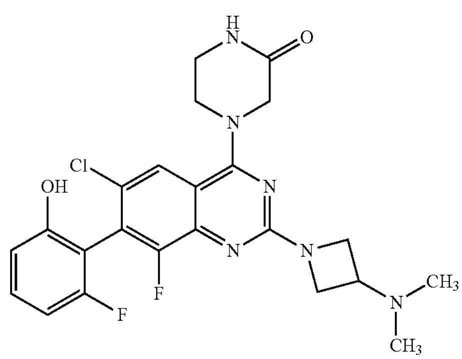 [SMILES: CN(C)C1CN(c2nc(N3CCNC(=O)C3)c3cc(Cl)c(-c4c(O)cccc4F)c(F)c3n2)C1] | 489.20 |
| 306 | 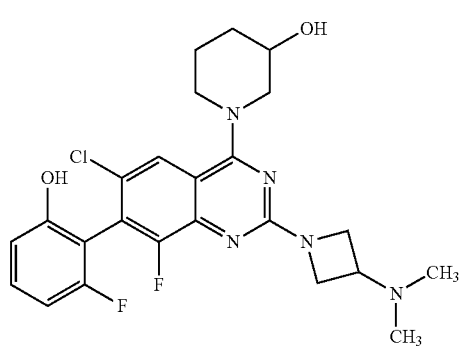 [SMILES: CN(C)C1CN(c2nc(N3CCCC(O)C3)c3cc(Cl)c(-c4c(O)cccc4F)c(F)c3n2)C1] | 490.2 |

TABLE 3-continued

| No. | Structure | [M + H]+ |
|---|---|---|
| 307 | 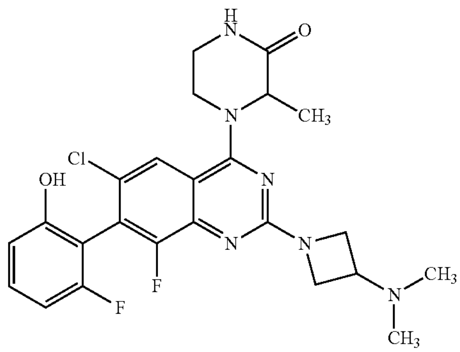 [SMILES: CC1C(=O)NCCN1c1nc(N2CC(N(C)C)C2)nc2c(F)c(-c3c(O)cccc3F)c(Cl)cc12] | 503.25 |
| 308 | 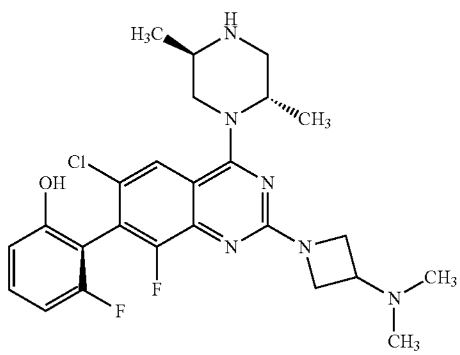 | 503.2 |
| 309 | 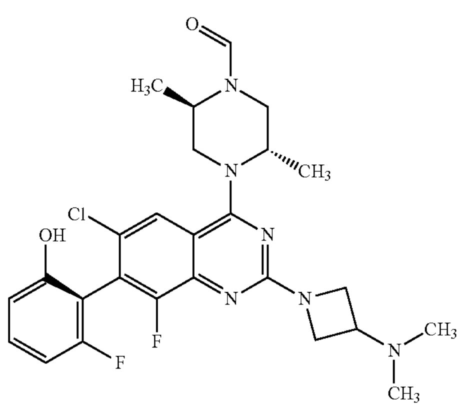 | 531.2 |
| 310 | 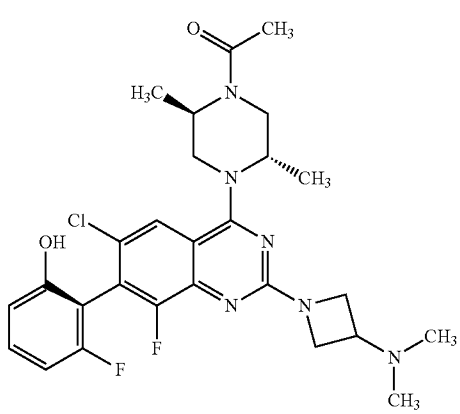 | 545.2 |

TABLE 3-continued
| No. | Structure | [M + H]+ |
|---|---|---|
| 311 | 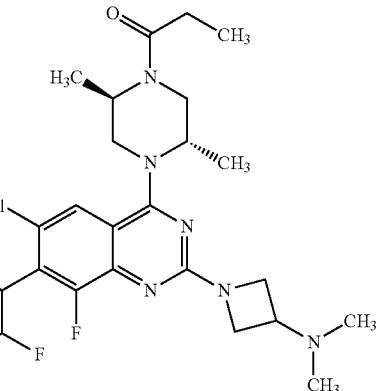 | 559.2 |
| 312 | 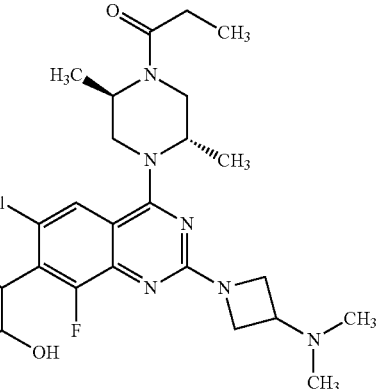 | 559.2 |
| 313 | 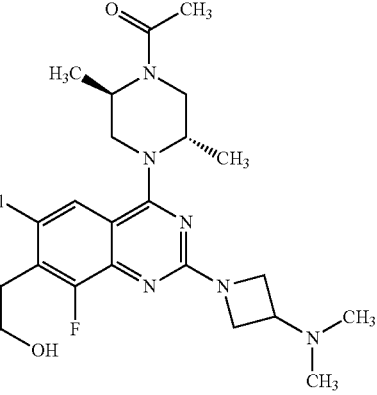 | 545.2 |
| 314 | 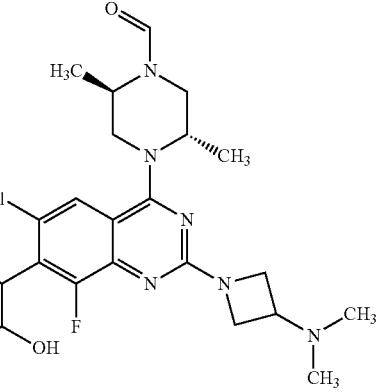 | 531.2 |

TABLE 3-continued
| No. | Structure | [M + H]+ |
|---|---|---|
| 315 | 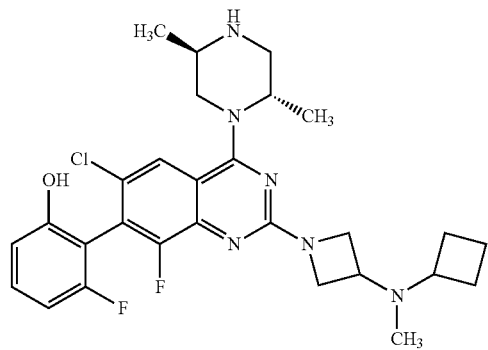 [SMILES: C[C@@H]1CN(c2nc(N3CC(N(C)C4CCC4)C3)nc3c(F)c(-c4c(O)cccc4F)c(Cl)cc23)[C@@H](C)CN1] | 542.7 |
| 316 | 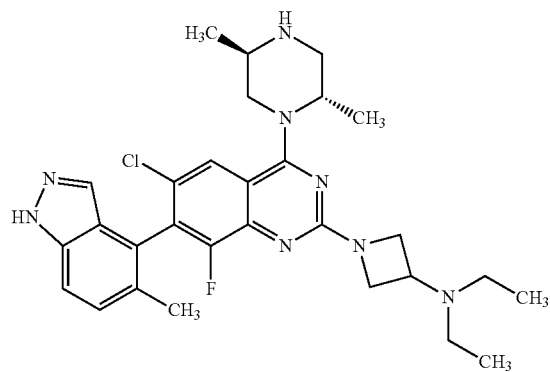 [SMILES: CCN(CC)C1CN(c2nc(N3C[C@@H](C)NC[C@@H]3C)c3cc(Cl)c(-c4c(C)ccc5[nH]ncc45)c(F)c3n2)C1] | 550.7 |
| 317 | 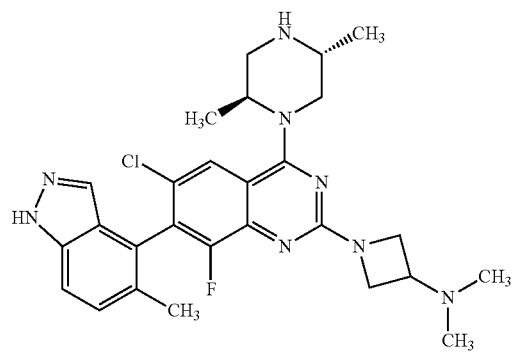 [SMILES: Cc1ccc2[nH]ncc2c1-c1c(Cl)cc2c(N3C[C@@H](C)NC[C@@H]3C)nc(N3CC(N(C)C)C3)nc2c1F] | 522.8 |
| 318 | 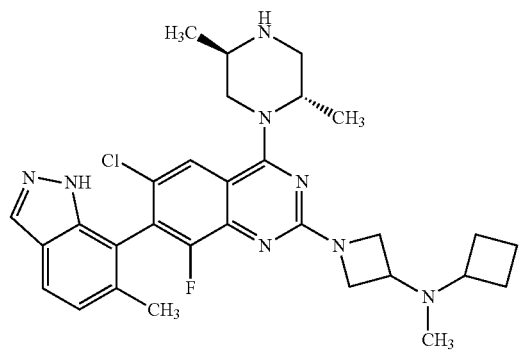 [SMILES: Cc1ccc2cn[nH]c2c1-c1c(Cl)cc2c(N3C[C@@H](C)NC[C@@H]3C)nc(N3CC(N(C)C4CCC4)C3)nc2c1F] | 563.3 |

TABLE 3-continued

| No. | Structure | [M + H]+ |
|---|---|---|
| 319 | 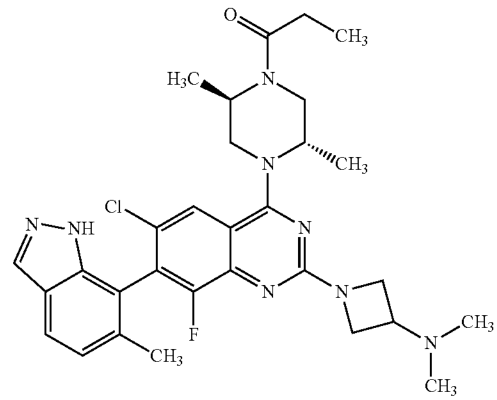 [SMILES: CCC(=O)N1C[C@H](C)N(c2nc(N3CC(N(C)C)C3)nc3c(F)c(-c4c(C)ccc5cn[nH]c45)c(Cl)cc23)C[C@H]1C] | 578.2 |
| 320 | 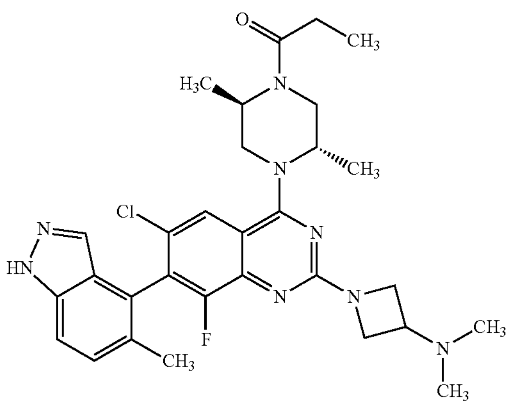 [SMILES: CCC(=O)N1C[C@H](C)N(c2nc(N3CC(N(C)C)C3)nc3c(F)c(-c4c(C)ccc5[nH]ncc45)c(Cl)cc23)C[C@H]1C] | 579.3 |
| 321 | 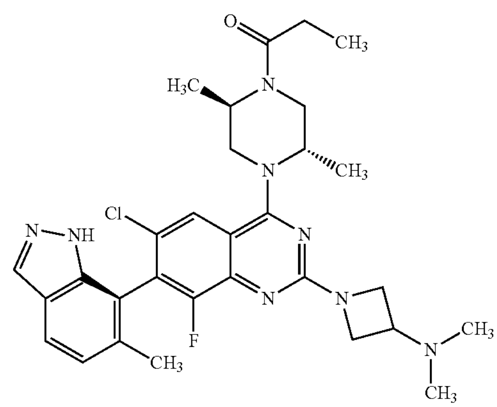 | 579.4 |
| 322 | 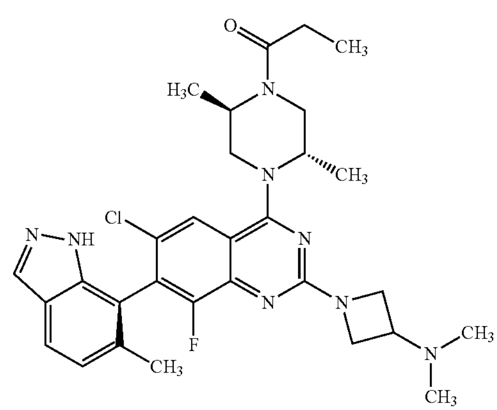 | 579.3 |

TABLE 3-continued

| No. | Structure | [M + H]+ |
|---|---|---|
| 323 | 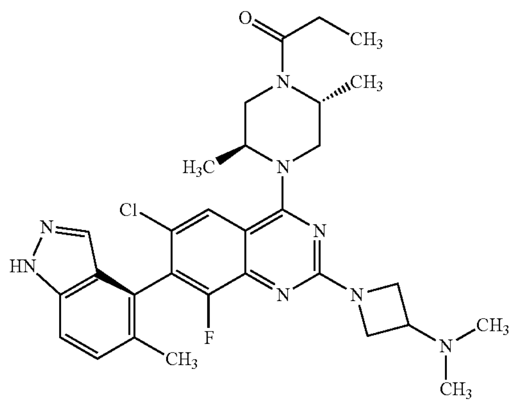 | 579.4 |
| 324 | 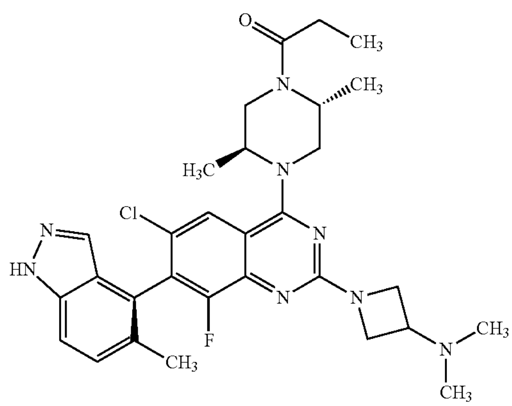 | 579.4 |
| 325 | 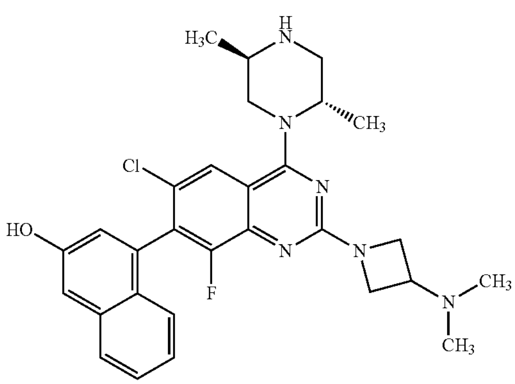 [SMILES: C[C@@H]1CN(c2nc(N3CC(N(C)C)C3)nc3c(F)c(-c4cc(O)cc5ccccc45)c(Cl)cc23)[C@@H](C)CN1] | 535.4 |
| 326 | 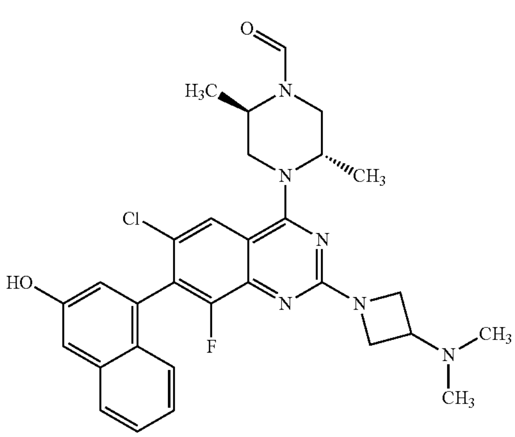 [SMILES: C[C@@H]1CN(c2nc(N3CC(N(C)C)C3)nc3c(F)c(-c4cc(O)cc5ccccc45)c(Cl)cc23)[C@@H](C)CN1C=O] | 563.4 |

TABLE 3-continued
| No. | Structure | [M + H]+ |
|---|---|---|
| 327 | 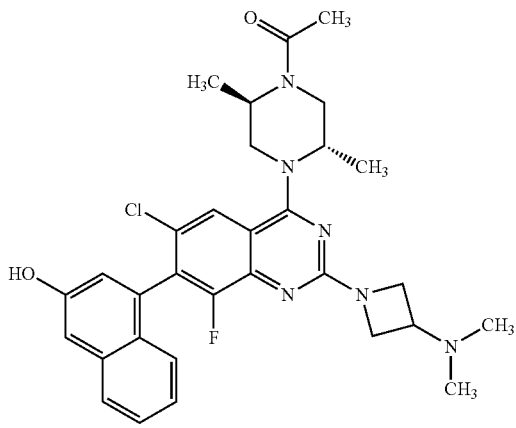 [SMILES: CC(=O)N1C[C@H](C)N(c2nc(N3CC(N(C)C)C3)nc3c(F)c(-c4cc(O)cc5ccccc45)c(Cl)cc23)C[C@H]1C] | 577.4 |
| 328 | 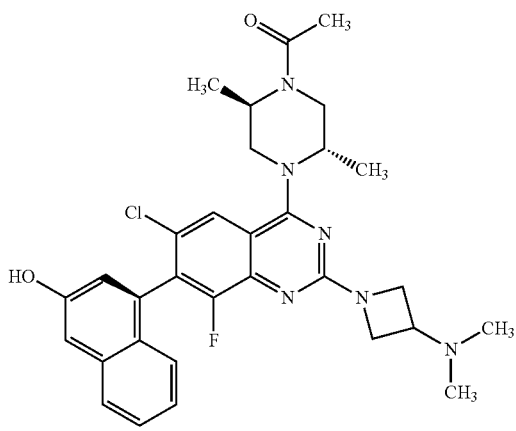 | 577.4 |
| 329 | 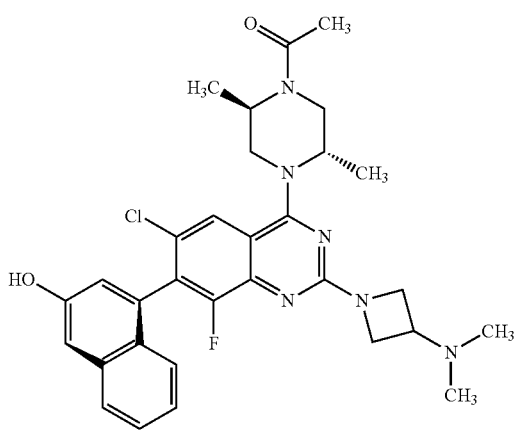 | 577.4 |

TABLE 3-continued

| No. | Structure | [M + H]+ |
|---|---|---|
| 330 | 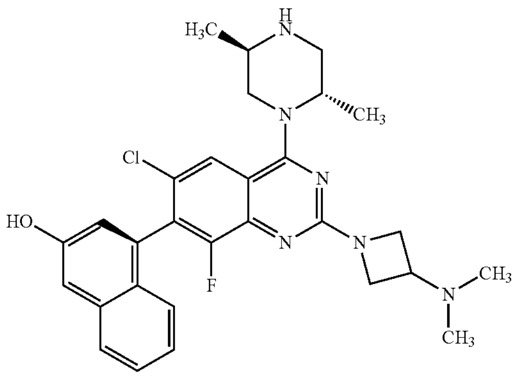 | 535.3 |
| 331 | 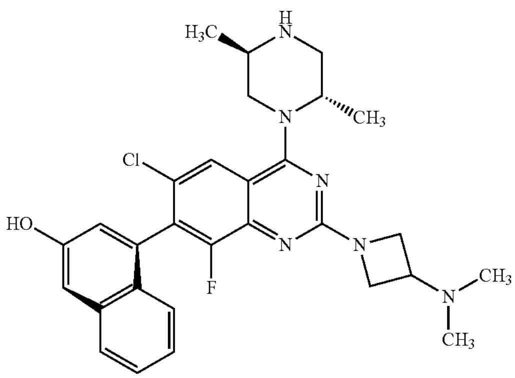 | 535.3 |
| 332 | 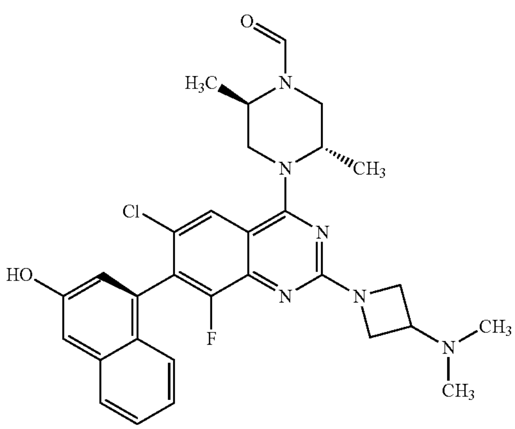 | 563.3 |
| 333 | 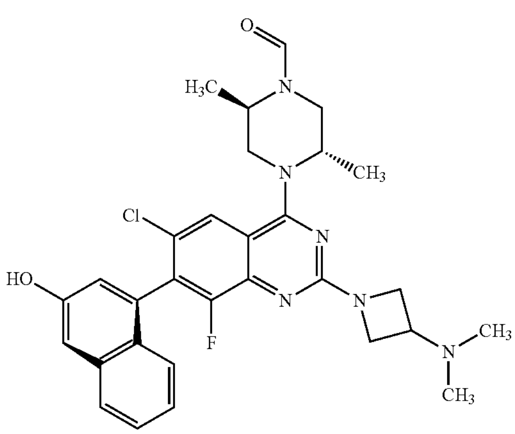 | 563.3 |

TABLE 3-continued
| No. | Structure | [M + H]+ |
|---|---|---|
| 334 | 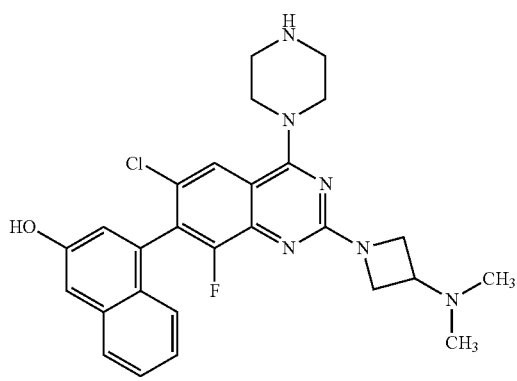 [SMILES: CN(C)C1CN(c2nc(N3CCNCC3)c3cc(Cl)c(-c4cc(O)cc5ccccc45)c(F)c3n2)C1] | 507.3 |
| 335 | 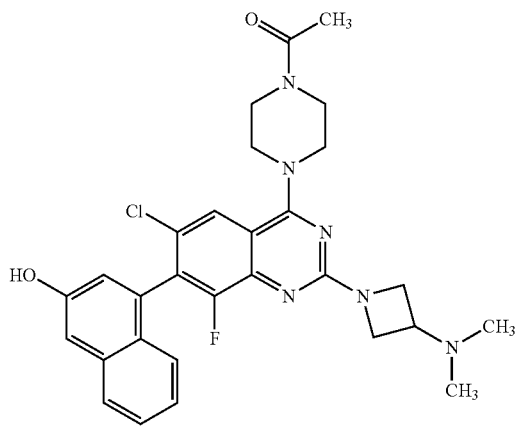 [SMILES: CC(=O)N1CCN(c2nc(N3CC(N(C)C)C3)nc3c(F)c(-c4cc(O)cc5ccccc45)c(Cl)cc23)CC1] | 549.4 |
| 336 | 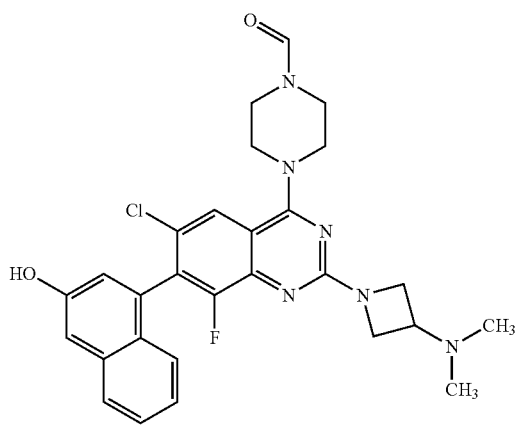 [SMILES: CN(C)C1CN(c2nc(N3CCN(C=O)CC3)c3cc(Cl)c(-c4cc(O)cc5ccccc45)c(F)c3n2)C1] | 535.3 |

TABLE 3-continued
| No. | Structure | [M + H]+ |
|---|---|---|
| 337 | 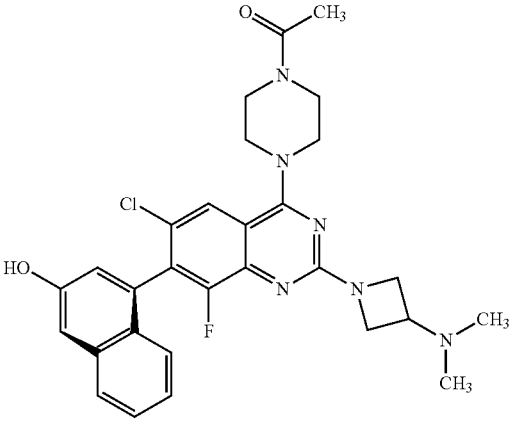 | 549.3 |
| 338 | 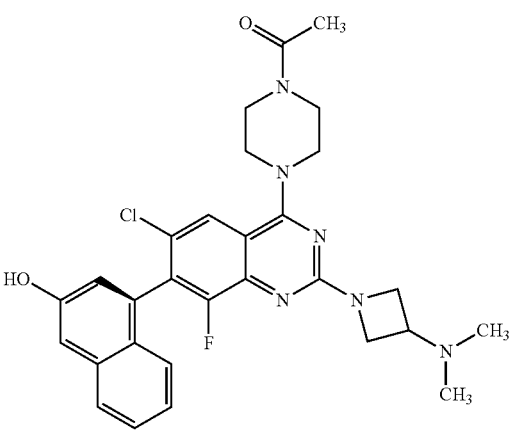 | 549.3 |
| 339 | 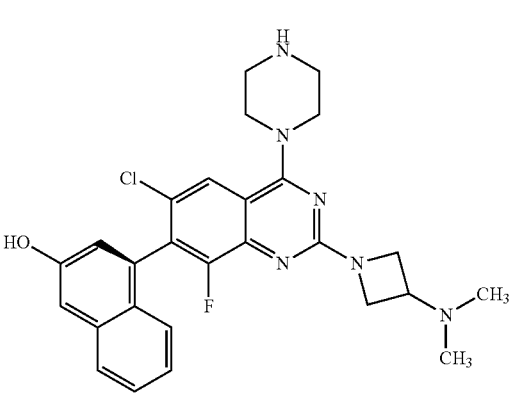 | 507.3 |
| 340 | 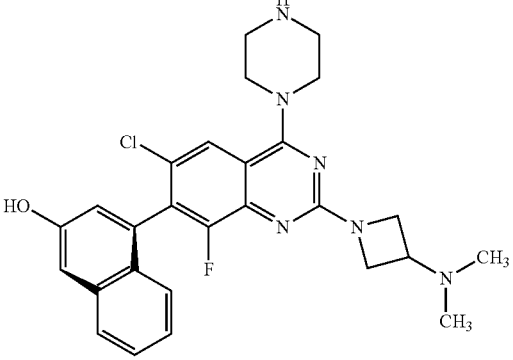 | 507.3 |

TABLE 3-continued

| No. | Structure | [M + H]+ |
|---|---|---|
| 341 | 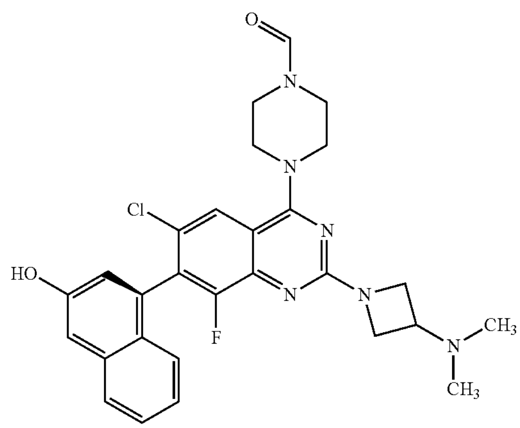 | 535.3 |
| 342 | 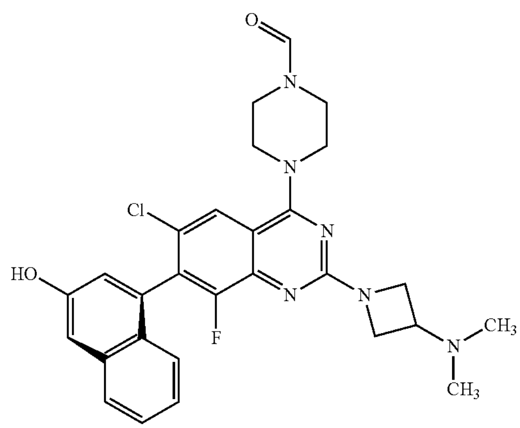 | 535.3 |
| 343 | 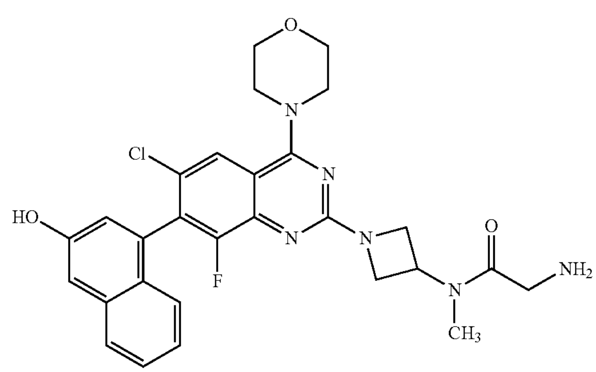 [SMILES: CN(C(=O)CN)C1CN(c2nc(N3CCOCC3)c3cc(Cl)c(-c4cc(O)cc5ccccc45)c(F)c3n2)C1] | 551.3 |
| 344 | 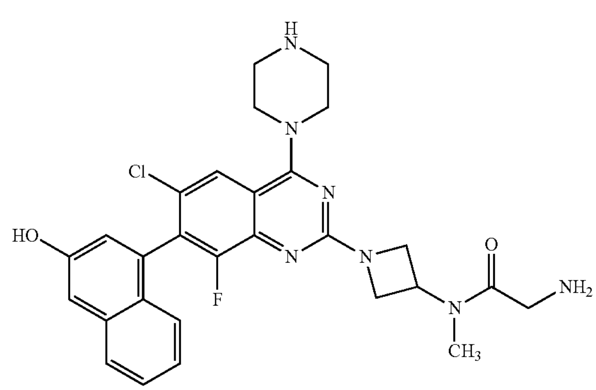 [SMILES: CN(C(=O)CN)C1CN(c2nc(N3CCNCC3)c3cc(Cl)c(-c4cc(O)cc5ccccc45)c(F)c3n2)C1] | 550.3 |

TABLE 3-continued
| No. | Structure | [M + H]+ |
|---|---|---|
| 345 | 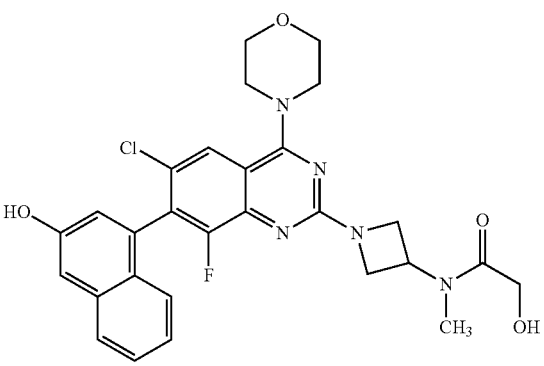 [SMILES: CN(C(=O)CO)C1CN(c2nc(N3CCOCC3)c3cc(Cl)c(-c4cc(O)cc5ccccc45)c(F)c3n2)C1] | 552.4 |
| 346 | 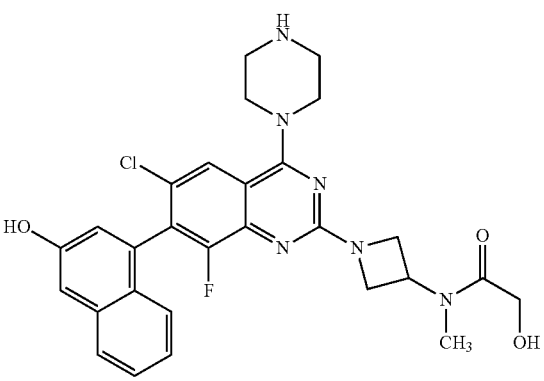 [SMILES: CN(C(=O)CO)C1CN(c2nc(N3CCNCC3)c3cc(Cl)c(-c4cc(O)cc5ccccc45)c(F)c3n2)C1] | 551.3 |
| 347 | 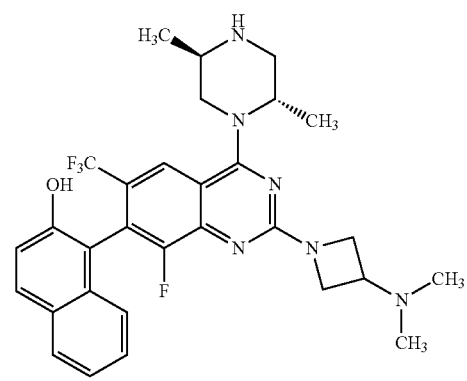 [SMILES: C[C@@H]1CN(c2nc(N3CC(N(C)C)C3)nc3c(F)c(-c4c(O)ccc5ccccc45)c(C(F)(F)F)cc23)[C@@H](C)CN1] | |
| 348 | 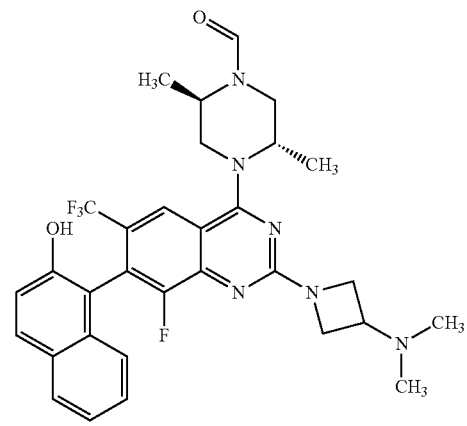 [SMILES: C[C@@H]1CN(c2nc(N3CC(N(C)C)C3)nc3c(F)c(-c4c(O)ccc5ccccc45)c(C(F)(F)F)cc23)[C@@H](C)CN1C=O] | |

TABLE 3-continued

| No. | Structure | [M + H]+ |
|-----|-----------|----------|
| 349 | 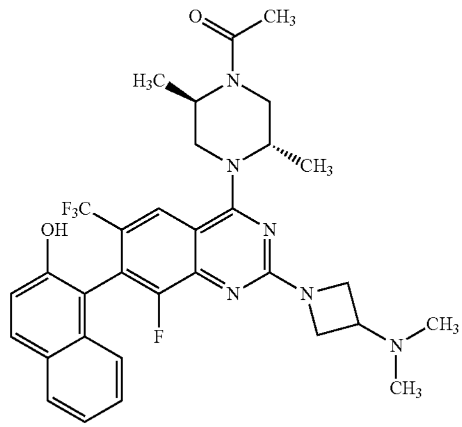 [SMILES: CC(=O)N1C[C@H](C)N(c2nc(N3CC(N(C)C)C3)nc3c(F)c(-c4c(O)ccc5ccccc45)c(C(F)(F)F)cc23)C[C@H]1C] | |
| 350 | 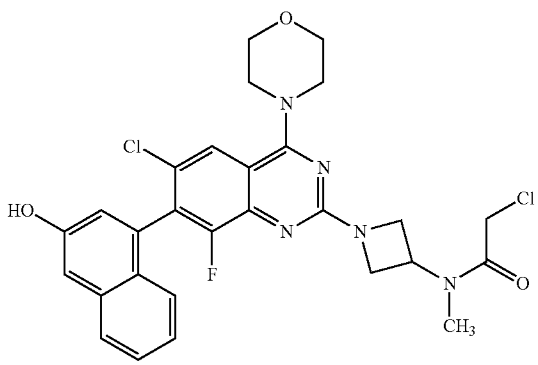 [SMILES: CN(C(=O)CCl)C1CN(c2nc(N3CCOCC3)c3cc(Cl)c(-c4cc(O)cc5ccccc45)c(F)c3n2)C1] | 570.3 |
| 351 | 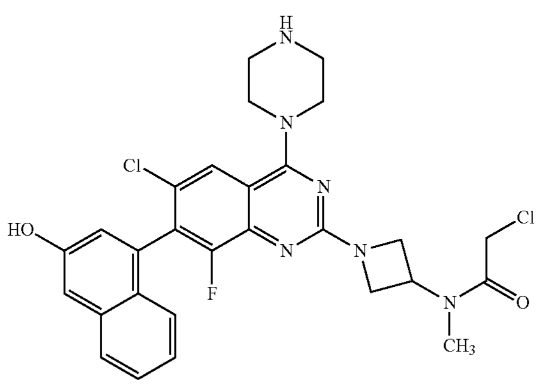 [SMILES: CN(C(=O)CCl)C1CN(c2nc(N3CCNCC3)c3cc(Cl)c(-c4cc(O)cc5ccccc45)c(F)c3n2)C1] | 569.3 |

PHARMACEUTICAL COMPOSITIONS

Other embodiments are directed to pharmaceutical compositions. The pharmaceutical composition comprises any one (or more) of the foregoing compounds and a pharmaceutically acceptable carrier. In some embodiments, the pharmaceutical composition is formulated for oral administration. In other embodiments, the pharmaceutical composition is formulated for injection. In still more embodiments, the pharmaceutical compositions comprise a compound as disclosed herein and an additional therapeutic agent (e.g., anticancer agent). Non-limiting examples of such therapeutic agents are described herein below.

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

The compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that are used in some embodiments. An exemplary dosage is 10 to 30 mg per day. The exact dosage will depend upon the route of administration, the form in which the compound is administered, the subject to be treated, the body weight of the subject to be treated, and the preference and experience of the attending physician.

In some embodiments, a compound of the disclosure is administered in a single dose. Typically, such administration will be by injection, e.g., intravenous injection, in order to introduce the agent quickly. However, other routes are used as appropriate. In some embodiments, a single dose of a compound of the disclosure is used for treatment of an acute condition.

In some embodiments, a compound of the disclosure is administered in multiple doses. In some embodiments, dosing is about once, twice, three times, four times, five times, six times, or more than six times per day. In other embodiments, dosing is about once a month, once every two weeks, once a week, or once every other day. In another embodiment a compound of the disclosure and another agent are administered together about once per day to about 6 times per day. In another embodiment the administration of a compound of the disclosure and an agent continues for less than about 7 days. In yet another embodiment the administration continues for more than about 6, 10, 14, 28 days, two months, six months, or one year. In some cases, continuous dosing is achieved and maintained as long as necessary.

Administration of the compounds of the disclosure may continue as long as necessary. In some embodiments, a compound of the disclosure is administered for more than 1, 2, 3, 4, 5, 6, 7, 14, or 28 days. In some embodiments, a compound of the disclosure is administered for less than 28, 14, 7, 6, 5, 4, 3, 2, or 1 day. In some embodiments, a compound of the disclosure is administered chronically on an ongoing basis, e.g., for the treatment of chronic effects.

In some embodiments, the compounds of the disclosure are administered in dosages. It is known in the art that due to intersubject variability in compound pharmacokinetics, individualization of dosing regimen is necessary for optimal therapy. Dosing for a compound of the disclosure may be found by routine experimentation in light of the instant disclosure.

In some embodiments, the compounds described herein are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

Provided herein are pharmaceutical compositions comprising a compound of Formula (I), (I-A), (I-B), (I-C), (II), (II-A), (II-B) or (II-C) and a pharmaceutically acceptable diluent(s), excipient(s), or carrier(s). In certain embodiments, the compounds described are administered as pharmaceutical compositions in which compounds of Formula (I), (I-A), (I-B), (I-C), (II), (II-A), (II-B) or (II-C) are mixed with other active ingredients, as in combination therapy. Encompassed herein are all combinations of actives set forth in the combination therapies section below and throughout this disclosure. In specific embodiments, the pharmaceutical compositions include one or more compounds of Formula (I), (I-A), (I-B), (I-C), (II), (II-A), (II-B) or (II-C).

A pharmaceutical composition, as used herein, refers to a mixture of a compound of Formula (I), (I-A), (I-B), (I-C), (II), (II-A), (II-B) or (II-C) with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of compounds provided herein are administered in a pharmaceutical composition to a mammal having a disease, disorder or medical condition to be treated. In specific embodiments, the mammal is a human. In certain embodiments, therapeutically effective amounts vary depending on the severity of the disease, the age and relative health of the subject, the potency of the compound used and other factors. The compounds described herein are used singly or in combination with one or more therapeutic agents as components of mixtures.

In one embodiment, one or more compounds of Formula (I), (I-A), (I-B), (I-C), (II), (II-A), (II-B) or (II-C) is formulated in an aqueous solutions. In specific embodiments, the aqueous solution is selected from, by way of example only, a physiologically compatible buffer, such as Hank's solution, Ringer's solution, or physiological saline buffer. In other embodiments, one or more compound described herein is/are formulated for transmucosal administration. In specific embodiments, transmucosal formulations include penetrants that are appropriate to the barrier to be permeated. In still other embodiments wherein the compounds described herein are formulated for other parenteral injections, appropriate formulations include aqueous or nonaqueous solutions. In specific embodiments, such solutions include physiologically compatible buffers and/or excipients.

In another embodiment, compounds described herein are formulated for oral administration. Compounds described herein are formulated by combining the active compounds with, e.g., pharmaceutically acceptable carriers or excipients. In various embodiments, the compounds described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulo se, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds described herein are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of at least one of the compounds described herein are formulated for buccal or sublingual administration. Formulations suitable for buccal or sublingual administration include, by way of example only, tablets, lozenges, or gels. In still other embodiments, the compounds described herein are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical compositions are formulated in a form suitable for parenteral injection as sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of the active compounds (e.g., compounds of Formula (I), (I-A), (I-B), (I-C), (II), (II-A), (II-B) or (II-C)) are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

In still other embodiments, the compounds of Formula (I), (I-A), (I-B), (I-C), (II), (II-A), (II-B) or (II-C) are administered topically. The compounds described herein are formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, the compounds of Formula (I), (I-A), (I-B), (I-C), (II), (II-A), (II-B) or (II-C) are formulated for transdermal administration. In specific embodiments, transdermal formulations employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of a compound described herein is accomplished by means of iontophoretic patches and the like. In certain embodiments, transdermal patches provide controlled delivery of a compound described herein. In specific embodiments, the rate of absorption is slowed by using rate-controlling membranes or by trapping the compound within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In other embodiments, the compounds of Formula (I), (I-A), (I-B), (I-C), (II), (II-A), (II-B) or (II-C) are formulated for administration by inhalation. Various forms suitable for administration by inhalation include, but are not limited to, aerosols, mists or powders. Pharmaceutical compositions of any compound described herein are conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatin for use in an inhaler or insufflator are formulated containing a powder mix of the compound and a suitable powder base such as lactose or starch.

In still other embodiments, the compounds of Formula (I), (I-A), (I-B), (I-C), (II), (II-A), (II-B) or (II-C) are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are optionally used as suitable. Pharmaceutical compositions comprising a compound described herein are manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and at least one compound of Formula (I), (I-A), (I-B), (I-C), (II), (II-A), (II-B) or (II-C), described herein as an active ingredient. The active ingredient is in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutical composition comprising at least one compound of Formula (I), (I-A), (I-B), (I-C), (II), (II-A), (II-B) or (II-C) illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, useful aqueous suspensions contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Certain pharmaceutical compositions described herein comprise a mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Useful pharmaceutical compositions also, optionally, include solubilizing agents to aid in the solubility of a compound of Formula (I), (I-A), (I-B), (I-C), (II), (II-A), (II-B) or (II-C). The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, useful pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, useful compositions also, optionally, include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other useful pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other useful compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other useful compositions include one or more antioxidants to enhance chemical stability where required. Suitable antioxidants include, by way of example only, ascorbic acid and sodium metabisulfite.

In certain embodiments, aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers useful herein. In certain embodiments, organic solvents such as N-methylpyrrolidone are also employed. In additional embodiments, the compounds described herein are delivered using a sustained-release system, such as semipermeable matrices of solid hydrophobic polymers containing the therapeutic agent. Various sustained-release materials are useful herein. In some embodiments, sustained-release capsules release the compounds for a few weeks up to over 100 days. Depending on the chemical nature and the biological stability of the therapeutic reagent, additional strategies for protein stabilization are employed.

In certain embodiments, the formulations described herein comprise one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

In some embodiments, the concentration of one or more compounds provided in the pharmaceutical compositions of the present disclosure is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of one or more compounds of the disclosure is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of one or more compounds of the disclosure is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of one or more compounds of the disclosure is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more compounds of the disclosure is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of one or more compounds of the disclosure is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g 0.15 g, 0.2 g 0.25 g, 0.3 g 0.35 g, 0.4 g 0.45 g, 0.5 g, 0.55 g, 0.6 g 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of one or more compounds of the disclosure is in the range of 0.0001-10 g, 0.0005-9 g, 0.001-8 g, 0.005-7 g, 0.01-6 g, 0.05-5 g, 0.1-4 g, 0.5-4 g, or 1-3 g.

Kits/Articles of Manufacture

For use in the therapeutic applications described herein, kits and articles of manufacture are also provided. In some embodiments, such kits comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from a variety of materials such as glass or plastic.

The articles of manufacture provided herein contain packaging materials. Packaging materials for use in packaging pharmaceutical products include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, the container(s) includes one or more compounds described herein, optionally in a composition or in combination with another agent as disclosed herein. The container(s) optionally have a sterile access port (for example the container is an intravenous solution bag or a vial having a stopper pierceable by a hypodermic injection needle). Such kits optionally comprising a compound with an identifying description or label or instructions relating to its use in the methods described herein.

For example, a kit typically includes one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included. A label is optionally on or associated with the container. For example, a label is on a container when letters, numbers or other characters forming the label are attached, molded or etched into the container itself, a label is associated with a container when it is present within a receptacle or carrier that also holds the container, e.g., as a package insert. In addition, a label is used to indicate that the contents are to be used for a specific therapeutic application. In addition, the label indicates directions for use of the contents, such as in the methods described herein. In certain embodiments, the pharmaceutical compositions is presented in a pack or dispenser device which contains one or more unit dosage forms containing a compound provided herein. The pack for example contains metal or plastic foil, such as a blister pack. Or, the pack or dispenser device is accompanied by instructions for administration. Or, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, compositions containing a compound provided herein formulated in a compatible pharmaceutical carrier are prepared, placed in an appropriate container, and labeled for treatment of an indicated condition.

Methods

The present disclosure provides a method of inhibiting Ras-mediated cell signaling comprising contacting a cell with an effective amount of one or more compounds disclosed herein. Inhibition of Ras-mediated signal transduction can be assessed and demonstrated by a wide variety of ways known in the art. Non-limiting examples include a showing of (a) a decrease in GTPase activity of Ras; (b) a decrease in GTP binding affinity or an increase in GDP binding affinity; (c) an increase in K off of GTP or a decrease in K off of GDP; (d) a decrease in the levels of signaling transduction molecules downstream in the Ras pathway, such as a decrease in pMEK level; and/or (e) a decrease in binding of Ras complex to downstream signaling molecules including but not limited to Raf. Kits and commercially available assays can be utilized for determining one or more of the above.

The disclosure also provides methods of using the compounds or pharmaceutical compositions of the present disclosure to treat disease conditions, including but not limited to conditions implicated by K-Ras, H-Ras or N-Ras mutation, H-Ras mutation and/or N-Ras mutation (e.g., cancer).

The disclosure also provides methods of using the compounds or pharmaceutical compositions of the present disclosure to treat disease conditions, including but not limited to conditions implicated by G12C G12D, G12S, G12V, and/or G13D mutations in K-Ras, H-Ras and/or N-Ras, (e.g., cancer).

In some embodiments, a method for treatment of cancer is provided, the method comprising administering an effective amount of any of the foregoing pharmaceutical compositions comprising a compound of Formula (I), (I-A), (I-B), (I-C), (II), (II-A), (II-B) or (II-C) to a subject in need thereof. In some embodiments, the cancer is mediated by a K-Ras, H-Ras or N-Ras G12C mutation. In other embodiments, the cancer is pancreatic cancer, colon cancer, MYH associated polyposis, colorectal cancer or lung cancer.

In some embodiments the disclosure provides method of treating a disorder in a subject in need thereof, wherein the said method comprises determining if the subject has a K-Ras, H-Ras or N-Ras G12C mutation and if the subject is determined to have the K-Ras, H-Ras or N-Ras G12C mutation, then administering to the subject a therapeutically effective dose of at least one compound of Formula (I), (I-A), (I-B), (I-C), (II), (II-A), (II-B) or (II-C) or a pharmaceutically acceptable salt, ester, prodrug, tautomer, solvate, hydrate or derivative thereof.

The disclosed compounds strongly inhibit anchorage-independent cell growth and therefore have the potential to inhibit tumor metastasis. Accordingly, in another embodiment the disclosure provides a method for inhibiting tumor metastasis, the method comprising administering an effective amount a pharmaceutical composition of comprising any of the compounds disclosed herein and a pharmaceutically acceptable carrier to a subject in need thereof.

Ras mutations including but not limited to K-Ras, H-Ras or N-Ras mutations have also been identified in hematological malignancies (e.g., cancers that affect blood, bone marrow and/or lymph nodes). Accordingly, certain embodiments are directed to administration of a disclosed compounds (e.g., in the form of a pharmaceutical composition) to a patient in need of treatment of a hematological malignancy. Such malignancies include, but are not limited to leukemias and lymphomas. For example, the presently disclosed compounds can be used for treatment of diseases such as Acute lymphoblastic leukemia (ALL), Acute myelogenous leukemia (AML), Chronic lymphocytic leukemia (CLL), small lymphocytic lymphoma (SLL), Chronic myelogenous leukemia (CML), Acute monocytic leukemia (AMoL) and/or other leukemias. In other embodiments, the compounds are useful for treatment of lymphomas such as all subtypes of Hodgkins lymphoma or non-Hodgkins lymphoma.

Determining whether a tumor or cancer comprises a Ras mutation including but not limited to a K-Ras, H-Ras or N-Ras mutation can be undertaken by assessing the nucleotide sequence encoding the Ras protein, by assessing the amino acid sequence of Ras protein, or by assessing the characteristics of a putative Ras mutant protein. The sequence of wild-type human Ras proteins including but not limited to K-Ras, H-Ras or N-Ras is known in the art, (e.g. Accession No. NP203524).

Methods for detecting a mutation in a Ras nucleotide sequence including but not limited to K-Ras, H-Ras or N-Ras nucleotide sequence are known by those of skill in the art. These methods include, but are not limited to, polymerase chain reaction-restriction fragment length polymorphism (PCR-RFLP) assays, polymerase chain reaction-single strand conformation polymorphism (PCR-SSCP) assays, real-time PCR assays, PCR sequencing, mutant allele-specific PCR amplification (MASA) assays, direct sequencing, primer extension reactions, electrophoresis, oligonucleotide ligation assays, hybridization assays, TaqMan assays, SNP genotyping assays, high resolution melting assays and microarray analyses. In some embodiments, samples are evaluated for Ras mutations including but not limited to K-Ras, H-Ras or N-Ras mutations by real-time PCR. In real-time PCR, fluorescent probes specific for the Ras mutation including but not limited to K-Ras, H-Ras or N-Ras mutation are used. When a mutation is present, the probe binds and fluorescence is detected. In some embodiments, the Ras mutation including but not limited to a K-Ras, H-Ras or N-Ras mutation is identified using a direct sequencing method of specific regions (e.g., exon 2 and/or exon 3) in the Ras gene or corresponding K-Ras, H-Ras or N-Ras gene, for example. This technique will identify all possible mutations in the region sequenced.

Methods for detecting a mutation in a Ras protein including but not limited to a K-Ras, H-Ras or N-Ras protein are known by those of skill in the art. These methods include, but are not limited to, detection of a K-Ras, H-Ras or N-Ras mutant using a binding agent (e.g., an antibody) specific for the mutant protein, protein electrophoresis and Western blotting, and direct peptide sequencing.

Methods for determining whether a tumor or cancer comprises a Ras mutation including but not limited to a K-Ras, H-Ras or N-Ras mutation can use a variety of samples. In some embodiments, the sample is taken from a subject having a tumor or cancer. In some embodiments, the sample is taken from a subject having a cancer or tumor. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is processed to a cell lysate. In some embodiments, the sample is processed to DNA or RNA.

The disclosure also relates to a method of treating a hyperproliferative disorder in a mammal that comprises administering to said mammal a therapeutically effective amount of a compound of the present disclosure, or a pharmaceutically acceptable salt, ester, prodrug, solvate, hydrate or derivative thereof. In some embodiments, said method relates to the treatment of cancer such as acute myeloid leukemia, cancer in adolescents, adrenocortical carcinoma childhood, AIDS-related cancers (e.g. Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myleoproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer, multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or Viral-Induced cancer. In some embodiments, said method relates to the treatment of a non-cancerous hyperproliferative disorder such as benign hyperplasia of the skin (e.g., psoriasis), restenosis, or prostate (e.g., benign prostatic hypertrophy (BPH)).

In certain particular embodiments, the disclosure relates to methods for treatment of lung cancers, the methods comprise administering an effective amount of any of the above described compound (or a pharmaceutical composition comprising the same) to a subject in need thereof. In certain embodiments the lung cancer is a non-small cell lung carcinoma (NSCLC), for example adenocarcinoma, squamous-cell lung carcinoma or large-cell lung carcinoma. In other embodiments, the lung cancer is a small cell lung carcinoma. Other lung cancers treatable with the disclosed compounds include, but are not limited to, glandular tumors, carcinoid tumors and undifferentiated carcinomas.

Subjects that can be treated with compounds of the disclosure, or pharmaceutically acceptable salt, ester, prodrug, solvate, tautomer, hydrate or derivative of said compounds, according to the methods of this disclosure include, for example, subjects that have been diagnosed as having acute myeloid leukemia, acute myeloid leukemia, cancer in adolescents, adrenocortical carcinoma childhood, AIDS-related cancers (e.g. Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myleoproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer, multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyo sarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or Viral-Induced cancer. In some embodiments subjects that are treated with the compounds of the disclosure include subjects that have been diagnosed as having a non-cancerous hyperproliferative disorder such as benign hyperplasia of the skin (e.g., psoriasis), restenosis, or prostate (e.g., benign prostatic hypertrophy (BPH)).

The disclosure further provides methods of modulating a mutant Ras including but not limited to a mutant K-Ras, H-Ras or N-Ras protein activity by contacting the protein with an effective amount of a compound of the disclosure. Modulation can be inhibiting or activating protein activity. In some embodiments, the disclosure provides methods of inhibiting protein activity by contacting the mutant Ras protein (for example, a Mutant K-Ras, H-Ras or N-Ras protein) with an effective amount of a compound of the disclosure in solution. In some embodiments, the disclosure provides methods of inhibiting the mutant Ras protein activity by contacting a cell, tissue, organ that express the protein of interest. In some embodiments, the disclosure provides methods of inhibiting protein activity in a subject including but not limited to rodents and mammal (e.g., human) by administering into the subject an effective amount of a compound of the disclosure. In some embodiments, the percentage modulation exceeds 25%, 30%, 40%, 50%, 60%, 70%, 80%, or 90%. In some embodiments, the percentage of inhibiting exceeds 25%, 30%, 40%, 50%, 60%, 70%, 80%, or 90%.

In some embodiments, the disclosure provides methods of inhibiting Ras activity including but not limited to K-Ras, H-Ras or N-Ras mutant activity in a cell by contacting said cell with an amount of a compound of the disclosure sufficient to inhibit the activity of Ras or a K-Ras, H-Ras or N-Ras mutant in said cell. In some embodiments, the disclosure provides methods of inhibiting Ras or mutant K-Ras, H-Ras or N-Ras activity in a tissue by contacting said tissue with an amount of a compound of the disclosure sufficient to inhibit the activity of mutant Ras or including but not limited to mutant K-Ras, H-Ras or N-Ras in said tissue. In some embodiments, the disclosure provides methods of inhibiting Ras including but not limited to mutant K-Ras, H-Ras or N-Ras activity in an organism by contacting said organism with an amount of a compound of the disclosure sufficient to inhibit the activity of Ras including but not limited to mutant K-Ras, H-Ras or N-Ras in said organism. In some embodiments, the disclosure provides methods of inhibiting Ras including but not limited to mutant K-Ras, H-Ras or N-Ras activity in an animal by contacting said animal with an amount of a compound of the disclosure sufficient to inhibit the activity of Ras including but not limited to mutant K-Ras, H-Ras or N-Ras in said animal. In some embodiments, the disclosure provides methods of inhibiting Ras including but not limited to mutant K-Ras, H-Ras or N-Ras activity in a mammal by contacting said mammal with an amount of a compound of the disclosure sufficient to inhibit the activity of Ras including but not limited to mutant K-Ras, H-Ras or N-Ras in said mammal. In some embodiments, the disclosure provides methods of inhibiting Ras including but not limited to mutant K-Ras, H-Ras or N-Ras activity in a human by contacting said human with an amount of a compound of the disclosure sufficient to inhibit the activity of Ras including but not limited to mutant K-Ras, H-Ras or N-Ras in said human. The present disclosure provides methods of treating a disease mediated by Ras including but not limited to mutant K-Ras, H-Ras or N-Ras activity in a subject in need of such treatment.

The present disclosure also provides methods for combination therapies in which an agent known to modulate other pathways, or other components of the same pathway, or even overlapping sets of target enzymes are used in combination with a compound of the present disclosure, or a pharmaceutically acceptable salt, ester, prodrug, solvate, tautomer, hydrate or derivative thereof. In one aspect, such therapy includes but is not limited to the combination of one or more compounds of the disclosure with chemotherapeutic agents, therapeutic antibodies, and radiation treatment, to provide a synergistic or additive therapeutic effect.

Many chemotherapeutics are presently known in the art and can be used in combination with the compounds of the disclosure. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

Non-limiting examples are chemotherapeutic agents, cytotoxic agents, and non-peptide small molecules such as Gleevec® (Imatinib Mesylate), Velcade® (bortezomib), Casodex (bicalutamide), Iressa® (gefitinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen, (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO). Where desired, the compounds or pharmaceutical composition of the present disclosure can be used in combination with commonly prescribed anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar.

This disclosure further relates to a method for using the compounds or pharmaceutical compositions provided herein, in combination with radiation therapy for inhibiting abnormal cell growth or treating the hyperproliferative disorder in the mammal. Techniques for administering radiation therapy are known in the art, and these techniques can be used in the combination therapy described herein. The administration of the compound of the disclosure in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g. At-211, I-131, I-125, Y-90, Re-186, Re-188, Sm-153, Bi-212, P-32, and radioactive isotopes of Lu). Suitable radiation sources for use as a cell conditioner of the present disclosure include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, the compounds of the present disclosure can render abnormal cells more sensitive to treatment with radiation for purposes of killing and/or inhibiting the growth of such cells. Accordingly, this disclosure further relates to a method for sensitizing abnormal cells in a mammal to treatment with radiation which comprises administering to the mammal an amount of a compound of the present disclosure or pharmaceutically acceptable salt, ester, prodrug, solvate, hydrate or derivative thereof, which amount is effective is sensitizing abnormal cells to treatment with radiation. The amount of the compound, salt, or solvate in this method can be determined according to the means for ascertaining effective amounts of such compounds described herein.

The compounds or pharmaceutical compositions of the disclosure can be used in combination with an amount of one or more substances selected from anti-angiogenesis agents, signal transduction inhibitors, antiproliferative agents, glycolysis inhibitors, or autophagy inhibitors.

Anti-angiogenesis agents, such as MMP-2 (matrix-metalloproteinase 2) inhibitors, MMP-9 (matrix-metalloproteinase 9) inhibitors, and COX-11 (cyclooxygenase 11) inhibitors, can be used in conjunction with a compound of the disclosure and pharmaceutical compositions described herein. Anti-angiogenesis agents include, for example, rapamycin, temsirolimus (CCI-779), everolimus (RAD001), sorafenib, sunitinib, and bevacizumab. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors useful in the disclosure are AG-3340, RO 32-3555, and RS 13-0830.

Autophagy inhibitors include, but are not limited to chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used.

The disclosure also relates to a method of and to a pharmaceutical composition for treating a cardiovascular disease in a mammal which comprises an amount of a compound of the disclosure, or a pharmaceutically acceptable salt, ester, prodrug, solvate, tautomer, hydrate or derivative thereof, or an isotopically-labeled derivative thereof, and an amount of one or more therapeutic agents use for the treatment of cardiovascular diseases.

Exemplary agents for use in cardiovascular disease applications are anti-thrombotic agents, e.g., prostacyclin and salicylates, thrombolytic agents, e.g., streptokinase, urokinase, tissue plasminogen activator (TPA) and anisoylated plasminogen-streptokinase activator complex (APSAC), anti-platelets agents, e.g., acetyl-salicylic acid (ASA) and clopidrogel, vasodilating agents, e.g., nitrates, calcium channel blocking drugs, anti-proliferative agents, e.g., colchicine and alkylating agents, intercalating agents, growth modulating factors such as interleukins, transformation growth factor-beta and congeners of platelet derived growth factor, monoclonal antibodies directed against growth factors, anti-inflammatory agents, both steroidal and non-steroidal, and other agents that can modulate vessel tone, function, arteriosclerosis, and the healing response to vessel or organ injury post intervention. Antibiotics can also be included in combinations or coatings comprised by the disclosure. Moreover, a coating can be used to effect therapeutic delivery focally within the vessel wall. By incorporation of the active agent in a swellable polymer, the active agent will be released upon swelling of the polymer.

In some embodiments, the compounds described herein are formulated or administered in conjunction with liquid or solid tissue barriers also known as lubricants. Examples of tissue barriers include, but are not limited to, polysaccharides, polyglycans, seprafilm, interceed and hyaluronic acid.

In some embodiments, medicaments which are administered in conjunction with the compounds described herein include any suitable drugs usefully delivered by inhalation for example, analgesics, e.g. codeine, dihydromorphine, ergotamine, fentanyl or morphine; anginal preparations, e.g. diltiazem; antiallergics, e.g. cromoglycate, ketotifen or nedocromil; anti-infectives, e.g. cephalosporins, penicillins, streptomycin, sulphonamides, tetracyclines or pentamidine; antihistamines, e.g. methapyrilene; anti-inflammatories, e.g. beclomethasone, flunisolide, budesonide, tipredane, triamcinolone acetonide or fluticasone; antitussives, e.g. noscapine; bronchodilators, e.g. ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino]methyl]benzenemethanol; diuretics, e.g. amiloride; anticholinergics e.g. ipratropium, atropine or oxitropium; hormones, e.g. cortisone, hydrocortisone or prednisolone; xanthines e.g. aminophylline, choline theophyllinate, lysine theophyllinate or theophylline; and therapeutic proteins and peptides, e.g. insulin or glucagon. It will be clear to a person skilled in the art that, where appropriate, the medicaments are used in the form of salts (e.g. as alkali metal or amine salts or as acid addition salts) or as esters (e.g. lower alkyl esters) or as solvates (e.g. hydrates) to optimize the activity and/or stability of the medicament.

Other exemplary therapeutic agents useful for a combination therapy include but are not limited to agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein include diuretics, vasopressin, agents affecting the renal conservation of water, rennin, angiotensin, agents useful in the treatment of myocardial ischemia, anti-hypertensive agents, angiotensin converting enzyme inhibitors, β-adrenergic receptor antagonists, agents for the treatment of hypercholesterolemia, and agents for the treatment of dyslipidemia.

Other therapeutic agents contemplated include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. Other therapeutic agents include antimicrobial agents, sulfonamides, trimethoprim-sulfamethoxazole quinolones, and agents for urinary tract infections, penicillins, cephalosporins, and other, β-lactam antibiotics, an agent comprising an aminoglycoside, protein synthesis inhibitors, drugs used in the chemotherapy of tuberculosis, *Mycobacterium avium* complex disease, and leprosy, antifungal agents, antiviral agents including nonretroviral agents and antiretroviral agents.

Examples of therapeutic antibodies that can be combined with a compound of the disclosure include but are not limited to anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immunomodulation, such as immunomodulators, immunosuppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and antiplatelet drugs.

For treating renal carcinoma, one may combine a compound of the present disclosure with sorafenib and/or avastin. For treating an endometrial disorder, one may combine a compound of the present disclosure with doxorubincin, taxotere (taxol), and/or cisplatin (carboplatin). For treating ovarian cancer, one may combine a compound of the present disclosure with cisplatin (carboplatin), taxotere, doxorubincin, topotecan, and/or tamoxifen. For treating breast cancer, one may combine a compound of the present disclosure with taxotere (taxol), gemcitabine (capecitabine), tamoxifen, letrozole, tarceva, lapatinib, PD0325901, avastin, herceptin, OSI-906, and/or OSI-930. For treating lung cancer, one may combine a compound of the present disclosure with taxotere (taxol), gemcitabine, cisplatin, pemetrexed, Tarceva, PD0325901, and/or avastin.

Further therapeutic agents that can be combined with a compound of the disclosure are found in Goodman and Gilman's "The Pharmacological Basis of Therapeutics" Tenth Edition edited by Hardman, Limbird and Gilman or the Physician's Desk Reference, both of which are incorporated herein by reference in their entirety.

The compounds described herein can be used in combination with the agents disclosed herein or other suitable agents, depending on the condition being treated. Hence, in some embodiments the one or more compounds of the disclosure will be co-administered with other agents as described above. When used in combination therapy, the compounds described herein are administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the disclosure and any of the agents described above can be simultaneously administered, wherein both the agents are present in separate formulations. In another alternative, a compound of the present disclosure can be administered just followed by and any of the agents described above, or vice versa. In some embodiments of the separate administration protocol, a compound of the disclosure and any of the agents described above are administered a few minutes apart, or a few hours apart, or a few days apart.

The following examples are given for the purpose of illustrating various embodiments of the disclosure and are not meant to limit the present disclosure in any fashion. The present examples, along with the methods and compositions described herein, are presently representative of preferred embodiments, are exemplary, and are not intended as limitations on the scope of the disclosure. Changes therein and other uses which are encompassed within the spirit of the disclosure as defined by the scope of the claims will occur to those skilled in the art.

EXAMPLES

Example 1: Synthesis of Compounds 22, 23, 17 and 18

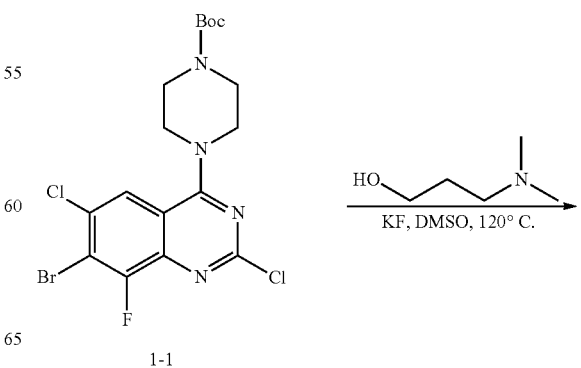

1-1

-continued

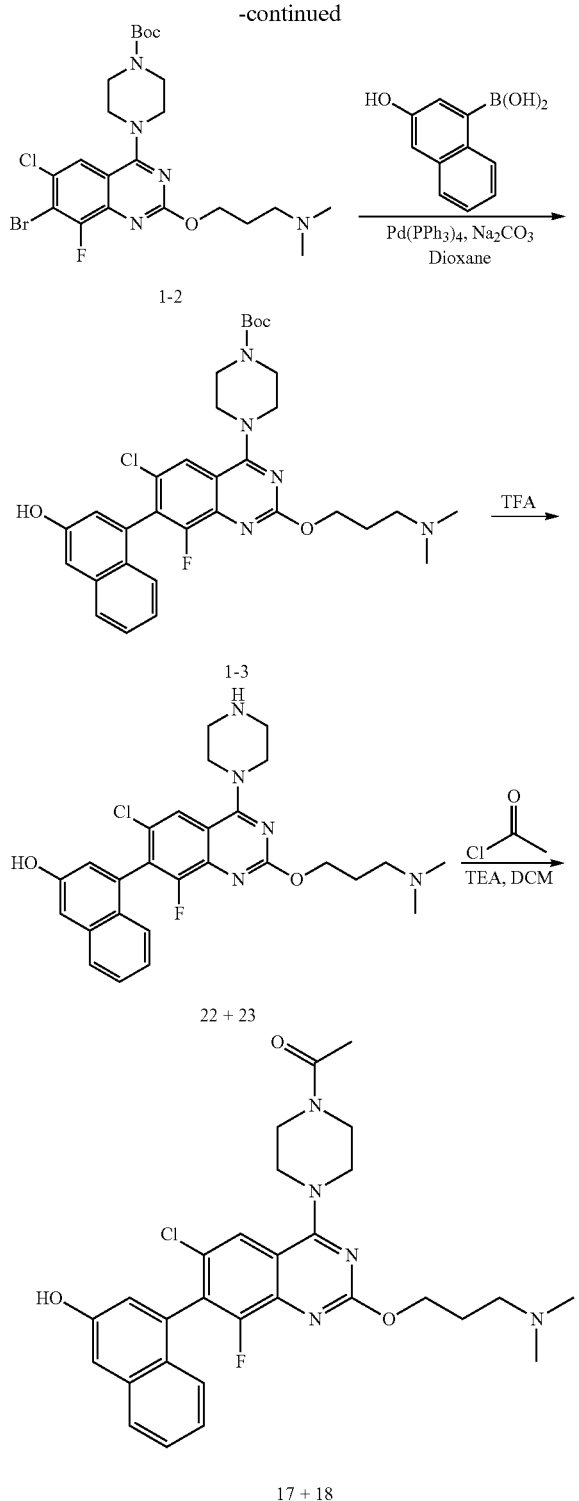

Step A: Preparation of 2-Amino-4-bromo-5-chloro-3-fluorobenzoic acid. To a solution of 2-amino-4-bromo-3-fluorobenzoic acid (17 g, 72.6 mmol) in DMF (200 mL) at room temperature was added NCS (10.2 g, 76.2 mmol). The resulting mixture was stirred at 70° C. for 16 h. The mixture was allowed to cool to room temperature and poured into cold brine. The precipitate was collected by filtration, rinsed with water and dried to afford the desired product as a white solid (14.6 g, 75% yield). ESI-MS m/z: 269.8 [M+H]$^+$.

Step B: Preparation of 7-Bromo-6-chloro-8-fluoroquinazoline-2,4(1H,3H)-dione. A mixture of 2-amino-4-bromo-5-chloro-3-fluorobenzoic acid (23.3 g, 110 mmol) and urea (68 g, 1100 mmol) was stirred at 200° C. for 4 h. The mixture was allowed to cool to room temperature. The solid was rinsed with boiling water 3 times, collected by filtration and dried to afford the desired product (24 g, 74% yield) as a gray solid.

Step C: Preparation of 7-Bromo-2,4,6-trichloro-8-fluoroquinazoline. The mixture of 7-bromo-6-chloro-8-fluoroquinazoline-2,4(1H,3H)-dione (14 g, 48 mmol) in POCl$_3$ (200 mL) and DIPEA (20 mL) was stirred at reflux for 16 h. The mixture was allowed to cool to room temperature and then concentrated in vacuo to remove POCl$_3$. The residue was purified by flash column chromatography on silica gel (2% ethyl acetate/petroleum ether) and then washed with HCl (1M) to afford the product (9 g, 57% yield) as a yellow solid.

Step D: Preparation of tert-Butyl 4-(7-bromo-2,6-dichloro-8-fluoroquinazolin-4-yl)piperazine-1-carboxylate (Compound 1-1). To a solution of 7-bromo-2,4,6-trichloro-8-fluoroquinazoline (9 g, 27.3 mmol) and Et$_3$N (11.4 mL, 82 mmol) in 1,4-dioxane (60 mL) at room temperature was added tert-butyl piperazine-1-carboxylate (5.07 g, 27.3 mmol), and the resulting mixture was stirred at 50° C. for 20 min. The mixture was allowed to cool to room temperature and partitioned between water and dichloromethane. The organic layer was washed with 1N HCl, water, saturated NaHCO$_3$ and brine, dried over Na$_2$SO$_4$ and concentrated in vacuo. The residue was triturated with a mixture of petroleum ether/ethyl acetate=5:1 to afford the desired product (12 g, 91.5% yield) as a light yellow solid. ESI-MS m/z: 447.2 [M+H]$^+$. $^1$H-NMR (400 MHz, CDCl$_3$) δ: 7.76 (d, J=1.8 Hz, 1H), 3.90-3.87 (m, 4H), 3.67-3.64 (m, 4H), 1.49 (s, 9H).

Step E: Preparation of tert-butyl 4-(7-bromo-6-chloro-2-(3-(dimethylamino)propoxy)-8-fluoroquinazolin-4-yl)piperazine-1-carboxylate (Compound 1-2). To a solution of tert-butyl 4-(7-bromo-2,6-dichloro-8-fluoroquinazolin-4-yl)piperazine-1-carboxylate (1.21 g, 2.5 mmol) and DIPEA (968 mg, 7.5 mmol) in DMSO (30 mL) at room temperature was added 3-(dimethylamino)propan-1-ol (516 mg, 5.0 mmol), and the resulting mixture was stirred at 130° C. for 3 h under N$_2$. The mixture was allowed to cool to room temperature and partitioned between water and EA. The organic layer was washed with brine, dried over Na$_2$SO$_4$ and concentrated in vacuo. The residue was triturated with a mixture of petroleum ether/ethyl acetate to afford the desired product (825 mg, 60.2% yield). ESI-MS m/z: 548.15 [M+H]$^+$.

Step F: Preparation of tert-butyl 4-(6-chloro-2-(3-(dimethylamino)propoxy)-8-fluoro-7-(3-hydroxynaphthalen-1-yl)quinazolin-4-yl)piperazine-1-carboxylate (Compound 1-3). To a stirred solution of tert-butyl 4-(7-bromo-6-chloro-2-(3-(dimethylamino)propoxy)-8-fluoroquinazolin-4-yl)piperazine-1-carboxylate (825 mg, 1.5 mmol) in 1,4-dioxane/H$_2$O (20 mL/5 mL), 3-hydroxynaphthalen-1-yl-1-boronic acid (846 mg, 4.5 mmol), Tetrakis(triphenylphosphine)palladium (173 mg, 0.15 mmol) and Na$_2$CO$_3$ (477 mg, 4.5 mmol) were added. The mixture was degassed and back-filled with N$_2$ several cycles and then stirred at 100° C. overnight. The mixture was partitioned between water and ethyl acetate. The organic layer was dried over anhydrous Na$_2$SO$_4$, filtered and concentrated in vacuo. The residue was purified by flash column chromatography on silica gel to afford the desired product (539 mg, 58.9% yield). ESI-MS m/z: 610.35 [M+H]$^+$.

Step G: Preparation of 4-(6-chloro-2-(3-(dimethylamino) propoxy)-8-fluoro-4-(piperazin-1-yl)quinazolin-7-yl)naphthalen-2-ol (Compounds 22 and 23). A solution of tert-butyl 4-(6-chloro-2-(3-(dimethylamino)propoxy)-8-fluoro-7-(3-hydroxynaphthalen-1-yl)quinazolin-4-yl)piperazine-1-carboxylate (300 mg, 0.492 mmol) in HCl/CH$_3$OH (15 mL) was stirred at RT for 1 h. The mixture was concentrated in vacuo. The residue was diluted with NH$_3$/CH$_3$OH and the solution was concentrated in vacuo. The residue was purified by prep-TLC to afford the desired product (230 mg, 95% yield). ESI-MS m/z: 510.20 [M+H]$^+$. $^1$H-NMR (400 MHz, DMSO-d$_6$) δ: 10.07 (s, 1H), 7.96 (s, 1H), 7.80-7.82 (d, J=8.0 Hz, 1H), 7.42-7.46 (m, 1H), 7.29-7.30 (d, J=2.4 Hz, 1H), 7.21-7.23 (m, 2H), 7.07-7.08 (d, J=2.4 Hz, 1H), 4.36-4.39 (m, 2H), 3.84 (m, 4H), 3.02-3.03 (m, 4H), 2.46-2.48 (m, 2H), 2.23 (s, 6H), 1.89-1.96 (m, 2H).

The two atropisomers were separated by chiral SFC separation using a CHIRALPAK AD-H column (50×250 mm, 5 μm) on preparative SFC-200 (Thar, Waters) instrument eluting with CO$_2$/methanol (50:50) at a flow rate of 130 g/min to afford Compounds 22 and 23, respectively.

Step H: Preparation of 1-(4-(6-chloro-2-(3-(dimethylamino)propoxy)-8-fluoro-7-(3-hydroxynaphthalen-1-yl) quinazolin-4-yl)piperazin-1-yl)ethanone (Compounds 17 and 18). To a solution of 4-(6-chloro-2-(3-(dimethylamino) propoxy)-8-fluoro-4-(piperazin-1-yl)quinazolin-7-yl)naphthalen-2-ol (125 mg, 0.246 mmol) and Et$_3$N (124 mg, 1.23 mmol) in DCM (8 mL) at 0° C., acetyl chloride (23 mg, 0.295 mmol) was added and the resulting mixture was stirred at 0° C. for 3 h. The mixture was allowed to cool to room temperature and partitioned between water and dichloromethane. The organic layer was washed with brine, dried over Na$_2$SO$_4$ and concentrated in vacuo. The residue was purified by prep-HPLC to afford the desired product (14 mg, 10% yield). ESI-MS m/z: 552.30 [M+H]$^+$. $^1$H-NMR (400 MHz, DMSO-d$_6$) δ: 8.24 (s, 1H), 8.01 (s, 1H), 7.80-7.82 (d, J=8.4 Hz, 1H), 7.43-7.46 (m, 1H), 7.29 (d, J=2.0 Hz, 1H), 7.21-7.22 (m, 2H), 7.07-7.08 (d, J=2.0 Hz, 1H), 4.36-4.39 (m, 2H), 3.86-3.93 (m, 8H), 2.54-2.57 (m, 2H), 2.29 (s, 6H), 2.07 (s, 3H), 1.93-1.98 (m, 2H).

The two atropisomers were separated by chiral SFC separation using a CHIRALPAK AD-H column (50×250 mm, 5 μm) on preparative SFC-200 (Thar, Waters) instrument eluting with CO$_2$/methanol (50:50) at a flow rate of 130 g/min to afford Compounds 17 and 18, respectively.

Example 2: Synthesis of Compound 75

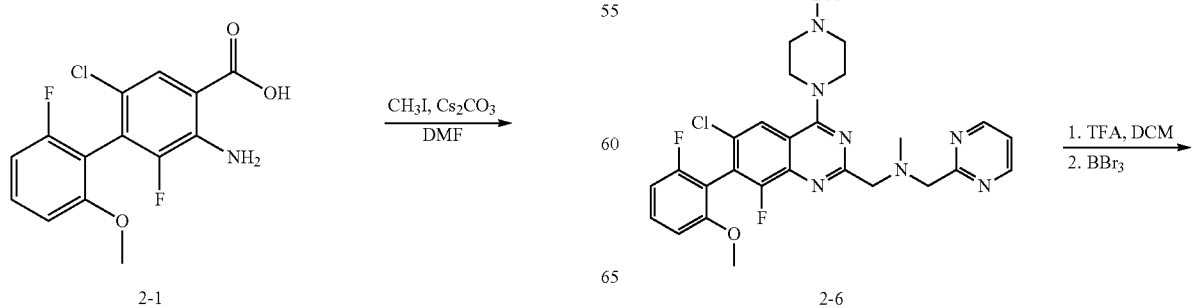

-continued

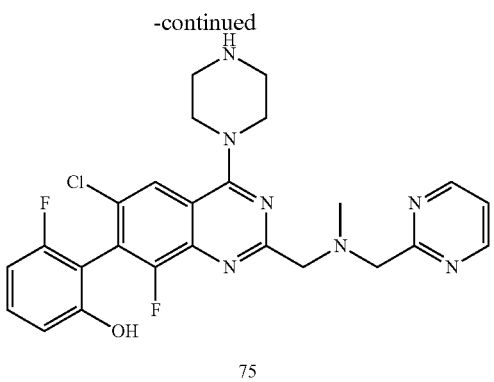

75

Step A: Preparation of 3-Amino-2,2'-difluoro-6'-methoxy-[1,1'-biphenyl]-4-carboxylic acid. To a stirred solution of 2-amino-4-bromo-3-fluorobenzoic acid (10 g, 43 mmol) in 1,4-dioxane (400 mL) and water (100 mL), 2-fluoro-6-methoxyphenylboronic acid (36 g, 213 mmol), tetrakis(triphenylphosphine)palladium (2.5 g, 2.15 mmol) and $Na_2CO_3$ (27 g, 258 mmol), were added. The mixture was degassed and back-filled with nitrogen several times, and then stirred at 100° C. overnight. The mixture was allowed to cool to RT and partitioned between water and ethyl acetate. The organic layer was discarded, and 1M HCl solution was added to the aqueous phase to adjust pH<3. The aqueous phase was extracted with ethyl acetate (200 mL×2), washed with brine, dried over $Na_2SO_4$ and concentrated in vacuo to afford the desired product (11 g, 92% yield). ESI-MS m/z: 280.1 $[M+H]^+$.

Step B: Preparation of 3-Amino-6-chloro-2,2'-difluoro-6'-methoxy-[1,1'-biphenyl]-4-carboxylic acid (Compound 2-1). To a solution of 3-amino-2,2'-difluoro-6'-methoxy-[1,1'-biphenyl]-4-carboxylic acid (11 g, 39.6 mmol) in N,N-dimethylformamide (100 mL) at RT, N-chlorosuccinimide (5.27 g, 39.6 mmol) was added and the resulting mixture was stirred at 100° C. for 1 h. The mixture was allowed to cool to RT, and then slowly added to $H_2O$ (300 mL). The mixture was filtered and the cake was dried to afford the desired product (11.5 g, 93.1% yield).

Step C: Preparation of Methyl 3-amino-6-chloro-2,2'-difluoro-6'-methoxy-[1,1'-biphenyl]-4-carboxylate (Compond 2-2). 3-Amino-6-chloro-2,2'-difluoro-6'-methoxy-[1,1'-biphenyl]-4-carboxylic acid (7.8 g, 29.2 mmol) and $Cs_2CO_3$ (28.5 g, 9.62 mmol) were dissolved in DMF (80 mL), $CH_3I$ (4.15 g, 29.2 mmol) was added and the resulting mixture was stirred at RT overnight. The mixture was partitioned between water and ethyl acetate. The organic layer was washed with brine, dried over $Na_2SO_4$ and concentrated in vacuo. The residue was purified by FC to afford the desired product (5.87 g, 61.3% yield) as an yellow solid.

Step D: Preparation of 6-chloro-2-(chloromethyl)-8-fluoro-7-(2-fluoro-6-methoxyphenyl)quinazolin-4-ol (Compound 2-3). Methyl 3-amino-6-chloro-2,2'-difluoro-6'-methoxy-[1,1'-biphenyl]-4-carboxylate (5.87 g, 20.9 mmol) and 2-chloroacetonitrile (7.89 g, 104 mmol) were dissolved in 1,4-dioxane (100 mL), and HCl gas was vapored into the solution for 1 h. The resultant solution was stirred at rt for 16 h. $H_2O$ was added and the product extracted with ethyl acetate. The organic layers were washed with brine, dried over $Na_2SO_4$ and concentrated. The residue was purified by by flash column chromatography on silica gel to afford the desire product (7.34 g, 94.7% yield). ESI-MS m/z: 370.95 $[M+H]^+$.

Step E: Preparation of 4,6-Dichloro-2-(chloromethyl)-8-fluoro-7-(2-fluoro-6-methoxyphenyl)quinazoline (Compound 2-4). 6-Chloro-2-(chloromethyl)-8-fluoro-7-(2-fluoro-6-methoxyphenyl)quinazolin-4-ol (7.34 g, 19.8 mmol) was dissolved in $POCl_3$ (50 mL), and DIPEA (5 mL) was added. The resulting solution was stirred at 110° C. for 16 h. The mixture was concentrated and diluted with ethyl acetate. The organic layer was concentrated in vacuo. The residue was purified by by flash column chromatography on silica gel to afford the desired product (6.4 g, 83% yield).

Step F: Preparation of tert-Butyl 4-(6-chloro-2-(chloromethyl)-8-fluoro-7-(2-fluoro-6-methoxyphenyl)quinazolin-4-yl)piperazine-1-carboxylate (Compound 2-5). A solution of 4,6-dichloro-2-(chloromethyl)-8-fluoro-7-(2-fluoro-6-methoxyphenyl)quinazoline (200 mg, 0.51 mmol) and tert-butyl piperazine-1-carboxylate (115 mg, 0.616 mmol) in DCM (15 mL) was stirred at RT overnight. The mixture was partitioned between water and DCM. The organic layer was washed with brine, dried over $Na_2SO_4$ and concentrated in vacuo. The residue was purified by flash column chromatography on silica gel to afford the desired product (200 mg, 72.2% yield).

Step G: Preparation of tert-Butyl 4-(6-chloro-8-fluoro-7-(2-fluoro-6-methoxyphenyl)-2-((pyrimidin-2-ylmethylamino)methyl)quinazolin-4-yl) piperazinel-carboxylate (Compound 2-6). To a solution of tert-butyl 4-(6-chloro-2-(chloromethyl)-8-fluoro-7-(2-fluoro-6-methoxyphenyl)quinazolin-4-yl)piperazine-1-carboxylate (200 mg, 0.37 mmol) and DIPEA (239 mg, 1.85 mmol) in i-PrOH (15 mL) at room temperature, N-methyl(pyrimidin-2-yl)methanamine hydrochloride (71 mg, 0.445 mmol) was added and the resulting mixture was stirred at reflux overnight. The mixture was allowed to cool to room temperature and concentrated in vacuo. The residue was partitioned between water and ethyl acetate. The organic layer was washed with brine, dried over $Na_2SO_4$ and concentrated in vacuo. The residue was purified by by flash column chromatography on silica gel to afford the desired product (169 mg, 72.8% yield). ESI-MS m/z: 626.30 $[M+H]^+$.

Step H: Preparation of 2-(6-Chloro-8-fluoro-2-((methyl (pyrimidin-2-ylmethyl)amino)methyl)-4-(piperazin-1-yl) quinazolin-7-yl)-3-fluorophenol (Compound 75). To a stirred solution of tert-butyl 4-(6-chloro-8-fluoro-7-(2-fluoro-6-methoxyphenyl)-2-((pyrimidin-2-ylmethylamino) methyl)quinazolin-4-yl) piperazinel-carboxylate (169 mg, 0.269 mmol) in dichloromethane (15 mL), was added TFA (5 mL). The mixture was stirred at RT for 2 h and then concentrated in vacuo. The residue was partitioned between ethyl acetate and $NaHCO_3$ solution. The organic layer was dried over $Na_2SO_4$ and concentrated in vacuo. The residue was dissolved in dichloromethane (20 mL) and cooled to −78° C. To this mixture, $BBr_3$ (673 mg, 2.69 mmol) was added and the resulting mixture was stirred for 2 h. The mixture was poured to ice water and extracted with ethyl acetate. The organic layer was washed with $NaHCO_3$, dried over $Na_2SO_4$ and concentrated in vacuo. The residue was purified by prep-TLC to afford the desired product (6 mg, 4.3% yield). ESI-MS m/z: 512.2 $[M+H]^+$. $^1$H-NMR (400 MHz, DMSO-$d_6$) δ: 8.77-8.81 (s, 2H), 8.00 (s, 1H), 7.32-7.38 (m, 2H), 6.73-6.82 (m, 2H), 4.06-4.23 (m, 8H), 3.16-3.23 (m, 4H), 2.64 (s, 3H).

Example 3: Synthesis of Compounds 127 and 128

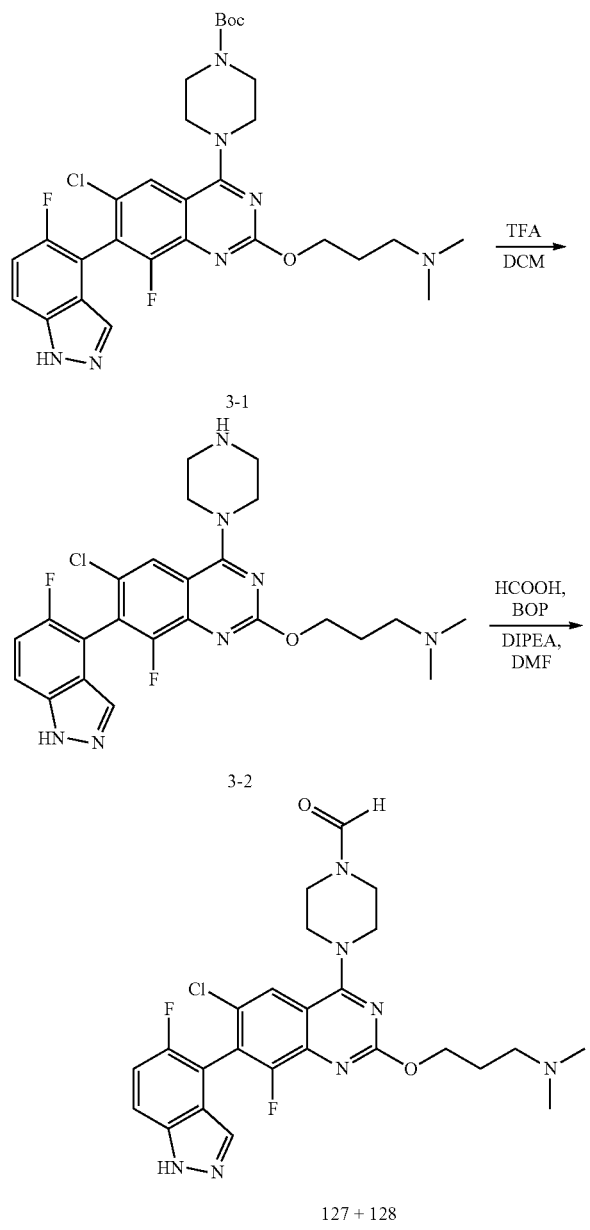

Compound 3-1 was prepared following the procedure for the synthesis of Compound 1-3 in Example 1, except that (5-methyl-1H-indazol-4-yl)boronic acid was used instead of (3-hydroxynaphthalen-1-yl)boronic acid in the Suzuki coupling step.

Step A: Preparation of 3-(6-Chloro-8-fluoro-7-(5-methyl-1H-indazol-4-yl)-4-(piperazin-1-yl)quinazolin-2-yloxy)-N,N-dimethylpropan-1-amine (Compound 3-2). A mixture of tert-butyl 4-(6-chloro-2-(3-(dimethylamino)propoxy)-8-fluoro-7-(5-methyl-1H-indazol-4-yl)quinazolin-4-yl)piperazine-1-carboxylate (580 mg, 0.97 mmol) in HCl/CH$_3$OH (15 mL) was stirred at RT for 2 h. The mixture was concentrated in vacuo and the residue was diluted with NH$_3$/CH$_3$OH. The mixture was concentrated in vacuo to afford the crude product which was used in the next step directly. ESI-MS m/z: 498.30 [M+H]$^+$; $^1$H-NMR (400 MHz, DMSO-d$_6$) δ: 13.20 (s, 1H), 7.96 (s, 1H), 7.56-7.59 (m, 2H), 7.37-7.40 (d, J=8.8 Hz, 1H), 4.35-4.39 (m, 2H), 3.80-3.82 (m, 4H), 2.96-3.00 (m, 4H), 2.42-2.45 (m, 2H), 2.16 (s, 6H), 1.87-1.94 (m, 2H).

Step B: Preparation of 4-(6-Chloro-2-(3-(dimethylamino)propoxy)-8-fluoro-7-(5-methyl-1H-indazol-4-yl)quinazolin-4-yl)piperazine-1-carbaldehyde (Compounds 127 and 128). To a solution of 3-(6-chloro-8-fluoro-7-(5-methyl-1H-indazol-4-yl)-4-(piperazin-1-yl)quinazolin-2-yloxy)-N,N-dimethylpropan-1-amine (150 mg, 0.30 mmol) and formic acid (21 mg, 0.45 mmol) in DMF (15 mL) at room temperature, BOP (200 mg, 0.45 mmol) and DIPEA (116 mg, 0.90 mmol) were added and the resulting mixture was stirred at RT overnight. The mixture was partitioned between water and ethyl acetate. The organic layer was washed with brine, dried over Na$_2$SO$_4$ and concentrated in vacuo. The residue was purified by prep-TLC to afford the desired product (35 mg, 22% yield). ESI-MS m/z: 526.25 [M+H]$^+$; $^1$H-NMR (400 MHz, DMSO-d$_6$) δ: 13.20 (s, 1H), 8.14 (s, 1H), 7.96-8.03 (m, 2H), 7.53-7.61 (m, 2H), 7.39-7.41 (d, J=8.8 Hz, 1H), 4.42-4.45 (m, 2H), 3.80-3.87 (m, 4H), 3.64 (m, 4H), 3.17-3.21 (m, 2H), 2.78 (s, 6H), 2.12-2.17 (m, 5H).

The two atropisomers were separated by chiral SFC separation using a CHIRALPAK AD-H column (50×250 mm, 5 μm) on preparative SFC-200 (Thar, Waters) instrument eluting with CO$_2$/methanol (50:50) at a flow rate of 130 g/min to afford compounds 127 and 128 respectively.

Example 4: Synthesis of Compounds 334 and 335

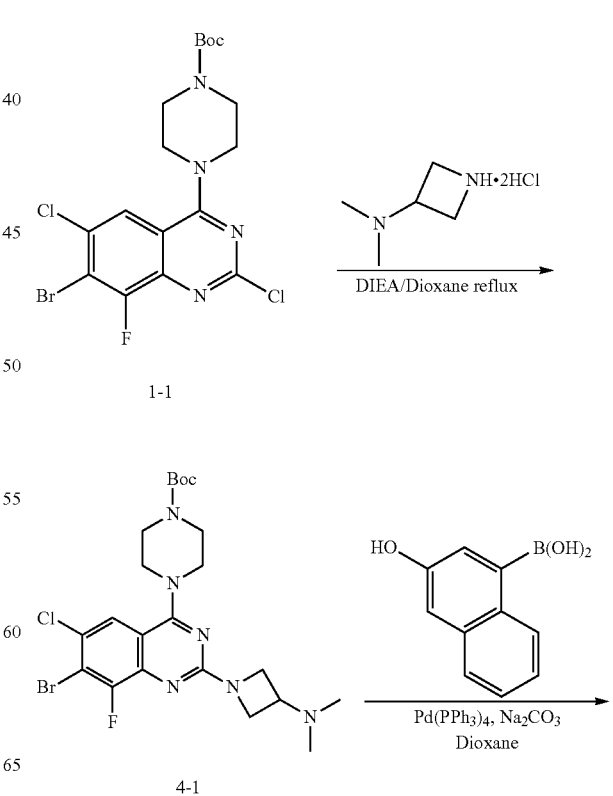

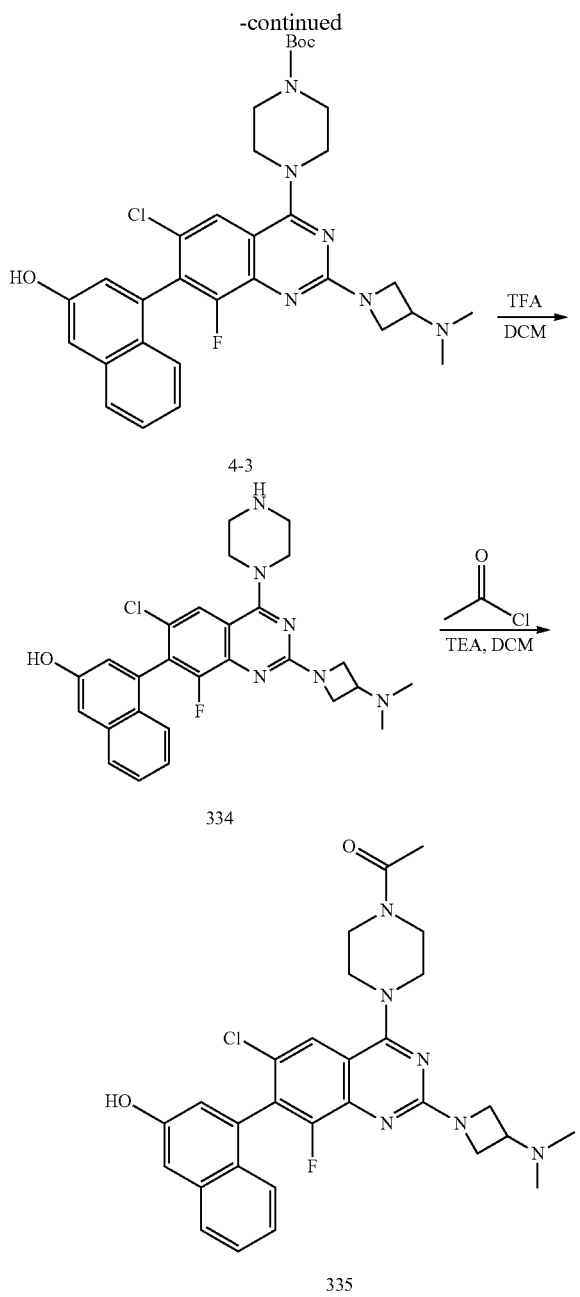

Step A: Preparation of tert-Butyl 4-(7-bromo-6-chloro-2-(3-(dimethylamino)azetidin-1-yl)-8-fluoroquinazolin-4-yl)piperazine-1-carboxylate (Compound 4-1). To a solution of tert-butyl 4-(7-bromo-2,6-dichloro-8-fluoroquinazolin-4-yl)piperazine-1-carboxylate (1.0 g, 2.08 mmol) and DIPEA (1.34 g, 10.4 mmol) in i-PrOH (100 mL) at room temperature, N,N-dimethylazetidin-3-amine dihydrochloride (4.29 g, 2.49 mmol) was added and the resulting mixture was stirred at 100° C. overnight. The mixture was concentrated in vacuo. The residue was purified by flash column chromatography on silica gel to afford the desired product (1.12 g, 100% yield). $^1$H-NMR (400 MHz, CDCl$_3$) δ: 7.76 (d, J=1.8 Hz, 1H), 3.90-3.87 (m, 4H), 3.67-3.64 (m, 4H), 1.49 (s, 9H).

Step B: Preparation of tert-Butyl 4-(6-chloro-2-(3-(dimethylamino)azetidin-1-yl)-8-fluoro-7-(3-hydroxynaphthalen-1-yl)quinazolin-4-yl)piperazine-1-carboxylate (Compound 4-3). To a stirred solution of tert-butyl 4-(7-bromo-6-chloro-2-(3-(dimethylamino)azetidin-1-yl)-8-fluoroquinazolin-4-yl)piperazine-1-carboxylate (1.12 g, 2.08 mmol) in 1,4-dioxane/H$_2$O (20 mL/5 mL), 3-hydroxynaphthalen-1-yl-1-boronic acid (895 mg, 4.79 mmol), Tetrakis(triphenylphosphine)palladium (276 mg, 0.23 mmol) and Na$_2$CO$_3$ (1.0 g, 9.5 mmol) were added. The mixture was degassed and back-filled with N$_2$ several cycles and then stirred at 100° C. overnight. The mixture was partitioned between water and ethyl acetate. The organic layer was dried over anhydrous Na$_2$SO$_4$, filtered and concentrated in vacuo. The residue was purified by flash column chromatography on silica gel to afford the desired product (1.0 g, 79% yield).

Step C: Preparation of 4-(6-Chloro-2-(3-(dimethylamino)azetidin-1-yl)-8-fluoro-4-(piperazin-1-yl)quinazolin-7-yl)naphthalen-2-ol (Compound 334). To a solution of tert-butyl 4-(6-chloro-2-(3-(dimethylamino)azetidin-1-yl)-8-fluoro-7-(3-hydroxynaphthalen-1-yl)quinazolin-4-yl)piperazine-1-carboxylate (1.0 g, 1.65 mmol) in DCM (15 mL) at RT, was added TFA (10 mL) and the resulting mixture was stirred for 1 h. The mixture was concentrated in vacuo. The residue was partitioned between sat NaHCO$_3$ solution and ethyl acetate. The organic layers were washed with brine, dried over Na$_2$SO$_4$ and concentrated in vacuo. The residue was purified by flash column chromatography on silica gel to afford the desired product (665 mg, 79% yield). ESI-MS m/z: 507.30 [M+H]$^+$; $^1$H-NMR (400 MHz, DMSO-d$_6$) δ: 10.02 (s, 1H), 7.79-7.81 (d, J=8.4 Hz, 1H), 7.75 (s, 1H), 7.41-7.45 (m, 1H), 7.26-7.27 (d, J=2.4 Hz, 1H), 7.21-7.22 (d, J=4.0 Hz, 1H), 7.03-7.04 (d, J=2.4 Hz, 1H), 4.08-4.12 (m, 2H), 3.85-3.89 (m, 2H), 3.67 (m, 4H), 3.11-3.14 (m, 1H), 2.92 (m, 4H), 2.11 (s, 6H).

Step D: Preparation of 1-(4-(6-Chloro-2-(3-(dimethylamino)azetidin-1-yl)-8-fluoro-7-(3-hydroxynaphthalen-1-yl)quinazolin-4-yl)piperazin-1-yl)ethanone (Compound 335). To a solution of 4-(6-chloro-2-(3-(dimethylamino)azetidin-1-yl)-8-fluoro-4-(piperazin-1-yl)quinazolin-7-yl)naphthalen-2-ol (110 mg, 0.22 mmol) in 2 N NaOH/THF (10 mL/10 mL) at 0° C., acetyl chloride (34 mg, 0.43 mmol) was added and the resulting mixture was stirred at RT for 1 h. The mixture was partitioned between water and ethyl acetate. The organic layer was washed with brine, dried over Na$_2$SO$_4$ and concentrated in vacuo. The residue was purified by prep-TLC to afford the desired product (14 mg, 10% yield). ESI-MS m/z: 549.35 [M+H]$^+$; $^1$H-NMR (400 MHz, DMSO-d6) δ: 10.01 (s, 1H), 7.79-7.83 (m, 2H), 7.42-7.46 (m, 1H), 7.27 (d, J=2.4 Hz, 1H), 7.21-7.22 (d, J=3.2 Hz, 2H), 7.04 (d, J=2.5 Hz, 1H), 4.10-4.14 (m, 2H), 3.87-3.91 (m, 2H), 3.68-3.79 (m, 8H), 3.15 (m, 1H), 2.13 (s, 6H), 2.07 (s, 3H).

Example 5: Biochemical and Cellular Assays of the Compounds

Inhibition of Cell Growth: The ability of a compound disclosed herein to inhibit Ras-mediated cell growth is assessed and demonstrated as follows. Cells expressing a wildtype or a mutant Ras are plated in white, clear bottom 96-well plates at a density of 5,000 cells per well. Cells are allowed to attach for about 2 hours after plating before a compound disclosed herein is added. After a certain time (e.g., 24 hours, 48 hours, or 72 hours of cell growth), cell proliferation is determined by measuring total ATP content using the Cell Titer Glo reagent (Promega) according to manufacturer's instructions. Proliferation EC50s are determined by analyzing 8 point compound dose responses at half-log intervals decreasing from 100 µM.

Inhibition of Ras-mediated signaling transduction: The ability of a compound disclosed herein to inhibit Ras-mediated signaling is assessed and demonstrated as follows. Cells expressing wild type or a mutant Ras (such as G12C, G12D, G12V, or G12A) are treated with or without (control cells) a subject compound. Inhibition of Ras signaling by one or more subject compounds is demonstrated by a decrease in the steady-state level of phosphorylated MEK, phosphorylated ERK, phosphorylated RSK, and/or Raf binding in cells treated with the one or more of the subject compounds as compared to the control cells.

Inhibition of Ras-mediated signaling transduction: The ability of a compound disclosed herein to inhibit Ras-mediated signaling is assessed and demonstrated as follows. Cells expressing wild type or a mutant Ras (such as G12C, G12D, G12V, or G12A) are treated with or without (control cells) a subject compound. Inhibition of Ras signaling by one or more subject compounds is demonstrated by a decrease in binding of Ras complex to downstream signaling molecules (for example Raf) in cells treated with the one or more of the subject compounds as compared to the control cells.

A compound of Table 1, Table 2 or Table 3 is tested according to the above procedures. The compound of Table 1, Table 2 or Table 3 is expected to inhibit Ras-mediated signaling transduction by one or more of the procedures described herein.

Example 6: Assessing Inhibition of Cell Proliferation by a Compound Disclosed Herein Two cancer cell lines, NCI H441 (human lung adenenocarcinoma cells comprising a G12V mutation) and MIA paca-2 (human pancreatic carcinoma comprising a G12C mutation) are used in this experiment. Both the cell lines are treated with a compound of Table 1, Table 2 or Table 3 at a concentration of 100 µM, 30 µM, 10 µM and 3 µM, and cell potency is measured as described in Example 5.

Example 7: Comparison of Cell Proliferation Inhibition by a Compound Disclosed Herein Three cell lines, NCI H441 (human lung adenenocarcinoma cells), NCI 1568 (lung adenenocarcinoma cells) and MIA paca-2 (human pancreatic carcinoma) are used in this experiment. Both the cell lines are treated with a compound of Table 1, Table 2 or Table 3 at a concentration of 100 µM, 30 µM, 10 µM and 3 µM, and cell potency is measured.

Example 8: SOS-Mediated Nucleotide Exchange Assays

GDP-loaded, hexahistidine tagged, truncated (1-169) KRAS proteins (WT or G12D) were used (stored in protein dilution buffer [20 mM HEPES pH=7.5, 150 NaCl, 1 mM MgCl$_2$]). 1 µL of the respective KRAS protein (1.88 µM stock, 0.125 µM final) was mixed with 10 µL of assay buffer (30 mM TRIS pH=7.5, 1.5 mM MgCl$_2$, 0.135 µM Bodipy-GDP [20 mM TRIS pH=7.5, 1.0 mM MgCl$_2$, 0.09 µM final]) and 1 µL of 15× compound stock in 30% DMSO (final DMSO conc. 2%). After 30 min incubation at room temperature, the exchange reaction was initiated by addition of 3 µL SOS(cat) (catalytic domain, 2.5 µM stock in protein dilution buffer, 0.5 µM final). The assay was carried out in black low-volume plates (Corning #4514) and fluorescence was monitored (485 nm excitation and 510 nm emission) for 45 minutes after initiation at 60-s intervals.

For data analysis, relative fluorescence values for each sample after subtracting the background values (before SOS addition) were plotted in graph pad. Rates were then calculated by fitting the data by non-linear regression (one phase association curve). Typically, 6 dilutions per compound (3-fold series, starting at 60 µM final) were measured. Calculated rates vs compound concentrations were fitted by non-linear regression (log(inhibitor) vs response-Variable slope (four parameters) fit) to determine IC$_{50}$ values.

Table 4 shows biological activities of selected compounds in an SOS-mediated nucleotide exchange assay. Compound numbers correspond to the numbers and structures provided in Tables 1, 2 and 3 and Examples 1-4.

TABLE 4

| | Less than 15 µM (++) | Greater than 15 µM (+) |
|---|---|---|
| Kras WT IC$_{50}$ (µM) | 18, 151, 158, 162, 170 | 22, 97, 108, 112, 120, 134, 147, 155, 156, 164, 165, 166, 171, 172, 173, 175, 176, 330, 339, 344, 346, 350, 351 |
| Kras G12D IC$_{50}$ (µM) | 22, 155, 156, 169, 172, 334, 339, 344 | 18, 97, 108, 112, 120, 134, 151, 158, 162, 164, 165, 166, 167, 168, 170, 171, 173, 174, 175, 176, 330, 346, 350, 351 |

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the invention. It is intended that the following claims define the scope of the invention and that methods and structures within the scope of these claims and their equivalents be covered thereby.

What is claimed is:
1. A compound of Formula (I-A):

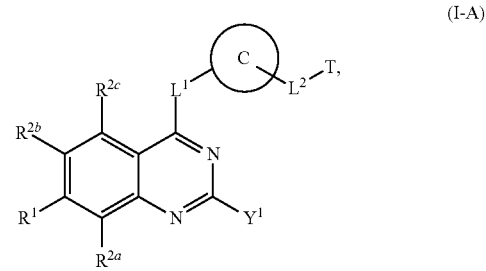

or a salt thereof, wherein:
R$^1$ is phenyl, naphthyl, or indazolyl, wherein phenyl, naphthyl, and indazolyl are independently optionally substituted with one or more substituents selected from halogen, —OR$^{52}$, —N(R$^{52}$)$_2$, C$_{1-6}$ alkyl, and C$_{1-6}$ haloalkyl;
R$^{2a}$ and R$^{2b}$ are each independently selected from hydrogen, halogen, and C$_{1-10}$ alkyl optionally substituted with one or more halogen;
R$^{2c}$ is hydrogen;

$Y^1$ is

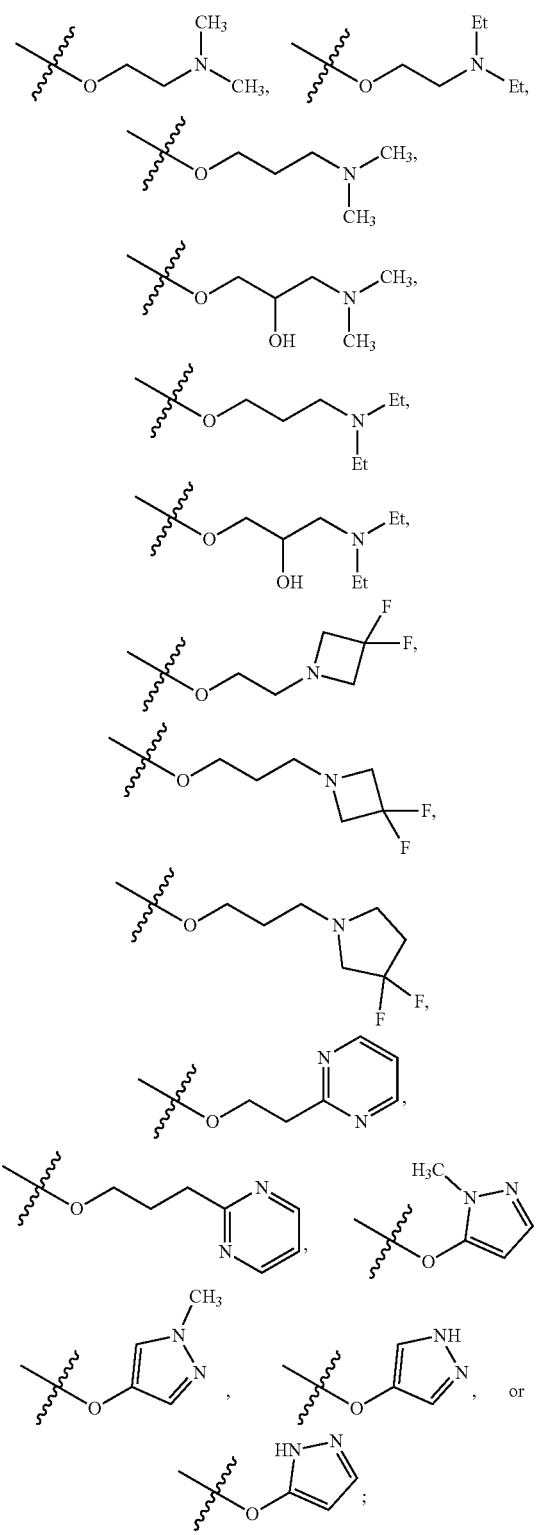

$L^1$ is a bond;
$L^2$ is selected from a bond and alkylene;
C is piperazinylene optionally substituted with one or more $R^{57}$;

T is hydrogen;
$R^{52}$ is independently selected at each occurrence from hydrogen and $C_{1-20}$ alkyl; and
$R^{57}$ is independently selected at each occurrence from:
halogen, —CN, —C(O)H, —C(O)$C_{1-6}$ alkyl, —C(O)NH$_2$, and $C_{1-10}$ alkyl optionally substituted at each occurrence with one or more substituents selected from —CN, —OH, and —C(O)NH$_2$; and
wherein the compound of Formula (I-A) is not:

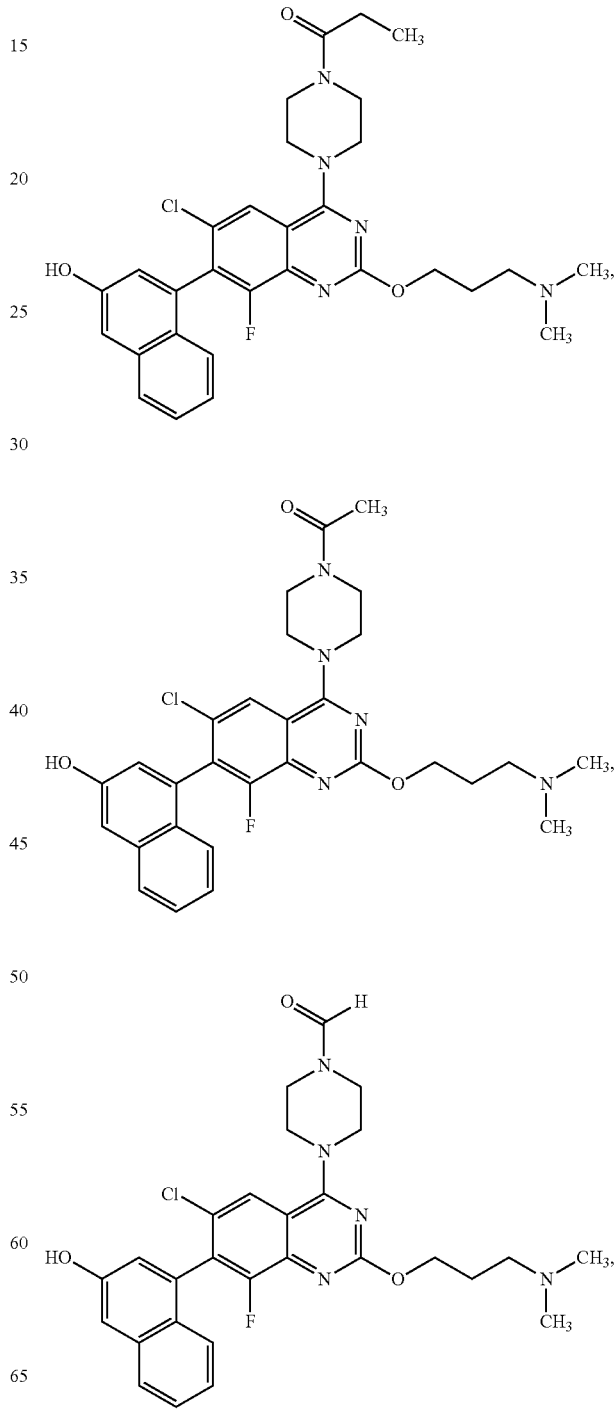

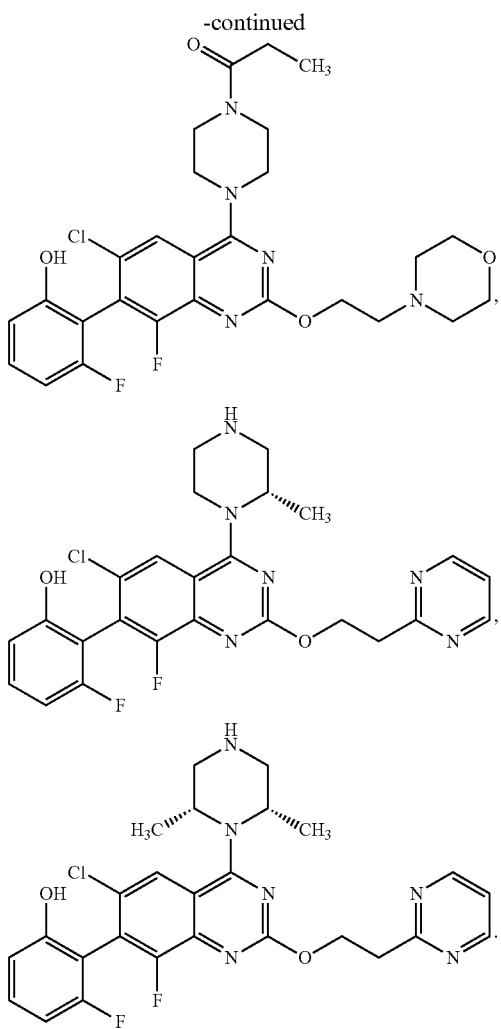

2. The compound of claim 1, wherein Y¹ is

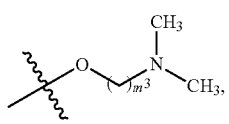

wherein m³ is an integer from 2 to 3.

3. The compound of claim 1, wherein R¹ is selected from phenyl, naphthyl, and indazolyl, each of which is optionally substituted with one or more substituents selected from halogen, —OR$^{52}$, —N(R$^{52}$)$_2$, and C$_{1-6}$ alkyl.

4. The compound of claim 1, wherein R¹ is selected from:

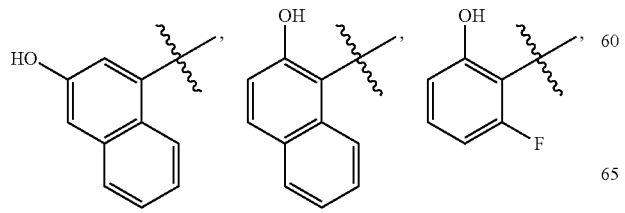

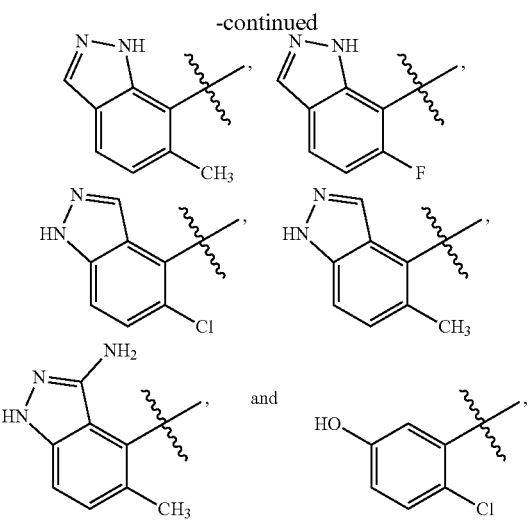

5. The compound of claim 1, wherein R$^{2a}$ and R$^{2b}$ are each independently selected from hydrogen, halogen, C$_{1-4}$ alkyl, and C$_{1-4}$ haloalkyl.

6. The compound of claim 1, wherein R$^{2a}$ is fluorine and R$^{2b}$ is chlorine.

7. The compound of claim 1, wherein R$^{57}$ is independently selected at each occurrence from —C(O)H, —C(O) C$_{1-6}$ alkyl, and C$_{1-6}$ alkyl.

8. The compound of claim 1, wherein L² is a bond.

9. The compound of claim 1, wherein:
R¹ is selected from phenyl, naphthyl, and indazolyl, optionally substituted with one or more substituents selected from halogen, —OH, and —CH$_3$;
R² and R$^{2b}$ are each independently selected from halogen; and
L² is a bond.

10. A substantially pure atropisomer of the compound of claim 1.

11. The compound of claim 1, wherein the compound, or a salt thereof, is selected from the group consisting of:

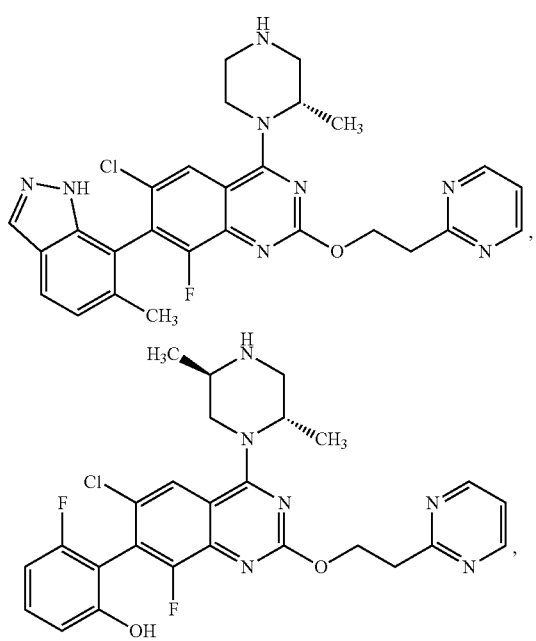

275
-continued
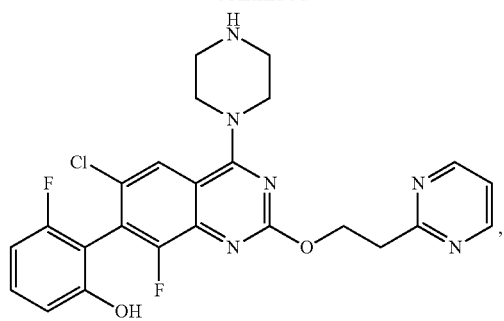
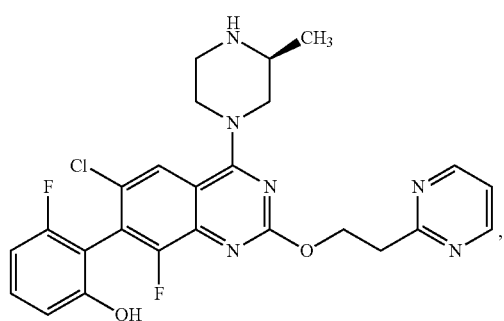
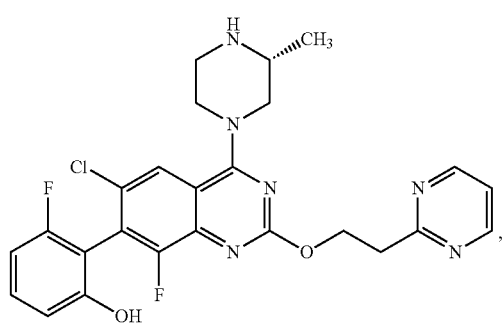
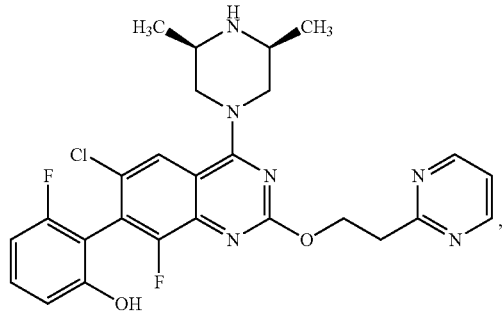
276
-continued
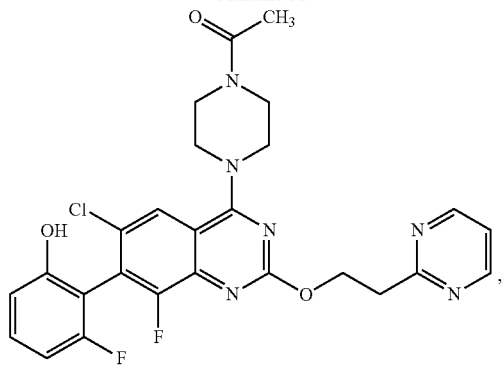
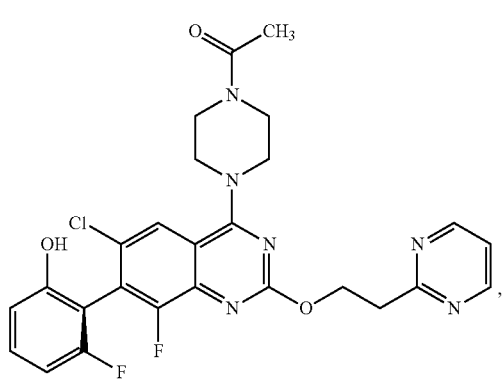
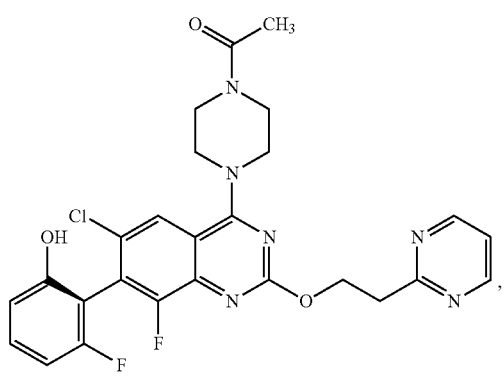
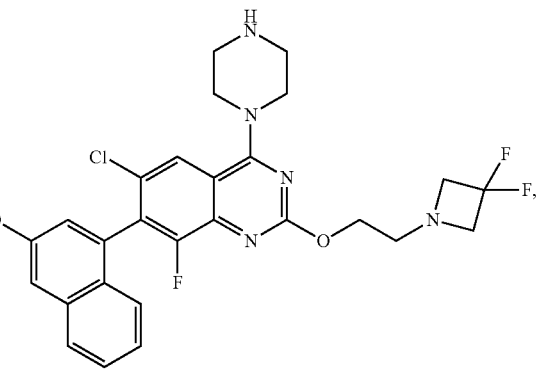

277
-continued
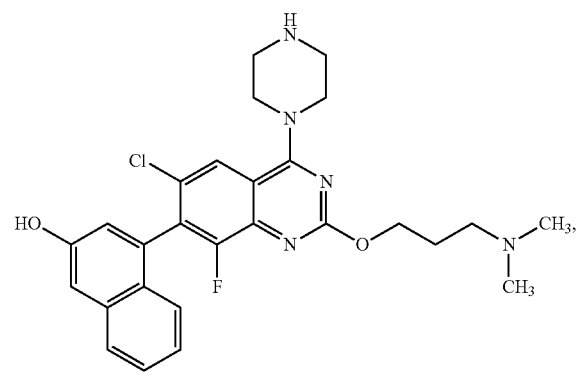
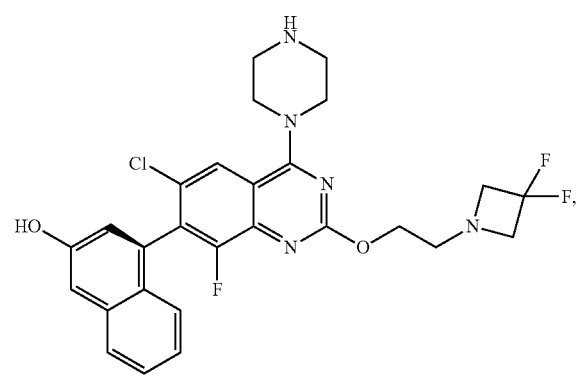
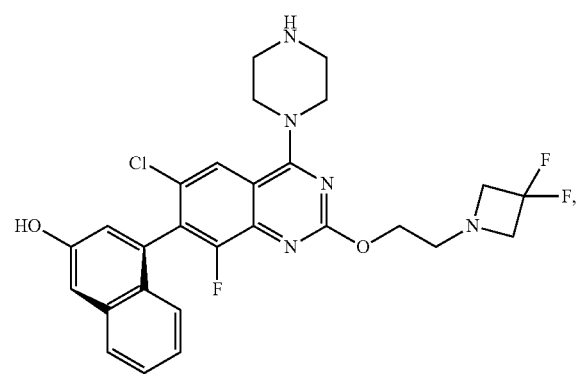
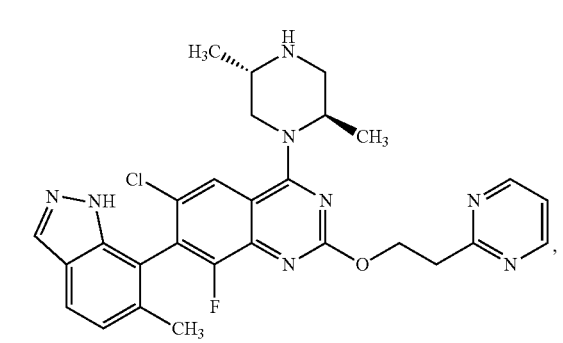
278
-continued
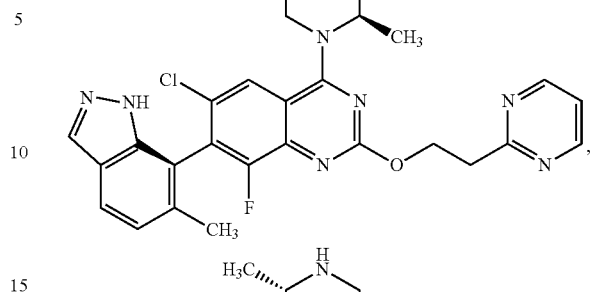
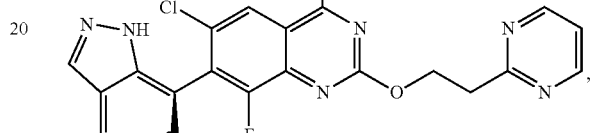
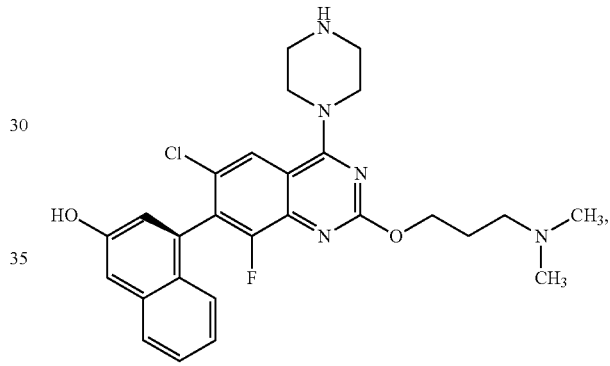
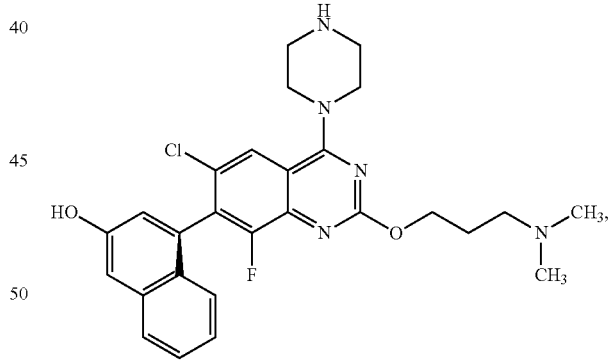
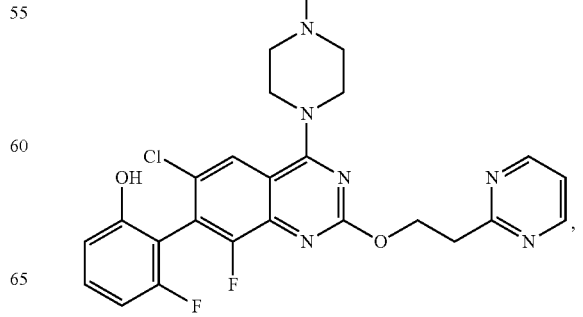

279
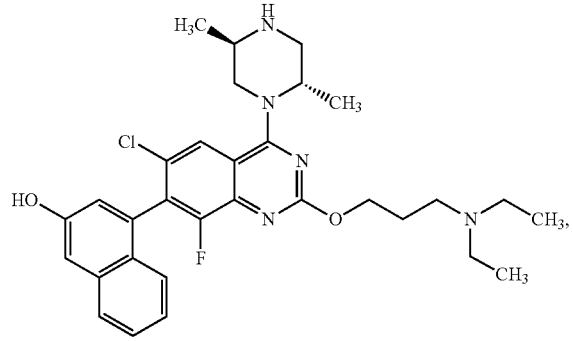
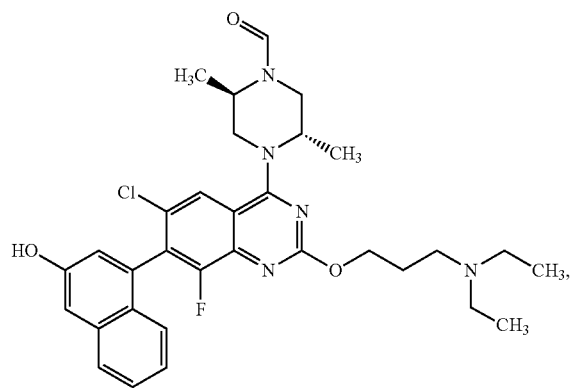
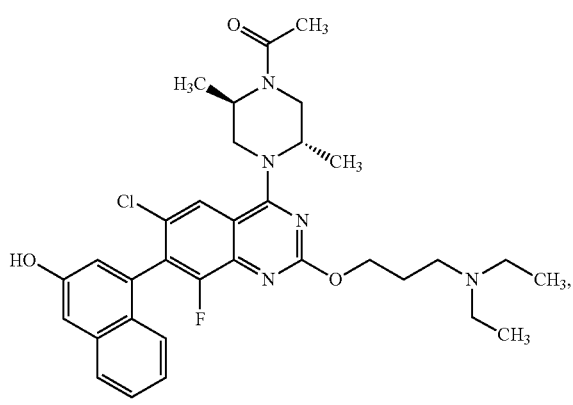
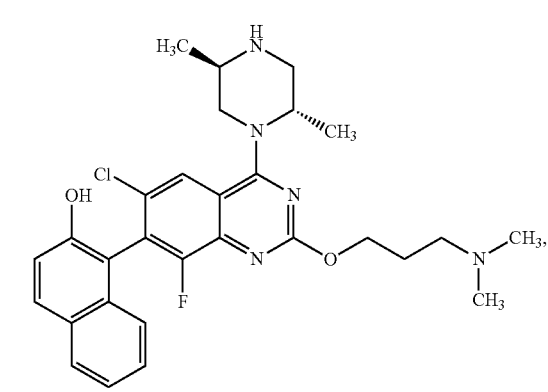
280
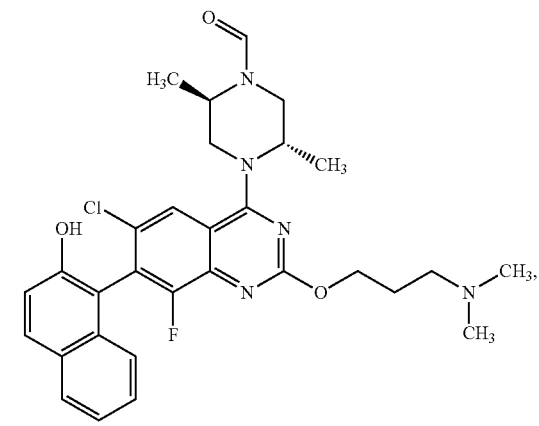
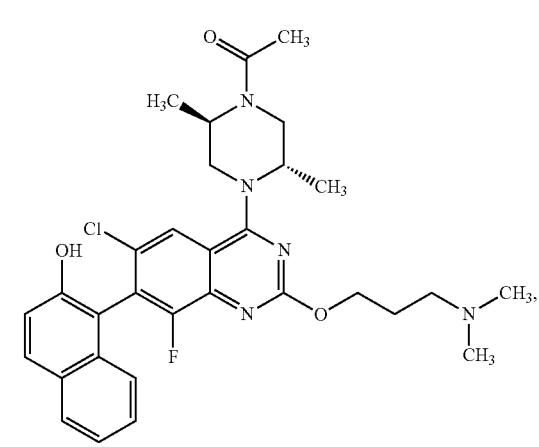
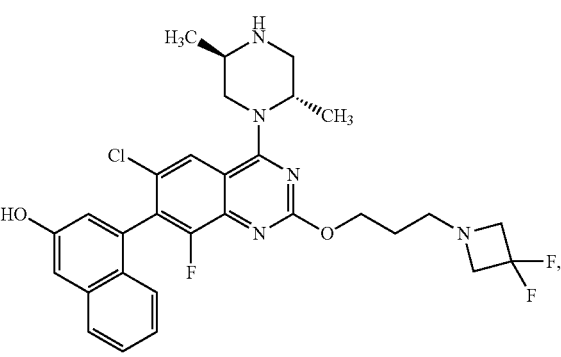
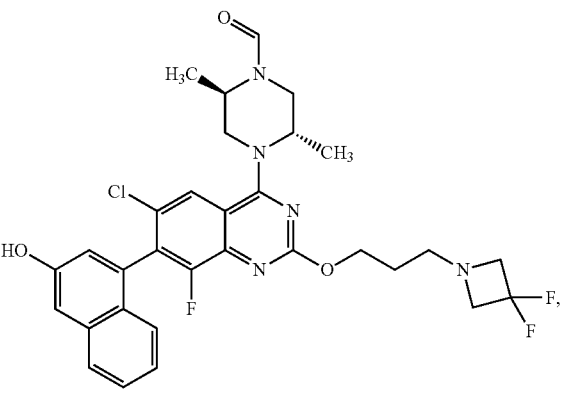

281
-continued
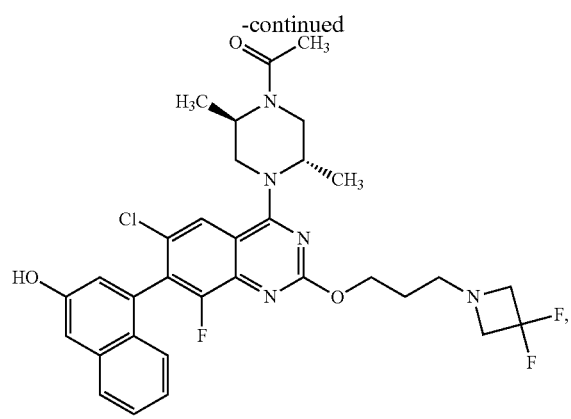
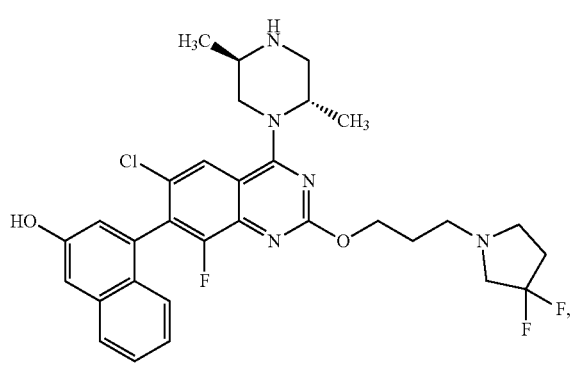
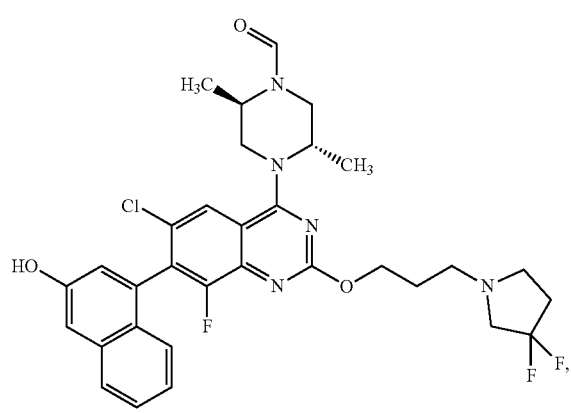
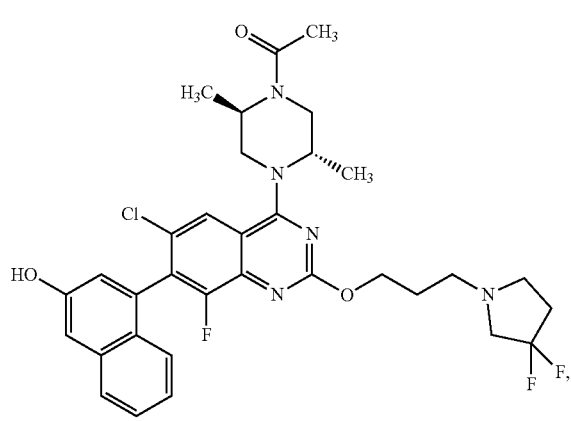
282
-continued
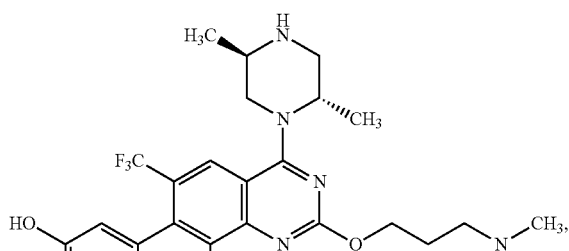
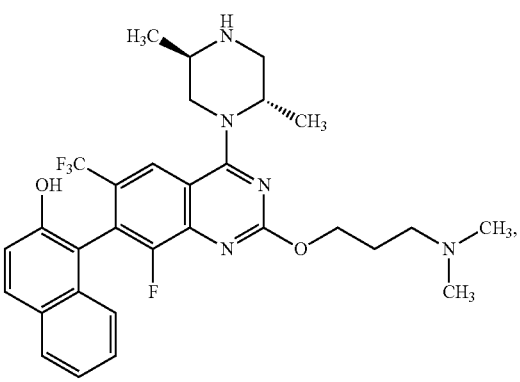
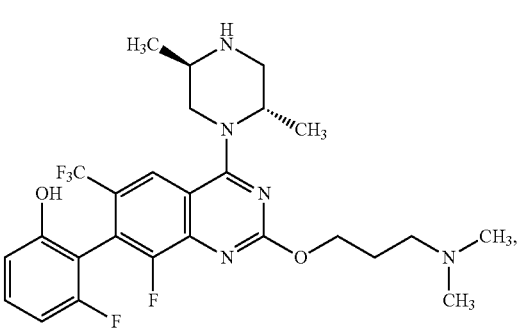
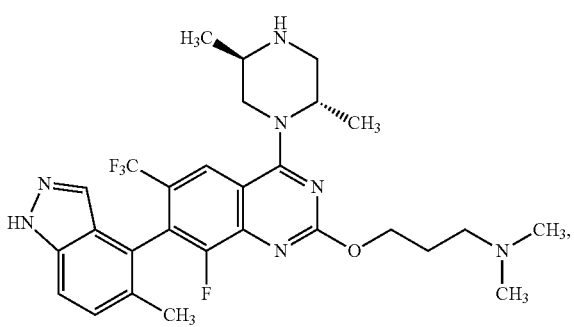

| 283 -continued | 284 -continued |
|---|---|
| 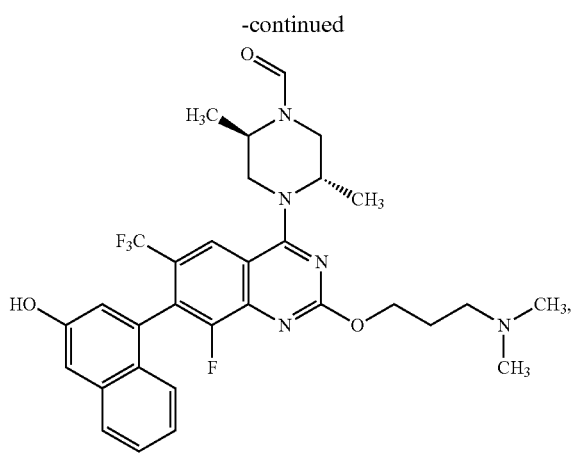 | 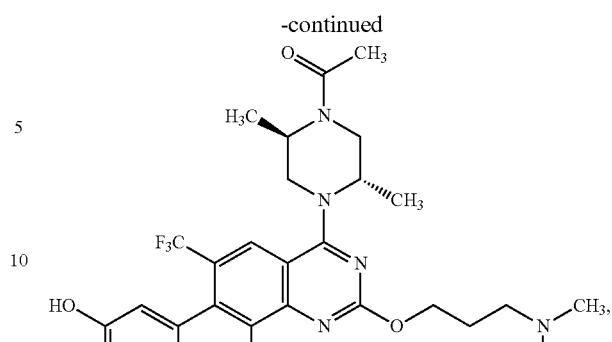 |
| 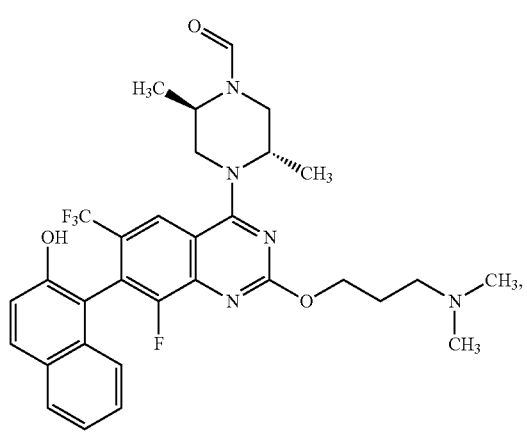 | 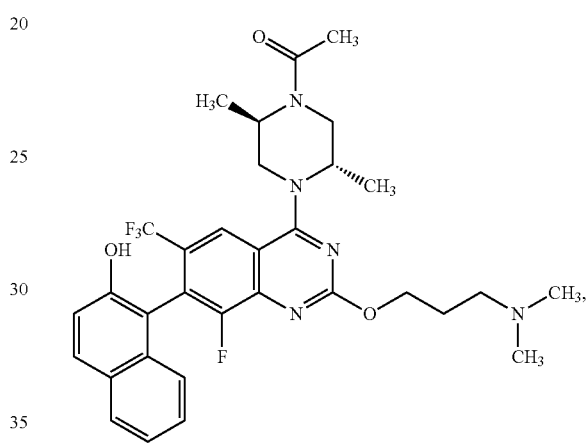 |
| 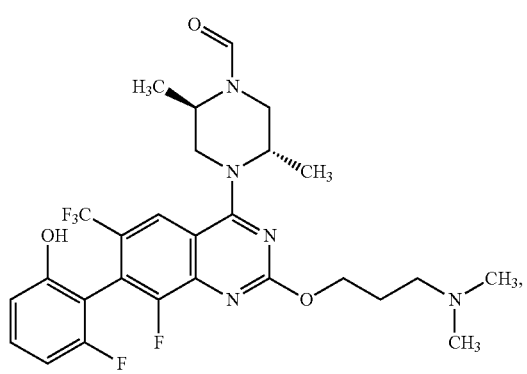 | 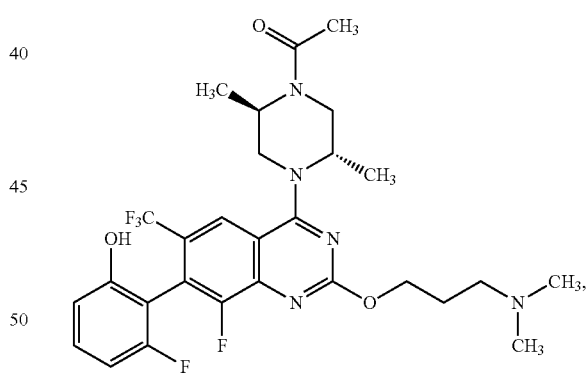 |
| 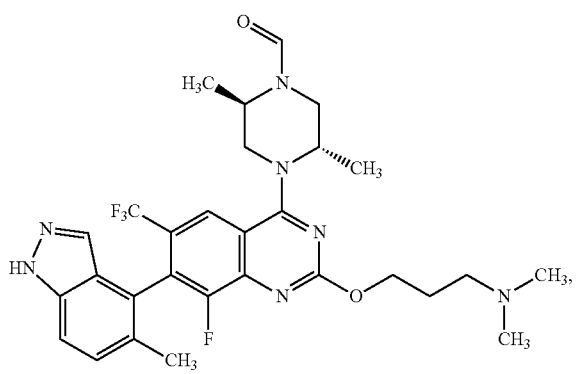 | 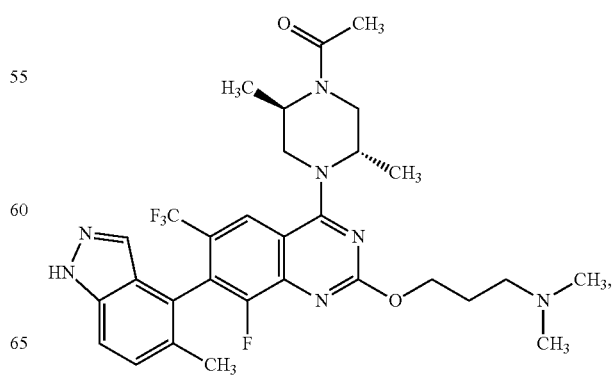 |

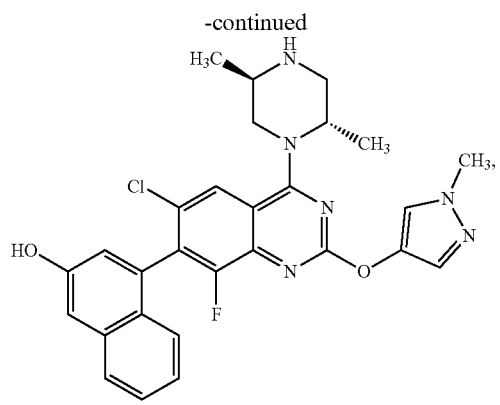
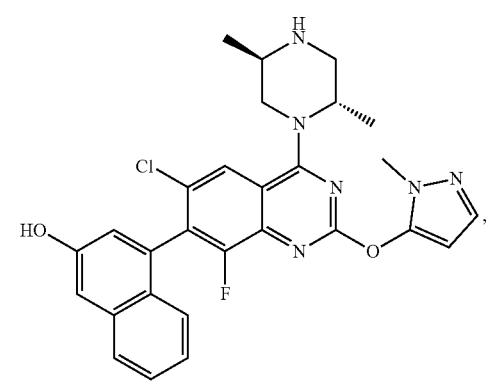
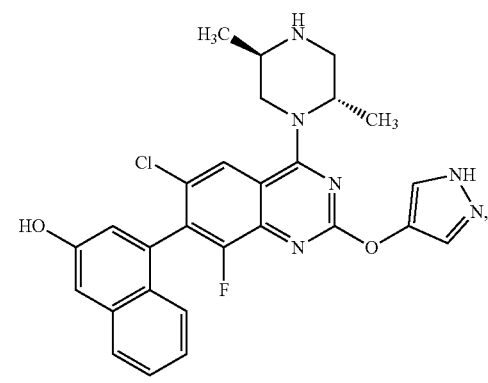
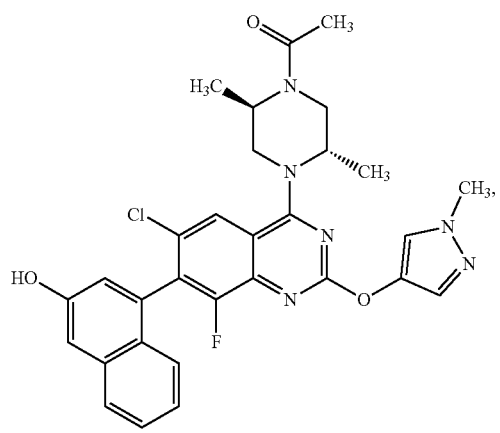
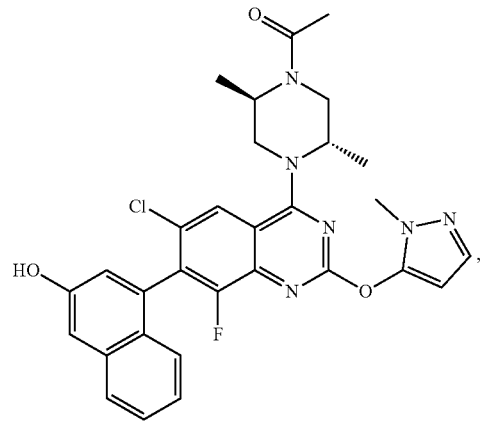
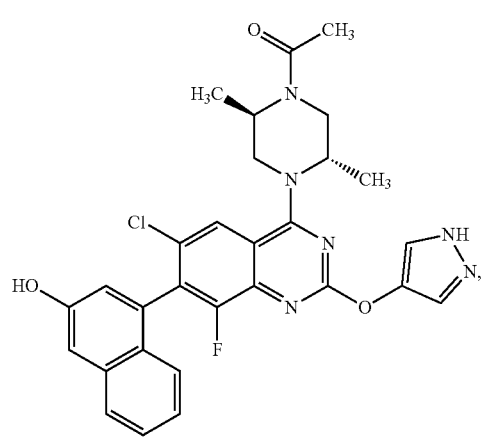
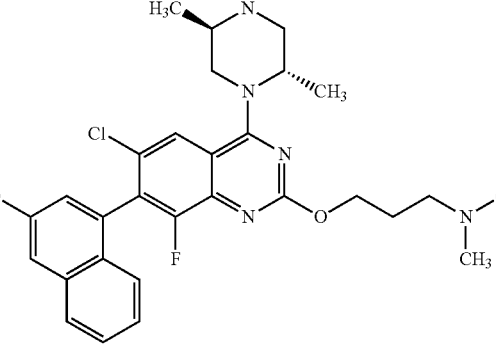
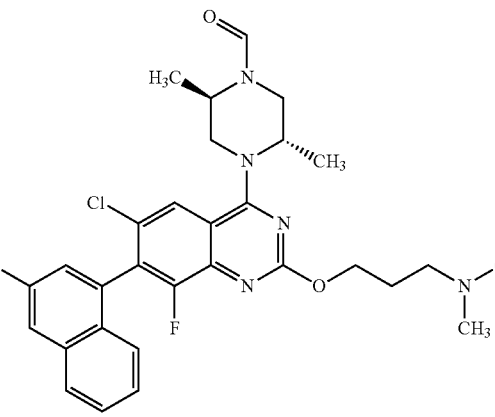

287
-continued

288
-continued

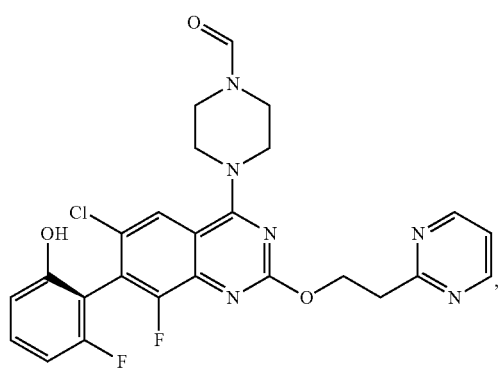
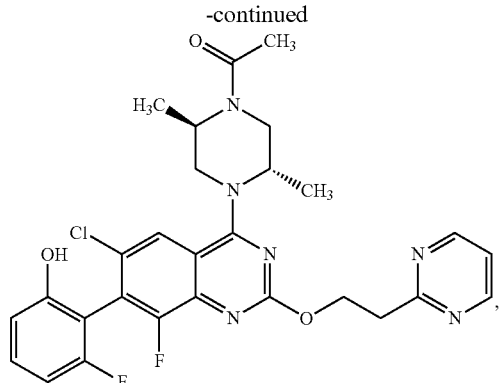
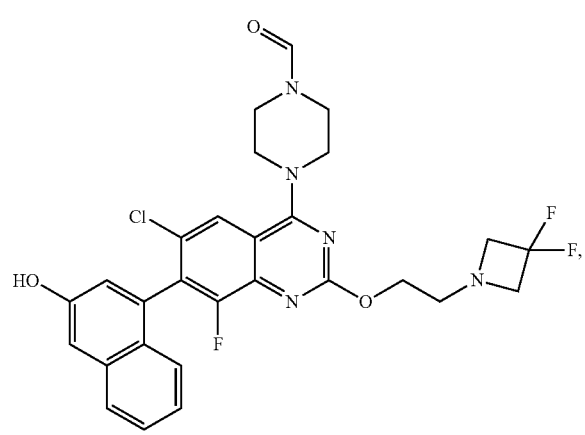
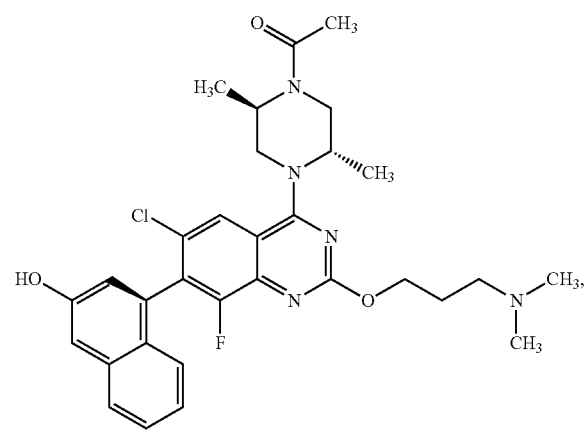
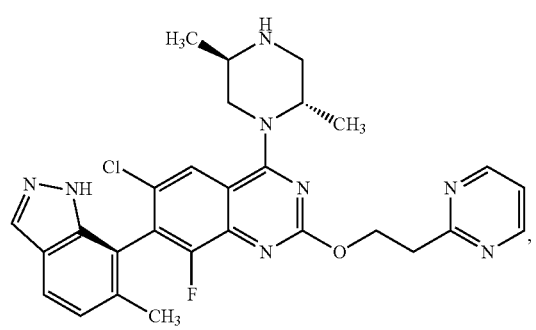
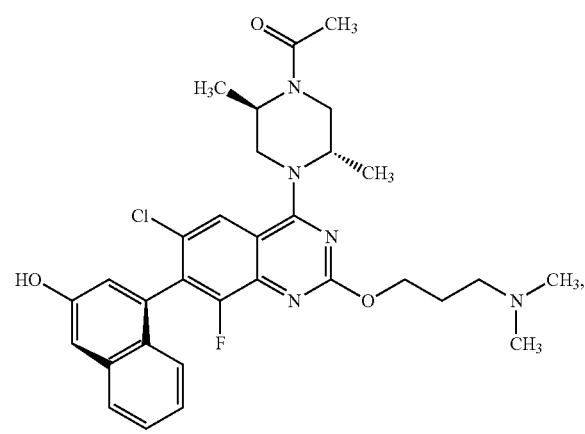
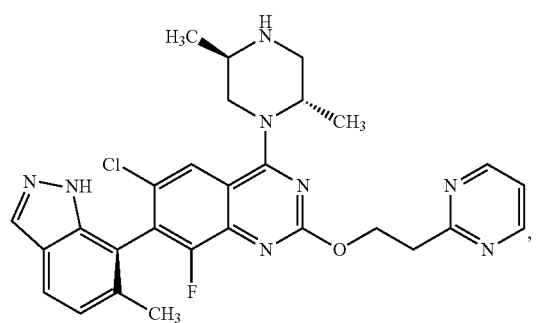
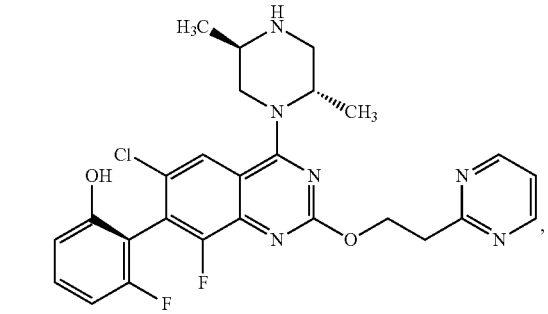

291
292
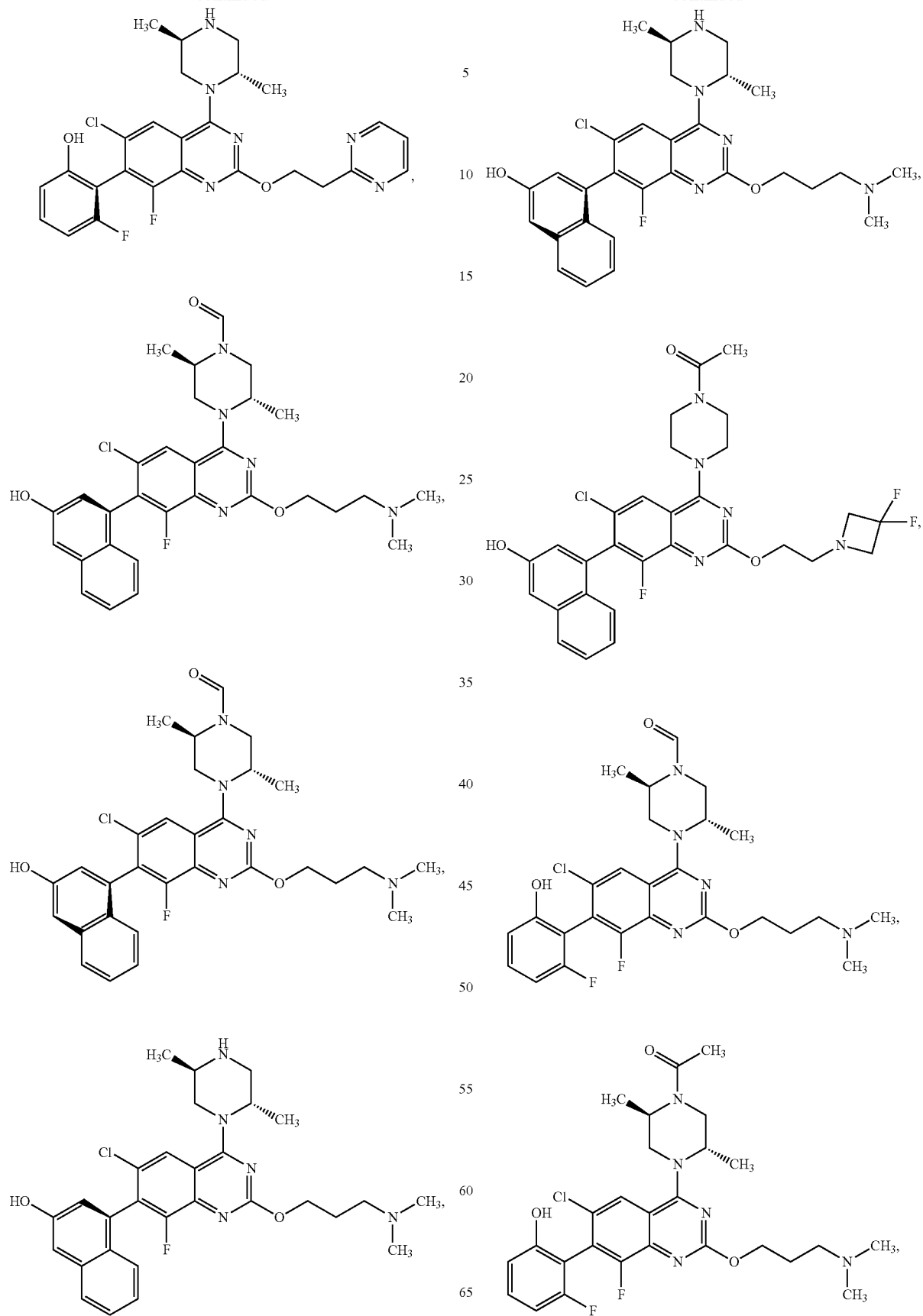

-continued
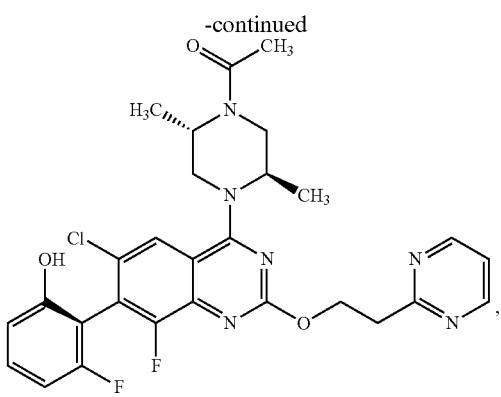
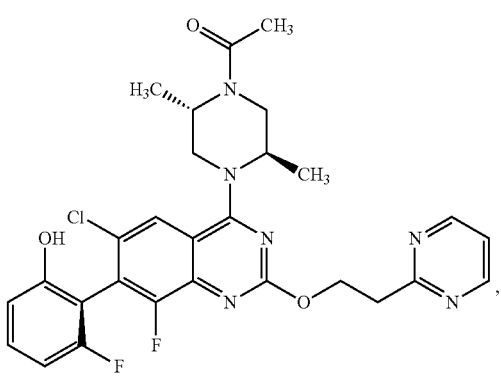
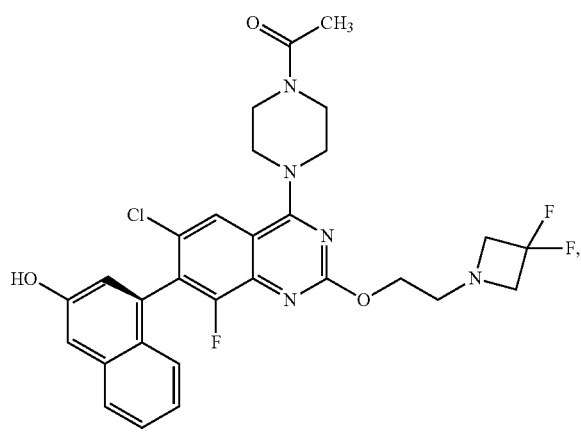
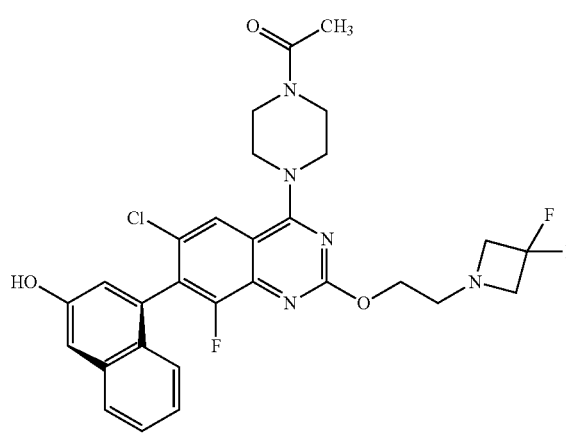
-continued
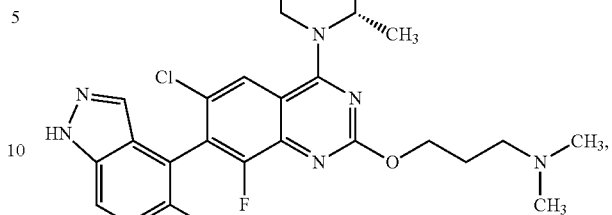
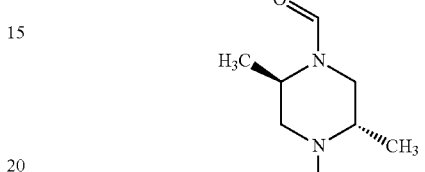
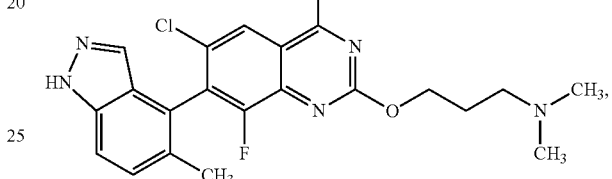
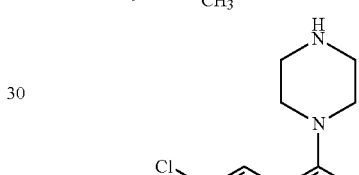
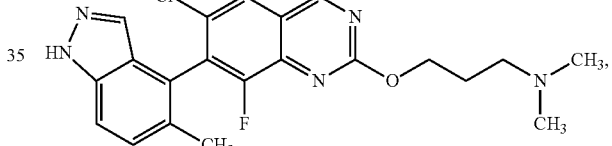
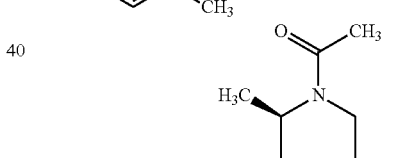
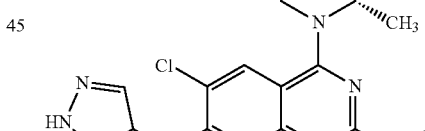
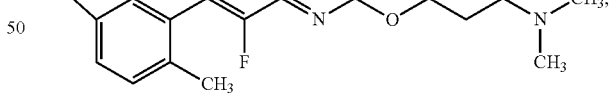
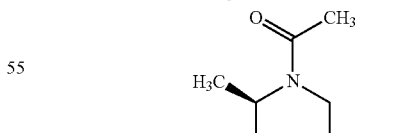
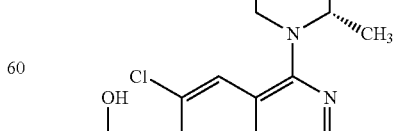
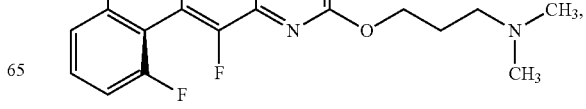

-continued
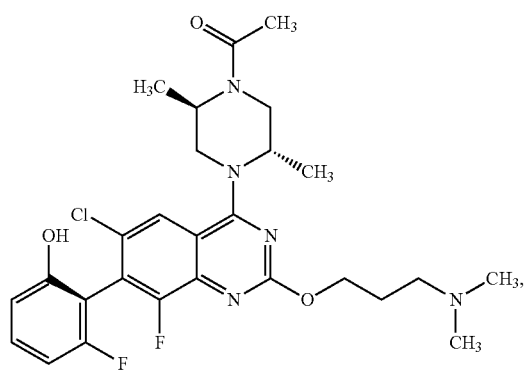
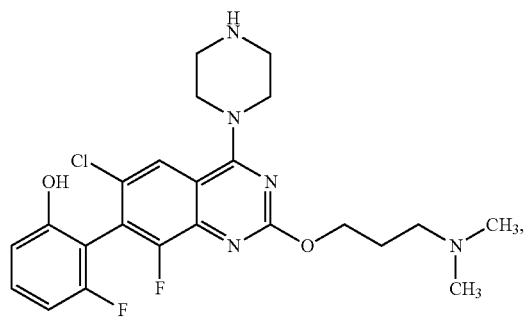
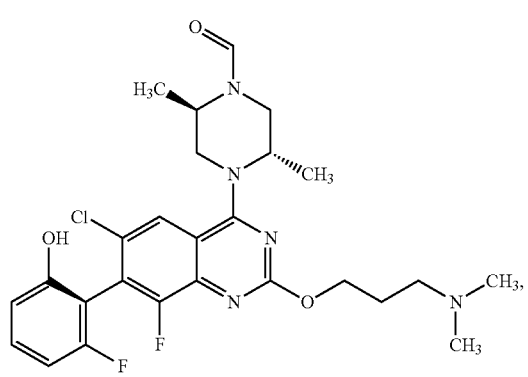
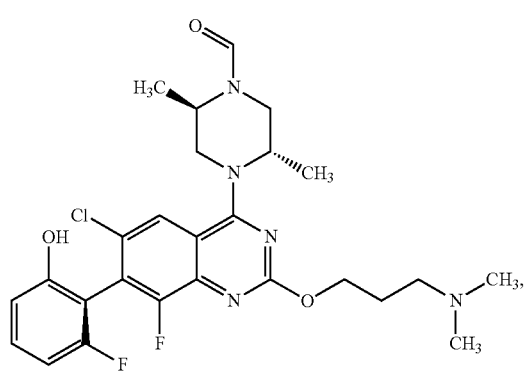
-continued
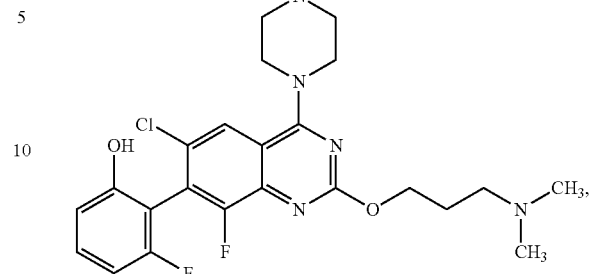
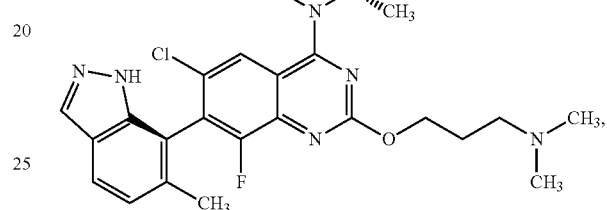
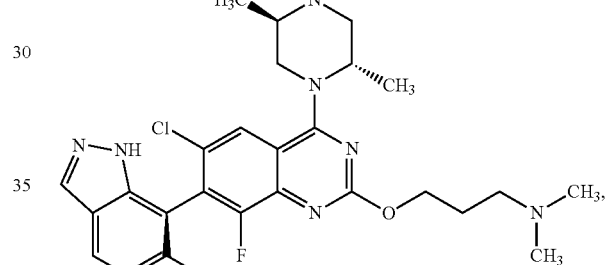
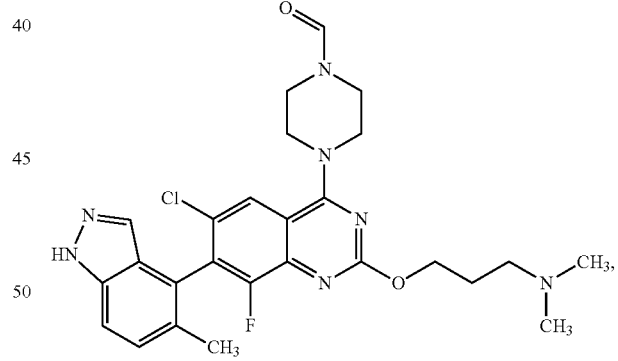
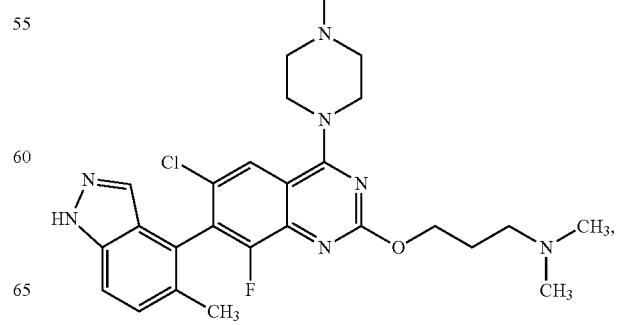

297
-continued
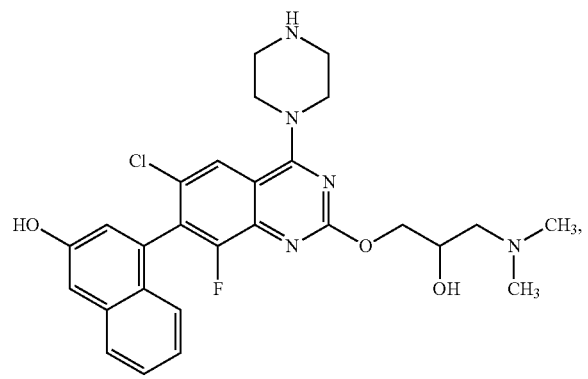
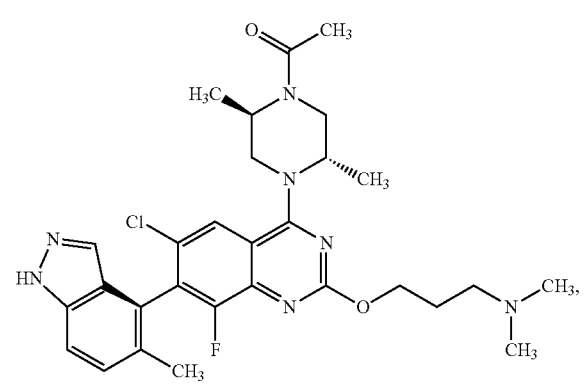
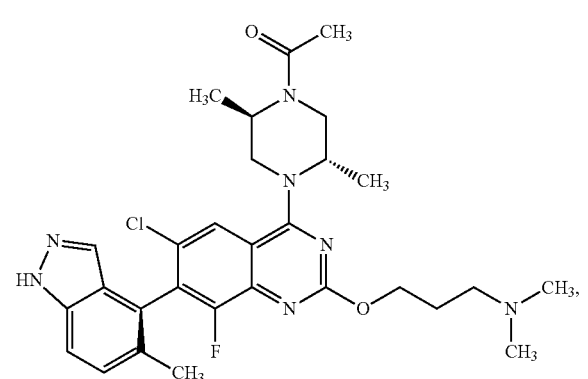
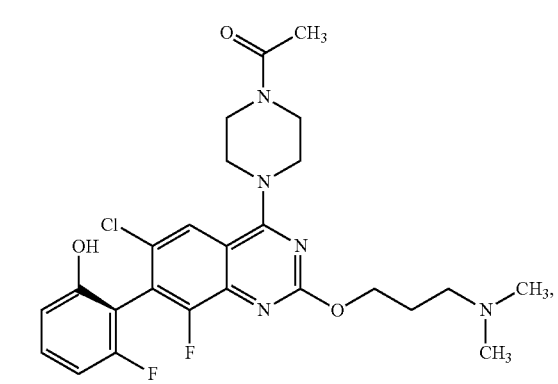
298
-continued
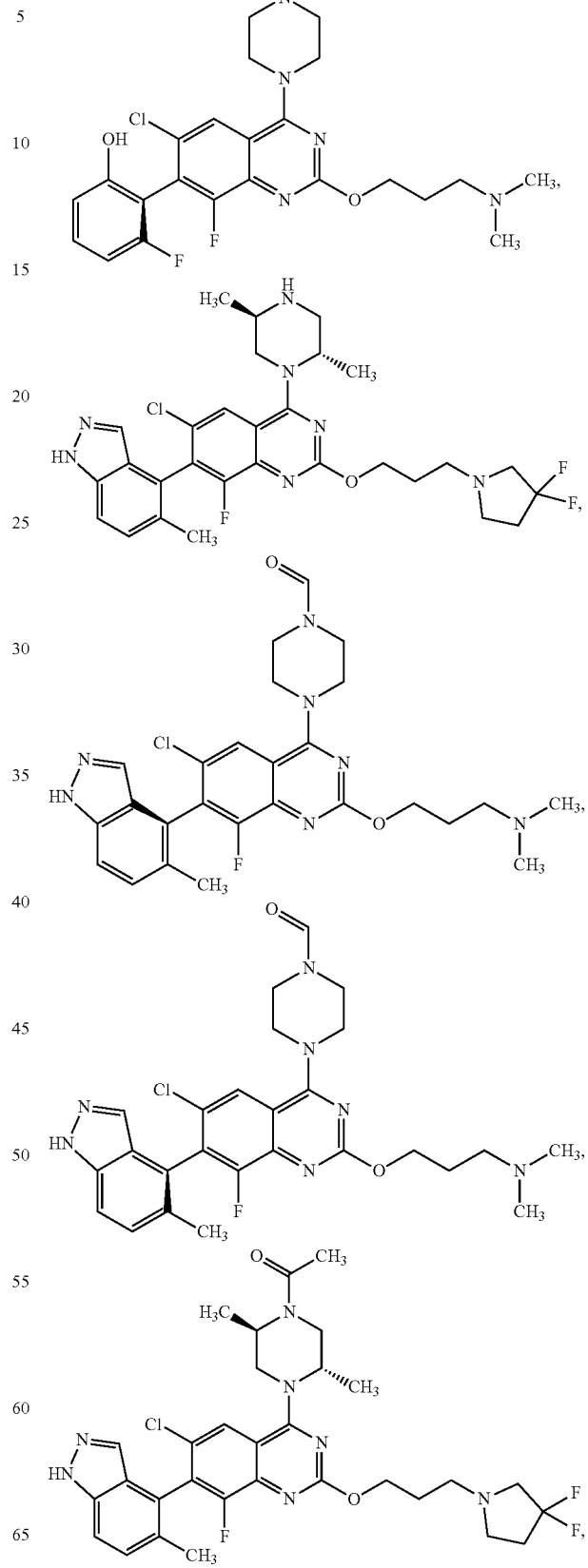

299
-continued
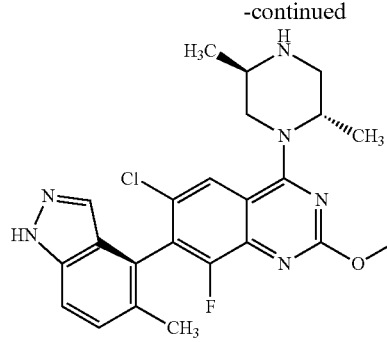
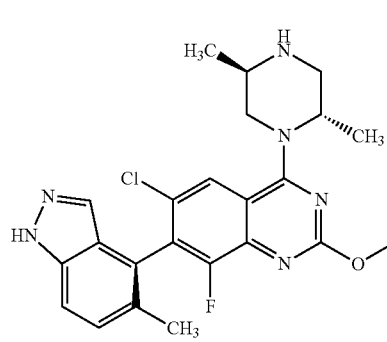
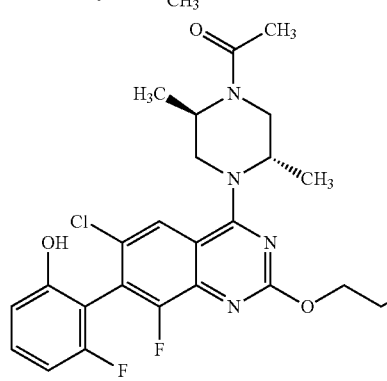
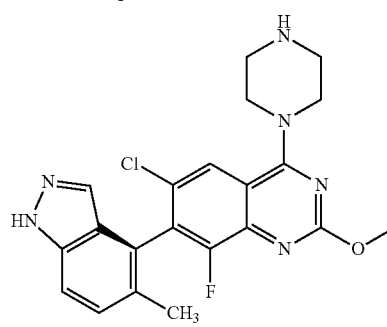
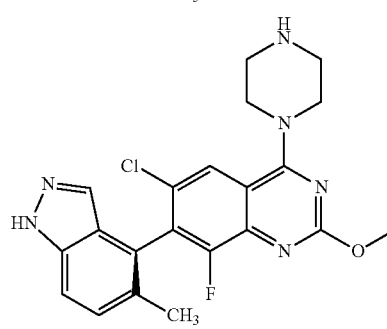
300
-continued
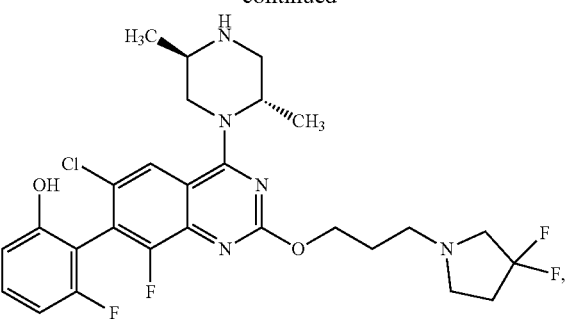
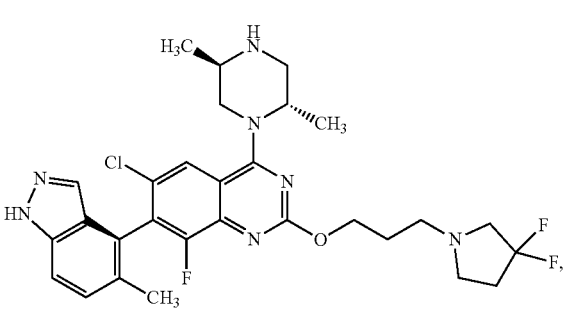
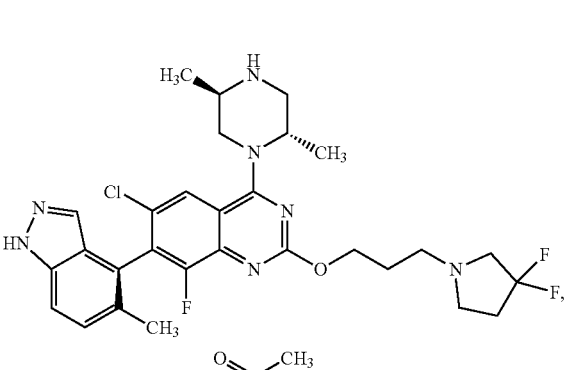
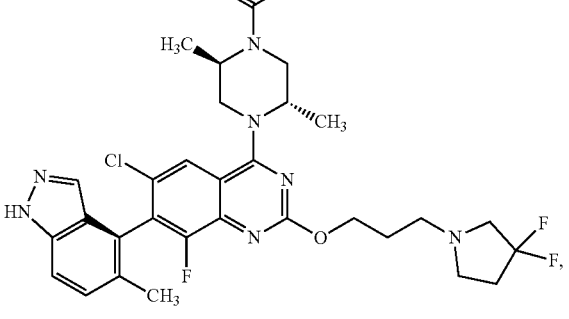
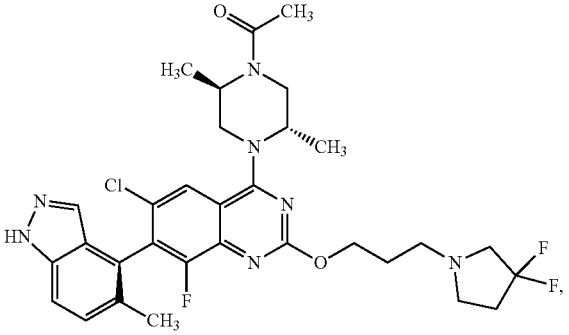

301
-continued
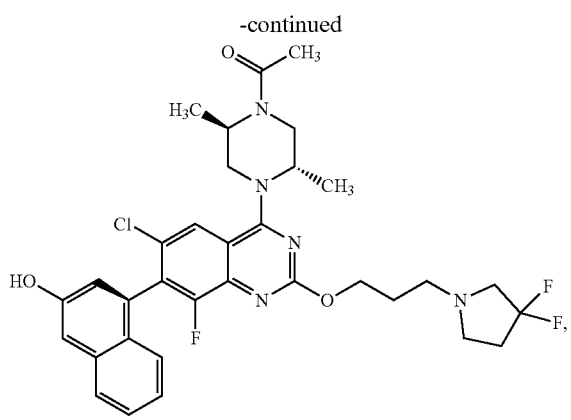
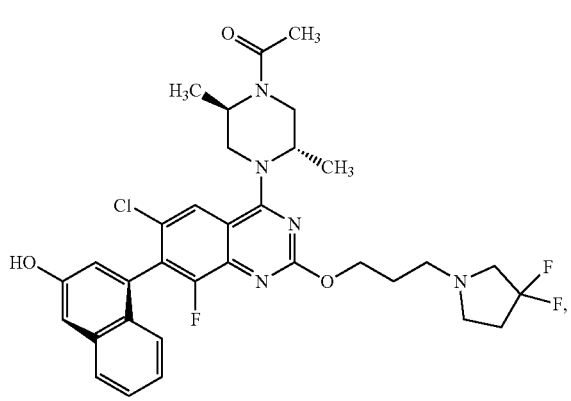
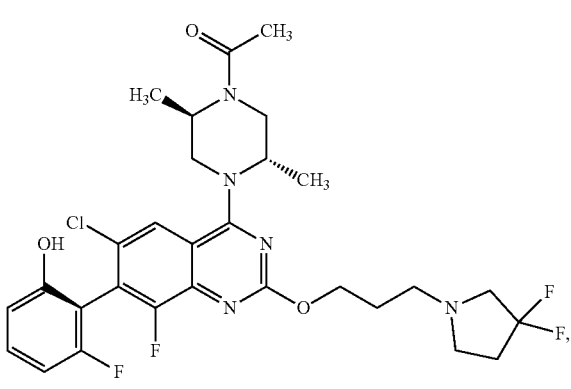
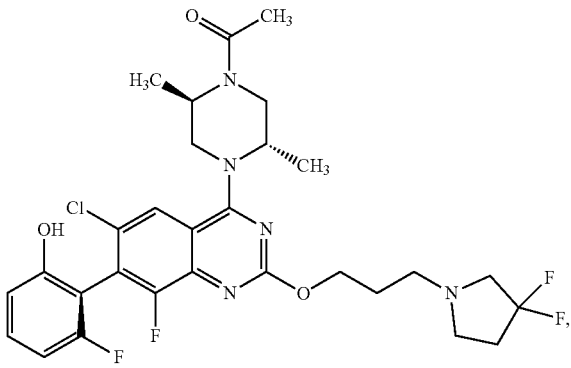
302
-continued
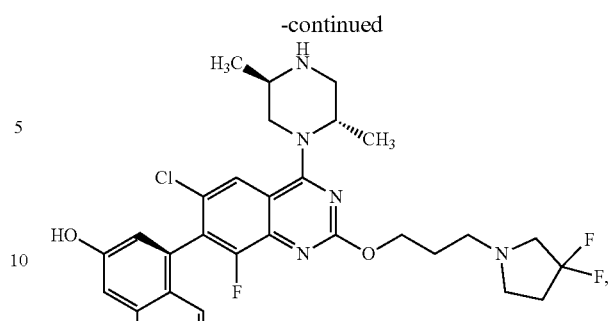
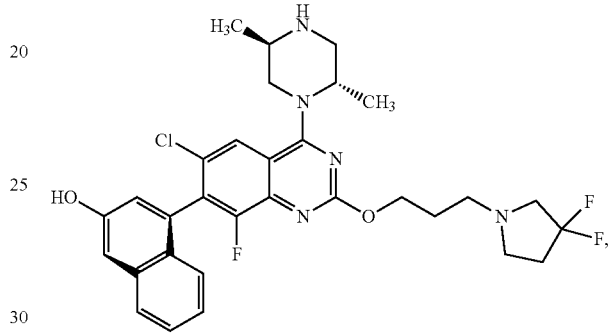
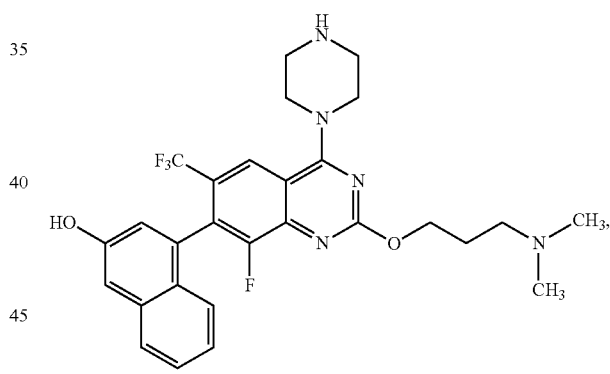
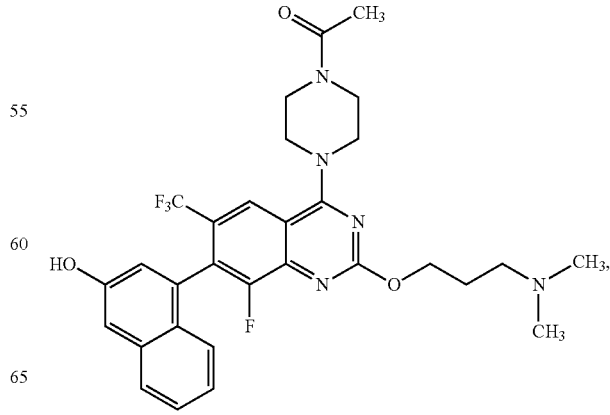

303
-continued
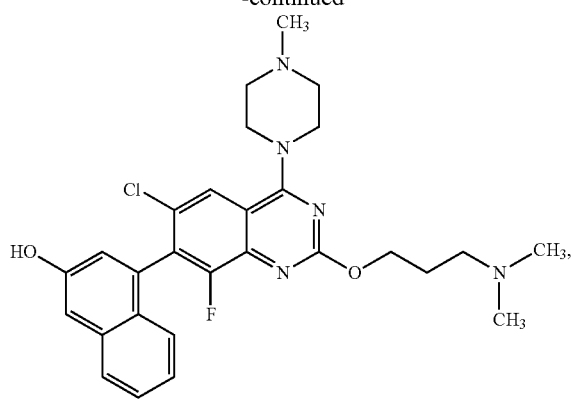
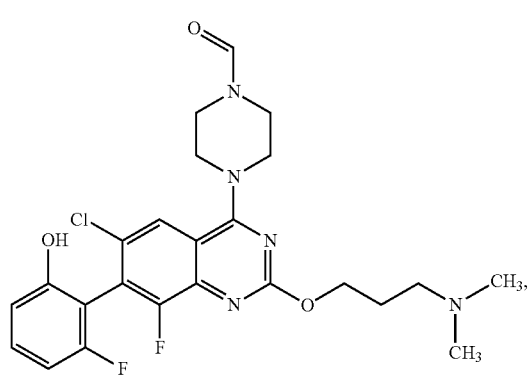
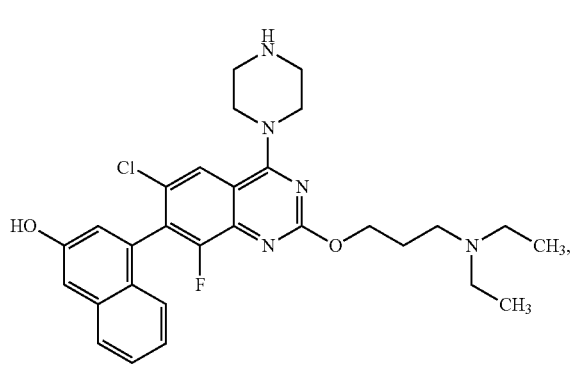
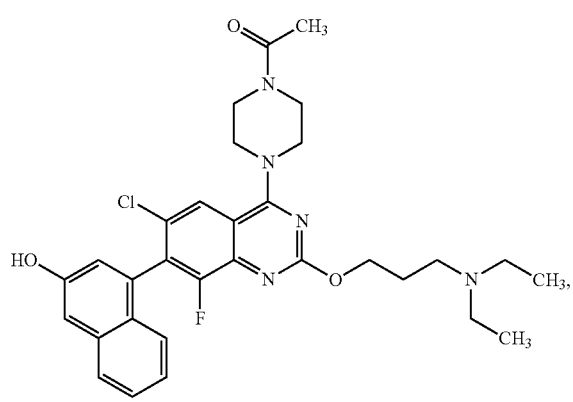
304
-continued
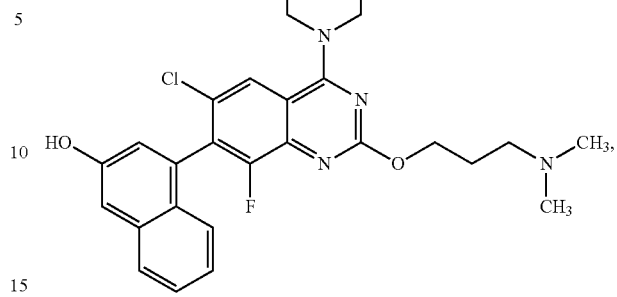
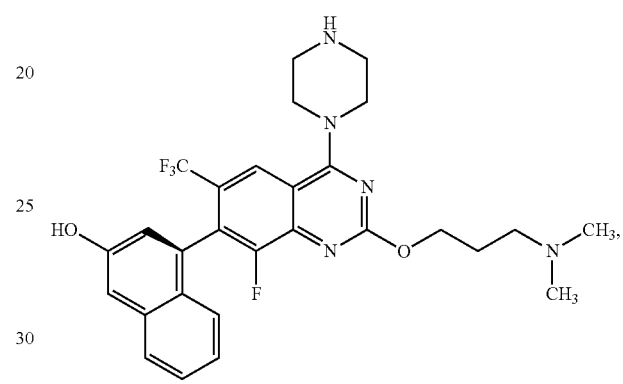
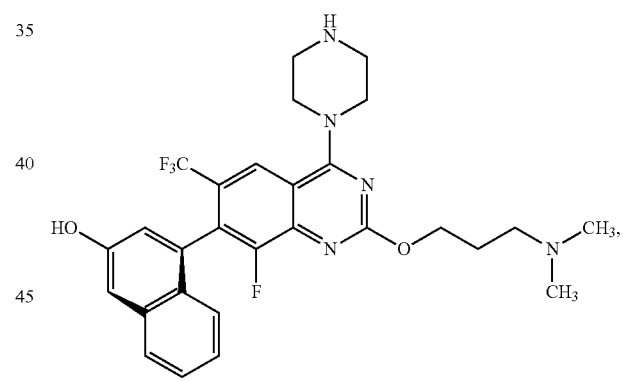
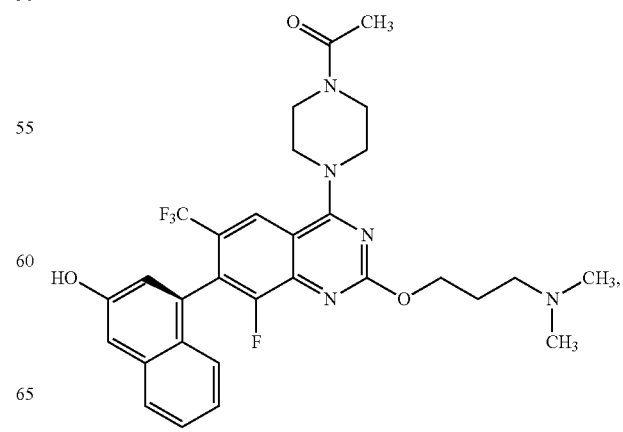

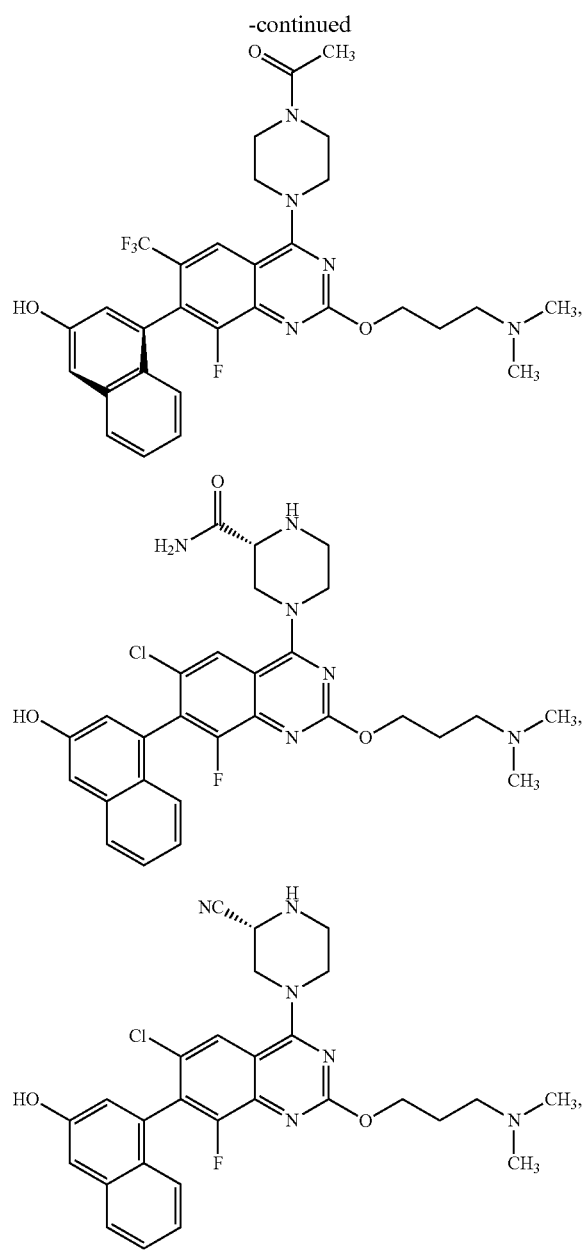
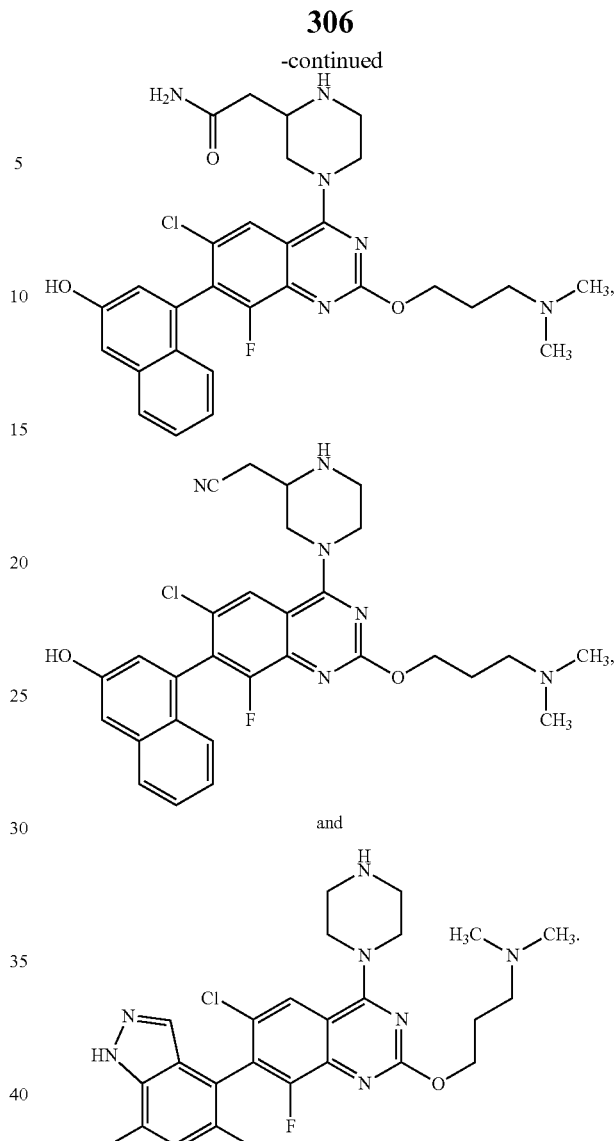
12. A pharmaceutical composition comprising a compound of claim 1, or a salt thereof, and a pharmaceutically acceptable carrier.
* * * * *